United States Patent [19]
Gradzki et al.

[11] Patent Number: 5,469,144
[45] Date of Patent: Nov. 21, 1995

[54] METHOD AND APPARATUS USING THRESHOLD TECHNIQUES FOR GENERATING AN ALARM IN A BIO-SENSOR

[75] Inventors: Pawel Gradzki, Lebanon, N.J.; Mark Kaynor; David Gruber, both of Christiansburg, Va.

[73] Assignee: Biological Monitoring, Inc., Blacksburg, Va.

[21] Appl. No.: 337,236

[22] Filed: Nov. 4, 1994

Related U.S. Application Data

[63] Continuation of Ser. No. 871,734, Apr. 21, 1992, abandoned, which is a continuation-in-part of Ser. No. 611,744, Nov. 13, 1990, abandoned.

[51] Int. Cl.⁶ .................................................. G01B 21/00
[52] U.S. Cl. .................................................. 340/603
[58] Field of Search ...................... 340/573, 603; 364/413.03, 413.05; 328/140; 324/76.39, 76.18, 76.25, 76.68; 119/2, 3, 4

[56] References Cited

U.S. PATENT DOCUMENTS 4,626,992  12/1986  Greaves .................................. 119/3 X
5,178,154  1/1993   Ackmann ........................ 364/413.03 X

FOREIGN PATENT DOCUMENTS 1083214  3/1984  U.S.S.R. ............................... 340/603

OTHER PUBLICATIONS

Ackmann, et al. "Non-Invasive Monitoring Techniques in Neuro-surgical Intensive Care". J. of Clinical Engineering, v 4, No. 4 (Oct.-Dec. 1979), 329-337.

*Primary Examiner*—Hezron E. Williams
*Assistant Examiner*—Christine K. Oda
*Attorney, Agent, or Firm*—Staas & Halsey

[57] ABSTRACT

A method for selecting and implementing waveform processing techniques for a Bio-Sensor®. The ventilatory cycles of a fish are used to determine when an alarm state is present. Threshold techniques used in the waveform processing include a dynamic threshold method and a static threshold method.

14 Claims, 3 Drawing Sheets

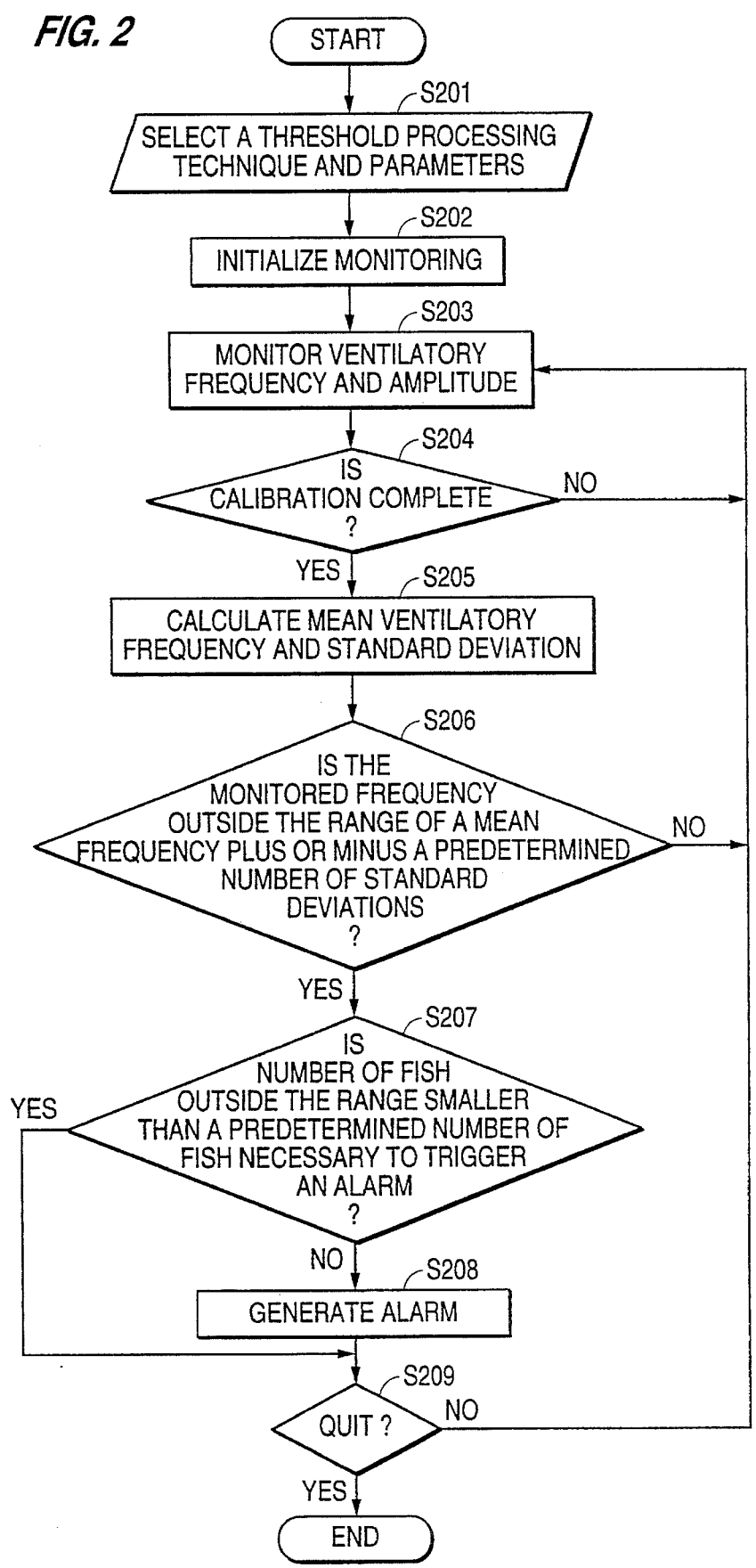

METHOD AND APPARATUS USING THRESHOLD TECHNIQUES FOR GENERATING AN ALARM IN A BIO-SENSOR

This application is a continuation of application Ser. No. 07/871,734, filed Apr. 21, 1992, now abandoned, which is a continuation-in-part of application Ser. No. 07/611,744, filed Nov. 13, 1990, now abandoned.

BACKGROUND OF THE INVENTION

The present invention is directed to a method of selecting and implementing threshold techniques for a Bio-Sensor® (a water quality monitoring system manufactured by Biological Monitoring, Inc. (BMI)) in which the threshold of a signal-filtering process is selected. The Bio-Sensor® is used, for example, in a system which detects the ventilatory frequency of fish used as biological sensors, for example, in a water quality monitoring system. The water quality monitoring system is described in U.S. Pat. No. 5,140,855, filed Nov. 13, 1990, U.S. Pat. No. 5,140,855 to Gruber et al., incorporated by reference herein. In addition, a Bio-Amp® employed in the system is described in U.S. Ser. No. 07/611,664, filed Nov. 13, 1990, now abandoned, by Harrison et al., incorporated by reference herein. The method of the present invention selects and implements different waveform processing techniques employing computer software developed to adequately process incoming signals.

SUMMARY OF THE INVENTION

It is an object of the present invention to provide a method in which one of two different waveform processing (threshold) techniques are selected and implemented.

It is another object of the present invention to provide a method which is used in selecting a waveform processing parameter from a menu.

It is yet another object of the present invention to provide a method to discriminate between ventilatory signals and other biological signals emitted by fish.

It is a further object of the present invention to select and implement various fish waveform processing techniques using computer software which identifies and assesses only the desired components of signals such as ventilatory behavior, specific body movements, etc.

The above objects are obtained by providing a software signal-filtering process used in determining ventilatory behavior. One of two waveform processing techniques, a static threshold method or a dynamic threshold method, is selected.

These objects, together with other objects and advantages which will be subsequently apparent, reside in the details of construction and operation as more fully hereinafter described and claimed, reference being had to the accompanying drawings forming a part hereof, wherein like reference numerals refer to like parts throughout.

BRIEF DESCRIPTION OF THE DRAWINGS

FIG. 2 is a flow chart of the operation of a Bio-Sensor® including selection of a threshold processing technique according to the present invention;

DESCRIPTION OF THE PREFERRED EMBODIMENT

Figure 1:
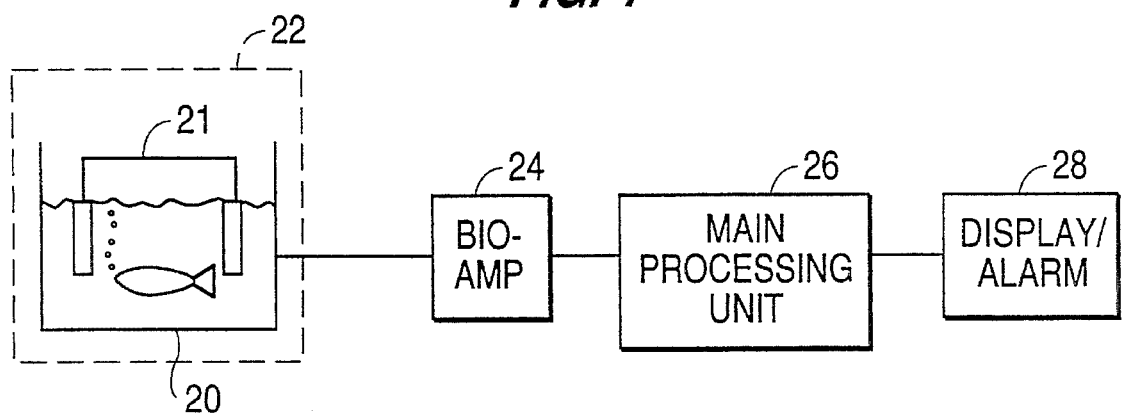
FIG. 1 is a block diagram of a Bio-Sensor® system using a threshold processing technique according to the present invention.

It has been demonstrated that what is toxic to fish is toxic to humans. Therefore, fish can serve as indicators of poor water quality which would be detrimental to aquatic ecosystems. These systems can be monitored to determine the quality of, for example, drinking water, as well as the quality of wastewater discharges and chemicals. The water and waste streams can also be monitored for the purposes of environmental audits.

The present invention provides the bases for developing computer software for analyzing fish ventilatory behavior and certain locomotor behaviors in biological automated and real time early warning water quality monitoring systems. Analog microvolt bio-electric signals, such as those generated by fish, can be amplified, filtered and interfaced to computers by employing appropriate hardware techniques such as a Bio-Amp®. The Bio-Amp® inputs a fish ventilatory signal to a computer interface. Such a device provides a computer's analog-to-digital converter with a consistent but not perfect signal-to-noise ratio. The signal represents a fish's breathing behavioral cycle and certain locomotor activity. The noise may originate from water movement, unwanted body movements and extraneous electrical signals. The use of a proper overall monitoring system as disclosed in the present invention (e.g., a Bio-Sensor®—manufactured by Biological Monitoring, Inc. (BMI)—a fish biological water quality monitor) will reduce most, but not all, of the noise. For example, the cabinet of the Bio-Sensor® housing the fish monitoring components acts as a Faraday cage, eliminating most extraneous electrical noise.

The ventilatory behavior for each fish in the water quality monitoring system of the present invention is used in statistical calculations in the Bio-Sensor®. The Bio-Sensor® of the present invention is a fish automated, real time water quality monitoring system. The system employs fish as sensors to detect the presence of poor water quality (e.g., the presence of toxics). The Bio-Sensor® assesses water quality by primarily monitoring fish ventilatory behavior. Certain locomotor behavior, such as quivers or episodes, and a fish's turning behavior or position in a monitoring tank can also be monitored and assessed. In the Bio-Sensor® individual fish are placed in separate monitoring chambers. Generally 8 to 12 fish are used, but more or less can be employed depending on the system.

Every living organism has a bio-electric field ($\mu v$) which is the result of the summation of its neuromuscular activity. The water in which aquatic organisms live serves as a conductor of the bio-electric field. This property enables the Bio-Sensor® system to receive or detect the bio-electric field by employing a pair of submerged, non-contact electrodes 21. Signals from the electrodes 21 are interfaced to a microcomputer system through a Bio-Amp® 24. The Bio-Amp® 24 includes a power supply and individual bio-amplifiers for each fish. Each bio-amplifier processes the bio-electric field signals from each fish, respectively, and converts the signals to analog signals varying in voltage over time and having a magnitude of ±10 volts suitable for computer interfacing. The bio-amplifiers process the signals so that changes in analog voltage represent components of a fish's ventilatory behavior and certain locomotor behavior components. After computer interface, software in the Bio-Sensor® 22 further processes the signals and assesses the signals for significant behavioral changes in either real time or on a subsequent basis. When operating on a real time basis, the Bio-Sensor® 22 generates alarm routines when a significant number of fish are assessed as behaving abnormally at the same time.

The basic components of a system for detecting the ventilatory behavior of a fish and sounding an alarm are shown by the block diagram in FIG. 1. A tank 20 having a fish therein is set up to be monitored in the Bio-Sensor® 22 of the present invention (only one tank is shown for simplicity).

As shown in FIG. 1, the two electrodes 21 are made of a single piece of stainless wire mesh (e.g., #316), fit into a teflon mount. The electrodes 21 are made of materials recommended by the U.S. Environmental Protection Agency for use in aquatic toxicity studies. The electrodes 21 receive signals from the bio-electric field generated by a fish. The Bio-Amp® processes the bio-electric signals as received by the electrodes 21 in monitoring chambers of the Bio-Sensor® 22. The Bio-Amp® detects the ventilatory behavior (breathing) of fish by detecting the bio-electrical signals (neuromuscular ventilatory signals) generated by the breathing of fish and amplifies the signal for use in for example, a water quality monitoring system. The fish are used as biological sensors. That is, as a fish ventilates (breathes), the sum of its neuromuscular activities generate bio-electrical signals. The strongest of these signals is the ventilatory signal. This signal, however, is not strong enough to be processed without amplification. Therefore, the analog bio-electrical signal, representing all ventilatory behavior and certain locomotor behaviors, is picked up by electrodes 21 in the Bio-Sensor® 22, and is amplified by the Bio-Amp® 24. The system includes a voltage tunable low-pass filter which can be set according to the desired functions of the system. A computer processing unit 26 receives a plurality of amplified ventilatory signals and performs threshold processing and various statistical calculations using Bio-Sensor® software, to determine whether an alarm state is present. A display 28 can visually and aurally issue an alarm based on the output from the computer processing unit 26.

The computer processing unit 26 receives a plurality of amplified analog ventilatory signals, which include data representing locomotor behavior of the fish, from bio-amplifiers in the Bio-Amp® 24 and performs various statistical calculations including threshold processing, using software, to determine whether an alarm state is present. A display 28 can visually and 15 aurally issue an alarm based on the output from the computer processing unit 26.

Cross-talk between different signals does not exist because the system is encapsulated in cabinetry which acts as a Faraday cage.

When fish monitoring is initiated, the software in the computer processing unit 26 has no statistical data to work with. Therefore, only after a predetermined number of assessment intervals have been processed can the statistical evaluation be initiated. (An assessment interval is an amount of time during which the number of ventilatory gill movements of a fish is counted. At the end of each assessment interval, the ventilatory behavior, mean ventilatory behavior and standard deviation, are calculated as a single statistical event.) That is, each channel of the Bio-Sensor® 22 must be calibrated. This calibration process includes determining mean ventilatory behavior and standard deviation for each channel. A calibration period lasts for an amount of time equal to the assessment interval multiplied by the number of samples required for a statistical event. The ventilatory behavior of a fish is determined based on how often it breathes, one inhalation and one exhalation are considered one cycle. The acceptable range of ventilatory behavior for each channel can be continuously re-adjusted by choosing different numbers of standard deviations taken around the ventilatory behavior mean if desired. The acceptable range is determined during calibration. Once a ventilatory behavior range for each fish is determined, analysis for determining an alarm state is commenced as discussed below.

The ventilatory behavior of a fish is compared to past ventilatory behavior values averaged over a predetermined number of assessment intervals, plus or minus a predetermined number of standard deviations. If the result of the statistical evaluation falls outside the ventilatory behavior range, a warning is generated. If the number of fish in simultaneous warning states is equal to or greater than a preset number, an alarm is generated. A predetermined number of fish must ventilate outside the ventilatory behavior range during the same time period to generate an alarm.

If any one fish generates a predetermined number of consecutive warnings, and an alarm is not generated, the statistical parameters for that channel are recalibrated. During recalibration that channel is not used in the determination of a generated alarm. After recalibration is complete, that channel is again included in the determination of the alarm state.

FIG. 2 is a flow chart of the operation of the Bio-Sensor® 22 according to the present invention. During the monitoring of the ventilatory behavior of a fish the analog ventilatory signals (or other locomotor behavior signals) are discriminated from other biological signals. The ventilatory signals have a higher amplitude than other biological signals. A discrimination operation is implemented using a threshold technique in which present data is compared to recent data using an unchanging module. The software of the present invention implements either one of two different threshold techniques S201 for the "threshold voltage" algorithm: a "static threshold method" or a "dynamic threshold method." A default function is provided such that the dynamic threshold method is selected when a selection input is not provided. The "static threshold method" and "dynamic threshold method" will be discussed hereinafter with respect to FIGS. 3 and 4. Step S202 initializes monitoring of a fish. Step S203 monitors ventilatory frequency and amplitude. Step S204 determines whether a calibration process is complete. If not, the process returns to step S203. If so, the process proceeds to step S205 in which a mean ventilatory frequency and standard deviation are calculated. Step S206 then determines whether the monitored ventilatory frequency is outside a mean frequency range plus or minus a predetermined number of standard deviations. If no, the process returns to step S203. If yes, step S207 then determines whether the number of fish outside the range is smaller than the predetermined number of fish necessary to trigger an alarm. If yes, then the process is completed in step S209, If no, an alarm is generated in step S208.

Figure 3:
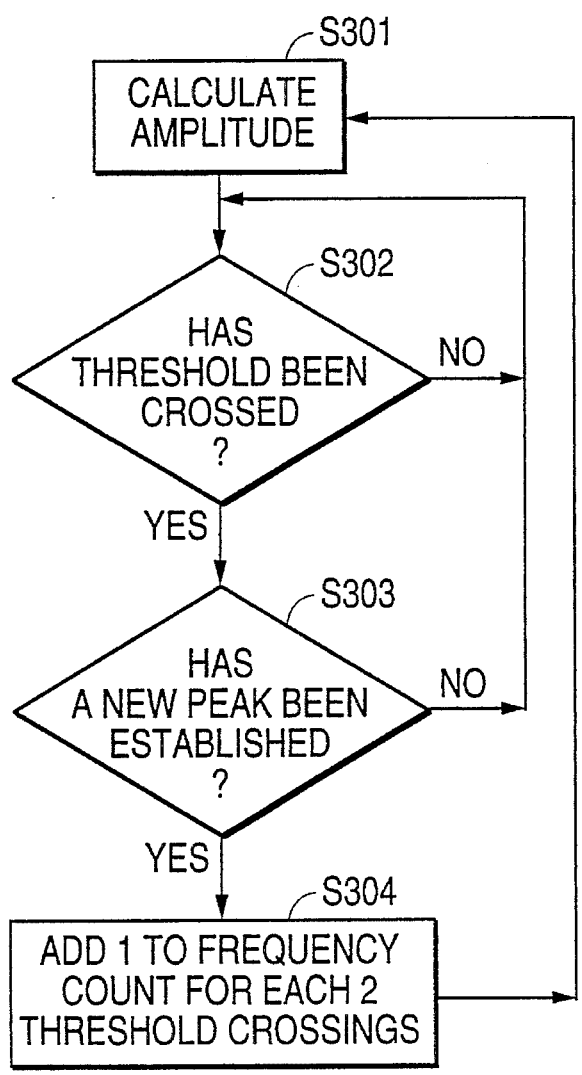
FIG. 3 is a flow chart of the operation of the static threshold method according to the present invention.

The static threshold method which uses a preset fixed threshold voltage value will now be explained. FIG. 3 is a flow chart of the operation of the static threshold method according to the present invention. It is first determined whether a threshold has been crossed (step S302). A threshold is crossed when a difference between a last established voltage peak and a present voltage sample is equal to the preset fixed threshold value. For two consecutive threshold crossings (a positive threshold crossing is one in which the signal crosses the preset fixed threshold going from the negative direction to the positive direction and a negative threshold crossing is one in which the signal crosses the preset fixed threshold going from the positive direction to the negative direction), one ventilatory cycle with respect to time (or breath) is counted.

As an example, assume that the voltage is increasing. Each consecutive higher voltage sample replaces the last as the highest established voltage. That is, it is determined in step S303 whether a new peak has been established. If so, the following occurs. Now assume that the voltage has increased to +2.46 volts and begins to decline. As the voltage declines from +2.46 volts, the static threshold algorithm retains +2.46 volts as the highest established voltage and compares each consecutive voltage sample +2.46 minus the preset fixed threshold value. Assuming the preset fixed threshold value is set at 0.25 volts, when the voltage reaches +2.21 volts (+2.46 volts–0.25 volts), the static threshold algorithm validates +2.21 volts as a valid peak to be counted as one-half of a frequency count. After the +2.21 volt peak is validated, the static threshold algorithm then retains each consecutive lower voltage sample as the lowest established voltage until the voltage again changes direction. Assume this occurs at −3.35 volts. As the voltage increases, each consecutive higher voltage sample is compared to −3.35 volts plus the preset fixed threshold value of 0.25 volts. When the voltage reaches −3.10 volts, the static threshold algorithm validates −3.35 volts as a valid peak to be counted as one-half of a frequency count. Thus, two threshold crossings, one positive and one negative, are required to increase the count by one as shown in step S304. Then, amplitude is recalculated (step S301).

Figure 4:
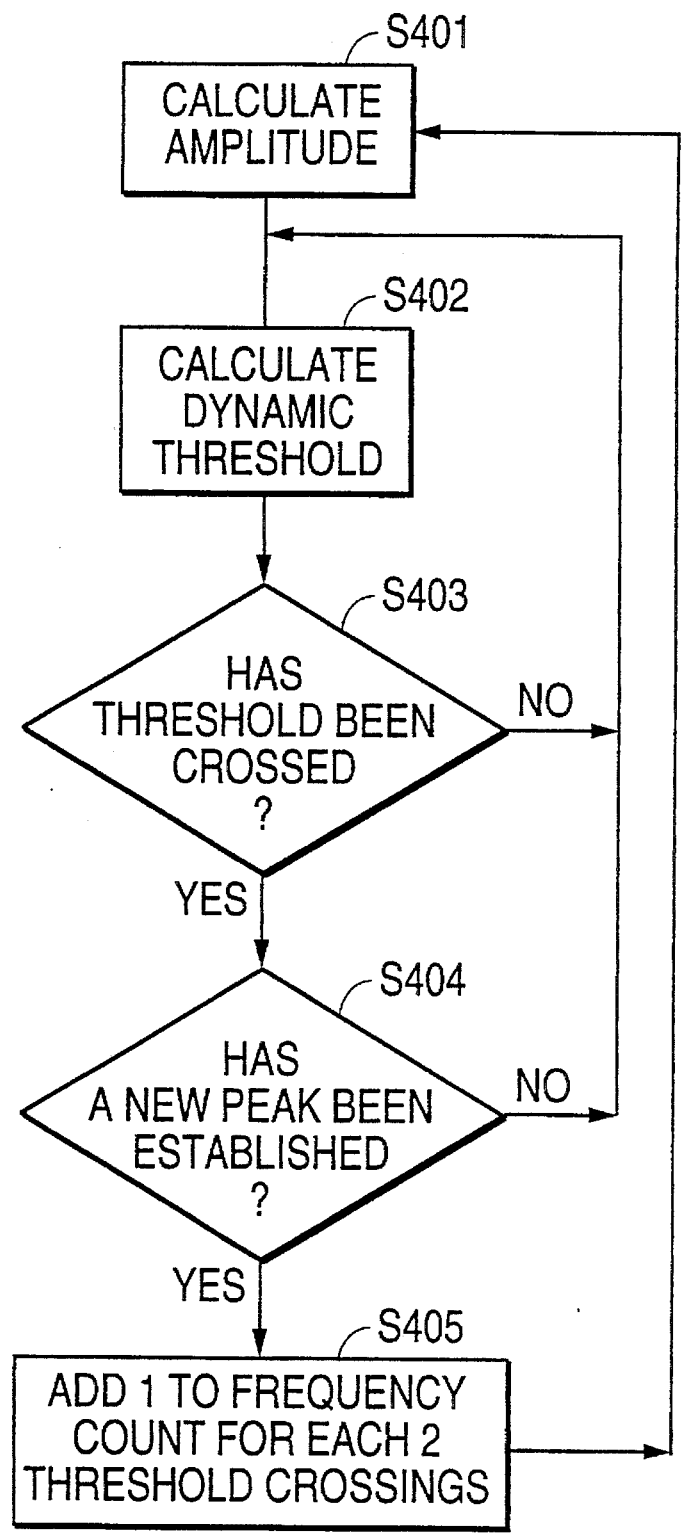
FIG. 4 is a flow chart of the operation of the dynamic threshold method according to the present invention.

The dynamic threshold method will now be explained. FIG. 4 is a flow chart of the dynamic threshold method according to the present invention. The dynamic threshold method employs a variable threshold voltage. The value of the dynamic threshold is determined in step S402 by a dedicated algorithm which uses the amplitude of the waveform and the time elapsed from a most recently validated peak. The algorithm uses the following formula:

$$V_T(t) = (V_{pp}/2) * A * e^{-t/T}$$

where $V_T$ is the dynamic threshold value in volts, $V_{pp}$ is the last cycle peak-to-peak voltage, A is the predetermined dynamic threshold as a percent of amplitude value, t is the time elapsed from the last threshold crossing in seconds, T is the dynamic threshold time constant value, and e is the base natural logarithm (2.7182818 ...).

$V_T$ is not a constant value, but rather is time-dependent, as denoted by $V_T(t)$. In FIG. 4, step 403 determines whether a threshold has been crossed.

A new value of $V_T(t)$ is determined for each change in voltage and is compared with the difference between the most recently validated peak and the preset voltage. This value is calculated independently for each individual fish. As an example, assume the following:

(a) the last peak-to-peak voltage was 5.00 volts;
(b) the time constant is 5.0 seconds;
(c) the dynamic threshold as a percent of amplitude is set to 50.0%; and
(d) the elapsed time from the last established peak is 2.0 seconds.

Therefore, $$\begin{aligned} V_T(t) &= (5.00/2) * 0.50 * 2.718^{-2/5} \\ &= (2.5) * 0.5 * 2.718^{-0.4} \\ &= 0.8379 \text{ volts} \end{aligned}$$

The present cycle must now change 0.8379 volts from the value of the last established peak prior to changing direction before another valid peak is established and it is determined in step S404 whether a new peak has been established. If so, step S405 adds a 1 to a frequency count for each two threshold crossings.

Assuming that the steady-state peak-to-peak voltage for a ventilatory cycle for a particular fish is 0.836 volts, then after the large 5.00 volt cycle previously described, the fish returns to its steady state ventilatory behavior. If the dynamic threshold (0.8379 volts) is not allowed to decay over time, the fish would continue breathing at its steady-state amplitude without registering a valid peak. This situation would result in the fish showing zero ventilatory behavior from this time on. In order to avoid this situation, the present software allows the dynamic threshold to decay (or decrease) over time. A predetermined parameter "dynamic threshold time constant" is employed which is that amount of time it takes for $V_T$ to decay e times if no valid peaks are established (the value $V_T$ will never go below the predetermined minimum threshold voltage). Step S401 calculated amplitude. As $V_T$ decays, it eventually becomes small enough to register a new peak at the steady state amplitude and frequency for this fish, or it becomes equal to the "predetermined minimum threshold voltage". As the amplitude decreases, so does the dynamic threshold.

The source code for the method of the present invention is attached hereto as an Appendix.

The foregoing is considered illustrative only of the principles of the present invention. Further, since numerous modifications and changes will readily occur to those skilled in the art, it is not desired to limit the invention to the exact construction and applications shown and described, and accordingly, all suitable modifications and equivalents may be resorted to, falling within the scope of the invention and the appended claims and their equivalents.

```
unit BMIDEnt;
{*********************************************************************}
{                                                                      }
{ Copyright (c) Biological Monitoring, Inc. 1987, 1990                 }
{                                                                      }
{*********************************************************************}

(*
ëëëëëëëëëëëëëëëëëëëëëëëëëëëëëëëëëëëëëëëëëëëëëëëëëëëëëëëëëëëëëëëëëëëëëëë£
¤                                                                     ¤
¤  GETSTRING - Returns a string of up length 12 to the calling routine. ¤
¤              Reads starting at the current pointer.                  ¤
¤                                                                     ¤
àëëëëëëëëëëëëëëëëëëëëëëëëëëëëëëëëëëëëëëëëëëëëëëëëëëëëëëëëëëëëëëëëëëëëëë¥
*)

interface uses
   Dos,
   Crt,
   Graph,
   BMIConst,
   mouse,
   BMIKey;

{
 GetString is used to get a string of characters in graphics
 mode.
}
procedure GetString   (        Leng : word;
                             CurPos : byte;
                            OrigStr : String;
                        var Result  : String;
                              Upper : boolean;
                             IsDate : boolean;
                             IsTime : boolean);

implementation

Type
   PosRec = record
      Ch  : char;
      X,Y : word;
   end;
   PosArray = array[1..255] of PosRec;

var
   OrigBkColor,
   OrigFGColor : byte;

{
 draws the cursor that tells where the next data point will go
}
procedure DrawTag (Index : byte;
```

```
                    ChPos   : PosArray;
                    TextInfo:TextSettingsType;
                    ShowIt  : boolean);
const  Tag_correction : array [1..5] of PointType=( (x:0;y:3),
                                                    (x:-2;y:3),
                                                    (x:-2;y:9),
                                                    (x:0;y:9),
                                                    (x:0;y:3));
var
  TH,
  TW             : word;
  Tag            : array [1..5] of PointType;
  LineInfo       : LineSettingsType;
  i              : byte;

begin
  TW := TextWidth ('H');
  TH := TextHeight ('/');

Tag[1].x := ChPos[Index].X + TW div 2;
  Tag[1].y := ChPos[Index].Y-(TH div 2);
  Tag[2].x := ChPos[Index].x - TW div 2;
  Tag[2].y := Chpos[Index].Y-(TH div 2);
  Tag[3].x := ChPos[Index].x - TW div 2;
  Tag[3].y := ChPos[Index].Y+(TH div 2);
  Tag[4].x := ChPos[Index].X + TW div 2;
  Tag[4].y := ChPos[Index].Y+(TH div 2);
  Tag[5].x := ChPos[Index].x + TW div 2;
  Tag[5].y := ChPos[Index].y-(TH div 2);

if TextInfo.Font = SansSerifFont then
     for i:=1 to 5 do begin
                    Tag[i].x:=Tag[i].x+Tag_correction[i].x;
                    Tag[i].y:=Tag[i].y+Tag_correction[i].y;
                    end;

OrigFGColor := GetColor;
  GetLineSettings (LineInfo);
  SetLineStyle (UserBitLn,0,NormWidth);
  if ShowIt then SetFillStyle (SolidFill,White)
          else
          SetFillStyle (SolidFill,OrigBkColor);
  FillPoly (SizeOf (Tag) div SizeOf (PointType),Tag);
  if showIt then SetColor(Blue) else SetColor (OrigFGColor);
  OutTextXY (ChPos[Index].x,ChPos[Index].y,ChPos[Index].Ch);
  SetColor (OrigFGColor);
  with LineInfo do
    SetLineStyle (LineStyle,Pattern,Thickness);
end;

{
 removes any spaces in a string
} function RemoveSpaces (S : String) : String;
begin
  while S[length(s)] = #32 do
    S := copy (S,1,length (S) -1);
  if Pos(' ',S) = 1 then while S[1] = ' ' do S := copy (S,2,length(S));
  RemoveSpaces := S;
```

```
end;

{*****************************************************************
   6/26/90 - new function and const follow - display ¯ to show length of
            string being edited.
*****************************************************************} const
  FillChar = #176;

function RemoveFillChar (S: String) : string;
begin
  while S[length(s)] = FillChar do
    S := copy (S,1,Length(s) -1);
  if pos (FillChar,S) = 1 then while S[1] = FillChar do S := copy (S,2,length(s)
  RemoveFillChar := S;
end;

{***************** END 6/26/90 addition **********************} procedure PrepString (Leng : byte; var Str1 : String);
var
  i    : byte;
begin
  Str1 := RemoveSpaces (Str1);
  while length (Str1) < Leng do str1 := str1 + FillChar;
end;

procedure GetString (       Leng    : word;
                            CurPos  : byte;
                            OrigStr : string;
                        var Result  : string;
                            Upper   : boolean;
                            IsDate  : boolean;
                            IsTime  : boolean);
var
  i,j,k      : byte;
  Key        : char;
  X1,Y1,TW   : word;
  TextInfo   : TextSettingsType;
  ChPos      : PosArray;
  Index      : byte;
  FG         : byte;
  Done       : boolean;
  FillInfo   : FillSettingsType;
begin
  Done := false;
  GetTextSettings (TextInfo);
  SetTextJustify (CenterText,CenterText);
  GetFillSettings(FillInfo);
  OrigBkColor := FillInfo.Color;
  X1 := GetX;
  Y1 := GetY;
  TW := TextWidth ('H');
  Result := copy (OrigStr,1,leng);
  PrepString (Leng,Result);
  FG := GetColor;
```

```
         if not FG = white then SetColor(white);
         for i := 1 to Leng do
         begin
            ChPos[i].X := X1 + ((i-1)*TW);
            ChPos[i].Y := Y1;
            if not Upper then ChPos[i].Ch := Result[i]
              else ChPos[i].Ch := upcase (Result[i]);
               OutTextXY (ChPos[i].X,ChPos[i].Y,ChPos[i].Ch);
         end;
         Index := CurPos;
         DrawTag (Index,ChPos,TextInfo,True);
         Result := OrigStr;
         MShown := true;
         repeat
            Key := GetKey;
            case Key of
               RArr : begin
                         DrawTag (Index,ChPos,TextInfo,False);
                         OutTextXY (ChPos[Index].X,ChPos[Index].Y,' ');
                         if Index < leng then inc (Index) else Index := 1;
                         DrawTag (Index,ChPos,TextInfo,True);
                      end;
               LArr : begin
                         DrawTag (Index,ChPos,TextInfo,False);
                         if Index > 1 then dec (Index) else Index := Leng;
                         DrawTag (Index,ChPos,TextInfo,True);
                      end;
         #32..#126 : begin
                         if IsDate then if Index in [3,6] then Key := '/';
                         if IsTime then if Index = 3 then Key := ':';
                         SetColor (OrigBkColor);
                         OutTextXY (ChPos[Index].X{+TW div 2},ChPos[Index].Y,ChPos[Index].
                         SetColor (OrigFGColor);
                         if not Upper then ChPos[Index].Ch := Key
                           else ChPos[Index].Ch := upcase (Key);
                         OutTextXY (ChPos[Index].X{+TW div 2},ChPos[Index].Y,ChPos[Index].
                         DrawTag (Index,ChPos,TextInfo,False);
                         if Index < Leng then inc (Index) else Index := 1;
                         DrawTag (Index,ChPos,TextInfo,True);
                      end;
               BkSp : begin
                         DrawTag (Index,ChPos,TextInfo,False);
                         if Index > 1 then
                         begin
                            i := Index;
                            dec (i);
                            ChPos[Leng+1].Ch := FillChar;
                            for Index := i to Leng do
                            begin
                               ChPos[Index].Ch := ChPos[Index+1].Ch;
                               DrawTag(Index,ChPos,TextInfo,False);
                            end;
                         end;
                         Index := i;
                         DrawTag (Index,Chpos,TextInfo,True);
                      end;
               Del  : begin
                         DrawTag (Index,ChPos,TextInfo,False);
                         ChPos[Leng+1].Ch := FillChar;
                         for i := Index to Leng do
```

```
                begin
                  ChPos[i].Ch := ChPos[i+1].Ch;
                  DrawTag(i,ChPos,TextInfo,False);
                end;
              DrawTag (Index,Chpos,TextInfo,True);
            end;

Esc,
      MEsc,
      Enter,
      MEnter : Done := true;

end;

until Done;
  DrawTag (Index,ChPos,TextInfo,false);
  MShown := false;
  with TextInfo do
    SetTextJustify (Horiz,Vert);
  if Key in [Esc,MEsc] then Result := OrigStr
  else
  begin
    Result := '';
    for i := 1 to Leng do Result := Result + ChPos[i].Ch;
    Result := RemoveFillChar (Result);
  end;
  if not FG = white then SetColor (FG);
end;

end.
unit bmiconst;
{*******************************************************************************}
{                                                                               }
{ Copyright (c) Biological Monitoring, Inc. 1987, 1990                          }
{                                                                               }
{ This unit contains global constants, types and variables required by other   }
{ modules                                                                       }
{                                                                               }
{*******************************************************************************}
interface
uses dos;
const
                        CompilationDateGlbConst = '31 October, 1991';
                        VersionNumStrGlbConst   = '5.10';

{$IFDEF SCOUTDAC}
                        DAC02BaseAddress    = $310; {Best guess - change }
                                                    {when installed     }
                        ScoutHiTemperature  = 40;   {Best guess in Deg.C.}
                        ScoutHiDissolvedO2  = 18;   {Best guess in mg/L  }
{$ENDIF}
                        RecoveryFileNameOne   = 'RECOVER1.HIS';
                        RecoveryFileNameTwo   = 'RECOVER2.HIS';
                        PowerLossSetupFileName = 'SETUP.HIS';
                        {$IFDEF EXP}
                        SetupFileName='bmi6012x.prf';
                        {$ELSE}
                        SetupFileName='bmi6008a.prf';
                        {$ENDIF}
```

```
                        Max_samples         = 100;

{digital IO assignments - 1/25/91 - MK}
                        BioAlarmOutput       = 0;
                        IntSamplerOutput     = 1;
                        PhysChemAlarmOutput  = 2;

{Input 0 is reserved for DMA trigger - DO NOT USE}
                        IntSamplerOverrideInput = 1;

{end digital assignments}
{$IFDEF EXP}
                        number_of_fish  =12;   { must be even for FFT !! }
{$ELSE}
                        number_of_fish  =8;    { must be even for FFT !! }
{$ENDIF}
{$IFDEF SCOUT}
     {$IFDEF SCOUTDAC}
                        number_of_Scout_parameters=2; {Marolyn's request 1/3/199
     {$ELSE}
                        number_of_Scout_parameters=4;
     {$ENDIF}
{$ENDIF}
{$IFDEF ANALOGPH}
                        number_of_analog_parameters=8;
{$ELSE}
                        number_of_analog_parameters=0;
{$ENDIF}

{$IFDEF SCOUT}
     {$IFNDEF ANALOGPH}
                        number_of_assignments=number_of_fish+number_of_Scout_Par
                        number_of_channels=number_of_fish;
     {$ELSE}
                        number_of_assignments= number_of_fish+
                                       number_of_Scout_Parameters+
                                       number_of_Analog_parameters;
                        number_of_channels=number_of_fish+number_of_analog_param {$ENDIF}
{$ELSE}
     {$IFDEF ANALOGPH}
                        number_of_assignments=number_of_fish+number_of_Analog_pa
                        number_of_channels=number_of_fish+number_of_analog_param
     {$ELSE}
                        number_of_assignments=number_of_fish;
                        number_of_channels=number_of_fish;
     {$ENDIF}
{$ENDIF}
                        acquisition_time =60; {seconds}
                        acquisition_period = 1.0*acquisition_time;
                                        {real seconds}
(*-           data_position    =500;
              Xst              =10;
              Y40              =12;
              Y30              =15;-*)
              Y20              =23;
```

```
                       Y10             =47;
  (*-                   Y3Y20            =69;
                       Y5Y20           =115;
                       Y7Y20           =161;
                       Y9Y20           =207;
                       Y10Y20          =230;-*)
                       Y11Y20          =253;
  (*-                   Y12Y20           =276;
                       Y13Y20          =299;
                       Y15Y20          =345;-*)
                       Y17Y20          =391;
  (*-                  Xsto            =333;-*)
                       Xmax            =639;
                       Ymax            =479;
                       Xcen            =319;
                       Xo              =64;
                       Yo              =384;
                       Xsize           =512;      { constants associated with
                       Ysize           =288;      { are set for VGA mode }
                       general         =0;
                       waveform_plot   =1;
                       spectrum_amplitude=2;
{$IFDEF SPECTRUM}
                       max_status      =3;  {
                                               how many screens in fish
                                               monitoring : spectrum,
                                               waveform display, general
                                               status }

FFT_max_vector_size=4096;
{$ELSE}
                       max_status      =2;   {
                                                only general status and
                                                waveform display screens
                                                this variable controls
                                                how many screens to display.
                                             }
{$ENDIF}
                       board_num       =0;
                       base_adr        =$300;
{$IFDEF MICROCHANNEL}
{ instructs the computer on how to set up the DAS-16 in terms of
  the DMA channel and interrupt level to handle DMA on both
  IBM microCHANNEL machines and non microCHANNEL machines } int_level       =9;
                       dma_level       =1;
{$ELSE}
                       int_level       =2;
                       dma_level       =1;
{$ENDIF}
                       chanlo          =0;
                       chanhi          =number_of_channels-1;
                       cycle           =1;
                       trigger         =1;
                       maxdirlimit     =10;
type

{$IFDEF SPECTRUM}
{
```

```
   data types necessary for performing the DFFT

} complex = record
               x,y:single;
          end;
complex_vector_type=array[0..FFT_max_vector_size] of complex;
complex_vector_ptr=^complex_vector_type;
real_vector_type=array[0..FFT_max_vector_size] of single;
real_vector_ptr=^real_vector_type;
complex_array_type=array[0..number_of_fish-1] of complex_vector_ptr;
{$ENDIF}

Realdatatype = record actual,min,max : real;end;
IntDataType  = record actual,min,max : integer;end;

{
  setup parameters for recording system parameters used in
  biological monitoring }
Biological       = record
                          Assessment_interval,
                          Sample_size,
                          Acceptable_std_dev,
                          Recalc_after_warnings,
                          Warnings_for_Alarm:IntDataType;
                          Minimum_frequency:RealDataType;
                          moving_average:boolean;
                          end;
{$IFDEF SCOUT}
{
 parameters used in keeping the upper and lower limits of
 the scout parameters and the actual value read from the
 scout during the last scan.
}
Scout_Physiochemical    = record
                          Temperature,
                          O2,
                          conductivity,
                          pH,
                          O2p,
                          battery :RealDataType;
                          Data_Valid:boolean;
                          Trigger:boolean;
                          end;
{$ENDIF}
{$IFDEF ANALOGPH}
{
 parameters used in keeping the upper and lower limits of
 the analog physiochemical parameters and the actual value
 received during the last scan of the analog equipment.
}
Analog_Physiochemical  = record
                          Ammonia,
                          Temperature,
                          pH,
```

```
                            conductivity,
                            O2,
                            turbidity,
                            extra1,
                            extra2,
                            O2p,
                            battery   :RealDataType;
                            cal       :array[0..number_of_ANALOG_parameters,1..2]
                            end;
{$ENDIF}

{
 keeps information on the waveform parameters such as using the dynamic
 threshold algorithm, what frequency to sample the A/D signals at and
 so forth.
}
         Waveform         = record
                            Sampling_frequency,
                            Min_threshold,
                            Time_constant,
                            Dynamic_threshold,
                            Corner_frequency  :RealDataType;
                            vector_size       :longint;
                            maxdirection      :intdatatype;
                               {must be power of 2 <=FFT_max_vector_size for FFT}
                            automatic_threshold
{$IFDEF SPECTRUM}
                            ,FFT
{$ELSE}

{$ENDIF}                    :boolean;
                            end;
{
 tells how a given channel is to be assessed. including:
 active    : fish is used to determine if an alarm has occured
 reference : fish is used as a control to compare against the active fish
 inactive  : the data for the fish is ignored in assessing biological
             alarms
}
      Channel_assignment  = array [0..number_of_assignments-1] of byte;
      sample_history_vector = array[0..number_of_fish-1] of longint;
      sample_history      = array[1..max_samples] of sample_history_vector;
(*-   Int_channel_data    = array[0..number_of_fish-1] of integer;-*)
      Real_channel_data   = array[0..number_of_fish-1] of real;
      Logic_channel       = array[0..number_of_fish-1] of boolean;

BooleanArray6       = array[1..6] of boolean;
      {
       tells which parameters will be written to the .BMI files
      }
      Printer_file_options = record
                             printopt,
                             fileopt  : BooleanArray6;
                             end;

{Communications subset added 22 Oct, 91 - MK - also see BMIINIT, MENULOGO}
         Communications   = record
                            Ring_back : boolean;
```

```
                              Tone_dial  : boolean;
                              Dial_wait  : IntDataType;
                              Num_rings  : IntDataType;
                           end;
{End communications subset change}

Miscellaneous   = record
                           Max_disp_frequency:RealDataType;
                           Alarm_duration : IntDataType;
                           Automatic_name : boolean;

{Mod to allow 1st two letters of auto period name to be changed. }
{22 Oct, 91 - MK - also BMIINIT, MENULOGO}
                           Period_prefix  : string[2];
{end mod}

ScreenSaveTime : IntDataType;
                           Password_set   : string;

{Communications subset added 22 Oct, 91 - MK - also see BMIINIT, MENULOGO}
                           Comm           : Communications;
{End communications subset change}

PrinterFileOpt : printer_file_options;
                        end;

Total_Data      = record
                           Bio:Biological;
{$IFDEF SCOUT}             Scout_Phys:Scout_Physiochemical;
{$ENDIF}
{$IFDEF ANALOGPH}          Analog_Phys:Analog_Physiochemical;
{$ENDIF}
                           Wave:Waveform;
                           Misc:Miscellaneous;
                           assignment:Channel_assignment;
                        end;

menu_text_type  = record
                           Assessment_interval,
                           Sample_size,
                           Acceptable_std_dev,
                           Recalc_after_warnings,
                           Warnings_for_Alarm,
                           Minimum_frequency,
                           moving_average,
                           Ammonia,
                           Temperature,
                           pH,
                           conductivity,
                           O2,
                           turbidity,
                           extra1,
                           extra2,
                           O2p,
                           Min_threshold,
                           Time_constant,
                           Dynamic_threshold,
                           Corner_frequency,
                           automatic_threshold,
{$IFDEF SPECTRUM}
```

```
                            FFT,
{$ELSE}

{$ENDIF}
                            Max_disp_frequency,
                            Alarm_duration,
                            Automatic_name,
                            ScreenSaveTime:string[50]
                            end;
{
The powerloss record records all the necessary information needed by
the program to restart when a powerloss has occurred.  It may be possible
if the outtage is brief enough that you can simply pick up where you
left off during monitoring.
}
    PowerLossRecord = record
      PeriodName          : string[12];
      Period_Freqs,
      Direction_changes,
      Period_Amplitudes   : sample_history;
      Period_Sum_Freq,
      Period_Sum_Amplitude,
      Last_Freq,
      sample_num,
      warning_count       : sample_history_vector;
      Warning,
      Calibration         : logic_channel;
      StartOfInterval     : DateTime;
      SDev                : array[0..number_of_fish -1] of real;
      last_amplitude      : real_channel_data;
      firstCycle          : boolean;
    end;

{
 To my knowledge this constant is not used but has been left here to
 insure compatibility.
}
const         menu_text : menu_text_type=
                        (Assessment_interval:    'Assessment interval [min]:
                         Sample_size:            'Sample size for statistica
                         Acceptable_std_dev:     'Number of acceptable stand
                         Recalc_after_warnings:  'Recalculate critical limit
                         Warnings_for_Alarm:     'Number of warnings for ala
                         Minimum_frequency:      'Minimum acceptable frequen
                         moving_average:         'Moving average:';
                         Ammonia:                'Ammonia';
                         Temperature:            'Temperature';
                         pH:                     'pH';
                         conductivity:           'Conductivity';
                         O2:                     'Dissolved O2';
                         turbidity:              'Turbidity';
                         extra1:                 'not used';
                         extra2:                 'not used';
                         O2p:                    '';
                         Min_threshold:          'Minimum threshold voltage
                         Time_constant:          'Dynamic threshold decay ti
                         Dynamic_threshold:      'Dynamic threshold as perce
```

```
{$IFDEF SPECTRUM}

{$ENDIF}
                         Corner_frequency:        '';
                         automatic_threshold:     'Use dynamic threshold:';

FFT:                     'Spectral analysis:';

Max_disp_frequency:      'Maximum displayed assessme
                         Alarm_duration:          'Alarm duration [s]:';
                         Automatic_name:          'Automatic period file name
                         ScreenSaveTime:          'Screen blanking time [min]

var
        status : word;
        powerlossrecoveryglb : boolean;

TimerNow          : longint absolute $40:$6C;

PL                : PowerLossRecord;

regs              : registers;

setup_data        : Total_data;

Setup_file        : file;

InitializePLRecGlB,

GoToMonitoring   :boolean;

{
          following variables are used to keep track of ventilatory
          behavior
        }
        {
          pospeak and negpeak keep track of the highest and lowest values
          seen on each channel to determine when a high or low peak
          has occured.
        }
        pospeak,
        negpeak,
        direction_change, { keeps track of the number of fish turns
                            during monitoring : STILL experimental
                            and not used fully }
        Amplitude,   { keeps track of the amplitude for each fish }
        threshold,   { keeps track of the decaying threshold value
                       which is used to smooth out "noisy" and erattic
                       signals which would lead to pre-mature peaks
                       and abnormal ventilatory frequency counts
                    }
        current_freq, { keeps track of the current ventilatory frequency
                        for each fish }
        old_sum_amplitude,
        sum_amplitude                             :sample_history_vector;
        { keeps track of the number of positve and negative peaks in each
          fish signal }
```

```
        poscount,
        negcount                                :array[0..number_of_fish-1] of wo
        dynamic_threshold                       :array[0..number_of_fish-1] of re
        direction,
        new_direction,
        rise                                    :logic_channel;
        old_direction                           :array[0..maxdirlimit] of logic_c
        oldrise                                 :boolean;
        AlarmSensorS1,AlarmSensorS2             :real_channel_data;
        {
        tells how long the data line will be when logged to the printer.
        This will help in preventing "wrap" and insuring that you have
        enough space on the disk to record the ventilatory data.
        }

Data_line_length_glb                    :integer;
{$IFDEF RAWDATA}
{ raw data record that tells how long to record raw data for.

}
type
        RawDataRecord = record
            CollectOK,
            DoCollect : boolean;
          NumSamples : longint;
          MaxSamples : longint;
            DataFile : text;
            Buffer   : array [1..32768] of char; { fix - 4/28/91 PG }
            Timer    : longint;
        end;

var
        RawDataRecGlb : RawDataRecord;

{$ENDIF}
implementation
end.unit BMIFlow;
interface
function FlowAlarm : boolean;
var
  bindata,error : integer;
begin
  d16_bins (0,bindata,error);
  if (bindata and 8) = 8 then FlowAlarm := true else FlowAlarm := false;
end;

end.unit BMIInit;
    {*******************************************************************}
    {                                                                   }
    { Copyright (c) Biological Monitoring, Inc. 1987, 1991              }
    {                                                                   }
    { This unit contains initialization, crash recovery and digital output }
    { procedures                                                        }
    {                                                                   }
    {*******************************************************************}
interface
uses
```

```
    filetool,
    bmimenux,
    bmiconst,
    das16,
    graph,
    filecopy,
{$IFDEF SCOUTDAC}
    dac_rtne,    {DAC 02 analog output board routine library}
{$ENDIF}
    dgt_rtne;                      {digital I/O routine library} var
{$IFDEF SCOUTDAC}
    DAC_02 : Dac02;      {DAC 02 object}
{$ENDIF}
    DGT_IO              :digitIO;    {digitIO object}
    (*-function DateToJulian (Year,Month,Day: word) : longint;-*)
procedure Initialize(var MetaPointer:Pointer;var current_menu:menu);
procedure Fetch_setup_data(fname:String);
procedure UpdatePowerLossFiles;
procedure RestoreDataFromPowerLoss(var Restored:Boolean);

implementation uses
    crt,
    menulogo,
    dos,
    bmikey,
    mouse
    (*-,
    u_header-*);
type
    (*-  PowerLossPtr = ^PowerLossRecord;-*)
    PowerLossFileType   =file of PowerLossRecord;
    procedure UpdatePowerLossFiles;
    var
        PLVar1,
        PLVar2                  :PowerLossFileType;
        (*-  i : integer;-*)
    begin
        Assign(PLVar1,RecoveryFileNameOne);
        Assign(PLVar2,RecoveryFileNameTwo);
        Rewrite(PLVar1);
        Rewrite(PLVar2);
        Write(PLVar1,PL);
        Write(PLVar2,PL);
        Close(PLVar1);
        Close(PLVar2);
    end;

function DateToJulian(Year,Month,Day:Word):LongInt;
    var
        T                       :LongInt;
    begin
```

```
    if(Year=1900) and(Month<=2)then
      begin
        if Month=1 then T:=Pred(Day)
        else T:=Day+30;
      end
    else
      begin
        if Month>2 then Dec(Month,3)
        else
          begin
            Inc(Month,9);
            Dec(Year);
          end;
        Dec(Year,1900);
        T:=(1461*LongInt(Year) div 4)+(153*Month+2) div 5+Day+58;
      end;
    DateToJulian:=T;
end;

procedure RestoreDataFromPowerLoss(var Restored:Boolean);

const
  Midnight           =24*60*60; { number of seconds elapsed between start of
                     midnight of that same day }
var
  PLVar              :PowerLossFileType;
  SRec               :SearchRec;

{ holds todays date and time and date of when the file was written and
  when the start of the last know assesment interval was }
  Today,
  FileDateAndTime    :DateTime;

S1,
  TempSec100,
  TempDayOfWeek      :Word;

FileDateJulian,
  CurrentDateJulian  :LongInt; { holds the date the history file was created
                     what day it is currently in julian day format}

ElapsedTimeinSeconds,
  Now,
  StartofLastInterval :LongInt;
  Passes,Result      :Integer; { holds the result of an I/O operation }
  (*-I : integer; -*)

begin
  Restored:=False;
  FindFirst('RECOVER*.HIS',AnyFile,SRec);
  if(DosError=0) and(SRec.Size=0)then FindNext(SRec);
    if DosError=0 then S1:=SRec.Size else Exit;
  if S1>0 then
    begin
      with Today do
        begin
          GetDate(Year,Month,Day,TempDayOfWeek);
          GetTime(Hour,Min,Sec,TempSec100);
        end;
```

```
    Fetch_setup_data(PowerLossSetupFileName);
{
 Set this flag to true so that regardless of when the power went
  off the program goes back into fish monitoring because the program
  terminated abnormally, this problem was uncovered in Canada when the
  power was off for longer than an assesment interval

MAJ 4/16/91 }

Restored:=True;
    Unpacktime(SRec.Time,FileDateAndTime);

with FileDateAndTime do
       FileDateJulian:=DateToJulian(Year,Month,Day);

with Today do
       CurrentDateJulian:=DateToJulian(Year,Month,Day);

{How many days has the power been off in days }
    if CurrentDateJulian-FileDateJulian<=1 then
      begin { Calculate number of elapsed seconds between midnight and the
        current time } with Today do
            Now:=LongInt(Hour)*3600+Min*60+Sec; {don't touch - PG}

{ Calculate number of elapsed seconds between midnight and the
        start of the last known assesment interval in the history file } with FileDateAndTime do
            StartofLastInterval:=LongInt(Hour)*3600+Min*60+Sec;
         {don't touch above code if you don't know typecasting - PG }

{ did the time between the start of the interval and the time of
        recover cross the midnight boundry ?} if CurrentDateJulian-FileDateJulian=1 then

{ Now + (Midnight - Then), is adding the time that elapsed
           between the start of the interval and midnight and then
           the elapsed time between midnight and now }

ElapsedTimeinSeconds:=Now+(Midnight-StartofLastInterval)
         else
            ElapsedTimeinSeconds:=Now-StartofLastInterval;

if ElapsedTimeinSeconds<=Setup_data.bio.assessment_interval.actual*6
            begin
               initializePLRECGLb := FALSE; { don't start over }
               restored := true;
            end
         else
           begin
              Restored:=True;
              InitializePLRecGlb:=True; { start over because it was outside
                                          an assesment interval }
           end;
```

```
              end;
            powerlossrecoveryglb := true;

{ grab the data anyway because it is useful in determining
            if a powerloss occured }

{ restore using data in history file }
            Passes:=0;
            Result:=1;          { set it to some arbitrary value to execute th
                       loop at least once }
            while(Result<>0) and(Passes<2)do
              begin
                Assign(PLVar,SRec.Name);
                Reset(PLVar);
                Read(PLVar,PL);
                Result:=IoResult;
                Inc(Passes);
                Close(PLVar);
                if Result<>0 then
                  begin
                    if SRec.Name=RecoveryFileNameOne then
                       SRec.Name:=RecoveryFileNameTwo
                    else
                       SRec.Name:=RecoveryFileNameOne;
                  end;
              end;
            if Result<>0 then
               InitializePLRecGlb:=True;

Restored:=True;

{ Restore the channels that were in calibration when monitoring
           was interrupted } end
       else
          if DosError=0 then
            begin
               Restored:=True;
               InitializePLRecGlb:=True;
            end;

end;

{
********************************************************************}
   procedure ShowHideLogo(Time:Word;graylevel:Integer;show:Boolean);
   var z(*-,stop -*)    :Integer;

procedure Fade_colors;
     begin
       SetRGBPalette(63,z,z,graylevel+(63-graylevel)*z div 63); {Restore White}
       Delay(Time div 128);
       SetRGBPalette(7,z*graylevel div 63,z*graylevel div 63,graylevel); {Restore
       Delay(Time div 128);
     end;
   begin
     if show then for z:=0 to 63 do Fade_colors
     else for z:=63 downto 0 do Fade_colors;
```

```
      end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ} procedure Fetch_setup_data(fname:String);
{
 procedure fetch_setup_data retrieves the defualt setup data file
 from the hard disk if possible.  If this retreival is not possible,
 fetch_setup_data will proceed to go by a set of predefined values.

This code was moved out of Initialize because certain parts of the
 set up data were needed before the graphics system initialized.
 MAJ 1/29/91
}
   var
      Setup_Exists         :Boolean; { fix }
      Result               :Word;
      i                    :Word;
   begin
      Assign(Setup_file,fname);
      if Exist(fname)then
         begin
            Reset(Setup_file,1);
            BlockRead(Setup_file,Setup_data,SizeOf(Setup_data),Result);
            Close(Setup_file);
            Setup_Exists:=SizeOf(Setup_data)=Result;
         end
      else Setup_Exists:=False;
      if not Setup_Exists then
         with Setup_data do
            begin
               with bio do
                  begin
                     assessment_interval.actual:=10;
                     Sample_size.actual:=6;
                     Acceptable_std_dev.actual:=4;
                     Recalc_after_warnings.actual:=4;
                     Warnings_for_Alarm.actual:=4;
                     Minimum_frequency.actual:=0.1;
                     Moving_average:=True;
                  end;

with wave do
                  begin
                     Min_threshold.actual:=0.25;
                     Time_constant.actual:=5;
                     Dynamic_Threshold.actual:=50.0;
                     Corner_frequency.actual:=8.0;
                     automatic_threshold:=True;
                     sampling_frequency.max   :=  30.0;
                     sampling_frequency.actual:=30.0;
                     sampling_frequency.min   :=  1.0;
                     Vector_Size:=Round(sampling_frequency.actual*acquisition_time);
                     maxdirection.actual:=maxdirlimit div 2;
{$IFDEF SPECTRUM}
                                 FFT:=FALSE;
{$ENDIF}
                  end;
```

```
              with misc do
                begin
                  Max_disp_frequency.actual:=3;
                  Alarm_duration.max := bio.assessment_interval.actual * 60;
                  Alarm_duration.actual:=1;
                  Alarm_duration.min := 1;
                  Automatic_name:=True;

{mod to allow period name prefix change - 22 oct, 91 - MK - also BMIINIT, MENULO
                  period_prefix := 'OP';
{end mod}

ScreenSaveTime.actual:=15;
                  Password_set:='@BMI!;';

{Communications subset 22 Oct, 91 - MK - see also BMICONST, MENULOGO}
                  with Comm do
                    begin
                      ring_back := true;
                      tone_dial := true;
                      dial_wait.min := 1;
                      dial_wait.max := 5;
                      dial_wait.actual := 1;
                      num_rings.min := 1;
                      num_rings.max := 8;
                      num_rings.actual := 3;
                    end;
{end communications subset changes} with PrinterFileOpt do
                    begin
                      printopt[1]:=True;
                      fileopt[1]:=True;

{change default for printer and data file options to Fav and Aav.
 Frequency data alone aren't much good for an operator to base an
 alarm assessment on without amplitude for comparison. - 22 Oct,91 - MK}
                      printopt[2]:=True;
                      fileopt[2]:=True;
                      for i:=3 to 6 do
                        begin
                          printopt[i]:=False;
                          fileopt[i]:=False;
                        end;
                    end;
{end print/file options change - MK, 22 Oct, 91}

Data_line_length_glb:=72;
{$IFDEF ANALOGPH}
                                Data_line_length_glb := Data_line_length_glb+40;
{$ENDIF}
{$IFDEF SCOUT}
                                Data_line_length_glb := Data_line_length_glb+27;
{$ENDIF}
                end;
{$IFDEF ANALOGPH}
                  with Analog_phys do
                    begin
                      for i:=0 to number_of_analog_parameters-1 do
                        begin
```

```
                              cal[i][1]:=0;
                              cal[i][2]:=0;
                              end;
                          Ammonia.min:=0;
                          Ammonia.max:=5;
                          Temperature.min:=0;

{$IFDEF FAHRENHEIT} {compile directive added by MK - 1/3/91}
                          Temperature.Max:=100;
{$ELSE}
                          Temperature.max:=40;
{$ENDIF}
                          O2.min:=0;
                          O2.max:=18;
                          pH.min:=0;
                          pH.max:=14;
                          Conductivity.min:=0;
                          Turbidity.min:=0;
{$IFDEF JTU} {compile directive added by MK - 1/3/91}
                          Turbidity.max:=500;
{$ELSE}
                          Turbidity.max:=500;
{$ENDIF}
                          extra1.min:=0;
                          extra1.max:=1000;
                          extra2.min:=0;
                          extra2.max:=1000;
                      end;
{$ENDIF}
{$IFDEF SCOUT}with Scout_phys do
                      begin
                      Temperature.min:=0;
                      Temperature.max:=40;
                      O2.min:=0;
                      O2.max:=18;
                      pH.min:=0;
                      pH.max:=14;
                      Conductivity.min:=0;
                      Conductivity.max:=25000;
                      end;
{$ENDIF} for i:=0 to number_of_assignments-1 do
           assignment[i]:=0;

{Change default assignments for channels 6 + 7 to Active for Sydney}
{Added following directive - 23 Oct, 91 - MK}
{$IFDEF ANALOGPH}
{End change}
         assignment[number_of_fish+number_of_analog_parameters-2]:=1;
         assignment[number_of_fish+number_of_analog_parameters-1]:=1;
{Change - 23 Oct, 91 - MK}
{$ENDIF}
{End change} end;
  end;

procedure Initialize(var MetaPointer:Pointer;var current_menu:menu);
  const graylevel     =40;
```

```
    var GrDriver,GrMode,
      ErrorCode           :Integer;
      mstat,nbut          :Word;
{$IFNDEF NOLOGO}
   (*-  Dummy            : boolean; {fix for function read_metafile}-*)
     {MK - 1/3/90                   }
{$ENDIF}
      i                   :Word;
  begin DosError:=0;
    Mstatus(mstat,nbut);
    if mstat=0 then TextExit('Mouse is not installed. Program aborted.');
    d16.init(base_adr,int_level,dma_level);
    if d16.err_code<>0 then begin
      WriteLn(d16.err_msg);        { write new procedure !!! PG}
      TextExit('D/A Initialization Error');
    end;
    GrDriver:=VGA;
    GrMode:=VGAHi;
    InitGraph(GrDriver,GrMode,'');
    ErrorCode:=GraphResult;
    case ErrorCode of
      -2:TextExit('VGA graphics card problem. Call BMI Inc. (703) 953-2821');
      -3:TextExit('No graphics driver');
      -4:TextExit('Invalid graphics driver');
      -5:TextExit('Insufficient memory to load graphics driver. Free some memory
    end;

SetTextJustify(CenterText,CenterText);
    SetRGBPalette(56,53,0,53);    {Modify DarkGray}
    ScreenSavedGLB:=False;
    LastKeypressGLB:=TimerNow;
    Mark(MetaPointer);            {mark heap before reading metafile}

{$IFNDEF NOLOGO}
    i:=1;
    if not current_menu.Read_metafile('logo2.cgm',i)then
      begin
        Closegraph;
        TextExit('LOGO2.CGM File '+IOcheck(i));
      end;
    SetRGBPalette(1,0,0,graylevel); {True Blue}
    SetRGBPalette(63,0,0,graylevel); {False white}
    SetRGBPalette(7,0,0,graylevel); {False LightGray}
    Logo(@current_menu);           { draw logo screen with big fish logo }
    Release(MetaPointer);          { kill big fish logo ]]}
    SetRGBPalette(59,0,0,graylevel);{False Light Cyan};
{   ShowHideLogo(3200,graylevel,True);}
    ShowHideLogo(1200,graylevel,True);
    SetColor(White);
    SetTextJustify(LeftText,CenterText);
    SetViewPort(2,Ymax-20,260,Ymax-2,ClipOn);
    OutTextXY(10,10,'Press space bar to continue...');
    SetViewPort(400,Ymax-20,635,Ymax-2,ClipOn);
    OutTextXY(10,10,'Compiled on '+CompilationDateGlbConst);
```

```
        if not GoToMonitoring then
          repeat until keypressed;
        ClearViewPort;
{       ShowHideLogo(3200,graylevel,False);}
        ShowHideLogo(1200,graylevel,False);
        ClearDevice;
        ShowHideLogo(0,graylevel,True);
        SetRGBPalette(59,0,$70,$70);{False Light Cyan};
{$ENDIF}

Data_line_length_glb:=CalcDataLineLength(Setup_data.misc.PrinterFileOpt);

{$IFDEF SCOUTDAC}
DAC_02.Init (DAC02BaseAddress,ScoutHiTemperature,ScoutHiDissolvedO2);
{$ENDIF}

DGT_IO.init(board_num);
    end;

end.
unit BMIKey;
{*******************************************************************************}
{                                                                               }
{ Copyright (c) Biological Monitoring, Inc. 1987, 1990                          }
{                                                                               }
{ This unit contains mouse and keyboard input and screen blanking procedures}
{                                                                               }
{*******************************************************************************}

(*
ëëëëëëëëëëëëëëëëëëëëëëëëëëëëëëëëëëëëëëëëëëëëëëëëëëëëëëëëëëëëëëëëëëëëëëëëëëëëëëëëëëf
¤                                                                              ¤
¤ GETKEY -   READKEY replacement, raises extended keys 128 to allow using      ¤
¤            function returning single character. Also checks time for         ¤
¤            screen blanking procedures. If KeyFull is defined, global         ¤
¤            constants can be used instead of ASCII values.                    ¤
¤                                                                              ¤
aëëëëëëëëëëëëëëëëëëëëëëëëëëëëëëëëëëëëëëëëëëëëëëëëëëëëëëëëëëëëëëëëëëëëëëëëëëëëëëëëëë¥
*)

interface uses
  Graph;

{ Define KeyFull to allow use of the following constants - mnemonics are    }
{ sometimes easier than remembering or looking up the various extended key  }
{ combinations - remember that 128 has been added to the actual extended    }
{ key code to allow GetKey to return a single character.                    }

{$DEFINE KeyFull}

{$IFDEF KeyFull} const
  F1  = #187;     AF1  = #232;     CF1  = #222;     SF1  = #212;
```

```
    F2  = #188;       AF2  = #233;       CF2  = #223;       SF2  = #213;
    F3  = #189;       AF3  = #234;       CF3  = #224;       SF3  = #214;
    F4  = #190;       AF4  = #235;       CF4  = #225;       SF4  = #215;
  { F5  = #191;       AF5  = #236;       CF5  = #226;       SF5  = #216; }
  { F6  = #192;       AF6  = #237;       CF6  = #227;       SF6  = #217; }
  { F7  = #193;       AF7  = #238;       CF7  = #228;       SF7  = #218; }
    F8  = #194; {     AF8  = #239;       CF8  = #229;       SF8  = #219; }
    F9  = #195; {     AF9  = #240;       CF9  = #230;       SF9  = #220; }
    F10 = #196; {     AF10 = #241;       CF10 = #231;       SF10 = #221; }

{ AltA = #158;      AltN = #177;       CtrlA = #1;        CtrlN = #14;}
  { AltB = #176;      AltO = #152;       CtrlB = #2;        CtrlO = #15;
  { AltC = #174;      AltP = #153;       CtrlC = #3;        CtrlP = #16;}
  { AltD = #160;      AltQ = #144;       CtrlD = #4;        CtrlQ = #17;}
  { AltE = #146;      AltR = #147;       CtrlE = #5;        CtrlR = #18;}
  { AltF = #161;}      AltS = #159;{     CtrlF = #6;        CtrlS = #19;}
  { AltG = #162;      AltT = #148;       CtrlG = #7;        CtrlT = #20;}
  { AltH = #163;      AltU = #150;       CtrlH = #8;        CtrlU = #21;}
  { AltI = #151;      AltV = #175;       CtrlI = #9;        CtrlV = #22;}
  { AltJ = #164;      AltW = #145;       CtrlJ = #10;       CtrlW = #23;}
  { AltK = #165;}      AltX = #173;{     CtrlK = #11;       CtrlX = #24;}
  { AltL = #166;      AltY = #149;       CtrlL = #12;       CtrlY = #25;}
  { AltM = #178;      AltZ = #172;       CtrlM = #13;       CtrlZ = #26;}

{ Alt1 = #248;}     UArr = #200;   {   CtrlLArr = #243;}
  { Alt2 = #249;}     DArr = #208;   {   CtrlRArr = #244;}
  { Alt3 = #250;}     LArr = #203;   {   AltLArr  = #243;}
  { Alt4 = #251;}     RArr = #205;   {   AltRArr  = #244;}
  { Alt5 = #252;
    Alt6 = #253;
    Alt7 = #254;
    Alt8 = #255;

HomeKey = #199;   CtrlHome  = #247; }  Enter = #13;
  { EndKey  = #207;   CtrlEnd   = #245; }  Esc   = #27;
  { PgUp    = #201;   CtrlPgUp  = #4;   }  BkSp  = #8;
  { PgDn    = #202;   CtrlPgDn  = #246; }  Del   = #211; {Ins = #210;}

{$ENDIF}

{Mouse button constants used in GetMouse}
const
    MEnter = #132;
  { MLeft  = #132;}
    MEsc   = #133;
  { MRight = #133;}

{global constants and variables for save screen} var
    LastKeypressGLB  : longint;    {time of last keypress}
    ScreenSavedGLB   : boolean;    {true if screen is saved}
```

```
type
(*-  St20 = string[20];-*)
  St40 = string[40];

procedure SaveScreen;
procedure RestoreScreen;
function GetKey : char;
procedure GetYNResponse (Prompt : St40; var Yes,Escd : boolean);
function AltPressed:boolean;

implementation uses
  Dos,
  Crt,
  BMIConst,
  oldview,
  Mouse;

const
   MBoth    = #131;
   SaveHotKey = #176; {AltB - use #xxx in case KEYFULL isn't defined above} var
   SavedPalette  : PaletteType;   {original palette for RestoreScreen} function AltPressed:boolean;
begin
    regs.ah:=2;
    Intr($16,regs);
    AltPressed:=regs.al and 8 = 8;
end;

function GetKbd : char;
(*-var
  key      : char;-*)
begin regs.ah:=0;
    Intr($16,regs);
    with regs do if al=0 then GetKbd:=Chr(128+ah) else GetKbd:=Chr(al);

{ Since this is an extended key and we only want to return one }
       { char for this function, we'll add 128 to the ASCII value of  }
       { the keypress thereby using the upper ASCII for extended keys.}
end;

function GetMouse : char;
var
(*-  Key   : char;-*)
  x,y,
  But : word;
begin
   mpos (But,x,y);          {get x,y, and button press - defined in mouse.pas}
```

```
      if (But > 0) then
      begin
        case But of
          1 : GetMouse := MEnter;
          2 : GetMouse := MEsc;
          3 : GetMouse := MBoth;
        end;

repeat mpos(But,x,y) until (But = 0);
                              {purge unwanted mouse button presses}
      end
      else GetMouse := #0;
    end;

procedure SaveScreen;

const  BlankPalette : PaletteType = (Size    : 16;
                                         Colors : (Black,Black,Black,Black,
                                                   Black,Black,Black,Black,
                                                   Black,Black,Black,Black,
                                                   Black,Black,Black,Black));
    begin
      ScreenSavedGLB := true;
      GetPalette (SavedPalette);     {save original palette}
      SetAllPalette (BlankPalette);         {display blank palette}
    end;

procedure RestoreScreen;
    begin
      SetAllPalette (SavedPalette); {restore original palette}
      ScreenSavedGLB := false;
    end;

function GetKey : char;
    var
      Key      : char;
      ThisTime : longint;

begin
      if setup_data.misc.ScreenSaveTime.actual > 0 then {skip the time check if}
                                                       {variable is set to 0}
      begin
        Thistime:=TimerNow;
        if Thistime mod 18=0 then
        if (ThisTime-LastKeypressGLB+1572480) mod 1572480 > longint(1092) *
            setup_data.misc.screenSaveTime.actual then
              if not ScreenSavedGLB then SaveScreen;
      end;
      if Keypressed then
      begin
        LastKeypressGLB := ThisTime;   {reset timer}
        Key := GetKbd;
        if not ScreenSavedGLB and (Key = SaveHotKey) then SaveScreen   {check for hot
        else if ScreenSavedGLB then
        begin
          RestoreScreen;
          Key := #0;
```

```
      end;
   end
   else if MShown then
   begin
     Key := GetMouse;
     if (Key in [MEsc,MEnter,MBoth]) then
     begin
        if ScreenSavedGLB then
        begin
           RestoreScreen;
           Key := #0;
        end;
        LastKeypressGLB := ThisTime;
     end;
   end
   else Key := #0;
   GetKey := Key;
end;

procedure GetYNResponse (Prompt : St40; var Yes,Escd : boolean);
var
   Done : boolean;
   Key  : char;
   But,
   mx,
   my,
   MinH,
   MaxH,
   MinV,
   MaxV : word;

const
   NoX1    = 400;
   NoX2    = 448;
   YesX1   = 480;
   YesX2   = 528 ;
(*- PromptX1 = 5;
    PromptX2 = 635;-*)
   Y1      = 430;
   Y2      = 474;
   YNBox : array [1..5] of PointType = ((x : 0 ; y : 0 ),
                                        (x : 48; y : 0 ),
                                        (x : 48; y : 24),
                                        (x : 0 ; y : 24),
                                        (x : 0 ; y : 0));

procedure DisplayYNPRompt;
begin
   SetViewPort(5,9*Y10-20,Xmax-5,Ymax-5,ClipOff);
   ClearViewPort;
   SetTextStyle(DefaultFont,HorizDir,1);
   SetTextJustify(CenterText,CenterText);
   while length (prompt) < 40 do
     prompt := ' '+prompt;
   OutTextXY(Xcen-100,Y20+20,Prompt);
   SetFillStyle (solidfill,9);
   SetViewport (NoX1,Y1+5,NoX2,Y2+5,ClipOn);
   FillPoly (SizeOf (YNBox) div SizeOf (PointType),YNBox);
   OutTextXY (28,13, '(N)o ');
   SetViewPort (YesX1,Y1+5,YesX2,Y2+5,ClipOn);
```

```
    FillPoly (SizeOf (YNBox) div SizeOf (PointType),YNBox);
    OutTextXY (24,13,'(Y)es');
    mvlimit (Y1+5,Y2-17);
    mhlimit (NoX1,YesX2-5);
    mput (NoX2+16,Y1+12);
end;

begin
  Escd := false;
  Done := false;
  View.save;
  MinV := MinVLim;
  MaxV := MaxVLim;
  MinH := MinHLim;
  MaxH := MaxHLim;
  SetColor(white);
  DisplayYNPrompt;
  MShow;
  repeat Key := GetKey; until (Key = #0);
  repeat
    Key := GetKey;
    if upcase (Key) in [RArr,LArr,Esc,MEsc,Enter,MEnter,'Y','N'] then
    begin
       case upcase (Key) of
          RArr   : mput (YesX1 + (YesX2-YesX1) div 2,Y1+(Y2-Y1) div 2);
          Larr   : mput (NoX1+(NoX2-NoX1) div 2,Y1+(Y2-Y1) div 2);

'Y'    : begin
                     Yes := true;
                     Escd := false;
                     Done := true;
                   end;
          'N'    : begin
                     Yes := false;
                     Escd := false;
                     Done := true;
                   end;
          Esc,
          MEsc   : begin
                     Yes := false;
                     Escd := true;
                     Done := true;
                   end;
          Enter,
          MEnter : begin
                     mpos (But,mx,my);
                     if ((mx > NoX1) and (mx < NoX2)) and
                        ((my > Y1) and (my < Y2)) then
                     begin
                       Yes := false;
                       Escd := false;
                       Done := true;
                     end
                     else if ((mx > YesX1) and (my < YesX2)) and
                             ((my > Y1) and (my < Y2)) then
                     begin
                       Yes := true;
                       Escd := false;
                       Done := true;
```

```
                        end
                      else write (#7);
                    end;
        end;  {case}
      end
      else if Key > #0 then write (#7);
    until Done;
    if mshown then
        mhide;
    SetViewPort(5,9*Y10-20,Xmax-5,Ymax-5,ClipOff);
    ClearViewPort;
    mvlimit (MinV,MaxV);
    mhlimit (MinH,MaxH);
    View.restore;
end;

end.
unit BMISecur;
{*********************************************************************}
{                                                                     }
{ Copyright (c) Biological Monitoring, Inc. 1987, 1990                }
{                                                                     }
{ Security unit. Do not distribute outside BMI!                       }
{ This function determines the proper hardware security key is attached to
  the computer.  If not the program exits pre-maturely.
 *********************************************************************}
interface USES graph;        {REQUIRED IN YOUR CODE}

(*-VAR
    TEST  :BOOLEAN;          {GLOBAL VARIABLE AS EXAMPLE OF CALL}-*)
{*********************************************************************}
FUNCTION KeyInstalled(*-(DUM:INTEGER)-*):BOOLEAN;   {DUM IS A DUMMY VARIABLE IN O
procedure SecurityExit;

implementation uses
   CRT,bmikey;

FUNCTION KeyInstalled(*-(DUM:INTEGER)-*):BOOLEAN;   {DUM IS A DUMMY VARIABLE IN O VAR
         ACK,I,J,K,TTEST    :INTEGER;      {I,J,K ARE FOR COUNTING}
         ORG_DAT                   :INTEGER;      {ORIGINAL DATA AND CONTROL BYTES
         PPORT,CTR,SEL  :ARRAY [1..3] OF INTEGER;
         CPORT,XX   :INTEGER;              {CPORT = CURRENT PORT IN USE}
         ACTFLAG    :BOOLEAN;                     {FLAG IF TRUE ACTIVATOR THERE}

BEGIN
{$IFDEF PROTECT}
         CTR[1]:=9;                                           {initial counter variabl
         CTR[2]:=18;
         CTR[3]:=41;
         SEL[1]:=13;                                                  {initial selecto
         SEL[2]:=17;
         SEL[3]:=33;
```

```
{ Get the parallel port numbers }
FOR I:=0 TO 2 DO
        PPORT[I+1]:=MEMW[0000:1032+2*I];

{ Invert the selector values }
FOR I:=1 TO 3 DO
        SEL[I]:=SEL[I] XOR 32;

TTEST:=0;               {INITIALIZE FOR ACK NEVER GOING HIGH}
ACTFLAG:=FALSE;         {ASSUME NO ACTIVATOR PRESENT}
FOR K:=1 TO 3 DO   {FOR 3 PARALLEL PORTS (PS 2 COMPATABILITY}
BEGIN
        CPORT:=PPORT[K];     {GET CURRENT PORT}
        IF CPORT<>0 THEN     {IF NOT ZERO THEN INTERROGATE}
        BEGIN
                ORG_DAT:=PORT[CPORT];   {SAVE ORIGINAL DATA BYTE}
                PORT[CPORT]:=128;       {POWER WITH RESET}
                DELAY(5);                       {ONLY NECESSARY DELAY}
                PORT[CPORT]:=192;       {KEEP POWER REMOVE RESET}
                FOR J:=1 TO 3 DO                {FOR 3 COUNTERS DO}
                BEGIN
                        FOR I:=1 TO CTR[J] DO    {USE CORRESPONDING SELEC
                        BEGIN
                                PORT[CPORT]:=SEL[J]+192;        {OUTPUT VA
                                PORT[CPORT]:=192;
                PORT[CPORT]:=224;           {ENABLE ACK FROM ACT. M}
                                DELAY(1);
                                XX:=PORT[CPORT+1] AND 64;    {CHECK TO
                                IF XX=64 THEN TTEST:=1;      {YES TTEST
                PORT[CPORT]:=192;            {CLEAR ACK ENABLE}
                        END;
                END;                            {FINISHED WITH PORT}
        PORT[CPORT]:=224;    {ENABLE ACK FROM ACT M}
                DELAY(5);            {ALLOW LINES TO SETTLE}
                ACK:=PORT[CPORT+1] AND 64;        {ACK RECIEVED ??? }
        PORT[CPORT]:=192;    {CLEAR ACK ENABLE}
                IF TTEST=1 THEN      {MAKE SURE WAS HIGH}
                        IF ACK=0 THEN ACTFLAG:=TRUE;    {YES}
                PORT[CPORT]:=SEL[3]+192;        {EXTRA COUNT FOR STRADDLE
                PORT[CPORT]:=192;
                DELAY(5);
                ACK:=PORT[CPORT+1] AND 64;         {CHECK ACK AGAIN}
                IF ACK=0 THEN ACTFLAG:=FALSE;      {IF LOW THEN INVALI
                PORT[CPORT]:=0;        {TURN OFF ACTIVATOR}
                PORT[CPORT]:=ORG_DAT;  {RESTORE DATA BYTE}
        END;                            {UNTIL ALL 3 PORTS PROCESSED}
    END;
   KeyInstalled:=ACTFLAG;             {RETURN VALUE TRUE IF THERE}
                {OTHERWISE FALSE}
{$ELSE}
  KeyInstalled := TRUE;
{$ENDIF}
END;       {END OF FUNCTION SECURITY} procedure SecurityExit;
var
  i,j(*-,k,l-*) : integer;
  Key : char;
  const
```

```
      box : array[1..5] of pointtype = ((x:100;y:100),
                                        (x:540;y:100),
                                        (x:540;y:300),
                                        (x:100;y:300),
                                        (x:100;y:100));
begin
  SetViewPort (0,0,GetMaxX,GetMaxY,ClipOn);
  ClearViewPort;
  SetFillStyle (SolidFill,4);
  FillPoly (SizeOf(Box) div SizeOf(PointType), box);
  SetTextJustify (CenterText,CenterText);
  SetTextStyle (TriplexFont,HorizDir,5);
  OutTextXY (320,150,'Security Violation');
  SetTextStyle (SansSerifFont,HorizDir,2);
  OutTextXY ( 320,250,'System Halted - Contact BMI');
  i := 1;
  while i < 2 do
  begin
    j := 0;
    while j < 5000 do
    begin
      sound (j);
      delay (2);
      nosound;
      inc (j,10);
    end;
    Key := GetKey;
    if Key = AltX then i := 2;
  end;
  HALT;
end;

END.

{*********************************************************************}
{                                                                     }
{    Program name: DAC_RTNE.PAS                                       }
{                                                                     }
{            Type: Unit                                               }
{                                                                     }
{         Version: 1.0                                                }
{        Revision: 1                                                  }
{                                                                     }
{           Title: Metrabyte DAC-02                                   }
{                                                                     }
{          Author: G.Mansbach                                         }
{                                                                     }
{            Date: November 20, 1990                                  }
{                                                                     }
{     Description: Data structures and routines for writing to DAC-02 board. }
{                  This is designed for use of more than 1 board.     }
{                                                                     }
{                                                                     }
{                                                                     }
{                                                                     }
```

```
{                                                                            }
{****************************************************************************}

Unit DAC_RTNE;

Interface
(*
                                          { ********* REMOVE ********** }
Var                                       { For ...                     }
   Port : Array[$300..$303] Of Byte;      {       ... Testing ...       }
                                          {                ... Only.    }
                                          { ********* REMOVE ********** }
*)

Type
{   Dac02Ptr      = ^Dac02;}  { Commented out by P. Gradzki 11/20/1990 }

Dac02         = Object
       port_addr       : Word;
       datum1_factor   : Real;
       datum2_factor   : Real;

PROCEDURE Init(address:Word;datum1_range,datum2_range:Real);
       PROCEDURE Write(datum1,datum2:Real);
    End;

Implementation

{*p**************************************************************************}
{                                                                            }
{    Name: Dac02.Init                                                        }
{                                                                            }
{    type: procedure                                                         }
{                                                                            }
{ Purpose: Set initial values for Metrabyte DAC-02 board. Base address is    }
{          established for future calls. Range conversion factors are        }
{          computed and saved.                                               }
{                                                                            }
{   Parms: address       Base address of output port.                        }
{          datum1_range  High value - low value                              }
{          datum2_range  High value - low value                              }
{                                                                            }
{  Inputs: none                                                              }
{                                                                            }
{ Outputs: none                                                              }
{                                                                            }
{****************************************************************************}

PROCEDURE Dac02.Init(address:Word;datum1_range,datum2_range:Real);
   Const out_rnge = 4095;            { 12 bits of data }
   Begin
      port_addr      := address;
      datum1_factor  := out_rnge/datum1_range;
      datum2_factor  := out_rnge/datum2_range;
   End;
```

```
{*p******************************************************************}
{                                                                      }
{    Name: Dac02.Write                                                 }
{                                                                      }
{    type: procedure                                                   }
{                                                                      }
{ Purpose: Write data to Metrabyte DAC-02 ports. Data received is assumed to }
{          be in the valid range and is converted without any checks.  }
{                                                                      }
{   Parms: datum1  Written to base address+0 and base address+1        }
{          datum2  Written to base address+2 and base address+3        }
{                                                                      }
{  Inputs: none                                                        }
{                                                                      }
{ Outputs: none                                                        }
{                                                                      }
{**********************************************************************}

PROCEDURE Dac02.Write(datum1,datum2:Real);
   Var
      out_int : Integer;
      Begin
         out_int           := Round(datum1*datum1_factor) and $0FFF;
                              {and $0FFF to keep value between 0 and 4095}
         out_int := 4095 - out_int;   {invert value for 4-20ma loop - 12/20/90 - MK}
         out_int := out_int shl 4;
         Port[port_addr+0] := Lo (out_int);
         Port[port_addr+1] := Hi (out_int);

out_int           := Round(datum2*datum2_factor) and $0FFF;
                              {and $0FFF to keep value between 0 and 4095}
         out_int := 4095-out_int;    {invert value for 4-20ma loop - 12/20/90 - MK}
         out_int := out_int shl 4;
         Port[port_addr+2] := Lo (out_int);
         Port[port_addr+3] := Hi (out_int);
      End;

End.

{**********************************************************************}
{                                                                      }
{    Program name: DGT_RTNE.PAS                                        }
{                                                                      }
{            Type: Unit                                                }
{                                                                      }
{         Version: 1.0                                                 }
{        Revision: 1                                                   }
{                                                                      }
{           Title: Metrabyte DASH-16 Digital IO                        }
{                                                                      }
{          Author: G.Mansbach                                          }
{                                                                      }
{            Date: November 20, 1990                                   }
{                                                                      }
{                                                                      }
{     Description: Data structures and routines for writing digital output }
{                  to DASH-16 board. Designed for multiple boards      }
```

```
{                                                                              }
{                                                                              }
{                                                                              }
{                                                                              }
{                                                                              }
{******************************************************************************}

Unit DGT_RTNE;

Interface
uses das16;
Type
      BooleanArray4  = array[0..3] of boolean;

digitIO       = Object
      board_num      : Integer;
      digit          : BooleanArray4;
      AlarmSet       : boolean;
      TimerStart     : longint;

PROCEDURE Init(board:Integer);
      FUNCTION  InDta:Boolean;
      FUNCTION  OutDta:Boolean;
      End;

Implementation
Uses bmiconst;
var    num:integer;

{*p****************************************************************************}
{                                                                              }
{    Name: digitIO.Init                                                        }
{                                                                              }
{    type: procedure                                                           }
{                                                                              }
{ Purpose: Set initial values for Metrabyte DASH-16 board. Board number is     }
{          established for future calls. Sets 0 on outputs.                    }
{                                                                              }
{   Parms: board           Board number of DASH-16 board.                      }
{                                                                              }
{  Inputs: none                                                                }
{                                                                              }
{ Outputs: none                                                                }
{                                                                              }
{******************************************************************************}
PROCEDURE digitIO.Init(board:Integer);
   Begin
      num:=0;
      d16.bous(num);
      for num:=0 to 3 do digit[num]:=FALSE;
      AlarmSet:=FALSE;
      End;

{*p****************************************************************************}
{                                                                              }
{    Name: digitIO.InDta                                                       }
```

```
{                                                                              }
{    type: function                                                            }
{                                                                              }
{ Purpose: Read digital data from Metrabyte DASH-16 digital input. Data        }
{          received is converted to boolean array.                             }
{                                                                              }
{   Parms: none                                                                }
{                                                                              }
{  Inputs: none                                                                }
{                                                                              }
{ Outputs: none                                                                }
{                                                                              }
{ Returns: TRUE indicates error / FALSE no error                               }
{                                                                              }
{*****************************************************************************}

FUNCTION digitIO.InDta:Boolean;
   Var
       in_val  : Integer;
       bin_val : Integer;

Begin
       d16.bins(in_val);
       bin_val := 1;
       For num := 0 To 3 Do Begin
           If (in_val And bin_val) > 0 Then digit[num] := TRUE Else digit[num] :=
           bin_val := bin_val shl 1;
           End;

If d16.err_code = 0 Then InDta := FALSE Else InDta := TRUE;
       End;

{*p***************************************************************************}
{                                                                              }
{    Name: digitIO.OutDta                                                      }
{                                                                              }
{    type: function                                                            }
{                                                                              }
{ Purpose: Write digital data to Metrabyte DASH-16 digital output. Data sent   }
{          is converted from boolean array.                                    }
{                                                                              }
{   Parms: none                                                                }
{                                                                              }
{  Inputs: none                                                                }
{                                                                              }
{ Outputs: none                                                                }
{                                                                              }
{ Returns: TRUE indicates error / FALSE no error                               }
{                                                                              }
{*****************************************************************************}

FUNCTION digitIO.OutDta:Boolean;
   Var
       out_val : Integer;
       bin_val : Integer;

Begin
       out_val := 0;
       bin_val := 1;
```

```
      For num := 0 To 3 Do Begin
         If digit[num] Then out_val := out_val Or bin_val;
         bin_val := bin_val shl 1;
         End;

d16.bous(out_val);

If d16.err_code = 0 Then OutDta := FALSE Else OutDta := TRUE;
      End;

End.
program dmatest;

uses
  crt,
  bmiconst,
  das16;

const
  Xtal = 10;
var
  rate : real;
  oldcount,
  count : word;
begin
  d16.init(base_adr,int_level,dma_level);
    if d16.err_code<>0 then begin
       WriteLn(d16.err_msg);        { write new procedure !!! PG}
       writeln('D/A Initialization Error');
    end;
  d16.malloc(AcquisitionData,Sizeof(Integer)*DMA_buf_count*2);
  rate :=6875;
  d16.aindma(AcquisitionData,chanlo,chanhi,Xtal,DMA_buf_count*2,rate);
                                       { start data acquisition }
  count:=0;
  clrscr;
    repeat
      oldcount:=count;
      {delay(100);}
      count := d16.count;
      write(count:8,#13);
      if (oldcount>count) then writeln(oldcount:8,count:8);
    until keypressed;

d16.dma_int_disable;
end.unit filetool;
{
===============================================================================

Copyright (c) Biological Monitoring, Inc. 1987, 1991

Unit    : FileTool

Purpose: Provides disk services that are used frequently

Programmer: Michael Johnson

Last Rev  : 5/24/91

===============================================================================
```

}

```
interface
uses
  dos;

{ checks for the existance of a filename before it overwrites it }
function Exist(Name:String):Boolean;

implementation
  function Exist(Name:String):Boolean;
  {
   Puprose:  Exist checks for the existence of a given filename.

Inputs:
   Name - contains the name of the file to be searched for.

Returns:
   True : if the file currently exists
   False: if the file does not exist
  }
  var
    SRec                :SearchRec;
  begin
    FindFirst(Name,AnyFile,SRec);
    Exist:=(DosError=0);
  end;

end.unit monitor;
interface
uses bmimenux,graph;
type monitor_periodOBJ = object procedure Display;
                    procedure RemoveDisallowedCharacters;
                    function FileCheck:boolean;
                    procedure GetFileName;
                    procedure AutoName(par_menu:pointer;
                                      CreateFiles,IsMidnight:boolean);

private
                      parent_menu:^menu;
                      item,
                      DataEntry         :string;
                      FilenameIsNull    :Boolean;

end;
procedure Monitor_period_name(par_menu:Pointer;item_:Word);
var Monitor_period:Monitor_periodobj;
implementation
uses bmiconst,dos,mouse,bmikey,bmident,u_header,oldview;
   {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
   procedure Monitor_PeriodObj.display;
      begin
        View.save;
        with parent_menu^ do
          SetViewPort(dataposition,ypos+2*ystep+1,Xmax-10,
                      ypos+3*ystep-1,ClipON);
```

```
    ClearViewPort;
    if setup_data.Misc.Automatic_name then SetColor(LightRed);
    settextjustify(LeftText,CenterText);
    with parent_menu^ do OutTextXY(margin,ystep div 2,Period_Name);
    View.restore;
  end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Monitor_periodobj.RemoveDisallowedCharacters;
const
    Allowed              =[#35,#45,#48..#57,#65..#90,#97..#122];
var
    i                    :Integer;
    Temp                 :String;
begin
  Temp:='';
  for i:=1 to Length(DataEntry) do
      if DataEntry[i] in Allowed then Temp:=Temp+DataEntry[i];
  DataEntry:=Temp;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Monitor_periodobj.FileCheck:Boolean;
   var SRec              :SearchRec;
       writeit,
       escd              :boolean;
   begin
     FileCheck:=False;
     FindFirst(parent_menu^.period_name+'.bmi',AnyFile,SRec);

if DOSError=0 then
       begin

{put here for because when called mouse not always visible,
        so I elected to show it then rehide it for clarity.
        MJ - 1/14/90 }
           if FilenameIsNull then
             mshow;
           if GoToMonitoring then   { skip filecheck if in recovery mode PG - 2/3/
             begin
               writeit:=TRUE;
               escd:=FALSE;
             end
           else
             begin
               SetBkColor(red);
               GetYNResponse('This filename already exists. Overwrite?',WriteIt,E
               SetBkColor(Blue);
             end;

{now hide the mouse again }
           if FilenameIsNull then
              if mshown then
                mhide;
           Filecheck:=writeit and not escd;
         end
   end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
    procedure Monitor_periodobj.GetFileName;
    var
      Changed            :Boolean;
```

```
    begin
{
  Added this line to hide the mouse again if the monitor period name
  was null when entering this function. This is because of the extra
  mouse show that is performed in this routine below that isn't cleared
  because this is called from fish_monitoring instead of the main menu where
  it is normall called from.
}
      if parent_menu^.Period_Name='' then
        begin
          if mshown then
             mhide;
          FilenameIsNull:=True;
        end
      else
        FilenameIsNull:=False;

{ end of change -- MJ -- 1/15/91 ----- } repeat
        SetViewPort(5,17*Y20,Xmax-5,Ymax-5,ClipON);
        SetTextStyle(DefaultFont,HorizDir,1);
        SetTextJustify(CenterText,CenterText);
        ClearViewPort;
        OutTextXY(Xcen,Y20,'Type monitor period name (8 characters max.) and pre
        OutTextXY(Xcen,Y10,'Use Backspace key to correct typing errors');
        parent_menu^.box(item);
        GetString(8,1,parent_menu^.Period_Name,DataEntry,True,False,False);
        RemoveDisallowedCharacters;
        if(DataEntry='NUL') or(DataEntry='PRN') or(DataEntry='CON') or(DataEntry
          (DataEntry='LPT1') or(DataEntry='LPT2') or(DataEntry='COM1') or(DataEntr
          (DataEntry='COM3') or(DataEntry='COM4')then
          begin
            DataEntry:='';
            Changed:=True;
          end;
        if Changed then
          begin
            parent_menu^.Period_Name:=DataEntry;
            Write(#7);
            display;
          end;
      until(DataEntry<>'') and not FileCheck;

SetViewPort(5,17*Y20,Xmax-5,Ymax-5,ClipON);
      ClearViewPort;
      parent_menu^.MouseChoice;
    end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{Added IsMidnight boolean to fix monitor period name overwrite - 4/10/91 - MK}
  procedure Monitor_periodobj.Autoname(par_menu:pointer;createfiles,ismidnight:b
  const
{$IFDEF EXP}
    prefix ='EX';
{$ELSE}
    prefix            ='OP';
{$ENDIF}
```

```
    var year,month,day,dayofweek:Word;
        ygr                     :String[4];
        mgr,dgr                 :String[2];
    begin
      parent_menu:=par_menu;
      GetTextSettings(TextInfo);
      GetDate(year,month,day,dayofweek);
      Str(year,ygr);
      ygr:=Copy(ygr,3,2);
      Str(month,mgr);
      if month<10 then mgr:='0'+mgr;
      Str(day,dgr);
      if day<10 then dgr:='0'+dgr;
      with parent_menu^ do
        begin
          if setup_data.Misc.Automatic_name then
             begin
             Old_Period_Name:=Period_Name;
             Period_Name:=prefix+mgr+dgr+ygr;
             end;
          if IsMidnight then
            begin
            if FileCheck then GetFileName;
            Header(parent_menu^);
            end
          else
          if CreateFiles then
            begin
          {   Period_Name:=Old_Period_Name;}
              Display;
              if FileCheck then GetFileName else parent_menu^.MouseChoice;
              Header(parent_menu^);
            end;
        end;
    end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
    {$F+}
      procedure Monitor_Period_Name(par_menu:Pointer;item_:Word);
      var
        XLoc,
        Yloc                    :Word;
        (*- Key    : char;-*)
      begin
        with Monitor_period do
            begin
            parent_menu:=par_menu;
            item:=item_;
            end;
        View.save;
        if setup_data.Misc.Automatic_name then with Monitor_period.parent_menu^ do
          begin (* inserted this change, so that if the user changed the name
               of the file with auto period name on, it would keep the name
               of the file for the user MAJ 4/11/91 *)

{         s1 := parent_menu^.period_name;} with Monitor_period do
```

```
                Autoname(parent_menu,check_for_old_file,FALSE);
        check_for_old_file:=False;

(* rest of the change, this checks to see if the name is the same
           and also checks to make sure that it is not in start up mode,
           and if it isn't in start up mode, the original filename is
           restored - MAJ 4/11/91 *)

{        if (parent_menu^.period_name <> s1) and (s1 <> '') then
            parent_menu^.Period_name := s1;
}
            end
        else Monitor_period.GetFileName;

Monitor_period.Display;
     mput(370,220);
     mshow;  { always turn the mouse cursor on so that it will be visible
                if the operator exits fish monitoring after a recovery from
                powerloss - MAJ 5/21/91
             }
     {if not GoToMonitoring then mshow;} { Hide cursor when recovering. 2/4/91 -
     with Monitor_period.parent_menu^ do Assign(Biofile,Period_Name+'.bmi');
     View.restore;
   end;
end.Program Nsffft;
{
Programmer: Michael Johnson
Project    : NSF Phase I This program is to perform spectral analysis on raw data collected.

}
uses
   crt;
const
   Blackmann_Harris_window:array[0..2]
   of Single           =(0.42323,0.49755,0.07922);
   {Minimum 3-term Blackmann_Harris window}
   max_status      =3;
   FFT_max_vector_size=4096;
   number_of_fish = 1;
   maxinput = 5.0 ; { this is 10.0 when data was collected with MCA
                     equipment } type
complex = record
               x,y:single;
          end;
complex_vector_type=array[0..FFT_max_vector_size] of complex;
complex_vector_ptr=^complex_vector_type;
real_vector_type=array[0..FFT_max_vector_size] of single;
real_vector_ptr=^real_vector_type;
complex_array_type=array[0..number_of_fish-1] of complex_vector_ptr;

var
   sampling_freq : integer;
```

```
  data : real;
  infile : text;
  filename : string;
  number_of_samples : longint;
  channum : integer;

function convert_to_raw_data(x : real) : integer;
begin
  convert_to_raw_data:=round(x*2048/maxinput);
end;

procedure get_and_print_header(var infile: text;
                               var number_of_samples : longint;
                               var channum : integer;
                               var sampling_freq : integer);
var
  Line,
  error : integer;
  text_data : string;
  index : integer;
begin
    for Line := 1 to 2 do { skip the useless header data }
      begin
        readln(infile,text_data);
        writeln(text_data);
      end;

readln(infile,text_data);
    delete(text_data,1,34);
    index := 1;
    while not (text_data[index] in ['a'..'z','A'..'Z'] )do
        inc(index);
    delete(text_data,index-1,length(text_data)-index);
    val(text_data,sampling_freq,error);

readln(infile,text_data); { fetch the line with the number of
                                samples } delete(text_data,1,34); { strip the comment text off the data }
    val(text_data,longint(number_of_samples),error); { convert the data }
    writeln('Number of samples = ',number_of_samples);
    readln(infile,text_data); { skip a blank line }
    readln(infile,text_data); { skip another one }
        readln(infile,text_data); { read the channel number }
    delete(text_data,1,5); { strip the channel comment }
    val(text_data,channum,error); { convert the text to a usefule number }
    writeln('This data came from channel ',channum);
end;

(*
Procedure Create_tables
         (var sincos,FFT2:complex_vector_ptr;
          var FFT_window:real_vector_ptr;
          nn:integer);
var  harm,
     cosa :extended;
     i    :integer;
BEGIN
```

```
    GetMem(sincos,nn*sizeof(complex));
    GetMem(FFT2,nn*sizeof(complex));
    GetMem(FFT_Window,nn*SizeOf(Single));
    harm := 2 * pi / nn;
    FOR i:= 0 TO nn - 1 DO
    BEGIN
         sincos^[i].y := -sin(harm * i );
         cosa:=cos(harm * i);
         sincos^[i].x := cosa;
         FFT_Window^[i]:= Blackmann_Harris_window[0]-
                          Blackmann_Harris_window[1]*cosa+
                          Blackmann_Harris_window[2]*(2*Sqr(cosa)-1);

end;
END;

procedure process_complex(var targeta,targeti,sincos_:complex;k:integer);
var prod:complex;
begin
IF k = 0 THEN
    prod:=targeta
    ELSE
    begin
    prod.x := targeta.x * sincos_.x - targeta.y * sincos_.y;
    prod.y := targeta.x * sincos_.y + targeta.y * sincos_.x;
    end;
targeta.x := targeti.x - prod.x;
targeta.y := targeti.y - prod.y;
targeti.x := targeti.x + prod.x;
targeti.y := targeti.y + prod.y;
end;

procedure Four(var target:complex_vector_type;sincos:complex_vector_ptr;
               nn:word;isign:integer);

VAR
  maxpower,arg,
  cntr,pnt0,pnt1,i,
  j,a,b,k              :integer;

PROCEDURE swap(VAR s1,
                   s2: complex);
var temp:complex;
begin
temp:=s1;
s1:=s2;
s2:=temp;
end;

BEGIN
  j := 0;
  for  i := 0 to nn - 2 do
  begin
     if i < j then swap(target[i],target[j]);
     k := nn div 2;
     while k <= j do
     begin
        Dec(j,k);
        k := k div 2;
```

```
      end;
    Inc(j,k);
  end;
maxpower := 0;
i := nn;
while i <> 1 do
begin
   Inc(maxpower);
   i := i div 2;
end;

a:=2 ; b := 1;
FOR cntr:= 1 TO maxpower DO
BEGIN
   pnt0 := nn DIV a;
   pnt1 := 0;
   FOR k := 0 TO b-1 DO
   BEGIN
      i:= k;
      WHILE i<nn DO
      BEGIN
         arg := i + b;
         process_complex(target[arg],target[i],sincos^[pnt1],k);
         Inc(i,a);
      END;
      Inc(pnt1,pnt0);
   END;
   a := 2 * a;
   b := b * 2;

END;

END;

procedure split_spectrum(var FFT1,FFT2:complex_vector_type;nn:word);
var i:word;
     rep,rem,aip,aim:single;
procedure split(var fft1i,fft1n,fft2i,fft2n:complex);
begin
rep:=fft1i.x+fft1n.x;
rem:=fft1i.x-fft1n.x;
aip:=fft1i.y+fft1n.y;
aim:=fft1i.y-fft1n.y;
fft1i.x:=rep;
fft1i.y:=aim;
fft1n.x:=rep;
fft1n.y:=-aim;
fft2i.x:=aip;
fft2i.y:=-rem;
fft2n.x:=aip;
fft2n.y:=rem;
end;

begin
fft2[0].x:=fft1[0].y;
fft1[0].y:=0;fft2[0].y:=0;

for i:=1 to nn div 2 -1 do split(fft1[i],fft1[nn-i],fft2[i],fft2[nn-i]);
         { 0.5 multiplying factor is skipped here.           }
            { It is taken into account in Data_processing.  }
```

```
end;
*)
procedure get_data_and_convert(var infile : text);
var
   data : real;
begin
    readln(infile,data);
    writeln('data = ',data:7:3,'   ',convert_to_raw_data(data));
end;

begin
{   write('Enter FileName to perform the FFT on ->');
    readln(filename);} filename := '05141654.r05';
    clrscr;
    assign(infile,filename);
    reset(infile);
    get_and_print_header(infile,number_of_samples,channum,sampling_freq);
    get_data_and_convert(infile);

end.unit timetool;
{
=======================================================================

Copyright (c) Biological Monitoring, Inc. 1987, 1991

Unit      : timetool

Purpose   : Provides time services that are used frequently

Programmer: Michael Johnson

Last Rev  : 5/24/91

=======================================================================
}
interface
  uses dos;
type
    delimeter = (dashes,slashes,spaces);
    date_format = (US,International);
    Year_format = (twodigit,fourdigit);
    am_pm = (give_am_pm,no_am_pm);
    time_format = (normal,military);
    show_seconds = (do_show_seconds,dont_show_seconds);

function date_string(delim : delimeter;
                     form  : date_format;
                     yform : year_format) : String;

function time_string(tf   : time_format;
                     ampm : am_pm;
                     ss : show_seconds) : string;

implementation
```

```
function time_string(tf    : time_format;
                     ampm  : am_pm;
                     ss    : show_seconds) : string;
var
  s1,s2 : string;
  oh,
  ch,
  cm,
  cs,
  c100s : word;
begin gettime(ch,cm,cs,c100s);

oh := ch; { save the orignal time so that we can tell later if it's
              am or pm } if tf = normal then
      if ch>12 then ch:=ch-12; { convert military time to normal time } str(ch,s1);
  if ch<10 then    { if the current hour is less than 10 then place a }
     s1 := '0'+s1; { leading 0 so that the time will be justified } s1 := s1+':';
  str(cm,s2);
  if cm<10 then    { if the current minute is less than 10 then place a }
     s2 := '0'+s2; { leading 0 so that the time will be justified }
  s1 := s1+s2;

if ss = do_show_seconds then
     begin
        s1 := s1+':';
        str(cs,s2);
        if cs<10 then    {if the current second is less than 10 then place a}
           s2 := '0'+s2; {leading 0 so that the time will be justified }
        s1 := s1 + s2;
     end;

if ampm = give_am_pm then
       if oh> 12 then
          s1 := s1 + ' P.M.'
       else
          s1 := s1 + ' A.M.';

time_string := s1; { return the string }
end;

function date_string(delim : delimeter;
                     form  : date_format;
                     yform : year_format) : String;
var s1,s2 : string;
  delim_char : char;
  cy,
  cd,
  cm,
  cdw : word;
```

```
begin
  getdate(cy,cm,cd,cdw);
  case delim of
      dashes  : delim_char := '-';
      slashes : delim_char := '/';
      spaces  : delim_char := ' ';
  end;

case form of
      US : begin
              { put the date into month-day format }
              str(cm,s1);
              if cm<10 then
                  s1 := '0'+s1;
              s1 := s1 + delim_char;
              str(cd,s2);
              if cd<10 then s2 := '0'+s2;
              s1 := s1+s2;
              s1 := s1 + delim_char;
          end;
      International : begin
                  { put the date into day-month format }
                  str(cd,s1);
                  if cd<10 then s1 := '0'+s1;
                  s1 := s1 + delim_char;
                  str(cm,s2);
                  if cm<10 then
                     s2 := '0'+s2;
                  s1 := s1+s2;
                  s1 := s1 + delim_char;
              end;
  end;

case yform of
    twodigit : begin
              { make the year a two digit year }
              str(cy-1900,s2);
              if cy-1900 <10 then
                  s2 := '0'+s2;
              s1 := s1+s2;
            end;
    fourdigit : begin
              { leave the year as a 4 digit year }
              str(cy,s2);
              s1 := s1+s2;
            end;
  end;

date_string := s1; { return the string }
end;

end.unit tp4fft;
{$N+}

INTERFACE uses
 bmiconst;
```

```
const
   Blackmann_Harris_window:array[0..2]
    of Single          =(0.42323,0.49755,0.07922);
   {Minimum 3-term Blackmann-Harris window}
   {yields very low spectral noise        }

Procedure Create_tables
         (var sincos,FFT2: complex_vector_ptr;
          var FFT_window:real_vector_ptr;
          nn:integer);

procedure Four(var target:complex_vector_type;sincos:complex_vector_ptr;
               nn:word;isign:integer);

procedure split_spectrum(var FFT1,FFT2:complex_vector_type;nn:word);

IMPLEMENTATION var temp:complex;
Procedure Create_tables
         (var sincos,FFT2:complex_vector_ptr;
          var FFT_window:real_vector_ptr;
          nn:integer);
var  harm,
     cosa :extended;
     i    :integer;
BEGIN
  harm := 2 * pi / nn;
  FOR i:= 0 TO nn - 1 DO
  BEGIN
       cosa:=cos(harm * i);
       if i<nn div 2 then
          begin  { only half of the vector is used for FFT - PG 6/6/91 }
           sincos^[i].x := cosa;
           sincos^[i].y := -sin(harm * i );
          end;
       FFT_Window^[i]:= Blackmann_Harris_window[0]-
                        Blackmann_Harris_window[1]*cosa+
                        Blackmann_Harris_window[2]*(2*Sqr(cosa)-1);

end;
END;

procedure process_complex(var targeta,targeti,sincos_:complex;k:integer);
begin
IF k = 0 THEN
   temp:=targeta
   ELSE
   begin
    temp.x := targeta.x * sincos_.x - targeta.y * sincos_.y;
    temp.y := targeta.x * sincos_.y + targeta.y * sincos_.x;
   end;
targeta.x := targeti.x - temp.x;
targeta.y := targeti.y - temp.y;
targeti.x := targeti.x + temp.x;
targeti.y := targeti.y + temp.y;
end;

procedure Four(var target:complex_vector_type;sincos:complex_vector_ptr;
```

```
                    nn:word;isign:integer);

VAR
  maxpower,arg,
  cntr,pnt0,pnt1,i,
  j,a,b,k            :integer;

PROCEDURE swap(VAR s1,
                   s2: complex);
begin
temp:=s1;
s1:=s2;
s2:=temp;
end;

BEGIN
  j := 0;
  for  i := 0 to nn - 2 do
  begin
    if i < j then swap(target[i],target[j]);
    k := nn div 2;
    while k <= j do
    begin
        Dec(j,k);
        k := k div 2;
    end;
    Inc(j,k);
  end;
  maxpower := 0;
  i := nn;
  while i <> 1 do
  begin
    Inc(maxpower);
    i := i div 2;
  end;

a:=2 ; b := 1;
  FOR cntr:= 1 TO maxpower DO
  BEGIN
    pnt0 := nn DIV a;
    pnt1 := 0;
    FOR k := 0 TO b-1 DO
    BEGIN
      i:= k;
      WHILE i<nn DO
      BEGIN
        arg := i + b;
        process_complex(target[arg],target[i],sincos^[pnt1],k);
        Inc(i,a);
      END;
      Inc(pnt1,pnt0);
    END;
    a := 2 * a;
    b := b * 2;

END;

END;
```

```
procedure split_spectrum(var FFT1,FFT2:complex_vector_type;nn:word);
var i:word;
    rep,rem,aip,aim:single;
procedure split(var fft1i,fft1n,fft2i,fft2n:complex);
begin
rep:=fft1i.x+fft1n.x;
rem:=fft1i.x-fft1n.x;
aip:=fft1i.y+fft1n.y;
aim:=fft1i.y-fft1n.y;
fft1i.x:=rep;
fft1i.y:=aim;
fft1n.x:=rep;
fft1n.y:=-aim;
fft2i.x:=aip;
fft2i.y:=-rem;
fft2n.x:=aip;
fft2n.y:=rem;
end;

begin
fft2[0].x:=fft1[0].y;
fft1[0].y:=0;fft2[0].y:=0;

for i:=1 to nn div 2 -1 do split(fft1[i],fft1[nn-i],fft2[i],fft2[nn-i]);
        { 0.5 multiplying factor is skipped here.      }
        { It is taken into account in Data_processing. } end;
END.
unit U_header;
{*****************************************************************}
{                                                                 }
{ Copyright (c) Biological Monitoring, Inc. 1987, 1990            }
{                                                                 }
{ This unit prints and writes to file the header information for datafile }
{                                                                 }
{*****************************************************************}
interface uses timetool,filetool,bmimenux;

function Printer_Status(number:word;var msg:string):boolean;

procedure Header(var current_menu:menu);

procedure calc_ScoutDataLoc(var ScoutDataLoc : integer);

implementation uses
  bmiconst,dos;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Printer_Status(number:word;var msg:string):boolean;
begin
regs.ah:=$02;
regs.dx:=number;
Intr($17,regs);
Printer_Status:=FALSE;
case regs.ah of
```

```
        $90 : begin
                Printer_Status:=TRUE;
                msg:='Printer is Ready.';
              end;
        $28 : msg:='Printer out of paper.';
        $C8 : msg:='Printer is turned off.';
        $0  : msg:='Printer is not Ready.';
        else
              msg:='Printer is disconnected.';
        end;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Printer_port(var stream:text):boolean;
var  Attr:word;
begin
GetFattr(stream,Attr);
Printer_port:=(Attr=$0);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
Procedure BMI_file_title(var target:text;Period_Name:string;
                           var NumHeaderLines:word);
(*-var Proprinter:boolean;-*)
begin
(*
Proprinter:=Printer_port(target);
 Append(target);
 if Proprinter then Write(target,#18);
 WRITELN(target,'ÜÔÔÔÔÔÔÔÔÔÔÔÔÔÔÔÔÔÔÔÔÔÔÔÔÔÔÔÔÔÔÔÔÔÔÔÔÔÔÔÔÔÔÔÔÔÔÔÔÔÔÔÔÔÜ');
 if Proprinter then
     writeln(target,'Ü         Bio-Sensor'+#27#83#0+'R'+#27#84+'
     else
     writeln(target,'Ü         Bio-Sensor(R)                    Ü');
 writeln(target,'Ü   (C)Copyright 1990 Biological Monitoring, Inc.  Ü');
 WRITELN(target,'ÜÉÉÉÉÉÉÉÉÉÉÉÉÉÉÉÉÉÉÉÉÉÉÉÉÉÉÉÉÉÉÉÉÉÉÉÉÉÉÉÉÉÉÉÉÉÉÉÉÉÜ');WRITELN(t
 Inc(NumHeaderLines,5);
 *)
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Bstr(b:boolean):string;
begin
if b then Bstr:='YES' else Bstr:='NO ';
end;

{****************************************************************}
{function ChannelAssignString
{Assigns the status of a given channel to a variable length string.    }
{Length depends on number of data selections to be echoed. Channel is the }
{fish # (0..7) and Num is the number of selections to be echoed.       }
{Called from precedure BMI_fileheader, below.                          }
{******************** 10/27/90 - MK **************************} function ChannelAssignString (Channel,DP,Num:integer):string;
var (*-  i:integer;-*)
   S:string;
begin
  case Num of
```

```
        0 : S := '';
        1 : case setup_data.assignment[Channel] of
                0 : S := '=A.  ';
                1 : S := '=R.  ';
                2 : S := '=I.  ';
            end;
        2 : case setup_data.assignment[Channel] of
                0 : S := ' = Active ';
                1 : S := ' = Ref.   ';
                2 : S := ' = Inact. ';
            end;
        3 : case setup_data.assignment[Channel] of
                0 : S := ' = Active      ';
                1 : S := ' = Reference   ';
                2 : S := ' = Inactive    ';
            end;
        4 : case setup_data.assignment[Channel] of
                0 : S := ' = Active        ';
                1 : S := ' = Reference     ';
                2 : S := ' = Inactive      ';
            end;
        5 : case setup_data.assignment[Channel] of
                0 : S := ' = Active          ';
                1 : S := ' = Referenc        ';
                2 : S := ' = Inactive        ';
            end;
        6 : case setup_data.assignment[Channel] of
                0 : S := ' = Active            ';
                1 : S := ' = Reference         ';
                2 : S := ' = Inactive          ';
            end;
    end;
    if ((DP=1) and setup_data.misc.PrinterFileOpt.printopt[6]) or
       ((DP=2) and setup_data.misc.PrinterFileOpt.fileopt[6])
           then S := S + ' ';
    ChannelAssignString := S;
end;

{******************************************************************}
{function DataTypeString                                            }
{Returns a label string for each type of data echoed.  Channel is the }
{fish # (0..7) and DP is passed a value of  1 for printer or 2 for file.}
{Called from procedure BMI-Fileheader, following.                   }
{****************** 10/27/90 - MK ******************************} function DataTypeString (Channel,DP : integer):string;
var
    i : integer;
    S : string;
begin
    S := '';
    for i := 1 to 6 do
    begin
        if DP = 1 then
        begin
            if setup_data.misc.PrinterFileOpt.printopt[i] then
                case i of
                    1 : S := S +'F'#27#83#1'AV'#27#84'  ';
```

```pascal
        2 : S := S +'A'#27#83#1'AV'#27#84'   ';
        3 : S := S +'F'#27#83#1'LM'#27#84'   ';
        4 : S := S +'A'#27#83#1'LM'#27#84'   ';
        5 : S := S +'M'#27#83#1'OV'#27#84'   ';
        6 : S := S +'S'#27#83#1'TD'#27#84'    '; {STD has 1 more space than the r
      end;
    end
    else if DP = 2 then
    begin
      if setup_data.Misc.PrinterFileOpt.fileopt[i] then
      case i of
        1 : S := S + 'Fav   ';
        2 : S := S + 'Aav   ';
        3 : S := S + 'Flm   ';
        4 : S := S + 'Alm   ';
        5 : S := S + 'Mov   ';
        6 : S := S + 'Std    '; {STD has 1 more space than the rest}
      end;
    end;
  end;
  DataTypeString := S;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ} procedure BMI_fileheader(var target      :text;
                               Period_name:string;
                           var NumHeaderLines:word;
                           var ScoutDataLoc : integer);

var        sep              :string[2];
           i,PrintNum,
           FileNum(*-,Len-*)    :integer;
(*-        ibuf             :array[1..5] of integer;
           rbuf             :array[6..11] of real;-*)
           chpr             :string;
{          rth,rtm,rts,rtu,
           year,month,day,dayofweek:word;}
begin
{    GetTime(rth,rtm,rts,rtu);
    GetDate(year,month,day,dayofweek);} if Printer_port (target) then chpr := #18'Bio-Sensor'#27#83#0'(R)'#27#84
      else chpr := 'Bio-Sensor(R)';
    write (target,chpr);
    write (target,'     Version ',VersionNumStrGlbConst);
    writeln (target,'     Copyright 1991     Biological Monitoring, Inc.');
    writeln (target);
    writeln(target,'LOG INFORMATION                 ');
    writeln(target);
    writeln(target,'Today''s date:         ',date_string(slashes,US,fourdigit));
{   if rtm<10 then sep:=':0' else sep:=':';}
    writeln(target,'Time of day:          ',time_string(military,no_am_pm,dont_sh
    writeln(target,'Monitor period name: ',Period_name);
    writeln(target);
    with setup_data do
    begin
      writeln(target,menu_text.assessment_interval:50,bio.assessment_interval.ac
      writeln(target,menu_text.sample_size:50,bio.sample_size.actual:4);
      writeln(target,menu_text.Acceptable_std_dev:50,bio.Acceptable_std_dev.actu
      writeln(target,menu_text.Recalc_after_warnings:50,bio.Recalc_after_warning
```

```
            writeln(target,menu_text.warnings_for_alarm:50,bio.warnings_for_alarm.actu
            writeln(target,menu_text.Minimum_frequency:50,bio.Minimum_frequency.actual
            writeln(target,menu_text.moving_average:50,Bstr(bio.moving_average):6);
            writeln(target,menu_text.automatic_threshold:50,Bstr(wave.automatic_thresh
            writeln(target,menu_text.min_threshold:50,wave.min_threshold.actual:7:2);
            writeln(target,menu_text.time_constant:50,wave.time_constant.actual:7:2);
            writeln(target,menu_text.dynamic_threshold:50,wave.dynamic_threshold.actua
            writeln(target,menu_text.max_disp_frequency:50,misc.max_disp_frequency.act
            writeln(target,menu_text.alarm_duration:50,misc.alarm_duration.actual:4);
            writeln(target,menu_text.automatic_name:50,Bstr(misc.automatic_name):6);
            writeln(target,menu_text.ScreenSaveTime:50,misc.ScreenSaveTime.actual:4);
{$IFDEF SPECTRUM}
            writeln(target,menu_text.FFT:50,Bstr(wave.FFT):6);
{$ENDIF}
       end;
       { START OF PATCH }
       writeln(target);
       Inc(NumHeaderLines);
{$IFDEF ANALOGPH}

{ moved this inside because you only want to print it when
         you have physiochemical params. MAJ 9/26/91
       }
       writeln(target,'Physiochemical parameter limits:           Min          Max'
       Inc(NumHeaderLines);
       { END OF PATCH }
       with setup_data.Analog_phys do
       begin
          writeln(target,menu_text.Ammonia:34,Ammonia.min:11:2,Ammonia.max:15:2);
          writeln(target,menu_text.Temperature:34,Temperature.min:11:2,Temperature.m
          writeln(target,menu_text.O2:34,O2.min:11:2,O2.max:15:2);
          writeln(target,menu_text.pH:34,pH.min:11:2,pH.max:15:2);
          writeln(target,menu_text.conductivity:34,conductivity.min:11:2,conductivit
          writeln(target,menu_text.Turbidity:34,Turbidity.min:11:2,Turbidity.max:15:
          writeln(target,menu_text.extra1:34,extra1.min:11:2,extra1.max:15:2);
          writeln(target,menu_text.extra2:34,extra2.min:11:2,extra2.max:15:2);
       end;
{$ENDIF}
{$IFDEF SCOUT}
       writeln(target,'Physiochemical parameter limits:           Min          Max
       With setup_data.Scout_phys do
       begin
          writeln(target,menu_text.Temperature:34,Temperature.min:11:2,Temperature.m
          writeln(target,menu_text.O2:34,O2.min:11:2,O2.max:15:2);

{ START OF PATCH }
       { these can be printed only when there aren't any physiochemical
         parameters.  It's only when there are physiochemical inputs that
         that they shouldn't be printed (such as the WATERLOO installation
         hence the IFNDEF MAJ 9/24/91 }

{$IFNDEF ANALOGPH}
          writeln(target,menu_text.pH:34,pH.min:11:2,pH.max:15:2);
          writeln(target,menu_text.conductivity:34,conductivity.min:11:2,conductivi
       {$ENDIF}
       { END OF PATCH }
       end;
{$ENDIF}

{********************* New header printout routine - 10/27/90 MK *********}
```

```
PrintNum := 0;
FileNum := 0;
for i := 1 to 6 do
begin
   if setup_data.misc.PrinterFileOpt.printopt[i] then inc (PrintNum);
   if setup_data.misc.PrinterFileOpt.fileopt[i] then inc (FileNum);
end;
if Printer_port (target) then
begin
   writeln (target,#15#27#88#0#240);
   write (target,'                    ');
   for i:= 0 to number_of_fish-1 do
   begin
     chpr := ChannelAssignString (i,1,PrintNum);
     write (target,i:2,chpr);
   end;
   writeln (target);
   write (target,' Date    Time   ');
   ScoutDataLoc := 16;
   for i := 0 to number_of_fish-1 do
   begin
     chpr := DataTypeString (i,1);
     write (target,chpr+'   ');
     ScoutDataLoc := ScoutDataLoc + (PrintNum * 5);
     if setup_data.misc.PrinterFileOpt.printopt[6] then
      inc (ScoutDataLoc);
     inc (ScoutDataLoc);
   end;
   {$IFDEF ANALOGPH}
   write (target,'  Amm    Temp    DO     pH    Cond    Turb');
   {$ELSE}
      {$IFDEF SCOUT}
{         write (target,'           Temp    DO   pH   Cond         ');}
         write (target,'  Temp    DO    pH    Cond      ');
      {$ENDIF}
   {$ENDIF}
  end
  else
{******************** New header file routine - 10/27/90 MK *************}
  begin
    write (target,'                    ');
    for i := 0 to number_of_fish-1 do
    begin
      chpr := ChannelAssignString (i,2,FileNum);
      write (target,i:2,chpr);
    end;
    writeln (target);
    write (target,' Date    Time   ');
    for i := 0 to number_of_fish-1 do
    begin
      chpr := DataTypeString (i,2);
      write (target,chpr+'   ');
    end;

{$IFDEF ANALOGPH}
    write (target,'  Amm    Temp    DO     pH    Cond    Turb');
    {$ENDIF}

{$IFDEF SCOUT}
    write (target,'   STemp    SDO');
```

```
        {$IFNDEF SCOUTDAC}
        write (Target,'    SpH    SCond');
        {$ENDIF}

{$ENDIF}
  end;
  writeln (target);
end;

procedure calc_ScoutDataLoc(var ScoutDataLoc : integer);
var
  PrintNum, i : integer;
begin
  PrintNum := 0;
  for i := 1 to 6 do
  begin
    if setup_data.misc.PrinterFileOpt.printopt[i] then inc (PrintNum);
  end;
    ScoutDataLoc := 16;
    for i := 0 to number_of_fish-1 do
    begin
      ScoutDataLoc := ScoutDataLoc + (PrintNum * 5);
      if setup_data.misc.PrinterFileOpt.printopt[6] then
        inc (ScoutDataLoc);
      inc (ScoutDataLoc);
    end;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Header(var current_menu:menu);
var     msg,msg1:string;
        DirInfo:SearchRec;
        HeaderLines:word;
        cy,cm,cd,cw : word;
begin
with current_menu do
  begin
  HeaderLines:=0;
  if(period_name <>pl.periodname) and (pl.periodname <> '') then
    begin
    getdate(cy,cm,cd,cw);
    if (cd=pl.startofinterval.day) and setup_data.Misc.Automatic_name then
        period_name := pl.periodname;
    end;

if (exist('*.his')) and (exist(Period_name+'.BMI')) then
    begin
      Assign(Biofile,Period_name+'.BMI');
      Append(biofile);
      msg := '***** POWER LOSS RECOVERY ON ';
      msg := msg + date_string(slashes,US,twodigit);
      msg := msg + ' AT ' + time_string(military,no_am_pm,do_show_seconds);
      msg := msg + ' *****';
      writeln(biofile,msg);
      close(biofile);
      if printer_status(0,msg1) then
         begin
            writeln(printer_output^,msg);
```

```
              end;
         end
      else
        begin
         if PL.PeriodName<>Period_Name then
           begin
           Assign(Biofile,Period_name+'.BMI');
           rewrite(Biofile);
           BMI_file_title(Biofile,Period_name,HeaderLines);
           BMI_fileheader(Biofile,Period_name,HeaderLines,ScoutDataLoc);
           close(Biofile);
           PL.PeriodName:=Period_Name;
           if Printer_Status(0,msg) then
              begin
              write(printer_output^,#13);
              BMI_file_title(printer_output^,Period_Name,HeaderLines);
              BMI_fileheader(printer_output^,Period_Name,HeaderLines,ScoutDataLoc);
              writeln(Printer_output^);
              end;
           if powerlossrecoveryglb then
              begin
              { show that a powerloss recovery occured over midnight }
              Append(biofile);
              msg := '***** POWER LOSS RECOVERY ON ';
              msg := msg + date_string(slashes,US,twodigit);
              msg := msg + ' AT ' + time_string(military,no_am_pm,do_show_seconds);
              msg := msg + ' *****';
              writeln(biofile,msg);
              close(biofile);
              if printer_status(0,msg1) then
                 begin
                     writeln(printer_output^,msg);
                 end;
              powerlossrecoveryglb:= false; {turn off powerloss recovery flag }
                end;
             end;
          end;
        NumHeaderLines:=HeaderLines;
        FindFirst(Period_Name+'.bmi',AnyFile,DirInfo);
        HeaderSize:=DirInfo.Size;
        end;
end;

end.
unit u_kermit;
interface uses disptool,
     unit_A0,
     unit_A1,
     unit_A2,
     unit_FT,
{$IFDEF DEBUG}
     printer,
{$ENDIF}
     bmidisp,
     crt;
type
     Kermit_config = record
                       MAXL,TIME,NPAD:byte;
```

```
                        PADC,EOL,QCTL:char;
                      end;
        Kermit_Obj = object
                      Local,Remote:Kermit_config;
                      incoming_type,
                      SOH_Char,
                      state:char;
                      First,
                      Erase_after_transfer,
                      start:boolean;
                      Filename:text;
                      protected_filename,
                      Received_data,
                      Data_to_Send,
                      Packet_to_Send,
                      Received_Packet:string;
                      Received_Packet_No,
                      Received_length,
                      Current_Packet_No:integer;
                      try,Failures_limit,
                      Modem_Port:word;
                      FTRecPtrLocal:_FTRecPtr;
                      procedure Read_Packet;
                      function Resend:word;
                      procedure Next_Packet;
                      function Datalink_Options(Location:Kermit_Config):string;
                      procedure Read_Datalink_Options;
                      procedure Transaction_Initialization;
                      function Send_Initialization:integer;
                      procedure Error(msg:string);
                      function Ack:integer;
                      function Nack:integer;
                      function Encode_char(ch:char):string;
                      procedure Decode;
                      procedure Start_File(FName:string);
                      function Send_Packet(Packet_Type:char):integer;
                      procedure Send_Data;
                      procedure Send_EOT;
                      procedure Send_EOF;
                      function Next_File_Exists:boolean;
                      procedure Task(var FTRecPtr:_FTRecPtr);
                      end;
implementation var     Dummy,NumWrit,
        CommErrorCode:word;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Chksum(Packet:string):char;
var     checksum,i:word;
begin    { by adding 32 any character is converted to readable range 32..127}
Checksum:=0;
for i:=2 to Ord(Packet[2])-31 do Inc(Checksum,Ord(Packet[i]));
Chksum:=Chr((Checksum+(Checksum and 192) div 64) and 63 +32);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Kermit_Obj.Read_Packet;
var     SOH_position,
        INQsize,PortStatus,
```

```
                checksum,
                NumRead:word;
                ReadTerm:boolean;
begin
Received_Packet_No:=-1; {in case of failure}
Received_Packet:='';
Received_data:='';
incoming_type:='T';
CommErrorCode:=__IQSizeA1(Modem_Port,INQsize,PortStatus);
with Remote do
CommErrorCode:=__RdTrmA2(Modem_Port,255,EOL,@Received_Packet[1],
                         time*91 div 5,nil,ReadTerm,NumRead,INQsize,PortStatus);
if CommErrorcode=_OK then
    begin
    Received_Packet[0]:=Chr(NumRead);
    SOH_Position:=Pos(SOH_Char,Received_Packet);
    if SOH_Position>0 then
        begin
        Received_Packet:=Copy(Received_Packet,SOH_Position,
                         length(Received_Packet)-SOH_Position+1);
        Received_length:=Ord(Received_Packet[2])-32;{Including checksum}
        Received_data:=Copy(Received_Packet,5,Received_length-3);
        Received_Packet_No:=Ord(Received_Packet[3])-32;
        Incoming_type:=Received_Packet[4];
        if Received_Packet[Received_length+2]<>
        Chksum(Received_Packet) then Incoming_type:='Q';
        end
        else Incoming_type:='Q';
    end;
{$IFDEF DEBUG}
writeln(lst,'IN='+incoming_type+Received_Packet);
{$ENDIF}
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Ctl(ch:char):char;
begin
Ctl:=Chr(Ord(ch) xor 64);
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Kermit_Obj.Resend:word;
begin
if Packet_to_Send='' then Resend:=Nack
                    else Resend:=Send_Packet(state);
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Kermit_Obj.Next_Packet;
begin
Current_Packet_No:=(Current_Packet_No+1) and 63;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Kermit_Obj.Datalink_Options(Location:Kermit_Config):string;
begin
with Location do
Datalink_Options:=Chr(MAXL+32)+Chr(Time+32)+Chr(NPAD+32)+
                  Chr(Ord(PADC) xor 64)+Chr(Ord(EOL)+32)+QCTL;
end;
```

```pascal
{ŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨ}
procedure Kermit_Obj.Transaction_Initialization;
var      i,j:integer;
begin
Received_Packet_No:=0;
Current_Packet_No:=0;First:=TRUE;
Packet_to_Send:='';Received_Packet:='';
with Local do    {what we want}
     begin
     MAXL:=94;
     Time:=4;
     NPAD:=0;
     PADC:=#0;
     EOL:=#13;
     QCTL:='#';
     end;
with Remote do   {default}
     begin
     MAXL:=80;
     Time:=5;
     NPAD:=0;
     PADC:=#0;
     EOL:=#13;
     QCTL:='#';
     end;
end;

{ŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨ}
function Kermit_Obj.Send_Initialization:integer;
begin
Data_to_Send:=Datalink_Options(Local);
state:='S';
Send_Initialization:=Send_Packet('S');
end;

{ŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨ}
procedure Kermit_Obj.Read_Datalink_Options;
var   len:integer;
begin
with Remote do
   begin
   len:=length(Received_data);
   if len>=1 then MAXL:=Ord(Received_data[1])-32;
   if MAXL<10 then MAXL:=80;
   if len>=2 then Time:=Ord(Received_data[2])-32;
   if Time<=0 then Time:=5;
   if len>=3 then begin
                  NPAD:=Ord(Received_data[3])-32;
                  if len>=4 then PADC:=Ctl(Received_data[4]);
                  end;
   if len>=5 then EOL:=Chr(Ord(Received_data[5])-32);
   if len>=6 then QCTL:=Received_data[6];
   first:=FALSE;
   end;
end;

{ŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨŨ}
function Kermit_Obj.Send_Packet(Packet_Type:char):integer;
var   Ldata:word;
```

```
begin
Send_Packet:=-1;
if state='E' then Exit;
Packet_to_Send:=SOH_Char+Chr(length(Data_to_Send)+35)+
                Chr(Current_Packet_NO+32)+Packet_type+Data_to_Send;
Packet_to_Send:=Packet_to_Send+Chksum(Packet_to_Send)+Local.EOL;
CommErrorCode:=_WrtStA1(Modem_port,Length(Packet_to_Send),
                        @Packet_to_Send[1],NumWrit);
if length(Packet_to_Send)>NumWrit then
    Send_Packet:=-1
    else
    Send_Packet:=NumWrit;
{$IFDEF DEBUG}
writeln(lst,'OUT='+Packet_to_Send);
{$ENDIF}
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Kermit_Obj.Error(msg:string);
begin
Data_to_Send:=msg;
Dummy:=Send_Packet('E');
state:='E';
Close(filename);
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Kermit_Obj.Ack:integer;
begin
Next_Packet;
Ack:=Send_Packet('Y');
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Kermit_Obj.Nack:integer;
begin
Data_to_Send:='';
Nack:=Send_Packet('N');
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Kermit_Obj.Encode_char(ch:char):string;
var  a7:byte;
begin
if ch>#126 then ch:=' ';  {convert 8-bit characters into spaces}
a7:=Ord(ch) and 127;
with Local do
if (a7<32) or (a7=127) then Encode_char:=QCTL+Ctl(ch)
                      else if a7=Ord(QCTL) then Encode_char:=QCTL+QCTL
                                           else Encode_char:=ch;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ} procedure Kermit_Obj.Decode;
var Decoded_data:string;
    i:integer;
    a7:byte;
begin
i:=0;
repeat
      Inc(i);
      if Received_Data[i]=Remote.QCTL then            { control prefix? }
```

```
      begin
      Inc(i);
      a7:=Ord(Received_Data[i]) and 127;
      if a7 in [63..95] then                    {encoded character ?}
         Received_Data[i]:=Ctl(Received_Data[i]);
      end;
   Decoded_Data:=Decoded_data+Received_Data[i];
until i>=length(Received_Data);
Received_Data:=Decoded_Data;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Kermit_Obj.Send_Data;
var i:integer;
    ch:char;
begin
Data_to_Send:='';
if not Eof(Filename) then
repeat
    Read(Filename,ch);
    Data_to_Send:=Data_to_Send+Encode_char(ch);
until eof(Filename) or (length(Data_to_Send)>=Local.MAXL-4);

{packet length includes SEQ,TYPE,CHECK bytes                      }
    {Slack of one byte protects packet if last is control character 0..31}

Next_Packet;

if Send_Packet('D')>0 then state:='D' else Error('data');

end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Kermit_Obj.Send_EOT;
begin
Next_Packet;
if FTRecPtrLocal^._CancelTrans then Error('aborted by Bio-Sensor(R).');
Data_to_Send:='';
if Send_Packet('B')>0 then state:='B' else Error('end of transmission');
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Kermit_Obj.Send_EOF;
begin
Next_Packet;
if (Received_data='X') or (Received_data='Z') then Data_to_Send:='D' {discard}
                                              else Data_to_Send:='';
if Send_Packet('Z')>0 then
   begin state:='Z';

Close(Filename);

if Erase_after_transfer and (Received_data<>'X') and (Received_data<>'Z')
      and (Pos(protected_filename,FTRecPtrLocal^._CurPathPtr^._FilePath)=0)
      and (Pos('.BMI',FTRecPtrLocal^._CurPathPtr^._FilePath)>0)
      then
           Erase(Filename); { erase the filename }
   end
 else Error('end of file');
```

```
end;
{ŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪ}
procedure Kermit_Obj.Start_File(FName:string);
begin
if first then Read_Datalink_Options; {before first file get Remote options}
Data_to_Send:=Fname;
Next_Packet;
if Send_Packet('F')>0 then state:='F' else Error('file header');
end;
{ŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪ}
function Kermit_Obj.Next_File_Exists:boolean;
begin
if first then Next_File_Exists:=TRUE
    else with FTRecPtrLocal^ do
            begin
             _CurPathPtr:=_CurPathPtr^._Next;
            if _CurPathPtr<>NIL then
               begin
               Assign(filename,_CurPathPtr^._FilePath);
               Reset(filename);
               Next_File_Exists:=TRUE;
               end
              else Next_File_Exists:=False;
            end;
end;
{ŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪ}
procedure Kermit_Obj.Task(var FTRecPtr:_FTRecPtr);
{ Sends one Kermit block at a time to RS232 port}
begin
if start then with FTRECPtr^ do
   begin
   FTRecPtrLocal:=FTRecPtr;           {Get file transfer record pointer}
   SOH_Char:=_SOH_Char;
   Failures_limit:=_MaxFailures;
   Modem_Port:=_PortNumber;
   Assign(Filename,_CurPathPtr^._FilePath);
   Reset(Filename);
   state:='S';
   try:=0;
   _CurrentOp:=_INI_SND_OP;
   CommErrorCode:=_IFlshAl(Modem_Port);
   CommErrorCode:=_OFlshAl(Modem_Port);
   Transaction_Initialization;
   if Send_Initialization<0 then Error('initalization');
   incoming_type:=#0;
   start:=FALSE;
   end;

Read_Packet;
display_message('','Kermit file '+FTRecPtrLocal^._CurPathPtr^._FilePath+'. Sendi
                     +state+'. Receiving:'+incoming_type+'.');
if (Received_Packet_No<>Current_Packet_No) or (state='E')
     or (incoming_type in ['N','T','Q']) then
     begin
     if (state='E') or (try>Failures_limit) then
        begin
        FTRecPtr^._CurrentOp:=_STOP_OP;
        if state in ['D','F','E'] then Close(Filename);
        Exit;
```

```
          end;
      if (incoming_type='N')
         and (Received_Packet_No=(Current_Packet_No+1) and 63) then
         incoming_type:='Y' else NumWrit:=Resend;
      Inc(try);
      Exit;
      end;

if incoming_type='E' then FTRecPtr^._CurrentOp:=_STOP_OP;

if incoming_type='Y' then with FTRecPtr^ do
   begin
   if Received_data='Z' then _CancelTrans:=TRUE;
   case state of              {decides what type of Kermit block to send}
       'S','Z': if Next_File_Exists and not _CancelTrans
                   then Start_File(_CurPathPtr^._FilePath)
                   else Send_EOT;

'D','F': if eof(Filename) or _CancelTrans or (Received_data='X')
                   then Send_EOF
                   else Send_data; {send more data}

'B': FTRecPtr^._CurrentOp:=_END_TRN_OP; {end transmission} end;
   end;
end;

end.unit U_scout;

{********************************************************************}
{                                                                    }
{ Copyright (c) Biological Monitoring, Inc. 1987, 1990               }
{                                                                    }
{ This is communication interface through RS-232C port with SCOUT(R) }
{ physiochemical monitor.                                            }
{                                                                    }
{********************************************************************} interface uses
      oldview,
      disptool,
      unit_A0,
      bmiconst,
      unit_A1,
      unit_A2,
      bmimenux,
      crt,
      graph;

type scout_states = (valid_data,data_error,reconnected,disconnected);

scoutobj = object
configured,
trigger : boolean;
error : word;
```

```
scout_state : scout_states;

procedure  Configuration(debugging : boolean);

procedure scan(var Scout_rec:scout_Physiochemical;var scout_msg:string;
               counter_reset : boolean);
function  _read(TermCh:char):string;
procedure _write(story:string); { i like the C conventioni *grin* }
procedure Setup;
function  Msg:string;
procedure Close;
procedure invoke;
private
        timer : longint;
        counter : integer;
        In_Qsize,
        Out_Qsize,
        PortStatus,
        NumRead             :word;
        Port_Options  :   _OptionRecord;
        { these functions are internal to the scout object
          MAJ-PG 6/28/91}
function Command(s:string):string;
end;

procedure scout_Calibration(parent_menu_ptr:pointer;item:word);

procedure water_display(var setup_data:Total_data;priority: boolean);

var
 scout : scoutobj;

implementation const  Out_Q = 64;
       In_Q  = 64;
       Port  =_COM2;
       Celsius    = TRUE;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure scoutobj.Setup;
begin
error:=0;
error:=__OpenA2(port,IN_Q,OUT_Q,0,0);
if error<>_OK then exit;
error:=__RetOpA2(port,port_options);
with port_options do
          begin
          _BaudRate:=300;
          _Parity:=_EVEN;
          _DataBits:=7;
          end;
error:=__SetOpA2(port,port_options);
error:=__IFlshA1(port);
error:=__OFlshA1(port);
timer:=timernow;
end;
```

```
procedure scoutobj.invoke;
begin
    if Error=0 then _Write(' M');
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function scoutobj._read(TermCh:char):string;
var    ReadTerm    :boolean;   {True if terminating character found}
       scout_String         :^string;
begin
New(scout_string);
scout_String^:='';
error:=__RdTrmA2(port,
       255,TermCh,@scout_string^[1],48,nil,ReadTerm,NumRead,IN_Qsize,PortStatus);
scout_string^[0]:=Chr(NumRead);
_read:=scout_string^;
Dispose(scout_string);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure scoutobj._write(story:string);
var    NumWrit:word;
begin
error:=__IFlshA1(port);
error:=__OQsizeA1(port,Out_Qsize);
if length(story)+Out_Qsize<Out_Q then
    error:=__WrtStA1(port,Length(story),@story[1],NumWrit)
  else
    error:=__OFlshA1(port);
{_write:=error;}
Delay(300);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure scoutobj.Close;
begin
error:=__CloseA2(port);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Delete_first_value(var datastr:string);
begin
Delete(datastr,1,Pos(' ',datastr));
while datastr[1]=' ' do Delete(datastr,1,1);
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function First_Value(var datastr:string):real;
var value:real;
    code : integer;
begin
Val(Copy(datastr,1,Pos(' ',datastr)-1),value,code);
if code=0 then First_Value:=value else First_Value:=-1.0;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure scoutobj.scan(var Scout_rec:scout_Physiochemical;var Scout_msg:string;
                        counter_reset : boolean);
var    ReadTerm    :boolean;   {True if terminating character found}
       Apos         :byte;
       scout_String         :^string;
begin
```

```
{   if scout_rec.data_valid and not counter_reset then exit;} if (scout_state=valid_data) and not counter_reset then exit;

if counter_reset then
   counter := 0;

{ only evaluate if at least 5 seconds elapsed since last call
  MAJ-PG 6/29/91
  but is overridden if scout.scan is called at the end of
  a minute of processing to insure that the scout is read
  MAJ 10/14/19}
if (timernow-timer<90) and (not counter_reset) then exit
   else
      timer := timernow;

if counter > 3 then
   begin
      configured := false;
      {cout_state := data_error;}
      exit;
   end;

if maxavail<sizeof(scout_string^) then
   begin
      display_message('','Not enough memory to read SCOUT(R) data');
      exit;
   end;

New(scout_string);
   Scout.trigger:=TRUE;
   scout_string^:='';
   Scout_rec.Data_Valid:=FALSE;
   scout_state:= data_error;

repeat
         error:=__RdTrmA2(port, { no timeout }
         255,#13,@scout_string^[1],0,nil,ReadTerm,NumRead,IN_Qsize,PortSta
         scout_string^[0]:=Chr(NumRead);
         Apos:=Pos('A',scout_string^);
   until (Apos>0) or (error>0);

if scout_string^='' then
      scout_state := disconnected;
   if scout_state <> disconnected then
   if ReadTerm and (Apos>0) then with setup_data.scout_phys do
      begin
         scout_string^:=Copy(scout_string^,Apos,length(scout_string^)-Ap
         Delete_first_value(scout_string^);   { Discard time string }
         Temperature.actual:=First_Value(scout_string^);
         Delete_first_value(scout_string^);
         pH.actual:=First_Value(scout_string^);
         Delete_first_value(scout_string^);
         conductivity.actual:=First_Value(scout_string^);
         { convert the conductivity value from milliSiemens to micromhos
         conductivity.actual := conductivity.actual * 1000;
         Delete_first_value(scout_string^);
         O2.actual:=First_Value(scout_string^);
         Scout_rec.Data_Valid:=TRUE;
```

```
                    scout_state:= valid_data;
                end;

error:=__IFlshA1(port);
        _Write(' M');
        Dispose(scout_string);

if not Scout_rec.data_valid then inc(counter);

if not configured and (Apos>0) then begin
            display_message('','SCOUT(R) is being configured');
            configuration(FALSE);
            if scout_state=reconnected then
                begin
                    display_message('','SCOUT(R) configured successfully');
                    invoke; {to get data}
                    scout_state := reconnected;
                    water_display(setup_data,FALSE);
                    _write(' M');
                    { victory for scout reconfiguration }
                    Sound(400);
                    delay(200);
                    Sound(440);
                    delay(200);
                    Sound(600);
                    delay(400);
                    delay(200);
                    NoSound;
                    {delay(1000);} { add a delay so that the new scout data can
                                    arrive before we read it. }
                end
                else
                begin
                    display_message('','SCOUT(R) configuration failed');
                    scout_rec.data_valid := false;
                    scout_state := data_error;
                end;
        end;

end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function scoutobj.Command(s:string):string;
var i      :integer;
    scout_String         :^string;
begin
New(scout_string);
scout_string^:='';
_write(' ');
for i:=1 to length(s) do
    begin
    scout_string^:=scout_string^+_read(#32);
    _write(s[i]);
    scout_string^:=scout_string^+_read(#10);
    end;
```

```
Command:=scout_string^;
Dispose(scout_string);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Scoutobj.Configuration(debugging : boolean);
var     Dummy,
        scout_String            :^string;
        trials : integer;
begin
New(scout_string);
New(Dummy);
TextBackground(Blue);
TextColor(White);
if debugging then
    begin
        write('Initializing SCOUT(R).');

end;
repeat
scout_string^:=_read(#8);
until scout_string^='';

trials:=0;
repeat
    _write(' ');
    scout_string^:=_Read(#32);
    inc(trials);
    if debugging then
        write('.');
until (scout_string^='TVPCS? ') or (trials>5);
if debugging then
    begin
    TextBackground(Black);
    writeln;

end;

if scout_string^='TVPCS? ' then
    begin
    if debugging then
        writeln('Please wait about 15 seconds...');
    _write('t');   {Time}
    scout_string^:=_read(#10);
    scout_string^:=scout_string^+_read(#32);
    _write('i');   {Interval}
    scout_string^:=scout_string^+_read(#10);
    scout_string^:=scout_string^+_read(#32);Delay(500);
    _write('000000'#13);   {24 hrs}
    scout_string^:=scout_string^+_read(#10);
    Dummy^:=_read(#10);
    scout_string^:=scout_string^+Command('vhd'); { Header disable         }
{$IFDEF FAHRENHEIT}
    scout_string^:=scout_string^+Command('vtf'); { Temperature in ½F      }
{$ELSE}
    scout_string^:=scout_string^+Command('vtc'); { Temperature in ½C      }
{$ENDIF}
    scout_string^:=scout_string^+Command('pdt'); { Disable all parameters }
    scout_string^:=scout_string^+Command('pep'); { Enable pH              }
    scout_string^:=scout_string^+Command('pec'); { Enable conductivity    }
    scout_string^:=scout_string^+Command('peo'); { Enable O2              }
```

```
    end;
if debugging then
    if length(scout_string^)<>202 then write(scout_string^);
configured:=length(scout_string^)=202;
if length(scout_string^)=202 then
        scout_state:=reconnected
    else
        scout_state:=disconnected;
Dispose(Dummy);
Dispose(scout_string);
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Scout_Calibration(parent_menu_ptr:pointer;item:word);
var       ch:char;
begin
RestoreCrtMode;
TextBackground(Blue);
ClrScr;
TextBackground(Red);
TextColor(White);
Write('Press Esc when finished');
TextBackground(Blue);
Window(5,5,75,24);
Scout.setup;
  repeat
  scout.error:=__RdChA1(port,ch,scout.In_Qsize,scout.PortStatus);
  if not (ch in [#0,#2]) then write(ch);
  if keypressed then
                begin
                ch:=ReadKey;
                if ch<>#0 then scout.error:=__WrtChA1(port,ch);
                end;
    until ch in [#27,#2];
scout.error:=__CloseA2(port);
if ch=#2 then begin
                writeln('SCOUT(R) is disconnected.');
                ch:=ReadKey;
                end;
Window(1,1,80,25);
SetGraphMode(GetGraphMode);
SetRGBPalette(56,53,0,53);   {Modify DarkGray}
SetBkColor(Blue);
menu(parent_menu_ptr^).redraw:=TRUE;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Scoutobj.Msg:string;
var       msg1,msg2:string;
begin
__ErrMsgA2(error,msg1,msg2);
Msg:='SCOUT(R): '+msg1+'.  '+msg2;
error:=0;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure water_display(var setup_data:Total_data;priority: boolean);
(*-type     rbuf         =array[0..7] of real;-*)
const   DY             =20;
var     back           :array[1..5] of pointtype;
        water_window_size,
```

```
            analog_water_window_size,
            Scout_water_window_size,    {vertical}
            i,
            Yloc            :integer;
(*-         phys_buf        :^rbuf;-*)
            phys_data       :string[8];
            analog_paramnum : integer;

begin
if status<> general then exit;
view.save;
{$IFDEF ANALOGPH}
analog_water_window_size:=0;

for i:=number_of_fish to number_of_fish+number_of_analog_parameters-1 do
{     if setup_data.assignment[i]=0 then Inc(analog_water_window_size);}
      { keep the analog display constant }
      Inc(analog_water_window_size);
{$ENDIF}
{$IFDEF SCOUT}
Scout_water_window_size:=0;

{$IFDEF ANALOGPH}
for i:=number_of_fish+number_of_analog_parameters to number_of_assignments-1 do
        {if setup_data.assignment[i]=0 then}
            Inc(Scout_water_window_size);
{     if analog_water_window_size=0 then water_window_size:=1
                                  else}
            water_window_size:=analog_water_window_size;
    SetViewPort(3*Xmax div 4,(7+water_window_size)*DY,Xmax-2,
        (9+water_window_size+number_of_scout_parameters)*DY,ClipOn);
{$ELSE}
for i:=number_of_fish to number_of_assignments-1 do
        {if setup_data.assignment[i]=0 then}
            Inc(Scout_water_window_size);
    SetViewPort(3*Xmax div 4,4*DY,Xmax-2,
        (6+number_of_scout_parameters)*DY,ClipOn);
{$ENDIF}
    clearviewport;
    back[1].x:=0;
    back[1].y:=0;
    back[2].x:=0;
    back[2].y:=DY*(2+Scout_water_window_size);
    back[3].x:=Xmax div 4 - 3;
    back[3].y:=back[2].y;
    back[4].x:=back[3].x;
    back[4].y:=0;
    back[5].x:=0;
    back[5].y:=0;

SetFillStyle(SolidFill,green);
    FillPoly(5,back);

if (not setup_data.Scout_phys.data_Valid) or (scout.scout_state <> valid_data) t
   begin
{$IFDEF ANALOGPH}
  (* these lines commented out because if for some reason the analogph or
      the scout goes off line the the window size will be incorrect
      and the display gets FUNKY - MAJ 06/25/91
```

```
    *)

(* SetViewPort(3*Xmax div 4,(8+analog_water_window_size)*DY,
                    Xmax-2,(11+analog_water_window_size)*DY,ClipOn);
    *)
{$ELSE}
    (*
    SetViewPort(3*Xmax div 4,4*DY,Xmax-2,7*DY,ClipOn);
    *)
{$ENDIF}

SetTextJustify(CenterText,CenterText);

case scout.scout_state of
      reconnected,
      valid_data :
        begin
           {SetFillStyle(SolidFill,lightgray);}
           SetFillStyle(SolidFill,Green);
           fillpoly(5,back);
           OutTextXY(80,DY,'   SCOUT(R)   ');
           OutTextXY(80,2*DY,' Configured ');
           outtextxy(80,9*dy div 2,'Please Wait ');
           outtextxy(80,5*dy,'for Data.     ');
        end;
      disconnected :
        begin
{           SetFillStyle(SolidFill,magenta);}
           SetFillStyle(SolidFill,Red);
           fillpoly(5,back);
              OutTextXY(80,5*DY div 2,'   SCOUT(R)   ');

OutTextXY(80,7*DY div 2,'Disconnected');
           display_message('','SCOUT(R) disconnected');
        end
      else
        begin
           SetFillStyle(SolidFill,red);
           fillpoly(5,back);
              OutTextXY(80,5*DY div 2,'   SCOUT(R)   ');

OutTextXY(80,7*DY div 2,'    ERROR    ');
           display_message('','SCOUT(R) ERROR');
        end;
      end;
     end
    else
     begin SetTextStyle(DefaultFont,Horizdir,1);
      SetTextJustify(CenterText,CenterText);
      SetColor(Yellow);
      OutTextXY(back[3].x div 2,DY,'SCOUT(R) WATER');
      SetColor(White);
      Yloc:=2*DY;

SetTextJustify(LeftText,CenterText);
      with setup_data.Scout_phys do
           begin
```

```
        if setup_data.assignment[number_of_fish+number_of_analog_parameters] = 0
        begin
          setcolor(white);
          Str(Temperature.actual:1:1,phys_data);
          OutTextXY(back[1].x +10,Yloc,'Temp. = '+phys_data);
          Inc(Yloc,DY);
        end
        else
        begin
          setcolor(white);
          OutTextXY(back[1].x +10,Yloc,'Temp. = Inactive');
          Inc(Yloc,DY);
        end;
        if setup_data.assignment[number_of_fish+number_of_analog_parameters+1] =
        begin
          setcolor(white);
          Str(O2.actual:1:1,phys_data);
          OutTextXY(back[1].x +10,Yloc,'  O2   = '+phys_data);
          Inc(Yloc,DY);
        end
        else
        begin
          setcolor(white);
          OutTextXY(back[1].x +10,Yloc,'  O2   = Inactive');
          Inc(Yloc,DY);
        end;

{$IFNDEF SCOUTDAC }

{
this code will only display the PH and conductivity if there is not
a scout dac module present within the software system MAJ 06/25/91
} if setup_data.assignment[number_of_fish+number_of_analog_parameters+2] =
        begin
          setcolor(white);
          Str(pH.actual:1:1,phys_data);
          OutTextXY(back[1].x +10,Yloc,'  pH   = '+phys_data);
          Inc(Yloc,DY);
        end
        else
        begin
          setcolor(white);
          OutTextXY(back[1].x +10,Yloc,'  pH   = Inactive');
          Inc(Yloc,DY);
        end;
        if setup_data.assignment[number_of_fish+number_of_analog_parameters+3] =
        begin
          setcolor(white);
          Str(conductivity.actual:1:0,phys_data);
          OutTextXY(back[1].x +10,Yloc,'Cond. = '+phys_data);
          Inc(Yloc,DY);
        end
        else
        begin
          setcolor(white);
          OutTextXY(back[1].x +10,Yloc,'Cond. = Incactive');
          Inc(Yloc,DY);
        end
```

```
{$ENDIF}
 {Marolyn's request 1/3/1990}
        end;
    end;
{$ENDIF} {SCOUT}
{$IFDEF ANALOGPH}
if analog_water_window_size=0 then water_window_size:=1
   else water_window_size:=analog_water_window_size;
back[1].x:=0;
back[1].y:=0;
back[2].x:=0;
back[2].y:=DY*(2+water_window_size);
back[3].x:=Xmax div 4 - 3;
back[3].y:=back[2].y;
back[4].x:=back[3].x;
back[4].y:=0;
back[5].x:=0;
back[5].y:=0;

SetViewPort(3*Xmax div 4,4*DY,Xmax-2,(6+water_window_size)*DY,ClipOn);
ClearViewPort;
SetTextStyle(DefaultFont,Horizdir,1);
SetFillStyle(SolidFill,green);
FillPoly(5,back);
SetTextJustify(CenterText,CenterText);
SetColor(Yellow);
OutTextXY(back[3].x div 2,DY,'ANALOG WATER');
SetColor(White);
if analog_water_window_size=0 then OutTextXY(back[3].x div 2,2*DY,'Inactive')
   else
   begin
   SetTextJustify(LeftText,CenterText);
   Yloc:=2*DY;

analog_paramnum := number_of_fish;  { used to step through the
                                        analog assignments to see which
                                        ones are active MAJ 07/05/91
                                      }
   with setup_data.Analog_phys do
        begin
        if setup_data.assignment[analog_paramnum]=0 then
        begin
        setcolor(white);
        Str(Ammonia.actual:1:2,phys_data);
        OutTextXY(back[1].x +10,Yloc,' Amm. = '+phys_data);
        end
        else
        begin
        setcolor(white);
        OutTextXY(back[1].x +10,Yloc,' Amm. = Inactive');
        end;

Inc(Yloc,DY);
        inc(analog_paramnum);

if setup_data.assignment[analog_paramnum]=0 then
        begin
        setcolor(white);
        Str(Temperature.actual:1:1,phys_data);
        OutTextXY(back[1].x +10,Yloc,'Temp. = '+phys_data);
```

```
end
else
  begin
  setcolor(white);
  OutTextXY(back[1].x +10,Yloc,'Temp. = Inactvie');
  end;

Inc(Yloc,DY);
inc(analog_paramnum);

if setup_data.assignment[analog_paramnum]=0 then
begin
setcolor(white);
Str(O2.actual:1:1,phys_data);
OutTextXY(back[1].x +10,Yloc,'   O2   = '+phys_data);
end
else
  begin
  setcolor(white);
OutTextXY(back[1].x +10,Yloc,'   O2   = Inactive');
  end;

Inc(Yloc,DY);
inc(analog_paramnum);

if setup_data.assignment[analog_paramnum]=0 then
begin
setcolor(white);
Str(pH.actual:1:1,phys_data);
OutTextXY(back[1].x +10,Yloc,'   pH   = '+phys_data);
end
else
 begin
 setcolor(white);
OutTextXY(back[1].x +10,Yloc,'   pH   = Inactive');
 end;

Inc(Yloc,DY);
inc(analog_paramnum);

if setup_data.assignment[analog_paramnum]=0 then
begin
setcolor(white);
Str(conductivity.actual:5:0,phys_data);
OutTextXY(back[1].x +10,Yloc,'Cond. = '+phys_data);
end
else
  begin
  setcolor(white);
  OutTextXY(back[1].x +10,Yloc,'Cond. = Inactive');
  end;

Inc(Yloc,DY);
inc(analog_paramnum);
if setup_data.assignment[analog_paramnum]=0 then
begin
setcolor(white);
Str(Turbidity.actual:1:1,phys_data);
OutTextXY(back[1].x +10,Yloc,'Turb. = '+phys_data);
```

```
                end
                else
                  begin
                    setcolor(white);
                    OutTextXY(back[1].x +10,Yloc,'Turb. = Inactive');
                  end;

Inc(Yloc,DY);
            inc(analog_paramnum);

SetTextJustify(CenterText,CenterText);
            setcolor(white);
            if analog_paramnum < number_of_fish+number_of_analog_parameters-1 then
                for i:=analog_paramnum to number_of_fish+number_of_analog_parameters-
                   begin
                     OutTextXY(back[3].x div 2,Yloc,'Not Used');
                     inc(yloc,DY);
                   end;
          end;
     end;
{$ENDIF}
view.restore;
end;

end.unit xmm; {for extended memory access}
           {Copyright Biological Monitoring, Inc. 1991}
           {Author: PG 5/18/1991}
interface
type
tripleword = record
              AX,BX,DX:word;
              end;
MoveDescription = record
                Length          :longint;
                SourceHandle    :word;
                SourceOffset    :longint;
                DestHandle      :word;
                DestOffset      :longint;
                end;

XMMObj = object
           initialized:boolean;
           error:byte;
           control:function:real;
           function Installed:boolean;
           function Version:longint;
           function RequestHMA(size:word):boolean;
           function ReleaseHMA:boolean;
           function GlobalEnableA20:boolean;
           function GlobalDisableA20:boolean;
           function EnableA20:boolean;
           function DisableA20:boolean;
           function QueryA20:boolean;
           function QueryLargestFree:word;
           function QueryTotalFree:word;
           function AllocateExtended(size:word;var handle:word):boolean;
           function FreeExtended(handle:word):boolean;
           function MoveExtended(var Description:MoveDescription):boolean;
           function LockExtended(handle:word):boolean;
           function UnLockExtended(handle:word):boolean;
```

```
            function GetHandleLength(handle:word):word;
            function GetHandleInfo(handle:word):word;
            function ReallocateExtended(handle,newsize:word):boolean;
            function RequestUMB(segment:word):boolean;
            function ReleaseUMB(segment:word):boolean;
         private
            res:real;
            function call_driver:boolean;
         end;
implementation
uses dos;

function XMMObj.call_driver:boolean;
begin
res:=control;
error:=tripleword(res).bx;
call_driver:=tripleword(res).ax=1;
end;

function XMMObj.Installed:boolean;
var regs:registers;
begin
if not initialized then with regs do
   begin
   ax:=$4300;   {Test for XMM}
   Intr($2F,regs);
   if al=$80 then
       begin
       ax:=$4310;   {Get control function}
       Intr($2F,regs);
       Addr(control):=ptr(es,bx);
       initialized:=TRUE;
       error:=0;
       end
       else Installed:=False;
   end
   else Installed:=FALSE;
end;

function XMMObj.version:longint;
begin
asm mov ah,ah end;
res:=control;
version:=tripleword(res).ax;
end;

function XMMObj.RequestHMA(size:word):boolean;
begin
asm
   mov ah,1
   mov dx,size
end;
RequestHMA:=call_driver;
end;

function XMMObj.ReleaseHMA:boolean;
begin
asm mov ah,2 end;
ReleaseHMA:=call_driver;
end;
```

```
function XMMObj.GlobalEnableA20:boolean;
begin
asm mov ah,3 end;
GlobalEnableA20:=call_driver;
end;

function XMMObj.GlobalDisableA20:boolean;
begin
asm mov ah,4 end;
GlobalDisableA20:=call_driver;
end;

function XMMObj.EnableA20:boolean;
begin
asm mov ah,5 end;
EnableA20:=call_driver;
end;

function XMMObj.DisableA20:boolean;
begin
asm mov ah,6 end;
DisableA20:=call_driver;
end;

function XMMObj.QueryA20:boolean;
begin
asm mov ah,7 end;
QueryA20:=call_driver;
end;

function XMMObj.QueryLargestFree:word;
begin
asm mov ah,8 end;
res:=control;
error:=tripleword(res).bx;
QueryLargestFree:=tripleword(res).ax;
end;

function XMMObj.QueryTotalFree:word;
begin
asm mov ah,8 end;
res:=control;
error:=tripleword(res).bx;
QueryTotalFree:=tripleword(res).dx;
end;

function XMMObj.AllocateExtended(size:word;var handle:word):boolean;
begin
asm
    mov ah,9
    mov dx,size
end;
Allocateextended:=call_driver;
handle:=tripleword(res).dx;
end;

function XMMObj.FreeExtended(handle:word):boolean;
begin
asm
```

```
    mov ah,0AH
    mov dx,handle
end;
FreeExtended:=call_driver;
end;

function XMMObj.MoveExtended(var Description:MoveDescription):boolean;
begin
asm
    mov ah,0BH
    mov si,word ptr Description
end;
MoveExtended:=call_driver;
end;

function XMMObj.LockExtended(handle:word):boolean;
begin
asm
    mov ah,0CH
    mov dx,handle
end;
LockExtended:=call_driver;
end;

function XMMObj.UnLockExtended(handle:word):boolean;
begin
asm
    mov ah,0DH
    mov dx,handle
end;
UnLockExtended:=call_driver;
end;

function XMMObj.GetHandleLength(handle:word):word;
begin
asm
    mov ah,0EH
    mov dx,handle
end;
res:=control;
error:=tripleword(res).bx*(1-tripleword(res).ax);
GetHandleLength:=tripleword(res).dx;
end;

function XMMObj.GetHandleInfo(handle:word):word;
begin
asm
    mov ah,0EH
    mov dx,handle
end;
res:=control;
error:=tripleword(res).bx*(1-tripleword(res).ax);
GetHandleInfo:=tripleword(res).bx;
end;

function XMMObj.ReallocateExtended(Handle,newsize:word):boolean;
begin
asm
    mov ah,0FH
    mov dx,handle
```

```
    mov bx,newsize
end;
ReallocateExtended:=call_driver;
end;

function XMMObj.RequestUMB(segment:word):boolean;
begin
asm
    mov ah,10H
    mov dx,segment
end;
RequestUMB:=call_driver;
end;

function XMMObj.ReleaseUMB(segment:word):boolean;
begin
asm
    mov ah,11H
    mov dx,segment
end;
ReleaseUMB:=call_driver;
end;
end.
program xmmtest;
uses xmm_unit;
var size:longint;
    num,handle:word;
    buf:string;
    XM:XMMObj;
begin
buf:='This is test';
size:=1; {kB}
XM.initialized:=FALSE;
if XM.Installed then num:=Hi(XM.version);
num:=XM.QueryLargestFree;
if XM.AllocateExtended(size,handle) then;
with XM.MoveX do
    begin
    length:=size*1024;
    sourcehandle:=0;
    sourceoffset:=longint(@buf);
    desthandle:=handle;
    destoffset:=0;
    end;
if XM.MoveExtended then
   begin
   buf:='This is new text';
   with XM.MoveX do
       begin
       length:=size*1024;
       sourcehandle:=desthandle;
       sourceoffset:=0;
       desthandle:=0;
       destoffset:=longint(@buf);
       end;
   if XM.MoveExtended then;
   end;
if XM.FreeExtended(handle) then;
end.unit xmm_unit; {for extended memory access}
        {Copyright Biological Monitoring, Inc. 1991}
```

```
            {Author: PG 5/18/1991}
interface
type
tripleword = record
             AX,BX,DX:word;
             end;

MoveDescription = record
                  Length        :longint;
                  SourceHandle  :word;
                  SourceOffset  :longint;
                  DestHandle    :word;
                  DestOffset    :longint;
                  end;

XMMObj = object
             initialized:boolean;
             error:byte;
             control:function:real;
             handle:array [0..31] of word;
             MoveX:MoveDescription;
             function Installed:boolean;
             function Version:longint;
             function RequestHMA(size:word):boolean;
             function ReleaseHMA:boolean;
             function GlobalEnableA20:boolean;
             function GlobalDisableA20:boolean;
             function EnableA20:boolean;
             function DisableA20:boolean;
             function QueryA20:boolean;
             function QueryLargestFree:word;
             function QueryTotalFree:word;
             function AllocateExtended(size:word;var newhandle:word):boolean;
             function FreeExtended(oldhandle:word):boolean;
             function MoveExtended:boolean;
             function LockExtended(lockhandle:word):boolean;
             function UnLockExtended(lockhandle:word):boolean;
             function GetHandleLength(oldhandle:word):word;
             function GetHandleInfo(oldhandle:word):word;
             function ReallocateExtended(oldhandle,newsize:word):boolean;
             function RequestUMB(var size,segment:word):boolean;
             function ReleaseUMB(segment:word):boolean;
           private
             res:real;
             function call_driver:boolean;
           end;
implementation
uses dos;

function XMMObj.call_driver:boolean;
begin
res:=control;
error:=tripleword(res).bx;
call_driver:=tripleword(res).ax=1;
end;

function XMMObj.Installed:boolean;
var regs:registers;
begin
if not initialized then with regs do
```

```
        begin
        ax:=$4300;   {Test for XMM}
        Intr($2F,regs);
        if al=$80 then
            begin
            ax:=$4310;   {Get control function}
            Intr($2F,regs);
            Addr(control):=ptr(es,bx);
            initialized:=TRUE;
            error:=0;
            end
            else Installed:=False;
        end
        else Installed:=FALSE;
end;

function XMMObj.version:longint;
begin
asm mov ah,ah end;
res:=control;
version:=tripleword(res).bx;
end;

function XMMObj.RequestHMA(size:word):boolean;
begin
asm
    mov ah,1
    mov dx,size
end;
RequestHMA:=call_driver;
end;

function XMMObj.ReleaseHMA:boolean;
begin
asm mov ah,2 end;
ReleaseHMA:=call_driver;
end;

function XMMObj.GlobalEnableA20:boolean;
begin
asm mov ah,3 end;
GlobalEnableA20:=call_driver;
end;

function XMMObj.GlobalDisableA20:boolean;
begin
asm mov ah,4 end;
GlobalDisableA20:=call_driver;
end;

function XMMObj.EnableA20:boolean;
begin
asm mov ah,5 end;
EnableA20:=call_driver;
end;

function XMMObj.DisableA20:boolean;
begin
asm mov ah,6 end;
DisableA20:=call_driver;
```

```
end;

function XMMObj.QueryA20:boolean;
begin
asm mov ah,7 end;
QueryA20:=call_driver;
end;

function XMMObj.QueryLargestFree:word;
begin
asm mov ah,8 end;
res:=control;
error:=tripleword(res).bx;
QueryLargestFree:=tripleword(res).ax;
end;

function XMMObj.QueryTotalFree:word;
begin
asm mov ah,8 end;
res:=control;
error:=tripleword(res).bx;
QueryTotalFree:=tripleword(res).dx;
end;

function XMMObj.AllocateExtended(size:word;var newhandle:word):boolean;
begin
asm
    mov ah,9
    mov dx,size
end;
Allocateextended:=call_driver;
newhandle:=tripleword(res).dx;
end;

function XMMObj.FreeExtended(oldhandle:word):boolean;
begin
asm
    mov ah,0AH
    mov dx,oldhandle
end;
FreeExtended:=call_driver;
end;

function XMMObj.MoveExtended:boolean;
begin
asm
    mov ah,0BH
    mov si,word ptr self
    add si,Movex
end;
MoveExtended:=call_driver;
end;

function XMMObj.LockExtended(lockhandle:word):boolean;
begin
asm
    mov ah,0CH
    mov dx,lockhandle
end;
LockExtended:=call_driver;
```

```
end;

function XMMObj.UnLockExtended(lockhandle:word):boolean;
begin
asm
    mov ah,0DH
    mov dx,lockhandle
end;
UnLockExtended:=call_driver;
end;

function XMMObj.GetHandleLength(oldhandle:word):word;
begin
asm
    mov ah,0EH
    mov dx,oldhandle
end;
res:=control;
error:=tripleword(res).bx*(1-tripleword(res).ax);
GetHandleLength:=tripleword(res).dx;
end;

function XMMObj.GetHandleInfo(oldhandle:word):word;
begin
asm
    mov ah,0EH
    mov dx,oldhandle
end;
res:=control;
error:=tripleword(res).bx*(1-tripleword(res).ax);
GetHandleInfo:=tripleword(res).bx;
end;

function XMMObj.ReallocateExtended(oldhandle,newsize:word):boolean;
begin
asm
    mov ah,0FH
    mov dx,oldhandle
    mov bx,newsize
end;
ReallocateExtended:=call_driver;
end;

function XMMObj.RequestUMB(var size,segment:word):boolean;
begin
asm
    mov ah,10H
    mov dx,word ptr size
end;
RequestUMB:=call_driver;
segment:=tripleword(res).bx;
size:=tripleword(res).dx;
end;

function XMMObj.ReleaseUMB(segment:word):boolean;
begin
asm
    mov ah,11H
    mov dx,segment
end;
```

```
ReleaseUMB:=call_driver;
end;
end.
unit bmimodem;
   {********************************************************************}
   {                                                                    }
   { Copyright (c) Biological Monitoring, Inc. 1987, 1991               }
   {                                                                    }
   { This unit contains procedures for remote graphic terminal and file }
   { transfer.                                                          }
   {                                                                    }
   {********************************************************************}
interface
uses
{.U-}
  unit_A0,
  Unit_A1,
  unit_A2,
  unit_MC,
  unit_FT,
{.U+}
  disptool,
  u_kermit,                         { Kermit file transfer   }
{$IFDEF SCOUT}
  U_scout,
{$ENDIF}
  graph,
  dos,
  bmiconst,
  bmimenux;
const Remote_prompt =#13#10'===>';
  Tek4010          =0;

type Screen_set    =record
                      Date_erase,
                      General_Status,
                      Water,
                      Fish_no,
                      FS_display,
                      Bars,
                      waveform           :Boolean;
                    end;
  Remote_states    =(Password_Query,File_query,Erase_files_query,Tek_mode,
                     Sending_Files,ANSI_mode,FT_protocol_query,Modem_off,
                     catchup_mode);
  RemoteRec        =record     {Remote connection variables}
                      Terminal_refresh,
                      BarUpdate,
                      Erase_after_transfer,
                      DCDHigh,OldDcd,
                      FullTekXYcoordinates,
                      ReadTerm           :Boolean;
                      initialize         :Screen_set;
                      HiMSR              :byte;
                      key                :Char;
                      Text_to_Send,
                      msg,Modem_In       :String;
                      Modem_out_Qsize,Modem_In_Qsize,
                      Password_attempts  :Word;
```

```
                    LastHiY,LastHiX,RespCode,
                    Terminal_type       :Integer;
                    Modem_Port_Options  :_OptionRecord;
                    PortStatus,
                    CommErrCode         :Word;
                    DirInfo             :SearchRec;
                  end;
RemoteObj       =object         {Remote modem object}
                    Data                :RemoteRec;
                    Command_state       :Remote_states;
                    ModemPtr            :_MRecPtr;
                    FTRecPtr            :_FTRecPtr;
                    Kermit_Protocol     :Boolean;
                    Kermit              : ^Kermit_Obj;
                    procedure Plot_Modem(x,y:Integer);
                    procedure Open_port;
                    procedure Modem_Setup;
                    procedure Modem_Cleanup(var current_menu:menu);
                    procedure Initialize_File_Transfer(var filename:String);
                    procedure Normal_file_Transfer(var protected_filename:St
                    procedure Lost_Carrier_File_Transfer_Cleanup(var protect
                    function DCD_Changed:Boolean;
                    procedure Modem_Carrier_Control;

procedure ModemErrMsg;
                    procedure Graph_message(msg1,msg2:String);
                    procedure Page_Erase;
                    procedure Color(col:Integer);
                    procedure Fill(col:Integer);
                    function Position(x,y:Integer):String;
                    function Vector(x,y:Integer):String;
                    procedure Erase_trace(y:Integer);
                    procedure Alarm_Start(Alarm_type:String);
                    procedure Alarm_Stop;
                    procedure Initialize_Graphmode(var Logo_polygon:polygon_
                    procedure Exit_Graphmode;
                    function Bar(x1,y1,x2,y2:Integer;frame:Char):String;
                    procedure Fish_no(channel:Integer);
                    procedure TekBar3D(x1,y1,x2,y2,depth,line_color,fill_col
                    procedure water_display(var setup_data:Total_data;priori
                    procedure General_Display(last_freq         :sample_hi
                                              last_amplitude    :real_chan
                                              var setup_data:Total_data;firs
                    procedure General_Status(var Logo_polygon:polygon_set;fi
                    procedure FS_display(frequency,amplitude,std_deviation:R
                    procedure TimeDateUpdate(x,y:Integer);
                    procedure Get_Password_Response(var current_menu:menu);
                    procedure Interpret_Command(command:Char;var current_men
                    function Terminal_Text(x,y:Integer;story:String):String;
                    procedure Poly(polygon:polygon_set;xref,yref:Integer);
                    procedure Plot_Refresh(x,y,ch      :Integer;
                                           last_freq :longint;
                                           last_amplitude,
                                           sdev                :Real);
                    procedure Plot_modem_setup(var current_menu:menu;
                                               x,y,ch           :Integer;
                                               last_freq        :longint;
                                               last_amplitude,
                                               sdev             :Real);
                    procedure Handler(var current_menu:menu;
```

```
                                       difference   : word;
                                       sampling_speed : real);
              private
              procedure Reset_Port_Baud_Rate;
              procedure Check_Files_for_transfer(var filename:String);
              procedure Command_Handler(var current_menu:menu);
            end;
procedure Send_to_Modem(story:String);

implementation uses
{.U-}
   (*-unit_A0,-*)               { interrupt driven asynchroneus RS-232 handler
   (*-    unit_FT,-*)           { Xmodem file transfer    }
   (*-    unit_MC,-*)           {    modem communication }
{.U+}
   crt,
   (*-    bmiinit,-*)
   timedate,
   files,
   bmidisp,
   bmikey,
   u_header;

const Modem_Port      =_COM1;
   Modem_Out_Q        =8192;
   Modem_In_Q         =128;
   vspace             =20;
   Tek4100            =1;
   Regis              =2;
var Chdata            :Char;
   FileCount,
   NumRead            :Word;
   FileCountStr       :String;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Send_to_Modem(story:String);
var CommErrCode,
    NumWrit           :Word;
begin
   CommErrCode:=__WrtStA1(Modem_Port,Length(story), @story[1],NumWrit);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function RemoteObj.Vector(x,y:Integer):String;
var Tek_X,Tek_Y,HiY,LoY,HiX,LoX,Extra:Integer;
    xstr,ystr         :String[3];

function XYencode   :String;
   var XYstr          :String[5];
   begin
      XYstr:=Chr(LoX);
      with Data do if(LastHiX<>HiX) or FullTekXYcoordinates then
        begin
           XYstr:=Chr(HiX)+XYstr;
           LastHiX:=HiX;
        end;
      XYstr:=Chr(LoY)+XYstr;
```

```
      with Data do if(LastHiY<>HiY) or FullTekXYcoordinates then
        begin
          XYstr:=Chr(HiY)+XYstr;
          LastHiY:=HiY;
        end;
      with Data do if FullTekXYcoordinates then FullTekXYcoordinates:=False;
      XYencode:=XYstr;
    end;

begin
  case Data.Terminal_type of
    Tek4010:begin
              Tek_X:=x*8 div 5; {VGA to Tek4010}
              Tek_Y:=(Ymax-y)*13 div 8; {VGA to Tek 4010}
              HiY:=Tek_Y shr 5 or $20;
              LoY:=Tek_Y and $1F or $60;
              HiX:=Tek_X shr 5 or $20;
              LoX:=Tek_X and $1F or $40;
              Vector:=XYencode;
            end;
    Tek4100:begin
              Tek_X:=x*32 div 5; {VGA to Tek4100}
              Tek_Y:=(485-y)*32 div 5; {VGA to Tek 4100}
              HiY:=Tek_Y shr 7 or $20;
              {for 12-bit resolution extra byte necessary}
              Extra:=Tek_Y and 3 shl 2+Tek_X and 3+96;
              LoY:=Tek_Y shr 2 and $1F or $60;
              HiX:=Tek_X shr 7 or $20;
              LoX:=Tek_X shr 2 and $1F or $40;
              Vector:=XYencode;
            end;

Regis:begin
            Str(x*5 div 4,xstr);
            Str(y,ystr);
            Vector:='V['+xstr+','+ystr+']';
          end;
  end;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Tek_Integer(i:Integer):String;
var S             :String[3];
begin
  S:='';
  if Abs(i)>1024 then S:=Chr(64+i div 1024 mod 64);
  if Abs(i)>16 then S:=S+Chr(64+i div 16 mod 64);
    if i>=0 then S:=S+Chr(48+i mod 16) else S:=S+Chr(32+(-i) mod 16);
  Tek_Integer:=S;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Color(col:Integer);
begin
  if Command_state<>Tek_mode then Exit;
  case Data.Terminal_type of
    Tek4100:Send_to_Modem(#27'ML'+Tek_Integer(col));
  end;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Fill(col:Integer);
begin
```

```pascal
      if Command_state<>Tek_mode then Exit;
      case Data.Terminal_type of
        Tek4100:Send_to_Modem(#27'MP'+Tek_Integer(col));
      end;
   end;
{ŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪ}
function RemoteObj.Position(x,y:Integer):String;
var xstr,ystr      :String[3];
begin
   case Data.Terminal_type of
     Regis:begin
             Str(x*5 div 4,xstr);
             Str(y,ystr);
             Position:='P['+xstr+','+ystr+']';
           end;
     Tek4010,
     Tek4100:Position:=#29+Vector(x,y);
   end;
end;

{ŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪ}
function RemoteObj.Terminal_Text(x,y:Integer;story:String):String;
var xstr,ystr      :String[3];
begin
   if length(story)=16 then
        story := story + ' ';    { this is a very quick patch to get around
                                   a bug with the vector routine that fails
                                   when the user (i.e. me and you) try to
                                   print a string that is exactly 16 chars.
                                   long --- MAJ 7/6/91 } case Data.Terminal_type of
     Regis:begin
             Str(x*5 div 4,xstr);
             Str(y,ystr);
             Terminal_Text:='T['+xstr+','+ystr+']T"'+story+'"';
           end;
     Tek4010:Terminal_Text:=Position(x,y)+#31+story+#29;
     Tek4100:Terminal_Text:=Position(x,y)+#27'LT'+
                            Tek_Integer(Length(story))+story;
   end;
end;
{ŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪ}
procedure RemoteObj.Page_Erase;
begin
   case Data.Terminal_type of
     Regis:Send_to_Modem('S(E)');
     Tek4010:Send_to_Modem(#27#12#29);
     Tek4100:Send_to_Modem(#27'KN0');
   end;
end;
{ŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪ}
procedure RemoteObj.Initialize_Graphmode(var Logo_polygon:polygon_set);
var Terminal_model_number:Integer;
begin
   Send_to_Modem(#27'%!0'#27'IQ?T'#10);
   with Data do
     begin
       CommErrCode:=__RdTrmA2(Modem_Port,10,#13, @Modem_In[1],50,nil,
                           ReadTerm,NumRead,Modem_In_Qsize,PortStatus);
```

```
        Modem_In[0]:=Chr(NumRead);
        if(NumRead>=5) and(Modem_In[1]='?')then
           Terminal_model_number:=((Ord(Modem_In[3])-32)*1024+
                                  (Ord(Modem_In[4])-32)*16+
                                  (Ord(Modem_In[5])-32) mod 16)
                                 *(1-2*Byte((Ord(Modem_In[5])-32) div 16 mod 2=0
        else Terminal_model_number:=0;
      end;
   if Terminal_model_number>=4107 then
     begin
        Command_state:=Tek_mode;
        Data.Terminal_type:=Tek4100;
     end
   else
     begin
        Send_to_Modem('Tektronix 4107 or higher model necessary...'+Remote_promp
        Exit;
     end;

Data.FullTekXYcoordinates:=True;
   Data.Terminal_refresh:=True;

case Data.Terminal_type of
     Regis:Send_to_Modem(#144'p');
     Tek4010:Send_to_Modem(#27'%!0'#29);
     Tek4100:begin
                with Data.initialize do
                  begin
                     General_Status:=True;
                     Water:=false;   { was true on 7/6/9 MAJ }
                     waveform:=True;
                     Date_erase:=True;
                     Bars:=True;
                  end;
                Data.BarUpdate:=False;
                Data.FullTekXYcoordinates:=True;
                Send_to_Modem(#27'LZ'#27'MC'+
                            Tek_Integer(50)+Tek_Integer(75)+Tek_Integer(15)+#2
                            #27'TM311'#27'TB0'+Tek_Integer(34)+'F4'#27'TG189K4
                {adjust redness   MAJ-MK 7/6/91 }
                Send_to_Modem(#27'TG!2'+tek_integer(120)+tek_integer(15)+tek_int {Set Tek mode, clear dialog area, set graphtext size,
                 set fixup level, enable and make visible dialog area,
                 set color mode, blue background,
                 set surface color map green-cyan -> dark green
                                       green-yellow -> dark yellow,
                 set invisible cursor, redefine color 10 to dark green,
                 redefine color 8 to brown, enter vector mode}

Page_Erase;

end;
     end;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Exit_Graphmode;
begin
   with Data do
     begin
```

```
        case Terminal_type of
          Regis:Send_to_Modem(#156);
          Tek4010:Send_to_Modem(#27#12#27'%!1');
          Tek4100:begin
                  Color(1);
                  Send_to_Modem(#27'RK!'#27'SK!'#27'KN0'#27'TG189M2C2F4:P>C2F4
                                #27'TB000'#31#27'LLB0'#27'%!1');
                  { delete views, segments, renew, restore surface color map,
                    restore background, restore 32 dialog lines, switch to ANSI }
                  end;
          end;
        Terminal_refresh:=False;
        Command_state:=ANSI_mode;
      end;
    Send_to_Modem(#13#10'View mode abandoned.'+Remote_prompt);
  end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function RemoteObj.Bar(x1,y1,x2,y2:Integer;frame:Char):String;
begin
  Bar:=#27'LP'+Vector(x1,y1)+frame+Vector(x1,y2)+Vector(x2,y2)+Vector(x2,y1)+#
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Graph_message(msg1,msg2:String);
begin
{if (msg1<>'') or (msg2<>'') then
    Send_to_Modem(#27'MC'+Tek_Integer(25)+Tek_Integer(38)+Tek_Integer(8));
 if msg1<>'' then
    Send_to_Modem(#27'MP0'+Bar(msgframe[0].x,msgframe[0].y,
                  msgframe[2].x,(msgframe[0].y+msgframe[2].y) div 2,'1')
                  +Terminal_Text(msgframe[0].x+5,(msgframe[0].y+msgframe[2].y) div
 if msg2<>'' then
    Send_to_Modem(#27'MP0'+Bar(msgframe[0].x,(msgframe[0].y+msgframe[2].y) div 2,
                  msgframe[2].x,msgframe[2].y,'1')
                  +Terminal_Text(msgframe[0].x+5,msgframe[2].y-3,msg2));
 if (msg1<>'') or (msg2<>'') then
    Send_to_Modem(#27'MC'+Tek_Integer(50)+Tek_Integer(75)+Tek_Integer(15));
 }
  Color(1);
  Send_to_Modem(#31#13#10#32+msg1+#13#10#32+msg2+#29);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Alarm_Start(Alarm_type:String);
begin
  if Command_state<>Tek_mode then Exit;
  Send_to_Modem(#27'TBG8C2F4'#7); {Make Red background}
  Color(1);
  Graph_message(Alarm_type+' alarm occured at '+timegr,'Water sample is collec
  if oldrise then Color(2) else Color(3);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Erase_trace(y:Integer);
begin
  if Command_state<>Tek_mode then Exit;
  with Data do
    case Terminal_type of
      Tek4100:begin
              FullTekXYcoordinates:=True; {to prevent errors due to line noi
              Send_to_Modem(#27'MP0'+Bar(Xo+2,Yo-2,Xo+Xsize,Yo-Ysize+2,'0')+
              {define erasing segment}
              {fill blue, begin panel, vectors, end panel}
```

```
            end;
      end;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Alarm_Stop;
begin
   if Command_state<>Tek_mode then Exit;
   Send_to_Modem(#27'TB0'+tek_integer(34)+'F4');   {Make Blue background}
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Poly(polygon:polygon_set;xref,yref:Integer);
var i,j               :Integer;
begin
   with polygon do
      for i:=1 to 5 do
         begin
            case Data.Terminal_type of
               Tek4010:Send_to_Modem(Position(points[i]^[1].x+xref,
                                              points[i]^[1].y+yref));
               Tek4100:Send_to_Modem(#27'MP!'#27'LP'+Vector(points[i]^[1].x+xref,
                                              points[i]^[1].y+yref)+'
            end;
            for j:=1 to count[i]do
               Send_to_Modem(Vector(points[i]^[j].x+xref,points[i]^[j].y+yref));
         end;
   if Data.Terminal_type=Tek4100 then Send_to_Modem(#27'LE');  {end panel}
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.water_display(var setup_data:Total_data;priority:Boolean);
(*-type     rbuf         =array[0..7] of real;-*)
const DY               =20;
var back               :array[1..5]of pointtype;
   water_window_size,
   analog_water_window_size,
   Scout_water_window_size,      {vertical}
   i,
   Yloc                :Integer;
   (*-    phys_buf     :^rbuf;-*)
   phys_data           :String[8];
   ViewPort            :ViewPortType;
      analog_paramnum : integer;
begin
{$IFDEF ANALOGPH}
   analog_water_window_size:=0;
   for i:=number_of_fish to number_of_fish+number_of_analog_parameters-1 do
      {if setup_data.assignment[i]=0 then} Inc(analog_water_window_size);
{$ENDIF}
   if not Data.initialize.Water then
      with Data do
         case Terminal_type of
            Tek4100:Send_to_Modem(#27'SKW0');  {delete date segment}
         end
   else Data.initialize.Water:=False;
   Send_to_Modem(#27'SOW0');
   send_to_modem(#27'MQ2');
   send_to_modem(#27'MG0');
{$IFDEF SCOUT}
   Scout_water_window_size:=0;
{$IFDEF ANALOGPH}
         for i:=number_of_fish+number_of_analog_parameters to number_of_assignmen
```

```
            {if setup_data.assignment[i]=0 then} Inc(Scout_water_window_size);
         if analog_water_window_size=0 then water_window_size:=1
         else water_window_size:=analog_water_window_size;
         with ViewPort do
            begin
               x1:=3*Xmax div 4;
               y1:=(7+water_window_size)*DY;
               x2:=Xmax-2;
               y2:=(9+water_window_size+Scout_water_window_size)*DY;
            end;
{$ELSE}
for i:=number_of_fish to number_of_assignments-1 do
        {if setup_data.assignment[i]=0 then} Inc(Scout_water_window_size);
   with ViewPort do
         begin
         x1:=3*Xmax div 4;
         y1:=4*DY;
         x2:=Xmax-2;
         y2:=(6+Scout_water_window_size)*DY;
         end;
{$ENDIF}
         back[1].x:=0;
         back[1].y:=0;
         back[2].x:=0;
         back[2].y:=DY*(2+Scout_water_window_size);
         back[3].x:=Xmax div 4-3;
         back[3].y:=back[2].y;
         back[4].x:=back[3].x;
         back[4].y:=0;
         back[5].x:=0;
         back[5].y:=0;

if (not setup_data.Scout_phys.data_Valid) or (scout.scout_state <> valid_dat
         begin
(*{$IFDEF ANALOGPH}
         with ViewPort do
            begin
               x1:=3*Xmax div 4;
               y1:=(7+analog_water_window_size)*DY;
               x2:=Xmax-2;
               y2:=(9+analog_water_window_size)*DY;
            end;
{$ELSE}
      with ViewPort do
         begin
         x1:=3*Xmax div 4;
         y1:=4*DY;
         x2:=Xmax-2;
         y2:=6*DY;
         end;
{$ENDIF} *)
            case scout.scout_state of
               reconnected,
               valid_data :
                  begin
                  Fill(-10);Color(1);
                     end;
                  disconnected:
                     begin
```

```
                        Fill(-2);Color(1)
                     end
                   else
                     begin
                        Fill(-2);Color(1);
                     end;
                end;
             with ViewPort do
                begin
                   Send_to_Modem(Bar(x1+back[1].x,y1+back[1].y,x1+back[3].x,y1+back[3].
                end;
             with ViewPort do
                begin
                   Send_to_Modem(Terminal_Text(x1,y1+2*DY,'    SCOUT(R)    '));
                   case scout.scout_state of
                   valid_data,
                   reconnected :
                      Send_to_Modem(Terminal_Text(x1,y1+3*DY,'   Configured   '));
                   disconnected :
                      Send_to_Modem(Terminal_Text(x1,y1+3*DY,' Disconnected'))
                   else
                      Send_to_Modem(Terminal_Text(x1,y1+3*DY,'     ERROR      '));
                   end;
                end;
          end
        else
          begin
             Fill(-10);Color(1);
             with ViewPort do
                begin
                   Send_to_Modem(Bar(x1+back[1].x,y1+back[1].y,x1+back[3].x,y1+back[3].

color(7);
                   Send_to_Modem(Terminal_Text(x1,y1+DY,' SCOUT(R) WATER'));
                   color(1);
                   Yloc:=2*DY;
                   with setup_data.Scout_phys do
                      begin Str(Temperature.actual:1:1,phys_data);
                         Send_to_Modem(Terminal_Text(x1+back[1].x+10,y1+Yloc,'Temp. = '+p
                         Inc(Yloc,DY);

Str(O2.actual:1:1,phys_data);
                         Send_to_Modem(Terminal_Text(x1+back[1].x+10,y1+Yloc,'   O2   = '+p
                         Inc(Yloc,DY);
{$IFNDEF SCOUTDAC }
{ these are only available when the scoutdac option is
   not present MAJ 06/26/91}
                         if number_of_scout_parameters >= 3 then
                            begin
                               Str(pH.actual:1:1,phys_data);
                               Send_to_modem(Terminal_Text(x1+back[1].x +10,y1+Yloc,'   pH
                               Inc(Yloc,DY);
                            end;
                         if number_of_scout_parameters >= 4 then
                            begin
                               Str(conductivity.actual:5:0,phys_data);
                               Send_to_modem(Terminal_Text(x1+back[1].x +10,y1+Yloc,'Cond.
```

```
                        Inc(Yloc,DY);
                end;
{$ENDIF}
            end;
        end;
      end;
{$ENDIF}
{$IFDEF ANALOGPH}
    if analog_water_window_size=0 then water_window_size:=1
    else water_window_size:=analog_water_window_size;
    back[1].x:=0;
    back[1].y:=0;
    back[2].x:=0;
    back[2].y:=DY*(2+water_window_size);
    back[3].x:=Xmax div 4-3;
    back[3].y:=back[2].y;
    back[4].x:=back[3].x;
    back[4].y:=0;
    back[5].x:=0;
    back[5].y:=0;

with ViewPort do
      begin
        x1:=3*Xmax div 4;
        y1:=4*DY;
        x2:=Xmax-2;
        y2:=(6+water_window_size)*DY;
      end;

Color(1);Fill(-10);
    with ViewPort do
     begin
        Send_to_Modem(Bar(x1+back[1].x,y1+back[1].y,x1+back[3].x,y1+back[3].y,'1
        color(7);
        send_to_modem(Terminal_Text(x1+back[1].x,y1+DY,'   ANALOG WATER'));
     end;
     color(1);
    if analog_water_window_size=0 then
      with ViewPort do
        Send_to_Modem(Terminal_Text(x1+back[1].x,y1+2*DY,'       Inactive'))
    else
      begin
        Yloc:=2*DY;
        analog_paramnum := number_of_fish; { used to step through the
                                            analog assignments }
{ make the text small }
Send_to_Modem(#27'MC'+Tek_Integer(42)+Tek_Integer(59)+Tek_Integer(12));
send_to_Modem(#27'MT'+Tek_Integer(1));
        with setup_data.Analog_phys do with ViewPort do
          begin
            if setup_data.assignment[analog_paramnum]=0 then
            begin
            send_to_Modem(#27'MT'+Tek_Integer(1));
            Str(Ammonia.actual:1:2,phys_data);
            Send_to_Modem(Terminal_Text(x1+back[1].x+10,y1+Yloc,' Amm. = '+phys_
            end
            else
             begin
            send_to_Modem(#27'MT'+Tek_Integer(15));
            Send_to_Modem(Terminal_Text(x1+back[1].x+10,y1+Yloc,' Amm. = Inactiv
```

```
    end;

Inc(Yloc,DY);
inc(analog_paramnum);

if setup_data.assignment[analog_paramnum]=0 then
begin
send_to_Modem(#27'MT'+Tek_Integer(1));
Str(Temperature.actual:1:1,phys_data);
Send_to_Modem(Terminal_Text(x1+back[1].x+10,y1+Yloc,'Temp. = '+phys_
end
else
    begin
send_to_Modem(#27'MT'+Tek_Integer(15));
    Send_to_Modem(Terminal_Text(x1+back[1].x+10,y1+Yloc,'Temp. = Inac
    end;
Inc(Yloc,DY);
inc(analog_paramnum);

if setup_data.assignment[analog_paramnum]=0 then
begin
send_to_Modem(#27'MT'+Tek_Integer(1));
Str(O2.actual:1:1,phys_data);
Send_to_Modem(Terminal_Text(x1+back[1].x+10,y1+Yloc,'  O2  = '+phys_
end
else
begin
send_to_Modem(#27'MT'+Tek_Integer(15));
Send_to_Modem(Terminal_Text(x1+back[1].x+10,y1+Yloc,'  O2  = Inactiv
end;

Inc(Yloc,DY);
inc(analog_paramnum);

if setup_data.assignment[analog_paramnum]=0 then
begin
send_to_Modem(#27'MT'+Tek_Integer(1));
Str(pH.actual:1:1,phys_data);
Send_to_Modem(Terminal_Text(x1+back[1].x+10,y1+Yloc,'  pH  = '+phys_
end
else
begin
send_to_Modem(#27'MT'+Tek_Integer(15));
Send_to_Modem(Terminal_Text(x1+back[1].x+10,y1+Yloc,'  pH  = Inactiv
end;

Inc(Yloc,DY);
inc(analog_paramnum);

if setup_data.assignment[analog_paramnum]=0 then
begin
send_to_Modem(#27'MT'+Tek_Integer(1));
Str(conductivity.actual:1:0,phys_data);
Send_to_Modem(Terminal_Text(x1+back[1].x+10,y1+Yloc,'Cond. = '+phys_
end
else
begin
send_to_Modem(#27'MT'+Tek_Integer(15));
Send_to_Modem(Terminal_Text(x1+back[1].x+10,y1+Yloc,'Cond. = Inactiv
end;
```

```
                    Inc(Yloc,DY);
                    inc(analog_paramnum);

if setup_data.assignment[analog_paramnum]=0 then
                    begin
                      send_to_Modem(#27'MT'+Tek_Integer(1));
                      Str(Turbidity.actual:1:1,phys_data);
                      Send_to_Modem(Terminal_Text(x1+back[1].x+10,y1+Yloc,'Turb. = '+phys_
                    end
                    else
                    begin
                      send_to_Modem(#27'MT'+Tek_Integer(15));
                      Send_to_Modem(Terminal_Text(x1+back[1].x+10,y1+Yloc,'Turb. = Inactiv
                    end;

Inc(Yloc,DY);
                    inc(analog_paramnum);
                    send_to_Modem(#27'MT'+Tek_Integer(9));
                    for i := analog_paramnum to  number_of_fish+number_of_analog_paramet
                       begin
                          Send_to_Modem(Terminal_Text(x1+back[1].x+10,y1+Yloc,'    Not
                          Inc(Yloc,DY);
                       end;
                    send_to_Modem(#27'MT'+Tek_Integer(1));
{ make the text big again }
   Send_to_Modem(#27'MC'+Tek_Integer(50)+Tek_Integer(75)+Tek_Integer(15));
          end;
       end;
{$ENDIF}
      Send_to_Modem(#27'SC');        {close segment W0} end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Fish_no(channel:Integer);
var chstr           :String[2];
begin
   Str(channel,chstr);
   Color(1);
   Send_to_Modem(#27'RC2');         {waveform view}
   if not Data.initialize.Fish_no then
     with Data do
        case Terminal_type of
           Tek4100:Send_to_Modem(#27'SKF0');  {delete fish number segment}
        end
     else
        Data.initialize.Fish_no:=False;
   Send_to_Modem(#27'SOF0'+Terminal_Text(10,20,'Fish No.'+chstr)+#27'SC');
   { open segment, put text and close segment }
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.FS_display(frequency,amplitude,std_deviation:Real;ch:Integ
   { frequency and standard deviation display }
var samplit,
    ssdev,
    sfreq                :String[5];
begin
   if Command_state<>Tek_mode then Exit;
   Send_to_Modem(#27'RC2');         {waveform view}
```

```
  Color(1);
  Str(frequency:4:2,sfreq);
  Str(amplitude:4:2,samplit);
    if PL.calibration[ch]then ssdev:='-----' else Str(std_deviation:5:3,ssdev)
  if not Data.initialize.FS_display then
    with Data do
      case Terminal_type of
        Tek4100:Send_to_Modem(#27'SKS0');   {delete statistical segment}
      end
  else
    Data.initialize.FS_display:=False;
  Send_to_Modem(#27'SOS0'+Terminal_Text(200,30,'Frequency = '+sfreq+' Hz')
              +Terminal_Text(200,30+vspace,'Amplitude = '+samplit+' V')
              +Terminal_Text(200,30+2*vspace,'Std. dev. = '+ssdev+' Hz')+#27
  { open segment, put text and data, and close segment }
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.TekBar3D(x1,y1,x2,y2,depth,line_color,fill_color:Integer);
begin
  Fill(-fill_color);
  Color(line_color);
  Send_to_Modem(Bar(x1,y1,x2,y2,'1')
              +#27'LP'+Vector(x1,y2)+'1'+Vector(x1+depth,y2-depth)+Vector(x2
              +Vector(x2,y2)+#27'LE');
  Fill(-line_color);
  Send_to_Modem(
    #27'LP'+Vector(x2,y2)+'1'+Vector(x2+depth,y2-depth)+
    +Vector(x2+depth,y1-depth)+Vector(x2,y1)+#27'LE');
  { assemble three panels into 3D-bar }
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.General_Display(last_freq:sample_history_vector;last_ampli
                                    var setup_data:Total_data;first_cycle,prio
var k,idisp,Barmax,Height,Ytop,Ybot:Integer;
    barfreq          :Real;
    stdata           :String[5];
    line_color,bar_color : integer;
begin
  if Command_state<>Tek_mode then Exit;
  Ybot:=Y17Y20;                     {frequency display}
  Ytop:=Ymax div 2;
  Height:=Ybot-Ytop;
  Barmax:=4*Height div 5;
  Send_to_Modem(#27'RC1');          {select view no 1}
  if not Data.initialize.Bars then Send_to_Modem(#27'SKB0')  {delete bar segmen
  else Data.initialize.Bars:=False;
  Send_to_Modem(#27'SOB0');         {open bar segment}
  if first_cycle then Send_to_Modem(Terminal_Text(200,200,'Collecting first sa
  else
    begin
      for k:=0 to number_of_fish-1 do
        if setup_data.assignment[k]<2 then {10 second interval}
          begin                {frequency bar}
            barfreq:=last_freq[k]/(2.0*acquisition_period);
            idisp:=Round(Height*barfreq/setup_data.misc.max_disp_frequency.act
            if idisp>Barmax then idisp:=Barmax;
            if idisp<0 then idisp:=0;
            if warning[k] then
              begin
```

```
                 bar_color := 7; { make bar yellow }
                 line_color := 9; { outline the bar in green }
              end
           else
              if pl.calibration[k] then
                 begin
                    bar_color := 1; { make the bar white }
                    line_color := 14; { outline the bar in black }
                 end
              else
                 begin
                    bar_color := 3; { make the bar green }
                    line_color := 10; { outline the bar in yellow }
                 end;

TekBar3D(Xmax div 5+k*Bar_spacing,Ytop+Height,
                   Xmax div 5+k*Bar_spacing+Bar_width,Ytop+Height-idisp,10,
                   line_color,bar_color);{3+4*Byte(warning[k])) }
           {green and dark green fill and line index}
           {if warning orange and yellow fill and line index}
           Str(barfreq:3:1,stdata);
           Color(1);              {white}
           Send_to_Modem(Terminal_Text(Xmax div 5+5+k*Bar_spacing,Ytop+Height
        end;                       {frequency bar}

Ybot:=Ymax div 2;              {amplitude display}
Ytop:=Y10+24;
Height:=Ybot-Ytop;
Barmax:=4*Height div 5;

for k:=0 to number_of_fish-1 do
   if setup_data.assignment[k]<2 then
      begin                     {amplitude bar}
        Str(last_amplitude[k]:3:1,stdata);
        idisp:=Round(Height*last_amplitude[k]/5*0.8);
        if idisp>Barmax then idisp:=Barmax;
        if warning[k] then
           begin
               bar_color := 7; { make the bar yellow }
               line_color:=9; { outline the bar in green }
           end
        else
           if pl.calibration[k] then
              begin
                  bar_color := 1; { make the bar white }
                  line_color := 14; { outline the bar in gray }
              end
           else
              begin
                  bar_color := 3; { make the bar green }
                  line_color := 10; { outline the bar in yellow }
              end;

TekBar3D(Xmax div 5+k*Bar_spacing,Ytop+Height,
                Xmax div 5+k*Bar_spacing+Bar_width,Ytop+Height-idisp,10,
                line_color,bar_color);{3+4*Byte(warning[k])) ;}
        {green and dark green fill and line index}
        {if warning orange and yellow fill and line index}
        Color(1);              {white}
        Send_to_Modem(Terminal_Text(Xmax div 5+5+k*Bar_spacing,Ytop+Height
```

```
            end;
        end;                                {first cycle}
    Send_to_Modem(#27'SC');                 {close bar segment}
    TimeDateUpdate(0,0);
    self.water_display(setup_data,priority);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.General_Status(var Logo_polygon:polygon_set;first_cycle,pr
var i                   :Integer;
   istr                 :String[2];
begin
   Data.Terminal_refresh:=False;
   if Command_state<>Tek_mode then Exit;
   if Data.initialize.General_Status then
      Send_to_Modem(#27'RC1'#27'KN1'#27'RA001'#27'RE1'#27'SO1')
      {select view#1,v.attrib,border vis., begin seg. 1} else
      begin
         Send_to_Modem(#27'KN1');   {renew view #1: general setup}
         if Data.BarUpdate then with PL do
            General_Display(last_freq,last_amplitude,warning,setup_data,
                        first_cycle,priority)
         else
            TimeDateUpdate(0,0);
         Data.BarUpdate:=False;
         Exit;
      end;

if(Data.Terminal_type<>Tek4100) or Data.initialize.General_Status then
      begin
         Color(1);
         Send_to_Modem(Terminal_Text(250,40,'GENERAL STATUS')+
                     Terminal_Text(30,140,'Amp. [V]')+Terminal_Text(30,300,'Fre
                     Terminal_Text(10,420,'Fish No.')+
                     #27'MC'+Tek_Integer(35)+Tek_Integer(70)+Tek_Integer(9)+
                     Position(0,Yo+45)+Vector(500,Yo+45)+Vector(500,Yo+65)+Vect
                     Terminal_Text(5,Yo+60,'Esc - quit View mode   Enter - fish
                     #27'MC'+Tek_Integer(50)+Tek_Integer(75)+Tek_Integer(12));
         for i:=0 to number_of_fish-1 do
            begin
               Str(i,istr);
               Send_to_Modem(Terminal_Text(140+i*Bar_spacing,420,istr));
            end;
         Poly(Logo_polygon,0,0);
      end;
   if Data.initialize.General_Status then
      begin
         Send_to_Modem(#27'SC');    {Close segment #1}
         with PL do General_Display(last_freq,last_amplitude,warning,setup_data,f
         Data.initialize.General_Status:=False;
      end;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.TimeDateUpdate(x,y:Integer);
begin
   if Command_state<>Tek_mode then Exit;
   if not Data.initialize.Date_erase then
      with Data do
         case Terminal_type of
```

```
          Tek4100:Send_to_Modem(#27'SKD0'); {delete date segment}
       end
    else
       Data.initialize.Date_erase:=False;
    Send_to_Modem(#27'SOD0'+Terminal_Text(500,35,Copy(timegr,1,8))
                +Terminal_Text(500,35+vspace,'    '+Copy(timegr,10,5))+#27'SC'+P
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Plot_Refresh(x,y,ch      :Integer;
                                 last_freq   :longint;
                                 last_amplitude,
                                 sdev              :Real);
begin
  if Command_state<>Tek_mode then Exit;
  Fish_no(ch);
  self.FS_display(last_freq/(2.0*acquisition_period),last_amplitude,sdev,ch);
  if oldrise then Color(2) else Color(3);
  Send_to_Modem(Position(x+Xo,y+Yo-Ysize)+#29);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Plot_modem_setup(var current_menu:menu;
                                     x,y,ch            :Integer;
                                     last_freq         :longint;
                                     last_amplitude,
                                     sdev              :Real);
const Arrow_width    =24;
      Arrow_length   =50;
begin
  if Command_state<>Tek_mode then Exit;
  Data.Terminal_refresh:=False;
  if Data.Terminal_type=Regis then Send_to_Modem('S(E)');

Color(1);
  {draw XY coordinates}
  if Data.Terminal_type=Tek4100 then
    if Data.initialize.waveform then
       Send_to_Modem(#27'RC2'#27'KN2'#27'RA001'#27'RE1'#27'SO2'#27'MP!'#27'LP'+
       {select view#2,v.attrib,border vis.,beg.seq.,fill white,beg.panel}
    else Send_to_Modem(#27'KN2') {renew view #2: waveform}
  else Send_to_Modem(Position(Xo+Xsize+2,Yo));
  if(Data.Terminal_type<>Tek4100) or Data.initialize.waveform then {X arrow}
    Send_to_Modem(Vector(Xo+Xsize+2,Yo-Arrow_width div 2)+
                  Vector(Xo+Xsize+2+Arrow_length,Yo)+
                  Vector(Xo+Xsize+2,Yo+Arrow_width div 2));
  if Data.initialize.waveform then Send_to_Modem(#27'LE'); {end panel}
  if(Data.Terminal_type<>Tek4100) or Data.initialize.waveform then
    Send_to_Modem(Vector(Xo+Xsize+2,Yo)+
                  Vector(Xo,Yo)+
                  Vector(Xo,Yo-Ysize div 2)+
                  Vector(Xo-5,Yo-Ysize div 2)+
                  Terminal_Text(Xo-10,Yo-Ysize div 2-5,'0')+ {0 tick on Y axis
                  Vector(Xo,Yo-Ysize div 2)+Vector(Xo,Yo-Ysize));
  if Data.Terminal_type=Tek4100 then
    if Data.initialize.waveform then
      Send_to_Modem(#27'LP'+Vector(Xo,Yo-Ysize)+'0') {begin panel}
    else
  else Send_to_Modem(Vector(Xo,Yo-Ysize));
  if(Data.Terminal_type<>Tek4100) or Data.initialize.waveform then {Y arrow}
    Send_to_Modem(Vector(Xo-Arrow_width div 2,Yo-Ysize)+
                  Vector(Xo,Yo-Ysize-Arrow_length)+
```

```
                         Vector(Xo+Arrow_width div 2,Yo-Ysize)+
                         Vector(Xo,Yo-Ysize));
  if Data.initialize.waveform then Send_to_Modem(#27'LE'); {end panel}
  if(Data.Terminal_type<>Tek4100) or Data.initialize.waveform then {Y label}
    Send_to_Modem(Terminal_Text(10,Yo-Ysize div 2-4*vspace,'A')+
                  Terminal_Text(10,Yo-Ysize div 2-3*vspace,'m')+
                  Terminal_Text(10,Yo-Ysize div 2-2*vspace,'p')+
                  Terminal_Text(10,Yo-Ysize div 2-1*vspace,'l')+
                  Terminal_Text(10,Yo-Ysize div 2-0*vspace,'i')+
                  Terminal_Text(10,Yo-Ysize div 2+1*vspace,'t')+
                  Terminal_Text(10,Yo-Ysize div 2+2*vspace,'u')+
                  Terminal_Text(10,Yo-Ysize div 2+3*vspace,'d')+
                  Terminal_Text(10,Yo-Ysize div 2+4*vspace,'e')+
                  {end Y label}
                  #27'MC'+Tek_Integer(35)+Tek_Integer(70)+Tek_Integer(9)+
                  Position(0,Yo+45)+Vector(500,Yo+45)+Vector(500,Yo+65)+Vector
                  Terminal_Text(5,Yo+60,'Esc - quit View mode   Arrow keys - ch
                  #27'MC'+Tek_Integer(50)+Tek_Integer(75)+Tek_Integer(12)+
                  Terminal_Text(Xo+Xsize div 2,Yo+30,'Time')); {X label}
  if(Data.Terminal_type<>Tek4100) or Data.initialize.waveform then
    Poly(current_menu.Logo_polygon,4*Xmax div 5,5*Ymax div 6); { BMI logo }
  if Data.initialize.waveform then
    begin
      Send_to_Modem(#27'SC');    { close segment }
      Data.initialize.waveform:=False;
    end;
  TimeDateUpdate(x,y);
  Plot_Refresh(x,y,ch,last_freq,last_amplitude,sdev);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Modem_Setup;
const Modem_Init_String='L0&C1&S1&J1';
begin
display_message('','Setting up the modem...');
  with Data do
    begin
      Terminal_refresh:=True;
      Erase_after_transfer:=False;
      DCDHigh:=False;OldDcd:=False;
      Text_to_Send:='';
      msg:='';Modem_In:='';
      Modem_out_Qsize:=0;
      Modem_In_Qsize:=0;
      Password_attempts:=0;
      PortStatus:=0;
      CommErrCode:=0;
      RespCode:=0;
      CommErrCode:=_RetOpA2(Modem_Port,Modem_Port_Options);
      Modem_Port_Options._BaudRate:=2400;
      CommErrCode:=_SetOpA2(Modem_Port,Modem_Port_Options);
      CommErrCode:=_IFlshA1(Modem_Port);
      CommErrCode:=_OFlshA1(Modem_Port);
      CommErrCode:=_MakeMC(ModemPtr,Modem_Port);
      if CommErrCode=_OK then
        with ModemPtr^ do
          begin
            {
              setup the kind of dialing the biosensor will do
              MAJ 10/22/91
            }
```

```
        if setup_data.misc.comm.tone_dial then
            _Dial_Prefix := 'DT'  { user is set up for touch-tone dialing }
        else
            _Dial_Prefix := 'DP'; { user is set up for pulse dialing }

{
          setup how long the modem will wait to get a dial
            tone before dialing
            MAJ 10/22/91
        }

_Dialtone_wait := setup_data.misc.comm.dial_wait.actual;

{ tell the biosensor to answer on a selected number of
            telephone rings MAJ 10/22/91}
        _Rings_To_Ans:=setup_data.misc.comm.num_rings.actual;
        _DialTone_Wait:=3;
        _DCD_Wait:=22;    {
                            this represents half of the time (in seconds)
                            that the modem will spend dialing a remote site
                            MAJ 8/21/91
                          }
        _Esc_GuardTime:=7000; {This is the place to change +++ delay}
        _Init_Baud:=2400;
        _Baud_to_try[1]:=2400;
        _Baud_to_try[2]:=2400;
        _Baud_to_try[3]:=2400;
        _Baud_to_try[4]:=1200;
        _Baud_to_try[5]:=300;
        _Baud_to_try[6]:= -1;
        _ConfigStr:=Modem_Init_String;
        _Reset:='&F';
      end;

if CommErrCode=_OK then CommErrCode:=__InitMC(ModemPtr,True,RespCode);
    RespCode:=CommErrCode;

if RespCode<>0 then Exit
                   else
                       begin
                       Command_state:=Password_query;
                       display_message('','Modem is ready.');
                       end;

if DCD_Changed then        {if modem off the hook}
      begin
        CommErrCode:=__HangUPMC(ModemPtr);
        Delay(500);
        Reset_Port_Baud_Rate;
        CommErrCode:=__InitMC(ModemPtr,True,RespCode);
        RespCode:=CommErrCode;
        CommErrCode:=__IFlshAl(Modem_Port);  { fix PG 7/7/1991 }
        Modem_in:='';                        { fix PG 7/7/1991 }
        if RespCode<>0 then Command_state:=Modem_off;
      end;
   end;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Open_Port;
```

```
begin
ModemPtr:=nil;
Command_state:=Modem_off;
with Data do CommErrCode:=__OpenA2(Modem_Port,Modem_In_Q,Modem_Out_Q,0,0);
Modem_setup;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Plot_Modem(x,y:Integer);
begin
  if Command_state<>Tek_mode then Exit;
  with Data do
    begin
      CommErrCode:=__OQsizeA1(Modem_Port,Modem_out_Qsize);
      if Modem_out_Qsize<Modem_Out_Q-50 then
        if x>Xo+2 then Send_to_Modem(Vector(x,y)); {plot waveform}
    end;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Modem_Cleanup(var current_menu:menu);
begin
if Command_state<>Modem_off then
  with Data do
    begin
      if Command_state=Sending_Files then
        begin
          FTRecPtr^._CancelTrans:=True;
          repeat
            Normal_file_Transfer(current_menu.Period_Name);
          until FTRecPtr=nil;
          display_message('',Text_to_Send);
          Send_to_Modem(Text_to_Send+#13#10);
        end;

if DCDHigh then
        begin
          Send_to_Modem('Monitoring aborted from local keybord.  Goodbye!...'#
          repeat
            CommErrCode:=__OQsizeA1(Modem_Port,Modem_out_Qsize)
          until Modem_out_Qsize=0;
          CommErrCode:=__HangUPMC(ModemPtr);
          Delay(500);
        end;
      ModemPtr^._Rings_To_Ans:=0;
      Reset_Port_Baud_Rate;
      CommErrCode:=__InitMC(ModemPtr,True,RespCode);
    end;
Data.CommErrCode:=__CloseA2(Modem_Port);

end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Modem_erase_after_transfer(var FTRecPtr:_FTRecPtr;var protected_file
var erase_target   :file;
  next_file         :_PathRecPtr;
begin
  next_file:=FTRecPtr^._PathListRoot;
  if next_file<>FTRecPtr^._CurPathPtr then
    repeat
      if(FTRecPtr^._CurPathPtr<>next_file) and
```

```
            ((FTRecPtr^._CurPathPtr<>next_file^._Next) or
             (next_file^._Next=nil))then
              begin
                if(Pos(protected_filename,next_file^._FilePath)=0) and
                (Pos('.BMI',next_file^._FilePath)>0)then
                  begin
                    Assign(erase_target,next_file^._FilePath);
                    Erase(erase_target);
                  end;

end;
          next_file:=next_file^._Next;
        until next_file=FTRecPtr^._CurPathPtr;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Normal_file_Transfer(var protected_filename:String);
begin
  if Kermit_Protocol then
    begin
      Kermit^.protected_filename:=protected_filename;
      Kermit^.Task(FTRecPtr);
    end
  else __TaskFT(FTRecPtr);

with FTRecPtr^ do
    begin
      if _CurrentOp in[_END_TRN_OP,_STOP_OP]then with Data do {end of file tra
        begin
          case _CurrentOp of
            _END_TRN_OP:if _CancelTrans then
                          Text_to_Send:='Modem file transfer aborted from Bio-
                        else
                          Text_to_Send:='Modem file transferred completed.';
            _STOP_OP:if _CancelTrans then
                        Text_to_Send:='Modem file transfer aborted from Bio-Sen
                     else
                        Text_to_Send:='Modem file transfer aborted.';
          end;
          if not Kermit_Protocol and Erase_after_transfer
          and(_PathListRoot<>nil)then
            Modem_erase_after_transfer(FTRecPtr,protected_filename);
          __ZapFT(FTRecPtr);
          if Kermit_Protocol then Dispose(Kermit);
          CommErrCode:=__IFlshAl(Modem_Port); {Clean up input buffer}
          CommErrCode:=__OFlshAl(Modem_Port); {Clean up output buffer}
          Modem_In:='';
          FTRecPtr:=nil;
          Command_state:=ANSI_mode;
          Send_to_Modem(#13#10#13#10#13#10#13#10+Remote_prompt);
        end;
    end;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Lost_Carrier_File_Transfer_Cleanup(var protected_filename:
begin
  with Data do
    begin
```

```
        if not Kermit_Protocol and Erase_after_transfer and(FTRecPtr^._PathListR
          Modem_erase_after_transfer(FTRecPtr,protected_filename);
          ZapFT(FTRecPtr);
        if Kermit_Protocol then Dispose(Kermit);
        CommErrCode:=__IFlshA1(Modem_Port); {Clean up input buffer}
        Modem_In:='';
        FTRecPtr:=nil;
        Text_to_Send:='Connection lost. Modem file transfer failed.';
        Command_state:=ANSI_mode;
      end;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure CheckModemResponse(test:String;var Response,LastResponse:String);
begin
   if Pos(test+#13,Response)>Pos(LastResponse,Response)then LastResponse:=test;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function RemoteObj.DCD_Changed:Boolean;
var MSR:word;
begin
   with Data do
      begin
        CommErrCode:=__RetOpA1(Modem_Port,18,MSR);
        HiMSR:=MSR shr 4;
        DCDHigh:=(MSR and _CD)=_CD;
        DCD_Changed:=OldDcd<>DCDHigh;
        OldDcd:=DCDHigh;
      end;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Reset_Port_Baud_Rate;
begin
   with Data do
      begin
        Modem_Port_Options._BaudRate:=ModemPtr^._Init_Baud;
        CommErrCode:=__SetOpA2(Modem_Port,Modem_Port_Options);
      end;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Modem_Carrier_Control;
var Response,BaudStr,
   LastResponse        :String;
   NewBaud
   (*-PortStatus-*)    :Word;
   (*-         j,OldRespCode:integer;-*)
begin                           {modem response}
   with Data do if Command_state<>Modem_off then
      begin
        CommErrCode:=__IQSizeA1(Modem_Port,Modem_In_Qsize,PortStatus);
        if Modem_In_Qsize>0 then
          begin
             CommErrCode:=__RespMC(ModemPtr,100,Response,NumRead);
             NewBaud:=0;
             CheckModemResponse('RING',Response,LastResponse);
             CheckModemResponse('CONNECT 2400',Response,LastResponse);
             CheckModemResponse('CONNECT 1200',Response,LastResponse);
```

```
            CheckModemResponse('CONNECT',Response,LastResponse);
            CheckModemResponse('NO CARRIER',Response,LastResponse);
            CheckModemResponse('NO DIALTONE',Response,LastResponse);
            CheckModemResponse('BUSY',Response,LastResponse);
            CheckModemResponse('NO ANSWER',Response,LastResponse);
            CheckModemResponse('ERROR',Response,LastResponse);
            CheckModemResponse('OK',Response,LastResponse);
            if LastResponse='CONNECT' then NewBaud:=300;
            if LastResponse='CONNECT 1200' then NewBaud:=1200;
            if LastResponse='CONNECT 2400' then NewBaud:=2400;
            if LastResponse='NO CARRIER' then
               begin
                  CommErrCode:=__HangUPMC(ModemPtr);
                  msg:='Modem disconnected.';
               end;
         end;

if not DCDHigh then         { carrier lost }
            begin
               Delay(1000);
               Reset_Port_Baud_Rate;
               CommErrCode:=__InitMC(ModemPtr,True,RespCode);
               Command_state:=Password_Query;
               Modem_In:='';
               msg:='Modem disconnected.';
            end;

if DCDHigh and(NewBaud<>Modem_Port_Options._BaudRate) and(NewBaud>0)then
            begin
               Modem_Port_Options._BaudRate:=NewBaud;
               CommErrCode:=__SetOpA2(Modem_Port,Modem_Port_Options);
               Str(NewBaud,BaudStr);
               if CommErrCode=_OK then msg:='Modem adjusted to '+BaudStr+' baud.';
            end;

if(NewBaud>0) and DCDHigh then
            begin
               Password_attempts :=0;
               key:=#0;
               Send_to_Modem(#13#10+
                   'Welcome to the Bio-Sensor(R) water quality monitoring system'#1
               Send_to_Modem(#13+'Password: ');
               Command_state:=Password_Query;
               CommErrCode:=__IFlshA1(Modem_Port); {Clean up input buffer}
               Modem_In:='';
               msg:='Bio-Sensor(R) is asking remote terminal for password.';
            end;
         display_message('',msg);
      end;                          {modem response}
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Get_Password_Response(var current_menu:menu);
var                           (*- j:integer; -*)
   dummy                :Boolean;
begin
   with Data do
      begin
         if(Pos(Modem_In,setup_data.misc.Password_set)>0) and(Length(Modem_In)>4)
         then
```

```
              begin
                Command_state:=ANSI_mode;
                Password_attempts := 0; { rest the number of password attempts }
(*{$IFDEF RINGBACK} *)
if setup_data.misc.comm.ring_back then
     begin
        Send_to_Modem(#13#10#13#10'Password correct.'#13#10#13#10);
        Send_to_Modem('Calling back... Have your modem in autoanswer mode'#13#
        Send_to_Modem('or type ATA and press <Enter> after the first RING.'#13
        display_message('','Calling back a remote terminal.');

Delay(500);

CommErrCode:=__HangUPMC(ModemPtr);
        CommErrCode:=__IFlshA1(Modem_Port); {Clean up input buffer}

Delay(500);
        CommErrCode:=__DialMC(ModemPtr,Copy(Modem_In,1,Length(Modem_In)-1),nil {           if RespCode=_OK_RESPONSE then Command_state:=Password_query if RespCode=_OK_RESPONSE then Command_state:=catchup_mode
        else
           Command_state:=Password_Query;

Modem_In:='';
        if Command_state<>Password_Query then
          begin
            Send_to_Modem(#13#13#10#10'Welcome back to the Bio-Sensor(R) Moni
            Send_to_Modem(#10#13#10#13#10'Please wait for the prompt. The Bio-Se
            Send_to_Modem('is processing data collected during the call back.');
            Command_state := catchup_mode;
          end
        else
          display_message('','Remote terminal has not responded.');Write(#7);
     end
(*{$ELSE} *)
   else
   command_state := catchup_mode;
(*{$ENDIF} *)

end
      else
        inc(Password_attempts);

if Password_attempts>6 then
          begin
            Send_to_Modem('Too many attempts. Goodbye!...');
            Delay(500);
            CommErrCode:=__HangUPMC(ModemPtr);
            Delay(500);
            Reset_Port_Baud_Rate;
            CommErrCode:=__InitMC(ModemPtr,True,RespCode);
            CommErrCode:=__IFlshA1(Modem_Port); {Clean up input buffer}
            Modem_In:='';
            Password_attempts:=0;
          end
      else
           if command_state = password_query then
```

```pascal
            begin
               Send_to_Modem('Incorrect password.'#13#10'Password: ');
               display_message('','Invalid password');
               Inc(Password_attempts);
               Modem_In := ''; {
                                    added this to reset the input string when an
                                    incorrect password was entered.  This created
                                    the problem where invalid passwords were kept
                                    making it nearly impossible to enter a correct
                                    until 80 had been entered MAJ 6/4/91
                               }
            end;

end;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Check_Files_for_transfer(var filename:String);
begin
   FileCount:=0;
   Delete(filename,Length(filename),1);
   FindFirst(filename,AnyFile,Data.DirInfo);
   if DosError=0 then Command_state:=Erase_files_query
   else
      begin
         Send_to_Modem('File(s) not found. Check the name and try again.'+Remot
         Command_state := ANSI_mode;
      end;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Initialize_File_Transfer(var filename:String);
   (*-var      NextInfo:SearchRec;-*)
begin
   with Data do
      begin
         if Kermit_Protocol then
            begin
               New(Kermit);              {allocate memory for Kermit}
               Kermit^.start:=True;
               Kermit^.Erase_after_transfer:=Erase_after_transfer;
            end;
         {Initialize file transfer control structure}

FTRecPtr:=__MakeFT(Modem_Port,_YMODEM,_FT_SEND,'',CommErrCode);

repeat
            __AddPthFT(FTRecPtr,DirInfo.Name);
            FindNext(DirInfo);
            Inc(FileCount);
         until(DosError<>0) or(FTRecPtr^._LastFTErr<>_OK);

Str(FileCount,FileCountStr);

if FTRecPtr^._LastFTErr<>_OK then
            Send_to_Modem('Warning: Not all files are being transferred due to mem
         Send_to_Modem(FileCountStr+' files are being transferred...'#13#10);

if Kermit_Protocol then
            Send_to_Modem('Sending... You have 50 seconds to start receiving.  '+
                      'Use Kermit protocol.'#13#10)
```

```
              else Send_to_Modem('Sending... You have 30 seconds to start receiving.
                            'Use YMODEM (batch) protocol.'#13#10);

Delay(500);

display_message('','File transfer through the modem in progress.');

Text_to_Send:='';

CommErrCode:=__IFlshAl(Modem_Port);
       end;
    end;
    {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
    procedure RemoteObj.Interpret_Command(command:Char;var current_menu:menu);
    var
       SizeStr
(*-           Text_to_Send,
                    Extra_Text_to_Send-*):String;

(*-           Past_data_length,
          Terminal_Model_number,
          code,i              :integer; -*)
          i : integer;
(*-           NumRecordsFile,
          NumRecordsOldFile,
          NumRecordsRequested :longint; -*)

{       Old_op_file          :text;}
       (*-          ReadTerm             :boolean;-*)
    begin
       with Data do
          case command of
             #13,'H':begin
                    Send_to_Modem('D - Download data (Ymodem or Kermit file transf
                    Send_to_Modem('G - Goodbye'#13#10);
                    Send_to_Modem('L - List files'#13#10);
                    {       Send_to_Modem('P - Past data screen dump'#13#10);}
                    Send_to_Modem('V - View graphic screens using Tektronix termin
                  end;
             'G':begin
                    Send_to_Modem(#13#10#13#10#13#10'Thank You for using the Bio-Senso
                    Delay(500);
                    CommErrCode:=__HangUPMC(ModemPtr);
                    Delay(500);
                    Reset_Port_Baud_Rate;
                    CommErrCode:=__InitMC(ModemPtr,True,RespCode);
                    CommErrCode:=__IFlshAl(Modem_Port); {Clean up input buffer}
                    Modem_In:='';
                    Command_state:=Password_Query;
                  end;
             'D':begin
                    Send_to_Modem('Type the filename to download or wildcard: ');
                    Command_state:=File_query;
                  end;
             'M':begin
                    Str(MemAvail,Text_to_Send);
                    Send_to_Modem('Memavail='+Text_to_Send);
                    Str(MaxAvail,Text_to_Send);
```

```
                    Send_to_Modem('  Maxavail='+Text_to_Send);
                    Str(DosError,Text_to_Send);
                    Send_to_Modem('  DosError='+Text_to_Send);
                    Str(InOutRes,Text_to_Send);
                    Send_to_Modem('  InOutRes='+Text_to_Send+Remote_prompt);
                end;
            'L':begin
                    FindFirst('*.bmi',AnyFile,DirInfo);
                    Send_to_Modem('The following data file(s) are available for downlo
                    FileCount:=0;
                    Text_to_Send:='';
                    if(DosError=0)then
                       repeat
                          Str(DirInfo.Size:7,SizeStr);
                          with DirInfo do
                             begin {next line added to align filenames on remote screen - 5/7
                                while Length(Name)<12 do Name:=' '+Name;
                                {}
                                Text_to_Send:=Text_to_Send+Name+SizeStr+'       ';
                             end;
                          if Length(Text_to_Send)>60 then
                             begin
                                Send_to_Modem(Text_to_Send+#13#10);
                                Text_to_Send:='';
                             end;
                          FindNext(DirInfo);
                          Inc(FileCount);
                       until(DosError<>0);
                    Send_to_Modem(Text_to_Send+#13#10);
                    Str(FileCount,FileCountStr);
                    Send_to_Modem(FileCountStr+' files'#13#10);
                    Diskinfo(@Text_to_Send,1);
                    Send_to_Modem(Text_to_Send+Remote_prompt);
                end;
(******************* DISABLED (Modification and debugging necessary) **********
            'P': begin                    {Dump past data over the modem}
                    FindFirst(current_menu.Period_Name^+'.bmi',AnyFile,DirInfo);
                    if DosError=0 then
                       begin
                       NumRecordsFile:=(DirInfo.Size-current_menu.HeaderSize) div bio_line
                       Send_to_Modem('How many minutes of data? : ');
                       Val(Read_Modem_String,Past_data_length,code);
                       if code=0 then
                          begin
                          NumRecordsRequested:= Past_data_length
                                     div setup_data.bio.assessment_interval.act
                          with current_menu do
                             begin
                             if NumRecordsRequested>NumRecordsFile then
                                begin
                                FindFirst(Old_Period_Name+'.bmi',AnyFile,DirInfo);
                                if DosError=0 then
                                   if DirInfo.Size>HeaderSize then
                                       begin
                                       Assign(OldBiofile,DirInfo.Name);
                                       NumRecordsOldFile:=(DirInfo.Size-HeaderSize) div b
                                       Reset(OldBioFile);
                                       for i:=1 to NumRecordsOldFile+NumHeaderLines-
```

```
                                    (NumRecordsRequested-NumRecordsFile) do
                                    Readln(OldBiofile);
                          for i:=1 to NumRecordsRequested-NumRecordsFile do
                              begin
                                  Readln(OldBiofile,Text_to_Send,Extra_text_to_S
                                  Send_to_Modem(Copy(Text_to_Send,1,80)+#13#10);
                                  {Send_to_Modem(Copy(Extra_text_to_Send,1,80)+#
                              end;
                          NumRecordsRequested:=NumRecordsFile;
                          Close(OldBiofile);
                          end
                          else if NumRecordsFile>0 then
                                  Send_to_Modem('Incomplete data available'#
                                  else
                        else Send_to_Modem('Previous data file not found'#13#
                  end;
               if NumRecordsFile>0 then
                  begin
                  Reset(Biofile);
                  for i:=1 to NumRecordsFile-NumRecordsRequested+NumHeader
                      if not Eof(Biofile) then Readln(Biofile);
                  if Eof(Biofile) then
                      Send_to_Modem('Incomplete data available'#13#10)
                      else
                      for i:=1 to NumRecordsRequested do
                          if not Eof(Biofile) then
                              begin
                              Readln(Biofile,Text_to_Send,Extra_text_to_Send
                              Send_to_Modem(Copy(Text_to_Send,1,80)+#13#10);
                              {Send_to_Modem(Copy(Extra_text_to_Send,1,80)+#
                              end;
                  Close(Biofile);
                  end
                  else Send_to_Modem('No data available yet');
               end; {current menu}
             end {code=0}
             else Send_To_Modem('Illegal characters.  Type only digits.');
          end {DosError}
          else Send_to_Modem(#7'Error.  Data file not found.');
       Send_to_Modem(Remote_Prompt);
       end;
*****************************************************************)
       'V':Initialize_Graphmode(current_menu.Logo_polygon); {Set graph mode} else Send_to_Modem('Command not recognized'+Remote_prompt);
       end;                              {case}
  end;
  {ŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪŪ}
  procedure RemoteObj.Command_Handler(var current_menu:menu);
  (*-var ReadTerm:boolean; -*)
  begin                                 {read input queue}
    with Data do
      begin CommErrCode:=__RdChAl(Modem_Port,Chdata,Modem_In_Qsize,PortStatus);
        if(CommErrCode<>_OK) or(Chdata=#0)then Exit;
        Chdata:=Upcase(Chdata);
        if(Chdata in[#8,#127]) and(Length(Modem_In)>0)then
          Delete(Modem_In,Length(Modem_In),1);
```

```
case Chdata of
  #8:if Modem_In<>'' then Send_to_Modem(#8);
  #127:if Modem_In<>'' then Send_to_Modem(#8#32#8);
end;
if Chdata in[#13,#27,#33..#90,#97..#122]then
   case Command_state of
      Tek_mode:if Chdata=#27 then
                  begin
                     CommErrCode:=__RdTrmA2(Modem_Port,1,'[', @Chdata,9,nil,
                                       NumRead,Modem_In_Qsize,PortStatu
                     if ReadTerm then
                        begin
                           CommErrCode:=__WaitChA1(Modem_Port,9,nil); {wait fo
                           CommErrCode:=__RdChA1(Modem_Port,Chdata,Modem_In_Qs
                           case Chdata of
                              'A':key:=Uarr;
                              'B':key:=Darr;
                              'C':key:=Rarr;
                              'D':key:=Larr;
                           end;
                        end
                     else Exit_Graphmode;
                     CommErrCode:=0;
                  end
               else key:=Chdata; {direct control through remote keyboard}

Password_Query:if Chdata=#13 then
                        begin
                           Modem_In:=Modem_In+';';
                           Get_Password_Response(current_menu);
                        end
                     else
                        begin
                           Modem_In:=Modem_In+Chdata;
                           Send_to_Modem('.');
                        end;
      ANSI_mode:begin
                  Send_to_Modem(Chdata);
                  Modem_In:=Modem_In+Chdata;
                  if Chdata=#13 then
                     begin
                        Send_to_Modem(#10);
                        Interpret_Command(Modem_In[1],current_menu);
                        Modem_In:='';
                     end;

end;
      File_query:begin
                  Send_to_Modem(Chdata);
                  Modem_In:=Modem_In+Chdata;
                  if Chdata=#13 then
                     begin
                        Send_to_Modem(#10);
                        Check_Files_for_transfer(Modem_In);
                        Modem_In:='';
                        if Command_state = Erase_files_Query then
                           begin
                              Send_to_Modem(#13#10'Erase files after transfe
                              Command_state:=Erase_files_query;
                           end;
```

```
                                end;
                        end;
        Erase_files_query:begin
                                Send_to_Modem(Chdata);
                                Modem_In:=Modem_In+Chdata;
                                if Chdata=#13 then
                                  begin
                                    Send_to_Modem(#10);
                                    Erase_after_transfer:=Modem_In[1]='Y';
                                    Modem_In:='';
                                    Send_to_Modem(#13#10'(Y)modem or (K)ermit fi
                                    Command_state:=FT_protocol_query;
                                  end;
                            end;
        FT_protocol_query:begin
                                Send_to_Modem(Chdata);
                                Modem_In:=Modem_In+Chdata;
                                if Chdata=#13 then
                                  begin
                                    Send_to_Modem(#10);
                                    Kermit_Protocol:=Modem_In[1]='K';
                                    Initialize_File_Transfer(Modem_In);
                                    Command_state:=Sending_Files;
                                    Modem_In:='';
                                  end;
                            end;
        end;                    {case}
        if Length(Modem_In)>80 then Modem_In:='';
      end;                      {with}
end;                            {remote command handler}
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.Handler(var current_menu:menu;
                                difference : word;
                                sampling_speed : real);
var
  dummy : boolean;
  s1 : string;
begin
with Data do
    case Command_state of
    Sending_files : begin {begin file transfer handler}
                        { current data file is not erased after transfer in
                    if HiMSR in [0,$F] then
                      begin
                      Lost_Carrier_File_Transfer_Cleanup(current_menu.Period
                      Command_state:=Modem_off;
                      Exit;
                      end;

if DCDHigh then
                      Normal_file_transfer(current_menu.Period_name) {modem
                    else
                      Lost_Carrier_File_Transfer_Cleanup(current_menu.Period if Text_to_Send<>'' then
                      begin
                      display_message('',Text_to_Send);
                      Send_to_Modem(Text_to_Send+Remote_prompt);
                      Text_to_Send:='';
                      end;
```

```
                            end;    {end file transfer handler}
   modem_off     : if ((HiMSR and 2)=2) and ((hiMSR and 4)<>4) then
                      modem_setup;
   Catchup_Mode  : begin
                      Send_to_Modem('.');
                      { see if we have caught up }
                      if difference <=
                           trunc(sampling_speed)
                             * number_of_channels div 2 then begin
                           command_state := ANSI_Mode;
                           display_message('','Remote session in progress.');
                           dummy:=Printer_status(0,msg);
                           if current_menu.printer_on then
                              Send_to_Modem(#13#10#10#9#9'Data echoed to print
                           else
                              Send_to_Modem(#13#10#10#9#9'Data not echoed to p
                           Send_to_Modem(#10#13#9#9'Type H and press Enter ke
                        end;
                     end else
             begin
                { the 8 below is to check to make sure that CD is present
                  in the status register of the UART and the not 4 is because
                  of the unique feature of the Northgate to stay online when
                  CD is present and RI is not when the modem is not powered
                  up MAJ-PG 7/1/91 } if ((HiMSR and 8)=8) and ((hiMSR and 4)<>4) then
                     if(difference > trunc(sampling_speed)*number_of_channels) and (c
                       begin
                          Modem_in := ''; { kill off any pending input }
                          command_state := Catchup_mode;
                          send_to_modem(#13#10'The Bio-Sensor(R) Software is processi
                       end
                     else
                        Command_Handler(current_menu);
           if HiMSR in [0,$F] then
              begin
              Command_state:=Modem_off;
              display_message('','Modem is off.');
              end;
           end;
        end; {case}
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoteObj.ModemErrMsg;
begin
   with Data do
      begin
         ErrMsgA2(CommErrCode,msg,Text_to_Send);
         display_message('','Modem: '+msg);
         msg:='';Text_to_Send:='';
         CommErrCode:=0;
      end;
end;

end.
```

```
unit bmidisp;
{******************************************************************}
{                                                                    }
{ Copyright (c) Biological Monitoring, Inc. 1987, 1991               }
{                                                                    }
{******************************************************************}
interface
uses
 u_scout,
 disptool,
 graph,
 bmiconst,
 bmimenux
         ;
const    Bar_width=200 div number_of_fish;
         Bar_spacing=352 div number_of_fish;

{ handles the screen during an alarm.  It turns the screen red and prints
  out which type of alarm has ocurred }
procedure Alarm_Display(Alarm_Type:string);

{ displays the general status screen inculding the frequency and amplitudes }
procedure General_Display(last_freq:sample_history_vector;last_amplitude:real_ch
           var setup_data:Total_data;priority : boolean);

{ displays the frequency and amplitude and standard deviations for a given
  fish on the waveform display screens.  The data displayed is from
  the previous minute of monitoring }
procedure FS_display(frequency,amplitude,std_deviation:real;ch:integer);
procedure Plot_setup(channum:integer;Xlabel,Ylabel:string;status:integer;
              frequency,amplitude,std_deviation:real;var refresh:boolean;
              var current_menu:menu;message:string);

{ experimental procedure that graphically depicts which way the fish is
  facing }
procedure Plot_fish_direction(fish_direction:boolean);

{ refresh procedure that tells the latest amplitude and frequency }
procedure Plot_refresh( channum:integer;{fish_direction:boolean;}
                       frequency,amplitude,std_deviation:real);

{ plot routine that draws the "background" of the general status display }
procedure General_Setup(var refresh,first_cycle:boolean;message:string;warning:l
              var setup_data:Total_data;priority:boolean;last_freq:sam
              last_amplitude:real_channel_data;var current_menu:menu);

{ system for displaying what a given set of Function keys do during
  monitoring }
procedure Fkey_display(legend_text:string;key_color,legend_color,backcolor:word)

{ displays the first cycle message that appears while the system is first
  collecting data to be used in assessing the ventilatory patterns. }
procedure First_Cycle_message;
implementation uses
dgt_rtne,bmiinit,
oldview,bmikey,timedate,
crt;(*-,dos,tp4d16-*)
```

```
const
        msgframe:array [0..4] of Pointtype=( (x:0;y:Ymax-36),(x:0;y:Ymax-12),
                                             (x:501;y:Ymax-12),
                                             (x:501;y:Ymax-36),(x:0;y:Ymax-36));

var Channelgr        :string[12];

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Fkey_display(legend_text:string;key_color,legend_color,backcolor:word)
const    frame_height=12;
        keyframe:array [0..4] of Pointtype=( (x:0;y:0),(x:0;y:frame_height),
                                             (x:Xmax;y:frame_height),
                                             (x:Xmax;y:0),(x:0;y:0));
begin
View.save;
setviewport(0,Ymax-frame_height,Xmax,Ymax,ClipOn);
setlinestyle(SolidLn,0,NormWidth);
SettextJustify(LeftText,CenterText);
SetColor(White);
SetFillStyle(SolidFill,backcolor);
fillpoly(5,keyframe);
MoveTo(16,frame_height div 2+1);
repeat
      SetColor(key_color);
      while legend_text[1]<>'-' do
            begin
            OutText(legend_text[1]);
            Delete(legend_text,1,1);
            end;
      SetColor(legend_color);
      repeat
            OutText(legend_text[1]);
            Delete(legend_text,1,1);
      until legend_text[1]=#13;
      Delete(legend_text,1,1);
until legend_text[1]=#10;
View.restore;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure FS_display(frequency,amplitude,std_deviation:real;ch:integer); { frequ
var       sfreq,samplit,ssdev   :string[5];
begin
SetViewPort(180,10,500,80,ClipOn);
ClearViewPort;
SetColor(White);
SetTextStyle(DefaultFont,HorizDir,2);
SetTextJustify(LeftText,CenterText);
Str(frequency:4:2,sfreq);
Str(amplitude:4:2,samplit);
if PL.calibration[ch] then ssdev:='-----' else Str(std_deviation:5:3,ssdev);
{ display the data }
OutTextXY(0,20,'Amplitude = '+samplit+' V');
OutTextXY(0,40,'Frequency = '+sfreq+' Hz');
OutTextXY(0,60,'Std. dev. = '+ssdev+' Hz');
SetViewPort(Xo+2,Yo-Ysize+2,Xo+Xsize,Yo-2,ClipOn);
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Plot_setup(channum:integer;Xlabel,Ylabel:string;status:integer;
           frequency,amplitude,std_deviation:real;var refresh:boolean;
```

```
                     var current_menu:menu;message:string);  { set up for waveform dis
const     arwidx           =35;      { arrows for horizontal and vertical axis }
          arlenx           =15;
          arwidy           =55;
          arleny           =9;
          trianx           :array[1..4] of pointtype =
                           ((x:Xo+Xsize+2;y:Yo+Ysize div arwidx),
                           (x:Xo+Xsize+Xsize div arlenx;y:Yo),
                           (x:Xo+Xsize+2;y:Yo-Ysize div arwidx),
                           (x:Xo+Xsize+2;y:Yo+Ysize div arwidx));
          triany           :array[1..4] of pointtype =
                           ((x:Xo+Xsize div arwidy;y:Yo-Ysize),
                           (x:Xo;y:Yo-Ysize-Ysize div arleny),
                           (x:Xo-Xsize div arwidy;y:Yo-Ysize),
                           (x:Xo+Xsize div arwidy;y:Yo-Ysize));
begin
SetViewPort(0,0,Xmax,Ymax,ClipOn);
ClearViewPort;
SetColor(White);
Frame;
SetFillStyle(SolidFill,White);
SetLineStyle(SolidLn,0,ThickWidth);
                                  { horizontal axis arrow }
FillPoly(4,trianx);
MoveTo(Xo+Xsize+2,Yo);
LineTo(Xo,Yo);                          { horizontal axis }
LineTo(Xo,Yo-Ysize);                    { vetical axis }
                                        { veritical axis arrow }
FillPoly(4,triany);
MoveTo(Xo,Yo-Ysize div 2);
SetTextJustify(CenterText,CenterText);   { set text attributes }
SetTextStyle(DefaultFont,HorizDir,1);
if status=waveform_plot then
   begin
   Line(Xo-5,Yo-Ysize div 2,Xo,Yo-Ysize div 2);   { 0 tick mark }
   OutTextXY(Xo-15,Yo-Ysize div 2,'0');
   SetTextJustify(LeftText,TopText);   { set text attributes }
{  OutTextXY(16,50,'Fish direction:');}
   end;

{ display directions for operator
OutTextXY(200,Yo+70,'Press Enter key for all channels display,');
OutTextXY(200,Yo+85,'arrows to change channel or Esc to abort');   }

SetTextStyle(SansSerifFont,VertDir,4);
SetTextJustify(CenterText,CenterText);
OutTextXY(Xo div 3,Yo-Ysize div 2,Ylabel);   { description of vertical axis}
SetTextStyle(SansSerifFont,HorizDir,4);
OutTextXY(Xo+2*Xsize div 4-30,Yo+34,Xlabel);{ description of horizontal axis}
SetViewPort(4*Xmax div 5,5*Ymax div 6,Xmax-5,Ymax-5,ClipOn);
SetLineStyle(SolidLn,0,NormWidth);
current_menu.Fish_Logo;             { Drawing the fish logo }
SetLineStyle(SolidLn,0,ThickWidth);          { Thickness of the plot}
SetViewPort(5,5,179,40,ClipOn);
Str(channum,channelgr);
ClearViewPort;
SetTextJustify(LeftText,CenterText);
OutTextXY(5,15,'Fish No.'+Channelgr);
FS_display(frequency,amplitude,std_deviation,channum);
current_menu.oldrtm:=100;
```

```
Time_update(@current_menu,0);
Date_update(@current_menu,0);
SetTextStyle(DefaultFont,HorizDir,1);
display_message(message,'');
{Fkey_display;}
SetFillStyle(SolidFill,Blue);
SetViewPort(Xo+2,Yo-Ysize+2,Xo+Xsize,Yo-2,ClipOn);
SetColor(Blue);
 end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Plot_fish_direction(fish_direction:boolean);
var msg:char;
begin
View.save;
if fish_direction then msg:='<' else msg:='>';
SetViewPort(136,50,144,58,ClipOn);
ClearViewPort;
SetColor(White);
SetTextStyle(DefaultFont,Horizdir,1);
SetTextJustify(CenterText,CenterText);
OutTextXY(4,4,msg);
View.Restore;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Plot_refresh (channum:integer;{fish_direction:boolean;}
                        frequency,amplitude,std_deviation:real);
begin
View.save;
Str(channum,channelgr);
SetTextJustify(LeftText,CenterText);
SetViewPort(5,5,179,40,ClipOn);
ClearViewPort;
SetTextStyle(SansSerifFont,HorizDir,4);
SetColor(White);
OutTextXY(5,15,'Fish No.'+Channelgr);
FS_display(frequency,amplitude,std_deviation,channum);
View.restore;
{Plot_fish_direction(fish_direction);}
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Alarm_Display(Alarm_Type:string); { Display the alarm }
begin
if ScreenSavedGLB then
   begin
    restorescreen;
    LastKeypressGLB := timernow; { simulate the keypress to turn on screen }
   end;
SetBkColor(Red);
Display_message(Alarm_type+' alarm occured at '+timegr,'Collecting a water sampl
Sound(300);
Delay(100);
Nosound;
Display_message('','A water sample has been collected');
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure ShadedBar3D(x1,y1,x2,y2,depth:integer);
var     BarBody          :array [1..7] of PointType;
        BarSide          :array [1..5] of PointType;
begin
```

```
BarBody[1].x:=x1;
BarBody[6].x:=x1;
BarBody[7].x:=x1;
BarBody[1].y:=y1;
BarBody[2].y:=y1;
BarBody[7].y:=y1;
BarBody[2].x:=x2;
BarBody[3].x:=x2;
BarBody[4].x:=x2+10;
BarBody[5].x:=x1+10;
BarBody[3].y:=y2;
BarBody[6].y:=y2;
BarBody[4].y:=y2-10;
BarBody[5].y:=y2-10;
BarSide[1].x:=x2;
BarSide[1].y:=y1;
BarSide[2].x:=x2+10;
BarSide[2].y:=y1-10;
BarSide[3].x:=x2+10;
BarSide[3].y:=y2-10;
BarSide[4].x:=x2;
BarSide[4].y:=y2;
BarSide[5].x:=x2;
BarSide[5].y:=y1;
DrawPoly(7,BarBody);
DrawPoly(5,BarSide);
FillPoly(5,BarSide);
SetFillStyle(SolidFill,GetColor+8);
FillPoly(7,BarBody);
Line(x1,y2,x2,y2);
SetFillStyle(SolidFill,GetColor);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure General_Display(last_freq:sample_history_vector;last_amplitude:real_ch
         var setup_data:Total_data;priority:boolean);

var      k,Ybot,Ytop,Height,Barmax,idisp :integer;
         barfreq                          :real;
         stdata                           :string[5];

begin
SetTextJustify(CenterText,CenterText);
Ybot:=Y17Y20;              {frequency display}
Ytop:=Ymax div 2;
Height:=Ybot-Ytop;
Barmax:=4*Height div 5;
SetViewPort(Xmax div 5,Ytop,3*Xmax div 4-3,Ybot,ClipOn);
ClearViewPort;
SetColor(LightGreen);
SetTextStyle(DefaultFont,Horizdir,1);
for k:=0 to number_of_fish-1 do
if setup_data.assignment[k]<2 then       {10 second interval}
   begin                  {frequency bar}
   barfreq:=last_freq[k]/(2.0*acquisition_period);
   idisp:=round(Height*barfreq/setup_data.misc.max_disp_frequency.actual*0.8);
   if idisp>Barmax then idisp:=Barmax;
   if idisp<0 then idisp:=0;
   if warning[k] then
             begin            {yellow bar}
             SetFillStyle(SolidFill,Brown);
```

```
              SetColor(Brown);
            end                  {yellow bar}
          else
            if PL.Calibration[k] then
              begin
                SetFillStyle(SolidFill,LightGray);
                SetColor(LightGray);
              end
            else
              begin
                { green bar }
                SetFillStyle(SolidFill,Green);
                SetColor(Green);
                { green bar }
              end;
    ShadedBar3D(k*Bar_spacing,Height,k*Bar_spacing+Bar_width,
         Height-idisp,10);
    Str(Barfreq:3:1,stdata);
    SetColor(White);
    OutTextXY(k*Bar_spacing+15,Height-idisp-20,stdata);
  end;                                {frequency bar}

Ybot:=Ymax div 2;     {amplitude display}
Ytop:=Y10+24;
SetViewPort(Xmax div 5,Ytop,3*Xmax div 4-3,Ybot,ClipOn);
Height:=Ybot-Ytop;
Barmax:=4*Height div 5;
ClearViewPort;
SetTextStyle(DefaultFont,Horizdir,1);

for k:=0 to number_of_fish-1 do
 if setup_data.assignment[k]<2 then
    begin                            {amplitude bar}
    Str(last_amplitude[k]:3:1,stdata);
    idisp:=round(Height*last_amplitude[k]/5*0.8);
    if idisp>Barmax then idisp:=Barmax;
    if warning[k] then
              begin             {yellow bar}
              SetFillStyle(SolidFill,Brown);
              SetColor(Brown);
              end               {yellow bar}
          else
            if PL.Calibration[k] then
              begin
                SetFillStyle(SolidFill,LightGray);
                SetColor(LightGray);
              end
            else
              begin
                { green bar }
                SetFillStyle(SolidFill,Green);
                SetColor(Green);
                { green bar }
              end;
    ShadedBar3D(k*Bar_spacing,Height,k*Bar_spacing+Bar_width,
         Height-idisp,10);

SetColor(White);
    OutTextXY(k*Bar_spacing+15,Height-idisp-20,stdata);
    end;
```

```
Water_display(setup_data,priority);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure First_Cycle_message;
begin
SetViewPort(200,200,440,300,ClipOn);
SetTextJustify(CenterText,CenterText);
OutTextXY(110,50,'Collecting first sample');
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure General_Setup(var refresh,first_cycle:boolean;message:string;warning:l
                        var setup_data:Total_data;priority:boolean;last_freq:sam
                        last_amplitude:real_channel_data;var current_menu:menu);
var       is,j,xpt,ypt       :integer;
          sis                :string[2];

begin
if refresh then
   begin
   xpt:=GetX;ypt:=GetY;
   refresh:=false;
   SetColor(White);
   SetLineStyle(SolidLn,0,NormWidth);
   Title('GENERAL STATUS',2);

{ Stop drawing the fish logo in psuedo 3d for faster performance for j:=1 to 3 do current_menu.Logo_polygon.color[j]:=LightGray;
   SetColor(LightGray);
   for is:= 25 downto 22 do
       begin
       SetViewPort(is,4,150,100,ClipOn);
       current_menu.Fish_Logo;
       end;
}
   for j:=1 to 3 do current_menu.Logo_polygon.color[j]:=White;
   SetColor(White);
   current_menu.Fish_Logo;
   SetViewPort(0,0,Xmax,Ymax,ClipOn);
   SetTextStyle(TriplexFont,HorizDir,4);
   OutText3DBoldXY(60,120,'Amp.',LightGray,3);
   OutText3DBoldXY(60,160,'[ V ]',LightGray,3);
   OutText3DBoldXY(60,280,'Freq.',LightGray,3);
   OutText3DBoldXY(60,320,'[ Hz ]',LightGray,3);
   OutText3DBoldXY(65,420,'Fish No.',LightGray,3);
   for is:=0 to number_of_fish-1 do
       begin
       Str(is,sis);
       OutText3DBoldXY(is*Bar_Spacing+140,420,sis,LightGray,3);
       end;
   SetTextStyle(DefaultFont,HorizDir,1);
{  Fkey_display;}
   SetFillStyle(SolidFill,Green);
   current_menu.oldrtm:=100;
   Time_update(@current_menu,0);
   Date_update(@current_menu,0);
   View.save;
   SetViewPort(130,60,620,90,ClipOn);
   SetColor(White);
```

```
    SetTextStyle(DefaultFont,HorizDir,1);
    display_message(message,'');
    View.restore;
    if first_cycle then begin
                First_Cycle_message;
                Water_Display(setup_data,priority);
                end
            else General_Display(last_freq,last_amplitude,warning,setup_data,prior
    end;

end;

end.unit bmifftx;
{********************************************************************}
{                                                                    }
{ Copyright (c) Biological Monitoring, Inc. 1987, 1990               }
{                                                                    }
{ This unit contains Fast Fourier Transformation algorithm for spectrum }
{ analysis                                                           }
{                                                                    }
{********************************************************************}
interface
uses bmid16x;

{
 Handles the DFFT for use in the spectral analysis sub-system present
 in the 6012X
}
procedure Four(var target:complex_vector_type;nn:word;isign:integer);

implementation procedure Four(var target:complex_vector_type;nn:word;isign:integer);
var     n,mmax,m,j,istep,i:word;
        wtemp,wr,wpr,wpi,wi,theta:double;
        tempr,tempi:single;

procedure swap_complex(var a,b:complex);
var c:complex;
begin
c:=a;a:=b;b:=c;
end;

begin
j:=1;
for i:=0 to nn-1 do
    begin
    if j>i then swap_complex(target[j],target[i]);
    m:=nn shr 1;
    while (m>=2) and (j>=m) do
                begin
                Dec(j,m);
                m:=m shr 1;
                end;
    Inc(j,m);
    end;

mmax:=1;
while nn>mmax do
                begin
```

```
                    istep:=2*mmax;
                    theta:=2*pi/mmax;
                    wtemp:=sin(0.5*theta);
                    wpr:=-2.0*sqr(wtemp);
                    wpi:=sin(theta);
                    wr:=1.0;
                    wi:=0.0;
                    for m:=0 to mmax-1 do
                        begin
                        i:=m;
                        while i<nn do
                                begin
                                j:=i+mmax;
                                tempr:=wr*target[j].x-wi*target[j].y;
                                tempi:=wr*target[j].y+wi*target[j].x;
                                target[j].x:=target[i].x-tempr;
                                target[j].y:=target[i].y-tempi;
                                target[i].x:=target[i].x+tempr;
                                target[i].y:=target[i].y+tempi;
                                Inc(i,istep);
                                end;
                        wtemp:=wr;
                        wr:=wtemp*wpr-wi*wpi+wr;
                        wi:=wi*wpr+wtemp*wpi+wi;
                        end;
                    mmax:=istep;
                    end;

end;
end.
unit bmimenux;
{*******************************************************************}
{                                                                   }
{ Copyright (c) Biological Monitoring, Inc. 1987, 1990              }
{                                                                   }
{ This unit contains generic menu object.  It is the main menuing system
  used in all of the setup screens.

The draw procedure is the handler that monitors the mouse, the keyboard
  and the dispatching of sub procedures that perform actions for the user
  such as getting parameter settings, passwords, and remote location
  phone numbers.
                                                                    }
{*******************************************************************}
interface uses
 das16,
 graph;
const
      max_polygons=6;
      max_menu=14;

type  polygon_type      =array[1..15000] of PointType;
      polygon_set       = record
                        color:array[1..max_polygons] of integer;
                        count:array[1..max_polygons] of word;
                        points:array[1..5] of ^polygon_type;
                        setnum:word;
```

```
                                    end;
            data_types   =(intgr,bool,float,data_range,calib_range,
                          story,dat,tim,two_chars,NoDataType);
       menu_element = record
                          description:string[60];
                          data_type:data_types;
                          data_ptr:pointer;
                          task:procedure(current_menu:pointer;item:word);
                        end;
       local_menu = object  bfont,bdirection,bcharsize,bmargin,oldrtm,
                            dataposition,ypos,xsize,ysize,margin,ystep:word;
                            redraw:boolean;
                            data:array [0..Max_Menu] of menu_element;
                            Logo_polygon:polygon_set;
                            function Read_Metafile(metafile:string;var size:word):boole
                            procedure Fish_Logo;
                            procedure MouseChoice;
                            procedure Box(item:integer;color,field_width :integer);
                            procedure erase_Box(item:integer;color :integer);
                            procedure draw( xorigin,yorigin,
                                           backcolor,forecolor,linethick,
                                           fillpattern,linestyle,
                                           font,direction,charsize:word;
                                           linespacing:real;items:word;parent:pointer)

end;
       local_menu_ptr     =^local_menu;
       menu = object(local_menu)
                          Period_Name:string[12];
                          Old_Period_Name:string[12];
                          Biofile:text;
                          printer_output   :^text;{ used to redirect printer output }
                          ScoutDataLoc            :integer;
                          DateStr:string[10];
                          HeaderSize,
                          NumHeaderLines:word;
                          Alarm_flag,
                          Printer_on:boolean;
                          procedure EraseEmptyFiles;
                        end;
       menu_ptr = ^menu;

var data_changed       :boolean;
       procedure TextBox(x1,y1,x2,y2,Fore,Back,TextSize:integer;Str1 : string);
       procedure TextExit(reason:string);
       procedure Title(TitleText:string;Depth3D:integer);
       procedure Frame;
       (*-procedure OutTextBoldXY (x,y:integer;TextString:string);-*)
       (*-procedure OutTextExtraBoldXY(x,y:integer;TextString:string);-*)
       procedure OutText3DExtraBoldXY(x,y:integer;TextString:string;Color3D:word;Depth3
       procedure OutText3DBoldXY(x,y:integer;TextString:string;Color3D:word;Depth3D:int
       procedure edit(current_menu:pointer;item:word);
       procedure Display (current_menu:pointer;item:word);
       implementation uses crt,dos,bmiconst,mouse,bmikey,bmident,oldview;

procedure TextBox (x1,y1,x2,y2,Fore,Back,TextSize:integer;Str1 : string);
       var
          Box       : array[0..4] of pointtype;
```

```
begin
  View.save;
  SetViewPort (0,0,GetMaxX,GetMaxY,ClipOn);
  Box[0].x := x1;  Box[0].y := y1;
  Box[1].x := x2;  Box[1].y := y1;
  Box[2].x := x2;  Box[2].y := y2;
  Box[3].x := x1;  Box[3].y := y2;
  Box[4] := Box[0];
  SetFillStyle (SolidFill,Back);
  SetColor (Fore);
  FillPoly (SizeOf (Box) div SizeOf (PointType), Box);
  SetTextJustify (CenterText,CenterText);
  SetTextStyle (SansSerifFont,HorizDir,TextSize);
  OutTextXY ((x2-x1) div 2 + x1,(y2-y1) div 2 + y1,str1);
  View.restore;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure TextExit(reason:string);
begin
TextBackground(Red);TextColor(White);
Write(reason);
TextBackground(Black);TextColor(LightGray);
write(#13);
Halt(100);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Frame;
begin
SetLineStyle(SolidLn,0,NormWidth);
Rectangle(0,0,639,479);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure OutTextBoldXY(x,y:integer;TextString:string);
begin
OutTextXY(x,y,TextString);
OutTextXY(x,y+1,TextString);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure OutTextExtraBoldXY(x,y:integer;TextString:string);
begin
OutTextXY(x,y,TextString);
OutTextXY(x-1,y-1,TextString);
OutTextXY(x-1,y,TextString);
OutTextXY(x,y+1,TextString);
OutTextXY(x-1,y+1,TextString);
OutTextXY(x+1,y-1,TextString);
OutTextXY(x+1,y+1,TextString);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure OutText3DBoldXY(x,y:integer;TextString:string;Color3D:word;Depth3D:int
var CurrentColor    :word;
    par             :integer;
begin
CurrentColor:=GetColor;
SetColor(Color3D);
for par:=1 to Depth3D do
if par mod 2=0 then
    OutTextBoldXY(x+par,y-par,TextString);
```

```
SetColor(CurrentColor);
OutTextBoldXY(x,y,TextString);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure OutText3DExtraBoldXY(x,y:integer;TextString:string;Color3D:word;Depth3
var CurrentColor    :word;
    par             :integer;
begin
CurrentColor:=GetColor;
SetColor(Color3D);
for par:=1 to Depth3D do
OutTextExtraBoldXY(x+par,y-par,TextString);
SetColor(CurrentColor);
OutTextExtraBoldXY(x,y,TextString);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Title(TitleText:string;Depth3D:integer);
begin
SetViewPort(0,0,Xmax,Ymax,ClipOn);
SetTextStyle(TriplexFont,HorizDir,4);
ClearViewPort;
Frame;
SetTextJustify(CenterText,CenterText);
OutText3DBoldXY(Xcen,Y20,TitleText,LightGray,Depth3D);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Local_menu.Fish_Logo;
var    i    :word;
begin
SetFillStyle(SolidFill,GetColor);
with Logo_polygon do
     for i:=1 to setnum do
         begin
         SetFillStyle(SolidFill,color[i]);
         fillpoly(count[i],points[i]^);
         end;

end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure local_menu.MouseChoice;
const back :array[1..5] of pointtype =
           ((x:0;y:0),(x:210;y:0),(x:210;y:Y10),(x:0;y:Y10),(x:0;y:0));
begin
SetColor(White);
View.save;
SetLineStyle(SolidLn,0,NormWidth);
SetViewPort(5,9*Y10+3,11*Xmax div 14,Ymax-5,ClipOn);
SetTextStyle(DefaultFont,HorizDir,1);
SetTextJustify(CenterText,CenterText);
if mshown then
Mhide;
ClearViewPort;
OutTextXY(4*Xmax div 7,Y20,                    'Choose desired option with the');
OutTextXy(4*Xmax div 7,Y20+TextHeight('H'),'mouse or the arrow keys         ');

SetTextStyle(TriplexFont,HorizDir,4);
SetFillStyle(SolidFill,Cyan);
FillPoly(5,back);
OutTextXY(100,Y20,'Bio-Sensor');
```

```
SetTextStyle(DefaultFont,HorizDir,1);
Circle (190,14,7);
OutTextXY(190,15,'R');
SetViewPort(4*Xmax div 5,17*Y20+12,Xmax-5,Ymax-5,ClipOn);
Fish_Logo;
View.restore;
Mshow;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function DataValString (data_type : data_types; data_ptr : pointer) : string;
(*-type
   A2D    = array[1..2] of real;-*)
var
   S1,S2    : string;
   BoolPtr  : ^Boolean;
   StrPtr   : ^string;
(*-  A2D_Ptr  : ^A2D;-*)
   Realdata : ^Realdatatype;
   IntData  : ^IntDataType;
   W,X,Y,Z  : word;
begin
   case Data_type of Bool  : begin
                     BoolPtr := data_ptr;
                     if BoolPtr^ then S1 := 'YES' else S1 := 'NO';
                     DataValString := S1;
                   end;
           Float : begin
                     Realdata := data_ptr;
                     str (Realdata^.actual:1:2,S1);
                     DataValString := S1;
                   end;
           Intgr : begin
                     IntData := data_ptr;
                     str (IntData^.actual,S1);
                     DataValString := S1;
                   end;

Calib_range : DataValString := '';
   Data_range  : begin
                     RealData:= data_ptr;
                     str (RealData^.min:1:2,S1);
                     str (RealData^.max:1:2,S2);
                     DataValString := S1+' - '+S2;
                 end;
        story,
    two_chars : begin
                     StrPtr := data_ptr;
                     DataValString := StrPtr^;
                 end;
           dat : begin
                     GetDate (W,X,Y,Z);
                     str (x,S1);
                     if x < 10 then S1 := '0'+S1;
                     str (y,S2);
                     if y < 10 then S2 := '0'+S2;
                     S1 := S1 + '/'+S2;
                     str (W,S2);
                     DataValString := S1+'/'+S2;
```

```
                    end;
         tim : begin
                    GetTime (W,X,Y,Z);
                    str (w,S1);
                    if W < 10 then S1 := '0'+S1;
                    str (x,S2);
                    if x < 10 then S2 := '0'+S2;
                    DataValString := S1 + ':'+S2;
               end;

NoDataType : DataValString := '';
  end;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure local_menu.Box(item:integer;color,field_width : integer);
var       BlueBox:array[0..4] of pointtype;
          l : integer;

begin
if (item=0) then exit;
SetViewPort(dataposition,ypos+(item-1)*ystep+1,Xmax-10,
            ypos+item*ystep-1+3,ClipOn);
SetTextStyle(bfont,bdirection,bcharsize);
SetTextJustify(LeftText,CenterText);
with self.data[item] do
    l:=Length(DataValString(data_type,data_ptr));
if field_width>l then l:=field_width;

ClearViewPort;
BlueBox[0].x:=0;
BlueBox[0].y:=0;
BlueBox[1].x:=0;
BlueBox[1].y:=ystep ; { was -2 }
if self.data[item].data_type<>Bool then
    BlueBox[2].x:=l*textwidth('H')+2*bmargin
else
    BlueBox[2].x := 0;

BlueBox[2].y:=ystep ; { was -2 }
BlueBox[3].x:=BlueBox[2].x;
BlueBox[3].y:=0;
BlueBox[4]:=BlueBox[0];
SetFillStyle(SolidFill,color);
if self.data[item].data_type<>Bool then
    FillPoly(5,BlueBox);
MoveTo(margin,Ystep div 2);

MoveTo(2*bmargin,ystep div 2);
end;

procedure local_menu.Erase_Box(item:integer;color : integer);
begin
if item=0 then exit;
View.save;
SetViewPort( dataposition,ypos+(item-1)*ystep+1,Xmax-10,
             ypos+item*ystep-1+3,ClipOn);
ClearViewPort;
setcolor(color);
```

```
bar(0,0,Xmax-10-dataposition,ystep);
View.restore;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function local_menu.Read_Metafile(metafile:string;var size:word):boolean;

type intbuftype = array[1..2048] of word;
     (*-vdctype=array[1..4] of word;-*)

var  FromF:file;
     Class,
     Identifier,
     Meta_Header,
     length,
     (*-max_length,-*)
     NumRead,
     flag,
     j,
     fillcolor:word;
     curpos:longint;
     intbuf:^intbuftype;
     i      :word;

begin
Logo_polygon.setnum:=0;
Assign(FromF,metafile);
Reset(FromF,1);
i:=IOResult;
if i=0 then
begin
while not Eof(FromF) do
      begin
      Curpos:=FilePos(FromF);
      BlockRead(FromF,Meta_Header,Sizeof(Meta_Header),NumRead);
      Meta_Header:=swap(Meta_Header);
      Class:=Meta_Header shr 12;
      Identifier:=(Meta_Header shr 5) mod 128;
      Length:=Meta_Header mod 32;

if length=31 then
              begin
              BlockRead(FromF,length,sizeof(length),NumRead);
              length:=swap(length);
              flag:=length shr 15;
              length:=length mod 32768;
                end;

if (class=4) and (identifier=7) then
         with Logo_polygon do
              begin
              Inc(setnum);
              if maxavail<length then begin
                 Closegraph;
                 TextExit('Out of memory.');
                 end;
              GetMem(points[setnum],length);
              if maxavail<sizeof(intbuf^) then begin
                 Closegraph;
                 TextExit('Out of memory.');
```

```
                    end;
                New(intbuf);
                BlockRead(FromF,intbuf^,length,NumRead);
                count[setnum]:=length div 4;
                for i:=1 to length div 2 do intbuf^[i]:=swap(intbuf^[i]);
                color[setnum]:=fillcolor;
                for i:=1 to count[setnum] do
                    if size=0 then
                        begin
                        points[setnum]^[i].x:=intbuf^[2*i-1] div 320;
                        points[setnum]^[i].y:=60-integer(intbuf^[2*i]) div 320;
                        end
                    else
                    begin
                        points[setnum]^[i].x:=intbuf^[2*i-1] div 250+30;
                        points[setnum]^[i].y:=100-integer(intbuf^[2*i]) div 250;
                    end;
                Dispose(intbuf);
                end
            else
                if (class=5) and (identifier=23) then begin
                    BlockRead(FromF,j,length,NumRead);
                    fillcolor:=(14+swap(j)) mod 16;
                    end
                else
                    begin
                    New(intbuf);
                    BlockRead(FromF,intbuf^,Length,NumRead);
                    Dispose(intbuf);
                    end;
        end;
Close(FromF);
Read_Metafile:=TRUE;
end
else Read_Metafile:=FALSE;
size:=i;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure local_menu.draw( xorigin,yorigin,
                    backcolor,forecolor,linethick,
                    fillpattern,linestyle,
                    font,direction,charsize:word;
                    linespacing:real;items:word;parent:pointer);

var j,i(*-,code-*):integer;
    back,tag              : array[1..5] of PointType;
    mbt,
    mx,
    my,
    (*-rtm,-*)
(*-    length,-*)
    current_length : word;
    Key                   : char;
    Index,
    LastPick
    (*-FColor-*)          : byte;
    Tag_margin            : integer;
```

```
        S1                              : string;
    cx,
    x1,y1,tw : word;
begin
tag_margin:=0;
LastPick := 1;
xsize:=0;
bfont:=font;bdirection:=direction;bcharsize:=charsize;
ypos:=yorigin;
SetTextStyle(font,direction,charsize);
SetTextJustify(LeftText,CenterText);
margin:=TextWidth('H') div 2;
bmargin:=margin;

for i:=1 to items do
            begin
            current_length:=TextWidth(data[i].description)+2*margin;
            if xsize<current_length then xsize:=current_length;
            end;

ystep:=Round(linespacing*TextHeight('H'));

ysize:=ystep*items;

back[1].x:=0;
back[1].y:=0;
back[2].x:=xsize;
back[2].y:=0;
back[3].x:=xsize;
back[3].y:=ysize;
back[4].x:=0;
back[4].y:=ysize;
back[5]:=back[1];

Logo_polygon:=local_menu(parent^).Logo_polygon;
        dataposition:=xorigin+xsize+margin;
redraw:=TRUE;
repeat
      if redraw then
                begin
                ClearDevice;
                Title(data[0].description,2);
                mvlimit(yorigin,yorigin+ysize-1);
                mhlimit(xorigin,xorigin+xsize-1);
                SetViewPort(xorigin,yorigin,Xmax-5,yorigin+ysize,ClipOn);
                SetFillStyle(Fillpattern,forecolor);
                SetLineStyle(linestyle,0,linethick);
                FillPoly(5,back);
                Line(0,0,xsize,0);
                SetTextStyle(font,direction,charsize);
                SetTextJustify(Lefttext,CenterText);
                data[items+1].task(nil,0); {paint extra items on screen}
                View.save;
                for i:= 1 to items do
                    begin
                    View.restore;
                    Line(0,i*ystep,xsize,i*ystep);
                    OutTextXY(margin,i*ystep-ystep div 2,data[i].description);
{                       S1 := '';}
                    S1 := DataValString (data[i].data_type,data[i].data_ptr);
```

```
              { patch applied to make the writing of text in the same
                place each time MAJ 6/20/91 }

SetViewPort( dataposition,ypos+(i-1)*ystep+1,Xmax-10,
                 ypos+i*ystep-1,ClipOn);
              SetTextJustify(LeftText,CenterText);
              {OutTextXY(margin,ystep div 2,S1);}
              cx := margin;
              for j := 1 to length(s1) do
                 begin
                    outtextxy(cx,ystep div 2,s1[j]);
                    cx := cx + textwidth('H');
                 end;

end;
        end;
MouseChoice;
dataposition:=xorigin+xsize+margin;
SetTextStyle(font,direction,charsize);
SetTextJustify(Lefttext,CenterText);
MPut(xsize+margin+3,yorigin + abs (LastPick * ystep) - ystep div 2);
mshow;
Key := #0;
repeat
  SetViewPort(dataposition,yorigin+ystep,Xmax-5,yorigin+2*ystep,ClipOn);
  data[0].task(@self,1); {clock}
  Key := GetKey;
  mpos(mbt,mx,my);
  Index:=1+(my-yorigin) div ystep;
  if (lastpick<>Index) or redraw then
     begin
     redraw:=FALSE;
     if mshown then
     mhide;
     SetViewPort(xorigin,yorigin,Xmax-5,yorigin+ysize,ClipOn);
     SetFillStyle(SolidFill,forecolor);
     tag[1].x:=tag_margin;
     tag[1].y:=(LastPick-1)*ystep+tag_margin;
     tag[2].x:=xsize-tag_margin;
     tag[2].y:=(LastPick-1)*ystep+tag_margin;
     tag[3].x:=xsize-tag_margin;
     tag[3].y:=LastPick*ystep-tag_margin;
     tag[4].x:=tag_margin;
     tag[4].y:=LastPick*ystep-tag_margin;
     tag[5]:=tag[1];
     FillPoly(5,tag);
     SetTextJustify(Lefttext,CenterText);
     OutTextXY(margin,LastPick*ystep-ystep div 2,data[LastPick].descriptio SetFillStyle(SolidFill,56);
     tag[1].x:=tag_margin;
     tag[1].y:=(index-1)*ystep+tag_margin;
     tag[2].x:=xsize-tag_margin;
     tag[2].y:=(index-1)*ystep+tag_margin;
     tag[3].x:=xsize-tag_margin;
     tag[3].y:=index*ystep-tag_margin;
     tag[4].x:=tag_margin;
     tag[4].y:=index*ystep-tag_margin;
     tag[5]:=tag[1];
```

```
            FillPoly(5,tag);
            OutTextXY(margin,Index*ystep-ystep div 2,data[Index].description);
            Mshow;
{            View.restore;}
            lastpick:=index;
          end;
    {GoToMonitoring is set in Main, and is true only if the time
     difference between current time and last time written to recovery file
     is < 10 minutes.} if GoToMonitoring then
        begin
          Index := 5;
          LastPick := 5;
          Key := Enter;
        end;

if Key in [Enter,MEnter,Esc,MEsc,UArr,DArr] then
           begin
             case Key of
               Enter,
               MEnter : begin
                          redraw:=FALSE;
                          if mshown then
                          Mhide;
                          LastPick := Index;
                          with data[Index] do task(@self,Index);
                         end;
               Esc,
               MEsc   : begin
                          Redraw := false;
                          if mshown then
                          mhide;
                          with data[items] do task (@self,items);
                          Index:=items;
                         end;
               UArr   : begin
                          LastPick:=Index;
                          if Index > 1 then dec (Index) else Index := items;
                          MPut (xsize+margin+3,yorigin+(ystep*Index)-ystep div 2)
                         end;

DArr   : begin
                          LastPick:=Index;
                          if Index < items then inc (Index) else Index := 1;
                          MPut (xsize+margin+3,yorigin+(ystep*Index)-ystep div 2)
                         end;

end; {case}
          end;
     until Key in [Enter,MEnter,Esc,MEsc];
until Index >= items;
local_menu(parent^).redraw:=TRUE;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure menu.EraseEmptyFiles;
var DirInfo:SearchRec;
begin
```

```
FindFirst(Period_Name+'.bmi',Anyfile,DirInfo);
    if (DosError=0) and (DirInfo.Size=0) then Erase(Biofile); {Erase empty file}
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function RemoveSpaces (S : string) : string;
var
  Temp : string;
  i : byte;
begin
  Temp := '';
  for i := 1 to length (S) do
    if not (S[i] in[' ',#176]) then Temp := Temp +S[i];
  RemoveSpaces := Temp;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function NumbersOnlyString (S : string) : string;
var
  Temp : string;
  i : byte;
begin
  Temp := '';
  for i := 1 to length (S) do
    if (S[i] in['0'..'9','.','-']) then Temp := Temp +S[i];
  NumbersOnlyString := Temp;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function IsInteger(S : string) : boolean;
var
  Index : integer;
  flag : boolean;
begin
   flag :=true;
   for Index:=1 to length(s) do
     if not (S[Index] in ['0'..'9']) then
        flag := false;
   IsInteger:=flag;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure ParseRangeString (S : string; var R1,R2 : real);
var
  Temp : string;
  Err  : integer;
begin
  Temp := copy (S,1,pos('-',S)-1);
  Temp := RemoveSpaces (Temp);
  val (Temp,R1,Err);
  if Err <> 0 then R1 := 0;
  Temp := copy (S,pos('-',S)+1,length(S));
  Temp := RemoveSpaces (Temp);
  val (Temp,R2,Err);
  if Err <> 0 then R2 := 0;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RangeError;
(*-var
  F,B,i : word;-*)
begin
  SetBkColor (Red);
```

```
    write (#7);
    Repeat until KeyPressed;
    SetBkColor (Blue);
    NoSound;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function CheckRange (S : string; R1,R2 : real) : boolean;
const
    HiAlk = 2000.0;
    HiTem = 100.0;
    HiDO  = 18.0;
    HipH  = 14.0;
    HiCnd = 25000.0;
    HiTur = 500.0;
    HiNot = 1000000.0;
var
    Temp : boolean;
(*- S1   : string[2];
    i    : byte;-*)
begin
    Temp := false;
    if R1 < R2 then
    case S[1] of
        'A' : Temp := (R1 >= 0) and (R2 <= HiAlk);
        'T' : case S[2] of
                'e' : Temp := (R1 >= 0) and (R2 <= HiTem);
                'u' : Temp := (R1 >= 0) and (R2 <= HiTur);
              end;
        'D' : Temp := (R1 >= 0) and (R2 <= HiDO);
        'p' : Temp := (R1 >= 0) and (R2 <= HipH);
        'C' : Temp := (R1 >= 0) and (R2 <= HiCnd);
        'n' : Temp := (R1 >= 0) and (R2 <= HiNot);
    end;
    if not Temp then RangeError;
    CheckRange := Temp;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
procedure Edit (current_menu:pointer;item:word);
{$F-}
type
    A2D = array [1..2] of real;
var
    R1,R2    : real;
    Tmp      : array[1..2] of integer;
    A2D_Ptr  : ^A2D;
    CalData  : A2D;
    S1,S2,S3 : string;
(*- Key     : char;-*)
    I1,
    Err
(*-
    Index,
    XLoc,
    YLoc,
    TW,TH
    -*) : integer;
    B1,B2,
    Escd     : boolean;
```

```
(*-  Tag       : array[1..5] of PointType;-*)
(*-  LineInfo : LineSettingsType;-*)
  NewRealData: RealDataType;
  Realdata : ^Realdatatype;
  IntData  : ^IntDataType;
  local_menu:^menu;
begin
local_menu:=current_menu;

{
 moved this out of edit so that we can check for any data change
 regardless of what the user does so that the proper set of events
 occurrs MAJ 2/26/91 data_changed := false;
2}

View.save;
SetViewPort(5,9*Y10,11*Xmax div 14,Ymax-5,ClipOn);
ClearViewPort;
SetTextJustify(CenterText,CenterText);
OutTextXY(Xcen,Y20,'Type desired value and press the Enter key');
View.restore;
{local_menu^.Box(item,LightBlue);}
with local_menu^.data[item] do
   case data_type of
      Float       : begin
                      RealData:=data_ptr;
                      repeat
                        local_menu^.Box(item,lightblue,20);
                        GetString (20,1,DataValString(float,Realdata),S1,false,false
                        val (S1,R1,Err);
                        if not ((R1>=Realdata^.min) and (R1<=Realdata^.max)) or (err
                          write (#7);
                      until ((R1>=Realdata^.min) and (R1<=Realdata^.max)) and (err=0
                      if Err = 0 then
                         begin
                           if R1<>Realdata^.actual then
                               data_changed := true;
                           Realdata^.actual:=R1;
                           end;
                      end;

Intgr       : begin
                      IntData:=data_ptr;
                      repeat
                        local_menu^.Box(item,lightblue,20);
                        GetString (20,1,DataValString (intgr,IntData),S1,false,false
                        if IsInteger(S1) then
                            val (S1,I1,Err)
                        else
                            I1 := IntData^.min -1;

if not ((I1>=IntData^.min) and (I1<=IntData^.max)) then
                          Write (#7);
                      until ((I1>=IntData^.min) and (I1<=IntData^.max));
                      if Err = 0 then
                         begin
                           if I1<>IntData^.actual then
                               data_changed := true;
```

```
                        IntData^.actual:= I1;
                    end;
                end;
Bool        : begin
                local_menu^.Box(item,lightblue,0);
                GetYNResponse (description,B1,Escd);
                data_changed := true;
                boolean(data_ptr^) := B1;
            end;
Data_range  : begin
                local_menu^.Box(item,lightblue,20);
                RealData:= data_ptr;
                GetString (20,1,DataValString (data_range,RealData),S1,false,f
                ParseRangeString (S1,NewRealData.min,NewRealData.max);
                B1 := CheckRange (description,NewRealData.min,NewRealData.max)
                if B1 then
                    begin
                    str (NewRealData.min:1:2,S2);
                    str (NewRealData.max:1:2,S3);
                    S1 := S2+' - '+S3;
                    RealData^:=NewRealData;
                    data_changed := true;
                    end;
            end;
Calib_range : begin
                local_menu^.Box(item,lightblue,20);
                A2D_Ptr := data_ptr;
                S1 := '';
                GetString (20,1,S1,S3,false,false,false);
                S3 := NumbersOnlyString (S3);
                val (S3,R1,Err);
                if Err = 0 then
                begin
                   caldata[1] := R1;
                   d16.ains (number_of_fish-1+item,Tmp[1]);
                end;
                B1 := d16.err_code = 0;
                GetString (20,length (S3) + 4,S3+' - ',S1,false,false,false)
                S3 := copy (S1,pos('-',S1)+1, length(S1));
                S3 := NumbersOnlyString (S3);
                val (S3,R2,Err);
                if Err = 0 then
                begin
                   caldata[2] := R2;
                   d16.ains (number_of_fish-1+item,Tmp[2]);
                end;
                B2 := d16.err_code = 0;
                if Tmp[2] > 0 then
                B1 := (((1.0*Tmp[1])/(1.0*Tmp[2])>1.1) or
                        ((1.0*Tmp[1])/(1.0*Tmp[2])<0.9) and B1 and B2)
                 else B1 := FALSE;
                if not B1 then
                begin
                   write (#7);
                   Sound(200);
                   Delay(300);
                   NoSound;
                end
                else
                begin
```

```
                            A2D_ptr^[1]:=(caldata[2]-caldata[1])/(Tmp[2] - Tmp[1]);
                            A2D_ptr^[2]:=caldata[1]-Tmp[1]*A2D_ptr^[1];
                            data_changed := true;
                          end;
                        end;

Story,
two_chars            : begin
                          local_menu^.Box(item,lightblue,27);
                          if data_type = two_chars then
                            GetString (2,1,DataValString (story,data_ptr),S1,TRUE,false,
                          else
                            GetString (27,1,DataValString (story,data_ptr),S1,false,fals
                          if S1<>string(data_ptr^) then
                              data_changed := true;
                          string(data_ptr^):=S1;
                          end;
   end;
ClearViewPort;
with local_menu^ do with data[item] do
  begin
   SetViewPort( dataposition,ypos+(item-1)*ystep+1,Xmax-10,
              ypos+item*ystep-1+3,ClipOn);
   clearviewport;
   s1:=DataValString(data_type,data_ptr);
   SetTextJustify(LeftText,CenterText);
   OutTextXY(margin,ystep div 2,s1);
   end;

end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
procedure Display (current_menu:pointer;item:word);
var    local_menu :^menu;
       s1         :string;
       j : integer;
       cx : word;
begin
local_menu:=current_menu;

{View.save;
SetViewPort(5,9*Y10,11*Xmax div 14,Ymax-5,ClipOn);
ClearViewPort;
SetTextJustify(CenterText,CenterText);
OutTextXY(Xcen,Y20,'Type desired value and press the Enter key');
View.restore;}
with local_menu^ do
  Box(item,lightblue,length(datavalstring(data[item].data_type,data[item].data_p ClearViewPort;
with local_menu^ do with data[item] do
     begin
      s1:= DataValString(data_type,data_ptr);
      SetTextJustify(LeftText,CenterText);
      cx := margin;
         for j := 1 to length(s1) do
              begin
```

```
                    outtextxy(cx,ystep div 2,s1[j]);
                    cx := cx + textwidth('H');
                  end;

end;
     end;

end.
unit das16;
{
  This object provides an interface to the DAS-16 functions so that
  a programmer can be insulated from the specifics of the microchannel
  and or ISA standard computers.
}
interface
uses
   graph;
const
{$IFDEF MICROCHANNEL}
DMA_buf_count          = 32000; {half of the buffer}
{$ELSE}
DMA_buf_count          = 16000; { half of the buffer}
{$ENDIF} type
DMA_buffer             = array[0..DMA_buf_count-1] of integer;
DMA_buf_type           = array [0..1] of ^DMA_buffer;
Parray                 = array [0..15] of integer;
D16Obj                 = object
                            mode,err_code,flag     :integer;
                            DMA_max_count,dmalev :word;
                            Parameters:Parray;
                            procedure ains(ch:integer;var x:integer);
                            procedure bous(num:integer);
                            procedure bins(var num:integer);
                            procedure init(basflagadr,int_level,dma_level:integer);
                            procedure dma_int_disable;
                            procedure aous(ch,x:integer);
                            procedure aindma(buffer:DMA_buf_type;chanlo,chanhi,Xtal,
                                    DMA_buf_count:word;rate:real);
                            function count : word;
                            function err_msg:string;
                            procedure malloc(var buffer:DMA_buf_type;size:longint);
                          end;
const
{$IFDEF MICROCHANNEL}
        max_input = 10.0;
{$ELSE}
        max_input = 5.0;
{$ENDIF} var
        D16                    : D16Obj;
        AcquisitionData        : DMA_buf_type;
implementation
uses crt;

{$IFDEF MICROCHANNEL}
   {$L tpucdasg} { link in the microchannel micro-das16-G driver }
{$ELSE}
```

```
    {$L turbopas}  { link in the das-16 for ISA style machines }
{$ENDIF} function tp_dasg(var mode:integer;var params:Parray;var err_code:integer):intege
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure d16obj.init(basflagadr,int_level,dma_level:integer);
begin
dmalev:=dma_level;
mode:=0;
{$IFDEF MICROCHANNEL }
parameters[0]:=basflagadr; { microchannel only needs the address of the
                             data acquisition board }
{$ELSE}
  parameters[0] := basflagadr; { set up the address of the board }
  parameters[1] := int_level;  { which interrupt to acquire data with }
  parameters[2] := dma_level;  { choose the DMA level used for data
                                 acquisition }
{$ENDIF} flag:=tp_dasg(mode,parameters,err_code);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure d16obj.dma_int_disable;
begin
if err_code<>0 then exit;
mode:=7;
flag:=tp_dasg(mode,parameters,err_code);
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function d16obj.count : word;
begin
  mode := 8;
  flag := tp_dasg(mode,parameters,err_code);
  count := word(parameters[2]);
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure d16obj.aous(ch,x:integer);
begin
if err_code<>0 then exit;
mode:=15;
if x<0 then x:=0;
if x>4095 then x:=4095;
parameters[0]:=ch;
parameters[1]:=x;
flag:=tp_dasg(mode,parameters,err_code);
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure d16obj.ains(ch:integer;var x:integer);
begin
if err_code<>0 then exit;
mode:=1;    {set channel}
parameters[0]:=ch;
parameters[1]:=ch;
flag:=tp_dasg(mode,parameters,err_code);
mode:=3;    { do one A/D conversion }
flag:=tp_dasg(mode,parameters,err_code);
```

```
x:=parameters[0];
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure d16obj.bous(num:integer);
begin
if err_code<>0 then exit;

mode:=13;

parameters[0]:=num;

flag:=tp_dasg(mode,parameters,err_code);

end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure d16obj.bins(var num:integer);
begin
if err_code<>0 then exit;
mode:=14;
flag:=tp_dasg(mode,parameters,err_code);
num:=parameters[0];
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure d16obj.aindma(buffer:DMA_buf_type;chanlo,chanhi,
                  Xtal,DMA_buf_count:word;rate:real);
var N,err,olderr:real;
    UB,swap,C1,C2,C1final,C2final:word;
    l : longint;
begin
if err_code<>0 then exit;
mode:=1;    {set channel}
parameters[0]:=chanlo;
parameters[1]:=chanhi;
flag:=tp_dasg(mode,parameters,err_code);
mode:=17;   {set timer rate}
N:=Xtal*1e6/(rate*(chanhi-chanlo+1));
err:=1e10;
olderr:=1e10;
C2:=1;
C1:=2;
{ changed the upper bound because when it goes to 65536 it "rolls"
  over to 0 and causes a division by zero error
  MAJ 5/13/91 }
UB:=65535;
if trunc(N) < UB then UB := trunc(N);
while (C1<UB) and (C2>0) and (err >0.5) do
    begin
    C2:=Round(N/C1);
    l:=longint(c1)*longint(c2);
    Err:=abs(N-l);
    if err<olderr then
        begin
        C1final:=C1;
        C2final:=C2;
        olderr:=err;
        end;
    Inc(C1);
```

```
        end;
    if c1final >c2final then
      begin
        swap := c1final;
        c1final := c2final;
        c2final := swap;
      end;
    while(c2final > 0) and (c2final mod 2 = 0) do
      begin
        c1final := c1final *2;
        c2final := c2final div 2;
      end;
parameters[0]:=integer(C1final);
parameters[1]:=integer(C2final);
flag:=tp_dasg(mode,parameters,err_code);
mode:=6;
DMA_max_count:=DMA_buf_count;
parameters[0]:=integer(DMA_buf_count);
parameters[1]:=integer(Seg(buffer[0]^));
parameters[2]:=1;
parameters[3]:=1;
parameters[4]:=0;
flag:=tp_dasg(mode,parameters,err_code);
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function d16obj.err_msg:string;
begin
   case err_code of
     -1 : err_msg:='Not enough memory for DMA buffer';
      0 : err_msg:='No Error';
      1 : err_msg:='Driver not initialized ';
      2 : err_msg:='Access Mode number out of range';
      3 : err_msg:='Invalid Base Address';
      4 : err_msg:='Invalid Interrupt Level';
      5 : err_msg:='Invalid DMA level';
      6,
      7 : err_msg:='Mux scan limits out of range';
      8 : err_msg:='Undefined Error -';
      9 : err_msg:='A/D timeout Error';
     10 : err_msg:='Counter Division Ratio 0 or 1 in mode 17 or 22';
     11 : err_msg:='Number of conversions is 0';
     12 : err_msg:='Counter configuration number out of range';
     13 : err_msg:='Digital output out of range';
     14 : err_msg:='D/A data out of range';
     15 : err_msg:='D/A channel number out of range';
     16 : err_msg:='Counter read operation not 0 or 1';
     17 : err_msg:='Starting convert number is negative!';
     18 : err_msg:='Word Count is 0 or negative in mode 9';
     19 : err_msg:='Tigger Mode not 0';
     20 : err_msg:='DMA operation already active';
     21 : err_msg:='DMA Page Wrap-Around';
     22 : err_msg:='Undefined Error -';
     23 : err_msg:='Trigger channel inconsistent with configuration';
     24 : err_msg:='Trigger Data out of range';
     25 : err_msg:='Slope Data not 0 or 1';
     26 : err_msg:='Gain code Data out of Range';
     27 : err_msg:='Function not available No PGA';
     28 : err_msg:='Single shot/recycle data not 0 or 1';
```

```
      end;
   end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure d16obj.malloc(var buffer:DMA_buf_type;size:longint);
var DummyPtr:pointer;
    unusable_space:longint;
begin
if err_code<>0 then exit;
unusable_space:= seg(HeapPtr^)*longint(16)+ofs(HeapPtr^);
unusable_space:= $10000 - unusable_space and $FFFF;
if unusable_space <> $10000 then GetMem(DummyPtr,unusable_space);

{
  changed the size of the acquisition buffers because they were not big
  enough..ie 32000 samples equals 64k, hence the reasone we were
  getting a "flat line" with more than 31000 samples... MAJ 5/15/91
}
if size<maxavail then
      begin
      New(buffer[0]);
      New(buffer[1]);
      end
    else
    err_code:=-1;
if unusable_space <> $10000 then FreeMem(DummyPtr,unusable_space);
end;

end.unit disptool;
{
 This function will write a string in the message area during monitoring,
 it is most useful in displaying values needed for debugging.
}
interface
uses
    bmiconst,
    graph;
procedure display_message(message1,message2:string);

implementation
uses oldview;
const
msgframe:array [0..4] of Pointtype=( (x:0;y:Ymax-36),(x:0;y:Ymax-12),
                                     (x:501;y:Ymax-12),
                                     (x:501;y:Ymax-36),(x:0;y:Ymax-36));

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure display_message(message1,message2:string);

begin
View.save;
SetViewPort(0,0,Xmax,Ymax,ClipOn);
setlinestyle(SolidLn,0,NormWidth);
SetColor(White);
drawpoly(5,msgframe);
SetColor(Yellow);
SetTextStyle(DefaultFont,HorizDir,1);
SetTextJustify(LeftText,CenterText);

if message1<>'' then
```

```
   begin
      SetViewPort(msgframe[0].x+1,msgframe[0].y+1,
               msgframe[2].x-1,(msgframe[0].y+msgframe[2].y) div 2,ClipOn);
      ClearViewPort;
      OutTextXY(8,7,message1);
   end;

if message2<>'' then
   begin
      SetViewPort(msgframe[0].x+1,(msgframe[0].y+msgframe[2].y) div 2+1,
               msgframe[2].x-1,msgframe[2].y-1,ClipOn);
      SetViewPort(1,Ymax-24,500,Ymax-13,ClipOn);
      ClearViewPort;
      OutTextXY(8,6,message2);
   end;
View.restore;
end;
end.unit files;
{*********************************************************************}
{                                                                     }
{ Copyright (c) Biological Monitoring, Inc. 1987, 1990                }
{                                                                     }
{*********************************************************************}
interface uses
graph;

{
 function calculates the amount of time remaining before the bio-sensor
 will be unable to log data to the fixed disk.
}
procedure Diskinfo(data_ptr:pointer;item:word);

implementation
uses
 bmiconst,
 oldview,
 dos;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Diskinfo(data_ptr:pointer;item:word);
const   DiskBox        :array[1..5] of PointType =((x:0;y:0),
                                                   (x:0;y:Y17Y20-Y11Y20),
                                                   (x:150;y:Y17Y20-Y11Y20),
                                                   (x:150;y:0),
                                                   (x:0;y:0));
var     Freeminutes,
        Freehours,
        Freedays,
        Freemonths,
        Freeyears,
        Freetime,
        FreeSpace      :longint;
        ms,
        hs,ds,mos,ys   :String[16];
        (*-datafile     :String[8];-*)
        SFreeminutes,
        SFreehours,
        SFreedays,
```

```
            SFreemonths,
            SFreeyears       :String[10];
            string_ptr       :^string;
begin
            FreeSpace:=DiskFree(0);
            Freetime:=Round(FreeSpace/
                        Data_line_length_glb*
                        setup_data.bio.assessment_interval.actual);
            Freeminutes:=Freetime mod 60;
            if Freeminutes =1 then ms:=' minute.' else ms:=' minutes.';
            Freehours:=(Freetime div 60) mod 24;
            if Freehours=1 then hs:=' hour.' else hs:=' hours.';
            Freedays:=(Freetime div 1440) mod 31;
            if Freedays=1 then ds:=' day.' else ds:=' days.';
            Freemonths:=(Freetime div 1440 div 31) mod 12;
            if Freemonths =1 then mos:=' month.' else mos:=' months.';
            Freeyears:=Freetime div 1440 div 366;
            if Freeyears =1 then ys:=' year.' else ys:=' years.';
            Str(Freeyears:2,SFreeyears);
            Str(Freemonths:2,SFreemonths);
            Str(Freedays:2,SFreedays);
            Str(Freehours:2,SFreehours);
            Str(Freeminutes:2,Sfreeminutes);
            SFreeyears:=SFreeyears+ys;
            SFreemonths:=SFreemonths+mos;
            SFreedays:=SFreedays+ds;
            SFreehours:=SFreehours+hs;
            SFreeminutes:=SFreeminutes+ms;

if item=0 then
            begin
            View.save;
            SetViewPort(440,Y11Y20,Xmax-5,Y17Y20,ClipOn);
            FillPoly(5,DiskBox);
            SetTextStyle(DefaultFont,HorizDir,1);
            SetTextJustify(LeftText,CenterText);
            OutTextXY(8,20,'Free disk space: ');
            OutTextXY(28,40,SFreeyears);
            OutTextXY(28,60,SFreemonths);
            OutTextXY(28,80,SFreedays);
            OutTextXY(28,100,SFreehours);
            OutTextXY(28,120,SFreeminutes);
            View.restore;
            end
            else
            begin
            string_ptr:=data_ptr;
            string_ptr^:='Free disk space: '+#13#10+
                        SFreeyears+#13#10+
                        SFreemonths+#13#10+
                        SFreedays+#13#10+
                        SFreehours+#13#10+
                        SFreeminutes+#13#10;
            end;

end;
end.unit filecopy;

{
```

This "task" handles the transfer of data to floppies during monitoring so
that the user does not have to exit fish monitoring to transfer
data.  It also provides an estimate of how many floppy diskettes will be
needed to make the transfer.

}

```
interface
uses    dos;
type buftype = array[1..10240] of char;
     File_Obj = object
                BMI_DirInfo:SearchRec;
                FileComplete:boolean;
                FromF,ToF:file;
                in_progress,
                start:boolean;
                NumRead,NumWritten,Total_filecount,
                oldfilecount,filecount                  :word;
                buf:^buftype;
                Extension,Period_name:string[12];
                function Transfer:string;
                function Next_File_Message:string;
                procedure Initialize(ext:string;var message2 : string);
                procedure Estimate(ext:string;var Exempt_name,message1,message2:
                end;
function IOcheck(IOError:word):string;

implementation
{$I-}
function IOcheck(IOError:word):string;
var  IOstr:string[3];
begin
case IOError of
        2: IOCheck:='Error: File not found';
        5: IOCheck:='Error: Too Many Files on Diskette.';
      150: IOcheck:='Error: Diskette is write protected.';
      100: IOcheck:='Error: Fixed disk read error.';
  101,103: IOcheck:='Disk full. Insert new diskette and press F4 again.';
      152: IOcheck:='Error: No diskette or diskette unformatted';
      154: IOcheck:='Error: CRC error in data transfer';
      156: IOcheck:='Error: Diskette seek error';
      157: IOcheck:='Error: Unknown media type';
      158: IOcheck:='Error: Sector not found';
      162: IOcheck:='Error: Diskette is not formatted';
        0: IOcheck:='';
   else begin
        Str(IOError,IOStr);
        IOcheck:='I/O Error: '+IOStr;
        end;
end;
end;

function Copy_to_dot(s:string):string;
begin
Copy_to_dot:=Copy(s,1,Pos('.',s)-1);
end;

procedure File_Obj.Initialize(Ext:string;var message2 : string);
begin
if Total_Filecount>0 then
```

```
      begin
         Extension:=Ext;
         Start:=True;
         in_progress:=True;
      end
   else
      if Ext = 'RAW' then
         message2 := 'No raw data files available for transfer.'
      else
         message2:='No data files available for transfer.';
end;

function File_Obj.Transfer:string;
var      IOError,DummyError:word;
begin
Transfer:='';
if start then
    begin
    start:=FALSE;
    filecount:=0;
    oldfilecount:=0;
    FindFirst('*.'+Extension,AnyFile,BMI_DirInfo);
    if DosError<>0 then
        begin
        Transfer:='Error: There are no data files in this path';
        Exit;
        end;
    if maxavail<sizeof(buf^) then
        begin
        Transfer:='Error: Not enough memory for file transfer.';
        exit;
        end
        else New(buf);

FileComplete:=TRUE;
    end
    else
    if FileComplete then FindNext(BMI_DirInfo);

if Copy_to_Dot(BMI_DirInfo.Name)=Period_Name then
    repeat
          FindNext(BMI_DirInfo)
    until (Copy_to_Dot(BMI_DirInfo.Name)<>Period_Name) or (DosError=18);

if DosError=18 then
    begin
    Dispose(buf);
    Transfer:='Data transferred to floppy successfully.';
    Exit;
    end;

if FileComplete and (DosError=0)  then
    begin
    Assign(FromF,BMI_DirInfo.Name);
    Reset(FromF,1);
    DummyError:=IOResult;
    Assign(ToF,'A:\'+BMI_DirINfo.Name);
    Rewrite(ToF,1);
    IOError:=IOResult;
    if IOError=0 then FileComplete:=FALSE else
```

```
            begin
            Close(FromF);
            DummyError:=IOResult;
            Close(ToF);
            DummyError:=IOResult;
            Dispose(buf);
            Transfer:=IOCheck(IOError);
            exit;
            end;
    end;

BlockRead(FromF,buf^,Sizeof(Buf^),NumRead);
IOError:=IOResult;
if IOError<>0 then
    begin
    Dispose(buf);
    Close(FromF);
    DummyError:=IOResult;
    Close(ToF);
    DummyError:=IOResult;
    Transfer:=IOCheck(IOError);
    Exit;
    end;
{$I-}
BlockWrite(ToF,buf^,NumRead,NumWritten);
IOError:=IOResult;
if (IOError=0) and (NumWritten=NumRead) and (NumRead=sizeof(buf^)) then
    Transfer:=''
    else
    begin
    Close(FromF);
    DummyError:=IOResult;
    Close(ToF);
    DummyError:=IOResult;
    if IOError=0 then
        if NumRead<sizeof(buf^) then
            if NumWritten=NumRead  then
                begin
                FileComplete:=TRUE;
                Erase(FromF);
                DummyError:=IOResult;
                Inc(filecount);
                Transfer:='';
                end
              else
                begin
                Dispose(buf);
                Erase(ToF);
                DummyError:=IOResult;
                Transfer:=IOCheck(103);
                end
          else if NumWritten<NumRead
                  then begin
                       Dispose(buf);
                       Erase(ToF);
                       DummyError:=IOResult;
                       Transfer:=IOCheck(103);
                       end
                  else
        else begin
```

```
                Dispose(buf);
                Erase(ToF);
                DummyError:=IOResult;
                Transfer:=IOCheck(IOError);
                end;
        end;
end;

function File_Obj.Next_File_Message:string;
var Fstr:string[3];
begin
if filecount<>oldfilecount then
    begin
    oldfilecount:=filecount;
    Str(Total_filecount-filecount,Fstr);
    Next_File_message:=BMI_Dirinfo.Name+' copied. '+Fstr+' file(s) left.';
    end;
end;

function storage(fname:string;var fcount:word):longint;  {in kilobytes}
{*********************************************************}
{*   Returns amount of storage required for files matching Path    *}
{*********************************************************}
var     DirInfo:SearchRec;
        TotalSize:longint;
begin
fcount:=0;
Totalsize:=0;
FindFirst(fname,AnyFile,DirInfo);
if (DosError=0) then
    begin
    TotalSize := DirInfo.Size div 1024 + 1;
    Inc(fcount);
    repeat
        FindNext(DirInfo);
        if (DosError=0) then
            begin
            Inc(TotalSize,DirInfo.Size div 1024 + 1);
            Inc(fcount);
            end;
    until(DosError<>0);
    end;
Storage:=TotalSize;
end;

procedure File_Obj.Estimate(ext:string;var Exempt_name,message1,message2:string)
var
        DiskSpace     :longint;
begin
  Period_name:=Exempt_name;
  Extension:=Ext;
  DiskSpace:= Storage('*.'+extension,Total_filecount)
            -Storage(Period_name+'.'+extension,filecount);
  Dec(Total_filecount,filecount);
  if Total_filecount=0 then
    begin
        message1:='';
        if Ext = 'RAW' then message2 := 'No raw data files available for transfer.
        else message2:='No data files available for transfer.';
        Exit;
```

```
      end;
   Str(DiskSpace,message2);
   Str(Total_filecount,message1);
   if ext = 'RAW' then message1:=message1+' raw data file(s) occupy '+message2+'
    else message1:=message1+' data file(s) occupy '+message2+' kbytes';
   Str(DiskSpace div 1420 +1,message2);
   if DiskSpace<=1420
    then
      begin
        if ext='RAW' then message2:='You need 1 HD diskette to move the raw data
          else
            message2:='You need 1 HD diskette to move data files'
      end
    else
      begin
        if ext = 'RAW' then message2:='You need '+message2+' HD diskettes to move
          else
            message2:='You need '+message2+' HD diskettes to move data files';
      end;
    end;

end.unit menulogo;
{**********************************************************************}
{                                                                      }
{ Copyright (c) Biological Monitoring, Inc. 1987, 1991                 }
{                                                                      }
{ This unit contains setup menu and submenus for all of
    the bio-sensor system paramters including waveform parameters,
    alarm sensitivty, and communications parameters

**********************************************************************}
{$IFDEF SPECTRUM}
{$N+}
{$ENDIF}
interface uses bmimenux,bmiconst,graph,das16;

(*-var short_printout:boolean;
     (*-polygon_big      :polygon_set;-*)
procedure Monitor_Period_Name(par_menu:Pointer;item:Word);
procedure Auto_name(var current_menu:menu;CreateFiles,IsMidnight:Boolean);
procedure Logo(parent_menu:local_menu_ptr);
procedure nothing(dummy:Pointer;item:Word);
procedure Change_Date(parent_menu:Pointer;item:Word);
procedure Change_time_of_day(parent_menu:Pointer;item:Word);
procedure Setup(parent_menu:Pointer;item:Word);
{$IFDEF ANALOGPH}
procedure Phys_scan;
{$ENDIF}
function CalcDataLineLength(PO:Printer_file_options):Integer;

{$IFDEF SPECTRUM}
procedure Plot_dB_grid(var refresh,first_cycle:boolean;skip:Integer;
                            vector_size,no_of_decades:Word);
procedure Amplitude_and_phase(var z:complex);

{$ENDIF}
var check_for_old_file:Boolean;
implementation
```

```
uses
  crt,
  bmikey,
  mouse,
  dos,
  bmident,
  oldview,
  (*-files,-*)
  u_header                            (*-,
tp4d16-*)

{$IFDEF SCOUT}
 ,U_SCOUT
{$ENDIF};

type DataEntryString=String;

procedure Warning_message(S:String);
    {Beep, draw a box, and write a message within the box}
  var
    (*-  i    : integer;-*)
    key                  :Char;
    (*-  nbuttons,mstat : word;-*)
  begin
    sound(300);
    delay(200);
    nosound;
    TextBox(40,150,600,210,white,red,1,S);
  { mouse status was changed to allow the user to press the mouse
    button to clear this warning - MAJ - 1/23/91 }
    if not mshown then
      mshown:=True;
    repeat
      key:=GetKey;
    until((key<>#0));
    mshown:=False;
  end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
  procedure Save_parameters(parent_menu:Pointer;item:Word);
{$F-}
  var
    (*-  Key   : char; -*)
    Escd,
    SaveIt               :Boolean;
    Result               :Word;
  begin
    if data_changed then
      begin
        GetYNResponse('Do you want to save this configuration ?',SaveIt,Escd);
        if not Escd and SaveIt then
          begin
            GetYNResponse('YES - Are you sure ?',SaveIt,Escd);
            if not Escd and SaveIt then
              begin
                Assign(Setup_file,SetupFileName); { fix - 4/28/91 PG }
                Rewrite(Setup_file,1);
                BlockWrite(Setup_file,setup_data,sizeof(setup_data),Result);
```

```
                    if result<>sizeof(setup_data) then write(#7);
                    Close(Setup_file);
                  end;
              end;
          end;
      menu(parent_menu^).redraw:=True;
    end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
  {$F+}
    procedure Channel_Assignments(par_menu:Pointer;item:Word);
  {$F-}
    const DY               =14;
      Top_margin           =60;
      (*-       Bottom_margin=400;-*)
      First_column         =208;
      Other_columns        =100;
      TotParm              =number_of_assignments;
      backbox              :array[1..5]of PointType=
      ((x:0;y:0),(x:Other_columns;y:0),
       (x:Other_columns;y:DY),(x:0;y:DY),(x:0;y:0));
      activity             :array[0..2]of String[9]=
      ('Active','Reference','Inactive');
      back                 :array[1..5]of PointType=
      ((x:0;y:Top_margin+1),
       (x:First_column;y:Top_margin+1),
       (x:First_column;y:Top_margin+number_of_assignments*DY),
       (x:0;y:Top_margin+number_of_assignments*DY),
       (x:0;y:Top_margin+1));
    var mmod,
      (*-j,-*)
      oldi,
      Yloc,
      (*-m,-*)
      xi,
      oldxi,
      i                    :Integer;
      key                  :Char;
      (*-     nobeep  :Boolean;-*)
      si                   :String[5];
      mbt,mx,my,
      VIndex,
      HIndex,
      HX,VY                :Word;
      parent_menu          : ^local_menu;

procedure Display_Channel_Assignment;
    var k                  :Integer;

begin if(i<number_of_fish)then mmod:=2 else mmod:=1;
      for k:=0 to mmod do
        begin
          if k=setup_data.assignment[i]then SetFillStyle(SolidFill,LightRed)
          else SetFillStyle(SolidFill,Cyan);
          SetLineStyle(SolidLn,0,ThickWidth);
          SetViewPort(First_column+k*Other_columns,Top_margin+i*DY,
                      First_column+(k+1)*Other_columns,Top_margin+(i+1)*DY-1,Cli
```

```
                ClearViewPort;
                FillPoly(5,backbox);
                if i<number_of_fish then OutTextXY(Other_columns div 2,DY div 2,activi
                else OutTextXY(Other_columns div 2,DY div 2,activity[2*k]);
            end;
    end;

begin
    i:=0;
    parent_menu:=par_menu;
    Mvlimit(Top_margin,Top_margin+(number_of_assignments+1)*DY-1);
    Title('CHANNEL ASSIGNMENTS',2);
    SetTextStyle(DefaultFont,HorizDir,1);
    OutTextXY(First_column div 2,Top_margin-DY,'Fish No.');
    SetFillStyle(SolidFill,Green);
    SetLineStyle(SolidLn,0,ThickWidth);
    FillPoly(5,back);
    for i:=0 to number_of_fish-1 do
      begin
        Str(i,si);
        OutTextXY(First_column div 2,Top_margin+i*DY+DY div 2,si);
      end;
    Yloc:=Top_margin+number_of_fish*DY+DY div 2;
    with menu_text do
      begin
{$IFDEF ANALOGPH}
        OutTextXY(First_column div 2,Yloc,Ammonia);Inc(Yloc,DY);
        OutTextXY(First_column div 2,Yloc,Temperature);Inc(Yloc,DY);
        OutTextXY(First_column div 2,Yloc,O2);Inc(Yloc,DY);
        OutTextXY(First_column div 2,Yloc,pH);Inc(Yloc,DY);
        OutTextXY(First_column div 2,Yloc,Conductivity);Inc(Yloc,DY);
        OutTextXY(First_column div 2,Yloc,turbidity);Inc(Yloc,DY);
        OutTextXY(First_column div 2,Yloc,extra1);Inc(Yloc,DY);
        OutTextXY(First_column div 2,Yloc,extra2);Inc(Yloc,DY);
{$ENDIF}
{$IFDEF SCOUT}
        OutTextXY(First_column div 2,Yloc,'SCOUT(R) '+Temperature);Inc(Yloc,DY);
        OutTextXY(First_column div 2,Yloc,'SCOUT(R) '+O2);Inc(Yloc,DY);
        if number_of_scout_parameters>=3 then OutTextXY(First_column div 2,Yloc,
        if number_of_scout_parameters>=4 then OutTextXY(First_column div 2,Yloc,
{$ENDIF}
      end;

for i:=0 to number_of_assignments-1 do
      Display_Channel_Assignment;

SetViewPort(0,0,Xmax,Ymax,ClipON);
    Line(0,Top_margin+number_of_fish*DY,First_column,Top_margin+number_of_fish*D
    Line(First_column+2*Other_columns,Top_margin+number_of_fish*DY,
         First_column+3*Other_columns,Top_margin+number_of_fish*DY);
    Line(First_column+Other_columns,Top_margin+number_of_assignments*DY,
         First_column+2*Other_columns,Top_margin+number_of_assignments*DY);
    SetViewPort(First_column,Top_margin+number_of_assignments*DY,
                First_column+Other_columns,Top_margin+(number_of_assignments+1)*
    ClearViewPort;
    SetLineStyle(SolidLn,0,ThickWidth);
    SetFillStyle(SolidFill,Cyan);
    FillPoly(5,backbox);
    OutTextXY(Other_columns div 2,DY div 2,'Done');
    parent_menu^.MouseChoice;
```

```
mput(First_column+Other_columns div 2,Top_margin+DY div 2);
mshow;
oldi:= -1;
data_changed:=False;
repeat
  repeat
    if my<Top_margin+number_of_fish*DY then Mhlimit(First_column,First_colum
    else if my>Top_margin+number_of_assignments*DY
    then Mhlimit(First_column,First_column+Other_columns-1)
    else Mhlimit(First_column,First_column+2*Other_columns-1);
    mpos(mbt,mx,my);

key:=GetKey;
    HIndex:=(mx-First_column) div Other_columns;
    VIndex:=(my-Top_margin) div DY;
    case key of
      UArr: case HIndex of
              0:if VIndex>0 then Dec(VIndex)
                  else VIndex:=TotParm;
              1:if VIndex>0 then Dec(VIndex)
                  else VIndex:=TotParm-1;
              2:if VIndex>0 then Dec(VIndex)
                  else VIndex:=number_of_fish-1;
            end;
      DArr: case HIndex of
              0:if VIndex<TotParm then Inc(VIndex)
                  else VIndex:=0;
              1:if VIndex<TotParm-1 then Inc(VIndex)
                  else VIndex:=0;
              2:if VIndex<number_of_fish-1 then Inc(VIndex)
                  else VIndex:=0;
            end;
      LArr: case VIndex of
              0..number_of_fish:if HIndex>0 then Dec(HIndex)
                                    else HIndex:=2;
              0..number_of_assignments:if HIndex=1 then HIndex:=0
                                            else HIndex:=1;
            end;
      RArr: case VIndex of
              0..number_of_fish:if HIndex<2 then Inc(HIndex)
                                    else HIndex:=0;
              0..number_of_assignments:if HIndex=1 then HIndex:=0
                                            else HIndex:=1;
            end;
      Esc,
      MEsc:begin
              parent_menu^.redraw:=True;
              if mshown then
                  mhide;
              Exit;
           end;
    end;
    HX:=First_column+(HIndex*Other_columns)+Other_columns div 2;
    VY:=Top_margin+(VIndex*DY)+DY div 2;
    if key in[UArr,DArr,LArr,RArr]then mput(HX,VY);
  until key in[Esc,MEsc,Enter,MEnter];
  i:=(my-Top_margin) div DY;
  xi:=(mx-First_column) div Other_columns;
  if i<TotParm then setup_data.assignment[i]:=xi;
  if((i<>oldi) or(oldxi<>xi))then
```

```
            begin
              if mshown then
                mhide;
              if i<TotParm then
                begin
                  Display_Channel_Assignment;
                  data_changed:=True;
                end;
              mshow;
              oldi:=i;
              oldxi:=xi;
            end
        until i=TotParm;
        parent_menu^.redraw:=True;
        if mshown then
            mhide;
    end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
    procedure nothing(dummy:Pointer;item:Word);
{$F-}
  begin
  end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
    procedure Back_to_Parent(parent_menu:Pointer;item:Word);
{$F-}
  begin
    local_menu(parent_menu^).redraw:=True;
  end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$IFDEF ANALOGPH}
{$F+}
    procedure Phys_Chem_Calibration(parent_menu:Pointer;item:Word);
{$F-}
    var current_menu     : ^local_menu;
        i                :Integer;
    begin
      New(current_menu);
      with current_menu^ do
        with menu_text do
          begin
            data[0].description:='ANALOG PHYSIOCHEMICAL CALIBRATION';
            data[0].task:=nothing;
            data[1].description:=Ammonia;
            data[2].description:=Temperature;
            data[3].description:=O2;
            data[4].description:=pH;
            data[5].description:=Conductivity;
            data[6].description:=turbidity;
            data[7].description:=extra1;
            data[8].description:=extra2;
            for i:=1 to number_of_analog_parameters do
              begin
                data[i].data_ptr:= @setup_data.analog_phys.cal[i][1];
                data[i].task:=Edit;
                data[i].data_type:=calib_range;
              end;
```

```
          data[number_of_analog_parameters+1].description:='Done';
          data[number_of_analog_parameters+1].task:=Back_to_Parent;
          data[number_of_analog_parameters+1].data_type:=NoDataType;
          data[number_of_analog_parameters+2].task:=nothing; ;
          redraw:=True;
          draw((Xmax+1) div 20,(Ymax+1) div 5,Blue,Magenta,NormWidth,
               SolidFill,SolidLn,DefaultFont,HorizDir,1,3,
               number_of_analog_parameters+1,parent_menu);
      end;
    Dispose(current_menu);
  end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
  {$F+}
    procedure Analog_Phys_Chem_Sensitivity(parent_menu:Pointer;item:Word);
  {$F-}
    var                              (*- sbuf    :string[20];-*)
      i                 :Word;
      current_menu      : ^local_menu;
    begin
      New(current_menu);

with current_menu^ do
        begin
          data[0].description:='ANALOG MONITOR SENSITIVITY';
          data[0].task:=nothing;
          with menu_text do
            begin
              data[1].description:=Ammonia;
              data[2].description:=Temperature;
              data[3].description:=O2;
              data[4].description:=pH;
              data[5].description:=Conductivity;
              data[6].description:=turbidity;
              data[7].description:=extra1;
              data[8].description:=extra2;
            end;
          with setup_data.analog_phys do
            begin
              data[1].data_ptr:= @Ammonia;
              data[2].data_ptr:= @Temperature;
              data[3].data_ptr:= @O2;
              data[4].data_ptr:= @pH;
              data[5].data_ptr:= @Conductivity;
              data[6].data_ptr:= @turbidity;
              data[7].data_ptr:= @extra1;
              data[8].data_ptr:= @extra2;
            end;
          for i:=1 to 8 do
            begin
              data[i].task:=Edit;
              data[i].data_type:=data_range;
            end;

data[number_of_analog_parameters+1].description:='Analog Physiochemical
          data[number_of_analog_parameters+1].task:=Phys_Chem_Calibration;
          data[number_of_analog_parameters+1].data_type:=NoDataType;
          data[number_of_analog_parameters+2].description:='Done';
          data[number_of_analog_parameters+2].task:=Back_to_Parent;
          data[number_of_analog_parameters+2].data_type:=NoDataType;
```

```
            data[number_of_analog_parameters+3].task:=nothing; ;
            draw((Xmax+1) div 20,(Ymax+1) div 5,Blue,Magenta,NormWidth,
                SolidFill,SolidLn,DefaultFont,HorizDir,1,3,
                number_of_analog_parameters+2,parent_menu);
        end;
      Dispose(current_menu);
    end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
  procedure Phys_scan;
  begin
    with setup_data.analog_phys do
      begin
        Ammonia.actual:=cal[1][1]*(AcquisitionData[0]^[8] shr 4-2048)+cal[1][2];
        Temperature.actual:=cal[2][1]*(AcquisitionData[0]^[9] shr 4-2048)+cal[2]
        O2.actual:=cal[3][1]*(AcquisitionData[0]^[10] shr 4-2048)+cal[3][2];
        pH.actual:=cal[4][1]*(AcquisitionData[0]^[11] shr 4-2048)+cal[4][2];
        Conductivity.actual:=cal[5][1]*(AcquisitionData[0]^[12] shr 4-2048)+cal[
        turbidity.actual:=cal[6][1]*(AcquisitionData[0]^[13] shr 4-2048)+cal[6][
        extra1.actual:=cal[7][1]*(AcquisitionData[0]^[14] shr 4-2048)+cal[7][2];
        extra2.actual:=cal[8][1]*(AcquisitionData[0]^[15] shr 4-2048)+cal[8][2];
      end;
  end;

{$ENDIF}
   {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$IFDEF SCOUT}
{$F+}
   procedure Scout_Phys_Chem_Sensitivity(parent_menu:Pointer;item:Word);
{$F-}
  var                         (*-   sbuf     :string[20]; -*)
     i                   :Word;
     current_menu        : ^local_menu;
  begin
    New(current_menu);
    with current_menu^ do
      begin
        data[0].description:='SCOUT(R) MONITOR SENSITIVITY';
        data[0].task:=nothing;
        with menu_text do
          begin
            data[1].description:=Temperature;
            data[2].description:=O2;
            data[3].description:=pH;
            data[4].description:=Conductivity;
          end;
        with setup_data.Scout_phys do
          begin
            data[1].data_ptr:= @Temperature;
            data[2].data_ptr:= @O2;
            data[3].data_ptr:= @pH;
            data[4].data_ptr:= @Conductivity;
          end;
        for i:=1 to number_of_scout_parameters do
          begin
            data[i].task:=Edit;
            data[i].data_type:=data_range;
          end;
        data[number_of_scout_parameters+1].description:='Scout(R) Physiochemical
        data[number_of_scout_parameters+1].task:=Scout_Calibration;
```

```
            data[number_of_scout_parameters+1].data_type:=NoDataType;
            data[number_of_scout_parameters+2].description:='Done';
            data[number_of_scout_parameters+2].task:=Back_to_Parent;
            data[number_of_scout_parameters+2].data_type:=NoDataType;
            data[number_of_scout_parameters+3].task:=nothing; ;
            draw((Xmax+1) div 20,(Ymax+1) div 5,Blue,Magenta,NormWidth,
                SolidFill,SolidLn,DefaultFont,HorizDir,1,3,
                number_of_scout_parameters+2,parent_menu);
        end;
      Dispose(current_menu);
    end;
{$ENDIF}
 {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$IFDEF SCOUT}
{$IFDEF ANALOGPH}
{$F+}
  procedure Choose_Physiochemical(parent_menu:Pointer;item:Word);
{$F-}
    var current_menu   : ^local_menu;
      (*-i:integer;-*)
    begin
      New(current_menu);
      with current_menu^ do
        begin
          data[0].description:='PHYSIOCHEMICAL SENSORS';
          data[0].task:=nothing;
          data[1].description:='SCOUT(R) monitor sensitivity';
          data[1].task:=Scout_Phys_Chem_Sensitivity;
          data[1].data_type:=NoDataType;
          data[2].description:='Analog monitor sensitivity';
          data[2].task:=Analog_Phys_Chem_Sensitivity;
          data[2].data_type:=NoDataType;
          data[3].description:='Done';
          data[3].task:=Back_to_Parent;
          data[3].data_type:=NoDataType;
          data[4].task:=nothing;
          draw((Xmax+1) div 20,(Ymax+1) div 5,Blue,Magenta,ThickWidth,
              SolidFill,SolidLn,SansSerifFont,HorizDir,4,1.6,3,parent_menu);
        end;
      Dispose(current_menu);
    end;
{$ENDIF}
{$ENDIF}
 {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
  procedure update_waveform_options(parent_menu:Pointer;item:Word);
{$F-}
    var
      original_sampling_freq : real;
    begin
    { save what the sampling frequency }
    original_sampling_freq := setup_data.wave.sampling_frequency.actual;

if parent_menu<> nil then Edit(parent_menu,item);
    with setup_data.wave do
{$IFDEF SPECTRUM}
        if FFT then
            begin
            vector_size:=Round(Exp(ln(2.0)*Int(
                    ln(sampling_frequency.actual*acquisition_time)/ln(2.0))));
```

```
                    {round to nearest lower power of 2}
          if vector_size>FFT_max_vector_size then vector_size:=FFT_max_vector_si
          sampling_frequency.actual:=vector_size/acquisition_time;
          corner_frequency.actual:=sampling_frequency.actual/4;
          if parent_menu<> nil then
             begin
                Display(parent_menu,2);   { update sampling frequency }
                Display(parent_menu,3); { update roll-off frequency }
             end;
          end
          else
{$ENDIF}

Vector_size:=Round(sampling_frequency.actual*acquisition_time);

{ make sure the roll off is at most 1/4 of sampling_frequency
       MAJ 5/17/91 } with setup_data.wave do if corner_frequency.max <> sampling_frequency.actual/4 then
             begin corner_frequency.max := sampling_frequency.actual /4;

{ if it's changed go with the maximum}
                if  original_sampling_freq <> sampling_frequency.actual then
                    corner_frequency.actual := corner_frequency.max
                else
                    if corner_frequency.actual > sampling_frequency.actual/4 then
                        corner_frequency.actual := sampling_frequency.actual/4;

if parent_menu<> nil then
             begin
                Display(parent_menu,2);   { update sampling frequency }
                Display(parent_menu,3); { update roll-off frequency }
             end
          end;

end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
   procedure Waveform_Options(parent_menu:Pointer;item:Word);
{$F-}
   const
{$IFDEF SPECTRUM}
      offset              =1;
{$ELSE}
offset = 0;
{$ENDIF}
   var current_menu    : ^local_menu;
   begin
     New(current_menu);
     with setup_data.Wave do
        with current_menu^ do
          begin
             data[0].description:='WAVEFORM PROCESSING PARAMETERS';
             data[0].task:=nothing;
{$IFDEF SPECTRUM}
```

```
            data[1].description:='Use spectral analysis:';
            data[1].task:=update_waveform_options;
            data[1].data_type:=bool;
            data[1].data_ptr:= @FFT;
{$ENDIF}
            data[1+offset].description:='Sampling frequency [Hz]:';
            data[1+offset].task:=update_waveform_options;
            data[1+offset].data_type:=Float;
{           Sampling_frequency.min:=1;
            Sampling_frequency.max:=300;}
            data[1+offset].data_ptr:= @sampling_frequency;
            data[2+offset].description:='Low-pass filter roll-off frequency [Hz]:'
            data[2+offset].task:=Update_waveform_options;
            data[2+offset].data_type:=Float;
            Corner_frequency.min:=1;
            Corner_frequency.max:=100;
            data[2+offset].data_ptr:= @corner_frequency;
            data[3+offset].description:='Use dynamic threshold:';
            data[3+offset].task:=Edit;
            data[3+offset].data_type:=bool;
            data[3+offset].data_ptr:= @automatic_threshold;
            data[4+offset].description:='Minimum threshold voltage [V]:';
            data[4+offset].task:=Edit;
            data[4+offset].data_type:=Float;
            Min_Threshold.min:=0.01;
            Min_Threshold.max:=5;
            data[4+offset].data_ptr:= @Min_Threshold;
            data[5+offset].description:='Dynamic threshold time constant [s]:';
            data[5+offset].task:=Edit;
            data[5+offset].data_type:=Float;
            Time_Constant.min:=0;
            Time_Constant.max:=86400;
            data[5+offset].data_ptr:= @Time_Constant;
            data[6+offset].description:='Dynamic threshold as percent of amplitude
            data[6+offset].task:=Edit;
            data[6+offset].data_type:=Float;
            Dynamic_threshold.min:=0;
            Dynamic_threshold.max:=100;
            data[6+offset].data_ptr:= @Dynamic_threshold;
{           maxdirection.min:=1;
            maxdirection.max:=maxdirlimit;
            data[7+offset].description:='Fish direction change threshold:';
            data[7+offset].task:=Edit;
            data[7+offset].data_type:=Intgr;
            data[7+offset].data_ptr:= @maxdirection;}
            data[7+offset].description:='Done';
            data[7+offset].task:=Back_to_Parent;
            data[7+offset].data_type:=NoDataType;
            data[8+offset].task:=Update_waveform_options;
            draw((Xmax+1) div 20,(Ymax+1) div 5,Blue,Magenta,NormWidth,
                SolidFill,SolidLn,DefaultFont,HorizDir,1,3,7+offset,parent_menu);
        end;
    Dispose(current_menu);
  end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
  procedure EditPassword(parent_menu:Pointer;item:Word);
{$F-}
```

```
const MaxPasswords   =8;
      min_password_length = 5;
type Password_type   =array[1..MaxPasswords]of String;
var
   current_menu          : ^local_menu;
   i                     :Integer;
   S1                    :String;
   S2                    :String[1];
   Password              : ^Password_type;
   password_too_short,
   Password_too_long     :Boolean;
begin
 Password_too_long:=true;
 Password_too_short := true;
 while password_too_long or password_too_short do
 begin
  New(current_menu);
  New(Password);
  Password_too_long:=False;
  Password_too_short := False;
  S1:=setup_data.Misc.Password_set;
  with current_menu^ do
     begin
        data[0].task:=nothing;
        data[0].description:='Edit Phone Number List';
        data[1].task := nothing;
        data[1].description := 'Passwords shorter than 5 chars. not accepted';
        data[1].data_type:=NoDataType;
        for i:=2 to MaxPasswords do
          begin
            if Pos(';',S1)>0 then Password^[i]:=Copy(S1,1,Pos(';',S1)-1)
            else Password^[i]:='';
            Str(i-1,S2);
            if Length(S1)>1 then S1:=Copy(S1,Pos(';',S1)+1,Length(S1))
            else S1:='';
            data[i].description:='Phone number '+S2;
            data[i].task:=Edit;
            data[i].data_type:=story;
            data[i].data_ptr:= @Password^[i];
          end;
        data[MaxPasswords+1].task:=Back_to_Parent;
        data[MaxPasswords+1].description:='Done';
        data[MaxPasswords+1].data_type:=NoDataType;
        data[MaxPasswords+2].task:=nothing;
        draw((Xmax+1) div 20,(Ymax+1) div 5,Blue,Magenta,NormWidth,
             SolidFill,SolidLn,DefaultFont,HorizDir,1,3,
             MaxPasswords+1,parent_menu);
     end;
  S1:='';
  for i:=2 to MaxPasswords do
    if Length(Password^[i])>0 then
       begin
         {
           fix to insure that the password is at least 5 characters in
           length to prevent easy detection MAJ 5/21/91
         } if length(password^[i]) < min_password_length then
            Password_too_short := true;
         if Length(Password^[i])+Length(S1)<255
```

```
            then S1:=S1+Password^[i]+';'
          else Password_too_long:=True;
          end;
      if Password_too_long then
        begin
        Write(#7);
        warning_message('Password Too Long - Changes Not recorded')
        end
      else
          if Password_too_short then
             begin
                Write(#7);
                warning_message('Password Too Short - Changes Not recorded')

end
          else
              setup_data.Misc.Password_set:=S1;
      Dispose(Password);
      Dispose(current_menu);
    end;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{communications parameters sub menu - 22 Oct, 91 - MK - also BMICONST, BMIINIT}
{$F+}
procedure EditComm(parent_menu:Pointer;item:Word);
{$F-}
var current_menu    : ^local_menu;
begin
  New(current_menu);
  with setup_data.Misc do
    with current_menu^ do
      begin
        data[0].description:='COMMUNICATION PARAMETERS';
        data[0].task:=nothing;
        data[1].description:='Edit phone number list';
        data[1].task:=EditPassword;
        data[1].data_type:=NoDataType;
        data[1].data_ptr:= current_menu;
        data[2].description:='Use ringback security';
        data[2].task:=Edit;
        data[2].data_type:=bool;
        data[2].data_ptr:= @comm.ring_back;
        data[3].description:='Use tone dialing';
        data[3].task:=Edit;
        data[3].data_type:=bool;
        data[3].data_ptr:= @comm.tone_dial;
        data[4].description:='Dial wait time [1-5 s]';
        data[4].task:=Edit;
        data[4].data_type:=intgr;
        data[4].data_ptr:= @comm.dial_wait;
        data[5].description:='Number of rings before answer [1-8]';
        data[5].task:=Edit;
        data[5].data_type:=intgr;
        data[5].data_ptr:=@comm.num_rings;
        data[6].description:='Done';
        data[6].data_type:=NoDataType;
        data[6].task:=Back_to_Parent;
        data[7].task:=nothing;
        draw((Xmax+1) div 20,(Ymax+1) div 5,Blue,Magenta,NormWidth,
```

```
                    SolidFill,SolidLn,DefaultFont,HorizDir,1,3,6,parent_menu);
        end;
     Dispose(current_menu);
  end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
  procedure File_options(parent_menu:Pointer;item:Word);
{$F-}
     {Menu to allow selection of what data are to be written to data file.   }
     {All six data options are allowed in file.                              }
     var
        i                      :Integer;
        current_menu           : ^local_menu;
     begin
        New(current_menu);
        with setup_data.Misc.PrinterFileOpt do
           with current_menu^ do
              begin
                 data[0].description:='DATA FILE OPTIONS';
                 data[0].data_type:=NoDataType;
                 data[0].task:=nothing;

data[1].description:='Write average frequency to data file';
                 data[2].description:='Write average amplitude to data file';
                 data[3].description:='Write last minute frequency to data file';
                 data[4].description:='Write last minute amplitude to data file';
                 data[5].description:='Write moving average to data file';
                 data[6].description:='Write standard deviation to data file';

{                 data[7].description:='Write fish direction changes to data file';
                 data[8].description:='Write std. dev. of fish direction changes to dat
                 for i:=1 to 6 do
                    begin
                       data[i].data_type:=bool;
                       data[i].data_ptr:= @fileopt[i];
                       data[i].task:=Edit;
                    end;

data[7].description:='Done';
                 data[7].data_type:=NoDataType;
                 data[7].task:=Back_to_Parent;
                 data[8].task:=nothing;

draw((Xmax+1) div 20,(Ymax+1) div 5,Blue,Magenta,NormWidth,
                    SolidFill,SolidLn,DefaultFont,HorizDir,1,3,7,parent_menu);
              end;
        Dispose(current_menu);
  end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
  procedure Print_options(parent_menu:Pointer;item:Word);
{$F-}
     {Menu to allow selection of which data are to be written to printer. If }
     {standard deviation = YES, then maximum selections = 3 else max = 4.    }
     var
        i,j                    :Integer;
        current_menu .         : ^local_menu;
        Done                   :Boolean;
```

```
begin
  Done:=False;
  New(current_menu);
  repeat
    with setup_data.Misc.PrinterFileOpt do
      with current_menu^ do
        begin
          data[0].description:='PRINTOUT OPTIONS';
          data[0].data_type:=NoDataType;
          data[0].task:=nothing;
          data[1].description:='*    Maximum of four may be set to "YES".  If
          data[1].data_type:=NoDataType;
          data[1].task:=nothing;
          data[2].description:='*       deviation is printed, then maximum is t
          data[2].task:=nothing;
          data[2].data_type:=NoDataType;
          data[3].description:=' ';
          data[3].data_type:=NoDataType;
          data[3].task:=nothing;
          data[4].description:='Print average frequency on printout';
          data[5].description:='Print average amplitude on printout';
          data[6].description:='Print last minute frequency on printout';
          data[7].description:='Print last minute amplitude on printout';
          data[8].description:='Print moving average on printout';
          data[9].description:='Print standard deviation on printout';
{
          data[10].description:='Print fish direction changes on printout';
          data[11].description:='Print std. dev. of fish direction changes on for i:=1 to 6 do
            begin
              data[i+3].data_type:=bool;
              data[i+3].data_ptr:= @printopt[i];
              data[i+3].task:=Edit;
            end;
          data[10].description:='Done';
          data[10].data_type:=NoDataType;
          data[10].task:=Back_to_Parent;
          data[11].task:=nothing;

draw((Xmax+1) div 20,(Ymax+1) div 5,Blue,Magenta,NormWidth,
               SolidFill,SolidLn,DefaultFont,HorizDir,1,3,10,parent_menu);

{Make sure no more than 4 items (3 if StdDev) are selected.    }
          {                            If # selected > max, then call    }
          {procedure Warning_message, above.                             } j:=0;
          for i:=1 to 6 do if printopt[i]then Inc(j);
       {$B-}
          if(j>4)then Warning_message('No more than four may be set to "YES".'
          else if(j>3) and printopt[6]then
            Warning_message('Max of three set to "YES" w/ StdDev.')
          else Done:=True;
          {B+} end;
  until Done;
  Dispose(current_menu);
end;
```

```
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
  procedure Miscellaneous_Options(parent_menu:Pointer;item:Word);
{$F-}
  var current_menu     : ^local_menu;
  begin
    New(current_menu);
    with setup_data.Misc do
      with current_menu^ do
        begin
          data[0].description:='MISCELLANEOUS OPTIONS';
          data[0].task:=nothing;
          data[1].description:='Maximum displayed assessment value [Hz]:';
          data[1].task:=Edit;
          data[1].data_type:=Float;
          Max_disp_frequency.min:=0.01;
          Max_disp_frequency.max:=100;
          data[1].data_ptr:= @Max_disp_frequency;
          data[2].description:='Alarm duration [s]:';
          data[2].task:=Edit;
          data[2].data_type:=Intgr;
          data[2].data_ptr:= @Alarm_duration;

data[3].description:='Automatic period file names:';
          data[3].task:=Edit;
          data[3].data_type:=bool;
          data[3].data_ptr:= @Automatic_name;

{mod to allow changing the 1st two letters of auto period name}
{22 Oct, 91 - MK - also BMICONST, BMIINIT}
          data[4].data_ptr := @period_prefix;
          data[4].description := 'Auto monitor period name prefix';
          data[4].data_type:=two_chars;
          data[4].task := edit;
{end mod}

ScreenSaveTime.min:=0;
          ScreenSaveTime.max:=60;
          data[5].data_ptr:= @ScreenSaveTime;
          data[5].description:='Screen blanking time [min]:';
          data[5].data_type:=Intgr;
          data[5].task:=Edit;
          data[6].description:={'Edit phone number list';}'Communications parame
          data[6].task:={EditPassword;}EditComm;
          data[6].data_ptr:=current_menu;
          data[6].data_type:=NoDataType;
          data[7].description:='Printout options';
          data[7].task:=Print_options;
          data[7].data_type:=NoDataType;
          data[7].data_ptr:=current_menu;
          data[8].description:='Data file options';
          data[8].task:=File_options;
          data[8].data_type:=NoDataType;
          data[8].data_ptr:=current_menu;
          data[9].description:='Done';
          data[9].task:=Back_to_Parent;
          data[9].data_type:=NoDataType;
          data[9].data_ptr:=current_menu;
          data[10].task:=nothing;
          draw((Xmax+1) div 20,(Ymax+1) div 5,Blue,Magenta,NormWidth,
```

```
                    SolidFill,SolidLn,DefaultFont,HorizDir,1,3,9,parent_menu);
      end;
    Dispose(current_menu);
  end;
  {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
  procedure Bio_Sensitivity(parent_menu:Pointer;item:Word);
{$F-}
  var                               (*-     ibuf :array[1..5] of integer;-*)
    (*-         i     :word;-*)
    current_menu       : ^local_menu;
  begin
    New(current_menu);
      with setup_data.Bio do
        with current_menu^ do
          begin
            data[0].description:='BIOLOGICAL ALARM SENSITIVITY';
            data[0].task:=nothing;
            data[1].description:='Assessment interval [min]:';
            data[1].task:=Edit;
            data[1].data_type:=Intgr;
            Assessment_interval.min:=1;
            Assessment_interval.max:=60;
            data[1].data_ptr:= @Assessment_interval;
            data[2].description:='Sample size for statistical evaluation:';
            data[2].task:=Edit;
            data[2].data_type:=Intgr;
            Sample_size.min:=2;
            Sample_size.max:=Max_samples;
            data[2].data_ptr:= @Sample_size;
            data[3].description:='Number of acceptable standard deviations:';
            data[3].task:=Edit;
            data[3].data_type:=Intgr;
            Acceptable_std_dev.min:=0;
            Acceptable_std_dev.max:=10;
            data[3].data_ptr:= @Acceptable_std_dev;
            data[4].description:='Recalculate critical limits after false warnings
            data[4].task:=Edit;
            data[4].data_type:=Intgr;
            Recalc_after_warnings.min:=1;
            Recalc_after_warnings.max:=1000;
            data[4].data_ptr:= @Recalc_after_warnings;
            data[5].description:='Number of warnings for alarm:';
            data[5].task:=Edit;
            data[5].data_type:=Intgr;
            Warnings_for_alarm.min:=1;
            Warnings_for_alarm.max:=number_of_fish;
            data[5].data_ptr:= @Warnings_for_alarm;
            data[6].description:='Minimum acceptable frequency [Hz]:';
            data[6].task:=Edit;
            data[6].data_type:=Float;
            Minimum_frequency.min:=0.001;
            Minimum_frequency.max:=100;
            data[6].data_ptr:= @Minimum_frequency;
            data[7].description:='Moving average';
            data[7].task:=Edit;
            data[7].data_type:=bool;
            data[7].data_ptr:= @Moving_average;
            data[8].description:='Done';
            data[8].task:=Back_to_Parent;
```

```
            data[8].data_type:=NoDataType;
            data[9].task:=nothing;
            draw((Xmax+1) div 20,(Ymax+1) div 5,Blue,Magenta,NormWidth,
                 SolidFill,SolidLn,DefaultFont,HorizDir,1,3,8,parent_menu);
         end;
      Dispose(current_menu);
      { check to see if the alarm duration is greater than the assessment
        interval and if so, clip the value to the duration of the assessment
        interval MAJ/MK 1023/91}
      with setup_data do
            begin
            if bio.assessment_interval.actual *60 < misc.alarm_duration.actual the
               begin
                    misc.alarm_duration.actual := bio.assessment_interval.actual * 6
               end;
            misc.alarm_duration.max := bio.assessment_interval.actual * 60;
            end;
   end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
   function CalcDataLineLength(PO:Printer_file_options):Integer;
   var
      i,j,L              :Integer;
   begin
      L:=16;                          {date and time use 16 spaces}
      for j:=1 to number_of_fish do
         begin
            with PO do
               begin
                  for i:=1 to 5 do
                     if fileopt[i]then Inc(L,6) else Inc(L,1);
                  if fileopt[6]then Inc(L,7) else Inc(L,1);
               end;
         end;
{$IFDEF ANALOGPH}
      L:=L+40;                        {six analog physiochemical parameters}
{$ENDIF}
{$IFDEF SCOUT}
      L:=L+27;                        {four Scout physiochemical parameters}
{$ENDIF}
      CalcDataLineLength:=L;
   end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
   procedure Setup(parent_menu:Pointer;item:Word);

(*-         const    back              :array[1..5] of PointType =
                                        ((x:0;y:0),(x:3*Xmax div 4;y:0),
                                         (x:3*Xmax div 4;y:26*Y40),(x:0;y:26*Y40),
                                         (x:0;y:0));
                     float_data = TRUE;
                     integer_data = FALSE; -*)
   var                                  (*-my,
                     code     :word;-*)
(*-                  i,
                     status   :integer;-*)
      current_menu              : ^local_menu;
   begin
      data_changed:=False;
      New(current_menu);
```

```
      with current_menu^ do
        begin
          data[0].description:='SETUP MENU';
          data[0].task:=nothing;
          data[1].description:='Biological Alarm Sensitivity';
          data[1].data_type:=NoDataType;
          data[1].task:=Bio_Sensitivity;
          data[2].description:='Physiochemical Sensors';
          data[2].data_type:=NoDataType;
{$IFDEF ANALOGPH}
{$IFDEF SCOUT}
          data[2].task:=Choose_Physiochemical;
{$ELSE}
              data[2].task:=Analog_Phys_Chem_Sensitivity;
{$ENDIF}
{$ELSE}
{$IFDEF SCOUT}
              data[2].task:=Scout_Phys_Chem_Sensitivity;
{$ELSE}
              data[2].task:=nothing;
              data[2].description:='Physiochemical Alarm not Available';
{$ENDIF}
{$ENDIF}
          data[3].description:='Waveform Processing Parameters';
          data[3].data_type:=NoDataType;
          data[3].task:=Waveform_Options;
          data[4].description:='Channel Assignments';
          data[4].data_type:=NoDataType;
          data[4].task:=Channel_Assignments;
          data[5].description:='Miscellaneous Options';
          data[5].data_type:=NoDataType;
          data[5].task:=Miscellaneous_Options;
          data[6].description:='Done';
          data[6].data_type:=NoDataType;
          data[6].task:=Save_parameters;
          data[7].task:=nothing;
          data_changed:=False;
          draw((Xmax+1) div 20,(Ymax+1) div 5,Blue,Magenta,ThickWidth,
               SolidFill,SolidLn,SansSerifFont,HorizDir,4,1.6,6,parent_menu);
        end;

Dispose(current_menu);
    menu(parent_menu^).oldrtm:=100; { greater than 59 to ensure time refreshing
    if setup_data.misc.Automatic_name then
             auto_name(menu(parent_menu^),false,false);
    check_for_old_file:=False;
    Data_line_length_glb:=CalcDataLineLength(setup_data.Misc.PrinterFileOpt);

end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ} procedure Change_time_of_day(parent_menu:Pointer;item:Word);
  var
    TStr,
    S1,S2            :String;
    Err              :Integer;
    h,m,S,d          :Word;
    Okay             :Boolean;
```

```
begin
  SetViewPort(5*Xmax div 14,9*Y10,11*Xmax div 14,Ymax-5,ClipON);
  ClearViewPort;
  SetTextStyle(DefaultFont,HorizDir,1);
  SetTextJustify(LeftText,CenterText);
  {OutTextXY(4 * Xmax div 7,Y20,'Enter new time (hours:minutes)');}
  OutTextXY(22,25,'Enter current time in 24 hour');
  outtextXY(22,35,'format');
  SetTextStyle(DefaultFont,HorizDir,6);
  SetTextJustify(CenterText,CenterText);

GetTime(h,m,S,d);
  Str(h,S1);
  if h<10 then S1:='0'+S1;
  Str(m,S2);
  if m<10 then S2:='0'+S2;
  TStr:=S1+':'+S2;
  Okay:=False;
  repeat
    menu(parent_menu^).box(item,lightblue,5);
    GetString(5,1,TStr,S2,False,False,True);
    S1:=Copy(S2,1,2);
    Val(S1,h,Err);
    if Err=0 then
      begin
        S1:=Copy(S2,4,2);
        Val(S1,m,Err);
        if Err=0 then
          begin
            if(h in[0..23]) and(m in[0..59])then
              begin
                TStr:=S2;
                SetTime(h,m,0,0);
                LastKeypressGLB:=(h*3600)+(m*60);
                Okay:=True;
              end
            else Write(#7);
          end;
      end
    else Write(#7);
  until Okay;
  with menu(parent_menu^)do
    SetViewPort(dataposition,ypos+(item-1)*ystep+1,Xmax-10,
                ypos+item*ystep-1+3,ClipON);
  ClearViewPort;
  with menu(parent_menu^)do OutTextXY(margin,ystep div 2,TStr);
  LastKeypressGLB:=TimerNow;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{Added IsMidnight boolean to fix monitor period name overwrite - 4/10/91 - MK}
  procedure Auto_name(var current_menu:menu;CreateFiles,IsMidnight:Boolean);

(* period name prefix mod - 22 Oct, 91 - MK - also BMICONST, BMIINIT, MENULOGO}
  const
{$IFDEF EXP}
    prefix     ='EX';
{$ELSE}
    prefix                  ='OP';
{$ENDIF}
```

```
  end period name mod*)

var year,month,day,dayofweek:Word;
    ygr                   :String[4];
    mgr,dgr               :String[2];
    prefix                :string[2];
  begin {period name mod - 22 Oct, 91 - MK}
    prefix := setup_data.misc.period_prefix;
{end mod}

GetDate(year,month,day,dayofweek);
    Str(year,ygr);
    ygr:=Copy(ygr,3,2);
    Str(month,mgr);
    if month<10 then mgr:='0'+mgr;
    Str(day,dgr);
    if day<10 then dgr:='0'+dgr;
    with current_menu do
      begin
        Old_Period_Name:=Period_Name;
        Period_Name:=prefix+mgr+dgr+ygr;
        if IsMidnight and CreateFiles and setup_data.Misc.Automatic_name then
          Header(current_menu)
        else if CreateFiles then
          begin
            Period_Name:=Old_Period_Name;
            Header(current_menu);
          end;
      end;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure RemoveDisallowedCharacters(var S:DataEntryString;var Fixed:Boolean);
const
  Allowed             =[#35,#45,#48..#57,#65..#90,#97..#122];
var
  i                   :Integer;
  Temp                :DataEntryString;
begin
  Fixed:=False;
  Temp:='';
  for i:=1 to Length(S)do
      if S[i]in Allowed then Temp:=Temp+S[i] else Fixed:=True;
  S:=Temp;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Monitor_Period_Name(par_menu:Pointer;item:Word);
var
  XLoc,
  Yloc                :Word;
  (*- Key    : char;-*)
  S1,
  S2                  :String;
  parent_menu         : ^menu;

function FileCheck(S:DataEntryString;FilenameIsNull:Boolean):Boolean;
  var SRec            :SearchRec;
    WriteIt,
    Escd                :Boolean;
```

```
    begin
      FileCheck:=False;
      FindFirst(S+'.bmi',AnyFile,SRec);

if DOSError=0 then
        begin

{put here for because when called mouse not always visible,
         so I elected to show it then rehide it for clarity.
         MJ - 1/14/90 }
          if FilenameIsNull then
            mshow;
          if GoToMonitoring then   { skip filecheck if in recovery mode PG - 2/3/
            begin
              WriteIt:=True;
              Escd:=False;
            end
          else
            begin
              SetBkColor(red);
              GetYNResponse('Monitor Period Name exists. Overwrite?',WriteIt,Esc
              SetBkColor(Blue);
            end;

{now hide the mouse again }
          if FilenameIsNull then
            if mshown then
              mhide;

if WriteIt and not Escd then parent_menu^.Period_Name:=S
          else FileCheck:=True;

end
      else parent_menu^.Period_Name:=S;

end;

procedure Period_name_display;
    begin
      with parent_menu^ do
        SetViewPort(dataposition,ypos+2*ystep+1,Xmax-10,
                    ypos+3*ystep-1+3,ClipON);
      ClearViewPort;
      if setup_data.Misc.Automatic_name then SetColor(LightRed);
      SetTextJustify(LeftText,CenterText);
      OutTextXY(parent_menu^.margin,parent_menu^.ystep div 2,parent_menu^.Period
      View.restore;
    end;

procedure GetFileName;
    var
      FilenameIsNull,
        Changed              :Boolean;
      begin
{
  Added this line to hide the mouse again if the monitor period name
  was null when entering this function.  This is because of the extra
  mouse show that is performed in this routine below that isn't cleared
  because this is called from fish_monitoring instead of the main menu where
  it is normall called from.
```

```
}
      if parent_menu^.Period_Name='' then
        begin
          if mshown then
            mhide;
          FilenameIsNull:=True;
        end
      else
        FilenameIsNull:=False;

{ end of change -- MJ -- 1/15/91 ----- } repeat
        { quick patch to fix the problem of where the fish logo is left
          when you enter monitor period logo; normally i would patch the
          code to display the fish, but that would require a LOT more
          work.
          }
        {
          set the area to be cleared to be the part of the BMI fishlogo
          that would still be visible
          MAJ 07/14/91
        }
        setviewport(Xmax-200,17*y20+y20-10,xmax-5,17*y20+y20,clipon);
        clearviewport;
        { end patch }
        SetViewPort(5,17*Y20+y20,Xmax-5,Ymax-5,ClipON);
        SetTextStyle(DefaultFont,HorizDir,1);
        SetTextJustify(CenterText,CenterText);
        ClearViewPort;
        OutTextXY(Xcen,Y20,'Type monitor period name (8 characters max.) and pre
        OutTextXY(Xcen,Y10,'Use Backspace key to correct typing errors');
        parent_menu^.box(item,lightblue,8);
        GetString(8,1,parent_menu^.Period_Name,S2,True,False,False);
        RemoveDisallowedCharacters(S2,Changed);
        if(S2='NUL') or(S2='PRN') or(S2='CON') or(S2='AUX') or
          (S2='LPT1') or(S2='LPT2') or(S2='COM1') or(S2='COM2') or
          (S2='COM3') or(S2='COM4')then
          begin
            S2:='';
            Changed:=True;
          end;
        if Changed then
          begin
            parent_menu^.Period_Name:=S2;
            Write(#7);
            Period_name_display;
          end;
      until(S2<>'') and not FileCheck(S2,FilenameIsNull);

SetViewPort(5,17*Y20+y20,Xmax-5,Ymax-5,ClipON);
      ClearViewPort;
      parent_menu^.MouseChoice;
    end;

begin
  parent_menu:=par_menu;
```

```
   View.save;
   check_for_old_file:=False;
   if setup_data.Misc.Automatic_name then with parent_menu^ do
      begin (* inserted this change, so that if the user changed the name
            of the file with auto period name on, it would keep the name
            of the file for the user MAJ 4/11/91 *)

s1 := parent_menu^.period_name;

Auto_name(parent_menu^,False,False);

(* rest of the change, this checks to see if the name is the same
            and also checks to make sure that it is not in start up mode,
            and if it isn't in start up mode, the original filename is
            restored - MAJ 4/11/91 *)

if (parent_menu^.period_name <> s1) and (s1 <> '') then
            parent_menu^.Period_name := s1;

Period_name_display;

if FileCheck(Period_Name,False)then GetFileName else parent_menu^.MouseC
      end
   else
      if not GotoMonitoring then
         GetFileName;

View.restore;
   Period_name_display;
   mput(370,220);
   mshow; { always turn the mouse cursor on so that it will be visible
            if the operator exits fish monitoring after a recovery from
            powerloss - MAJ 5/21/91
          }
   {if not GoToMonitoring then mshow;} { Hide cursor when recovering. 2/4/91 -
   with parent_menu^ do Assign(Biofile,Period_Name+'.bmi');
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Logo(parent_menu:local_menu_ptr);
var j                  :Word;

procedure Logo_circle(x,y,r:Integer);
   begin
      SetFillStyle(SolidFill,LightGray);
      SetColor(LightGray);
      Circle(x,y,r);
      Circle(x,y,r+3);
      FloodFill(x-r-1,y,LightGray);
      Circle(x-1,y+1,r);
      Circle(x-1,y+1,r+3);
      FloodFill(x-r-2,y+1,LightGray);
      Circle(x-2,y+2,r);
      Circle(x-2,y+2,r+3);
      FloodFill(x-r-3,y+2,LightGray);
      SetFillStyle(SolidFill,white);
      SetColor(white);
      Circle(x-3,y+3,r);
```

```
      Circle(x-3,y+3,r+3);
      FloodFill(x-r-4,y+3,white);
    end;

begin
    SetBkColor(Blue);SetColor(LightCyan);
    OutTextXY(GetmaxX div 2,GetmaxY div 2,'Please wait ...');
    SetColor(white);
    SetTextStyle(TriplexFont,HorizDir,9);
    Frame;
    OutText3DExtraBoldXY(Xcen,1*Ymax div 10,'Bio-Sensor',LightGray,4);
    SetTextStyle(TriplexFont,HorizDir,4);
    Logo_circle(Xmax-42,2*Ymax div 30,18);
    OutText3DBoldXY(Xmax-45,2*Ymax div 30,'R',LightGray,3);
{$IFDEF EXP}
OutText3DBoldXY(Xcen,5*Ymax div 20,'Model 6012X    Version '+VersionNumStrGlbCons
{$ELSE}
    OutText3DBoldXY(Xcen,5*Ymax div 20,'Model 6008A    Version '+VersionNumStrGlb
{$ENDIF}
{    Logo_circle(200,170,14);}

OutText3DBoldXY(Xcen,7*Ymax div 20,'c Copyright 1991',LightGray,3);
    Logo_circle(Xcen-(textwidth('c Copyright 1991') div 2)+(textwidth('c') div 2

OutText3DBoldXY(Xcen,9*Ymax div 20,'Biological Monitoring, Inc.',LightGray,3
    OutText3DBoldXY(Xcen,11*Ymax div 20,'All Rights Reserved',LightGray,3);
    OutText3DBoldXY(Xcen,13*Ymax div 20,'P.O. Box 184, Blacksburg, VA 24063',Lig
    OutText3DBoldXY(Xcen,15*Ymax div 20,'ph. (703) 953-2821',LightGray,3);
    with parent_menu^.logo_polygon do for j:=1 to 3 do color[j]:=LightGray;
    SetColor(LightGray);
    for j:=3 downto 1 do
      begin
        SetViewPort(3*Xmax div 8+j-20,7*Ymax div 9-3,5*Xmax div 8,Ymax,ClipON);
        parent_menu^.Fish_Logo;
      end;
    with parent_menu^.logo_polygon do for j:=1 to 3 do color[j]:=white;
    SetColor(white);
    SetViewPort(3*Xmax div 8-20,7*Ymax div 9,5*Xmax div 8,Ymax,ClipON);
    parent_menu^.Fish_Logo;
    SetViewPort(0,460,Xmax,Ymax,ClipON);
    SetTextStyle(DefaultFont,HorizDir,1);
    SetTextJustify(CenterText,CenterText);
  end;
  {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$IFDEF SPECTRUM}
  procedure Amplitude_and_phase(var z:complex);
    {var        temp:single;}
  begin
    {temp:=z.x;}
    z.x:=Sqrt(Sqr(z.x)+Sqr(z.y));
{
if temp<>0 then z.y:=arctan(z.y/temp) else if z.y<>0 then
                                           z.y:=pi/2*abs(z.y)/z.y
                                           else z.y:=0;
calculation of the phase angle is disabled
}
  end;
  {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
  procedure Plot_dB_grid(var refresh,first_cycle:boolean;skip:Integer;
                         vector_size,no_of_decades:Word);
```

```
      var xlabelposition        :Integer;
          dBstr                 :String[5];
          i                     :Integer;
      begin
{     refresh:=FALSE;   at PG's request 5/9/91 }

View.save;
      SetLineStyle(DottedLn,0,NormWidth);
      with view_port_setting do SetViewPort(x1,y1,x2,y2,ClipOff);
      SetTextJustify(RightText,CenterText);
      SetTextStyle(DefaultFont,HorizDir,1);
      for i:=0 to no_of_decades-1 do
        begin
          Str(i*10:2,dBstr);
          if i>0 then dBstr:='-'+dBstr;
          SetColor(white);
          OutTextXY(Xsize+56,i*Ysize div no_of_decades,dBstr+' dB');
          SetColor(LightGray);
          Line(0,i*Ysize div no_of_decades,Xsize,i*Ysize div no_of_decades);
        end;
      SetColor(white);
      SetLineStyle(SolidLn,0,ThickWidth);
      SetTextJustify(CenterText,CenterText);
      if skip<0 then skip:=0;
      for i:=1 to 7 do
        begin
          Str(vector_size/1024*i/(skip+1):5:2,dBstr);
          xlabelposition:=(LongInt(Xsize)*240*i) div 2048;
          OutTextXY(xlabelposition,Ysize+15,dBstr);
          Line(xlabelposition,Ysize,xlabelposition,Ysize+5);
        end;
      if not setup_data.Wave.FFT then
          OutTextXY(Xsize div 2,Ysize div 2-10,'Spectral analysis is turned off');
      if first_cycle then
          OutTextXY(Xsize div 2,Ysize div 2-10,'Collecting first sample');
      View.restore;
    end;
{$ENDIF} procedure Change_Date(parent_menu:Pointer;item:Word);
  var
    S1,S2,DStr           :String;
    Done                 :Boolean;
    oy,om,od,                        (*-ow,-*)
    y,m,d,w              :Word;
    Err                  :Integer;
    current_menu         : ^menu;
    cx : word;
    j : integer;
  begin
    current_menu:=parent_menu;
    SetViewPort(5*Xmax div 14,9*Y10,11*Xmax div 14,Ymax-5,ClipON);
    SetTextStyle(DefaultFont,HorizDir,6);
    SetTextJustify(CenterText,CenterText);
    ClearViewPort;
    OutTextXY(Xcen,Y20,'Enter new date (month/day/year)');
    SetViewPort(5*Xmax div 14,9*Y10,11*Xmax div 14,Ymax-5,ClipON);
    ClearViewPort;
```

```
SetTextStyle(DefaultFont,HorizDir,1);
SetTextJustify(LeftText,CenterText);
OutTextXY(22,25,'Enter new date in');
OutTextXY(22,35,'(month/day/year) format ');
SetTextStyle(DefaultFont,HorizDir,6);
SetTextJustify(CenterText,CenterText);
GetDate(y,m,d,w);
oy:=y;
om:=m;
od:=d;
Str(m,S1);
if m<10 then S1:='0'+S1;
DStr:=S1;
Str(d,S1);
if d<10 then S1:='0'+S1;
DStr:=DStr+'/'+S1;
Str(y,S1);
DStr:=DStr+'/'+S1;
repeat
   Done:=True;
   current_menu^.box(item,lightblue,10);
   GetString(10,1,DStr,S2,False,True,False);
   S1:=Copy(S2,1,2);
   Val(S1,m,Err);
   S1:=Copy(S2,4,2);
   Val(S1,d,Err);
   S1:=Copy(S2,7,4);
   Val(S1,y,Err);
{$B+}
   if(not(m in[1..12]) or
       not(d in[1..31]) or
       ((y<1980) or(y>2076)))then
     Done:=False
   else
     begin
       case m of
         4,6,9,11:Done:=(d<=30);
         2:Done:=(d<=28) or((d=29) and(y mod 4=0));

end;
     end;
{$B-} if Done then SetDate(y,m,d) else Write(#7);
until Done;
with current_menu^ do
   begin
     SetViewPort(dataposition,ypos+(item-1)*ystep+1,Xmax-10,
                 ypos+item*ystep-1+3,ClipON);
     ClearViewPort;
     display(parent_menu,item);

oldrtm:=100;
   end;

{
   if the date changed then make check_for_old_file true,
   this will insure if automatic monitor period name generation
   is on, the data file will not be accidentally overwritten.
   02/05/91 - MAJ
```

```
      }
      if not((od=d) and(om=m) and(oy=y))then
         if setup_data.misc.automatic_name then
           begin
              auto_name(current_menu^,false,false);
              display(parent_menu,item+2);
           end;
      end;

end.
Unit Mouse;
{
 This is the mouse unit that the program uses to interface with the
 the mouse.  These are the standard function calls as defined by the
 microSOFT mouse interface.
}
Interface (*-     type curarray = array[0..31] of word;
        procedure mshape(xhot, yhot : word; var cursor : curarray);-*)
        procedure mstatus(var mstat, nbuttons : word);
        procedure mshow;
        procedure mhide;
        procedure mpos(var mbt, mx, my : word);
        procedure mput(mx,my : word);
        procedure mvlimit(minpos, maxpos : word);
        procedure mhlimit(minpos, maxpos : word);
(*-       procedure mtext(select,mask1,mask2 : word);-*)
        procedure Flush_Keyboard_Buffer;

{ôôôôôôôôôôôôôôôôôôôôôôôôôôôôôôôôôôôôôôôôôôôôôôôôôôôôôôôôôôôôôôôôôôôô}
var
  MShown  : boolean;
  MinVLim,                         {needed for SRPKEY and SRPDENT}
  MaxVLim,                         {MShown set in mshow and mhide}
  MinHLim,                         {Lim variables set in mvlimit and mhlimit}
  MaxHLim : word;
{ôôôôôôôôôôôôôôôôôôôôôôôôôôôôôôôôôôôôôôôôôôôôôôôôôôôôôôôôôôôôôôôôôôôô}

Implementation

Uses
        bmiconst,
        dos;

(*-procedure mshape;
{ xhot and yhot pixel designations for the cursor hot spot. cursor is the array
 containing the cursor shape.  curarray is array type defined as
 ARRAY[0..31] OF INTEGER } begin
   with regs do
     begin
        ax := 9;
        bx := xhot;
        cx := yhot;
        dx := Ofs(cursor[0]);
        es := Seg(cursor[0])
```

```
      end;
   intr($33, regs)
end; -*)

procedure mstatus;
{ returns mouse status and resets mouse parameters.  mstat=0 if mouse is not
  installed. -1 otherwise.  nbuttons is number of buttons enabled, =2 } begin
   regs.ax := 0;
   intr($33, regs);
   with regs do
   begin
      mstat := ax;
      nbuttons := bx
   end
end;

procedure Flush_Keyboard_Buffer;
var
  Regs : registers;
begin
  with Regs do
  begin
    AX := 3078;
    DX := 255;
  end;
   intr ($21,Regs);
end;

procedure mshow;
{ show mouse cursor } begin
   Flush_keyboard_buffer;
   regs.ax := 1;
   intr($33, regs);

{*********************************************}
   {New global variable                          }
   {*********************************************}

MShown := true;
   {*********************************************}
end;

procedure mhide;
{ hide mouse cursor } begin
   regs.ax := 2;
   intr($33, regs);

{*********************************************}
   {New global variable                          }
   {*********************************************}

MShown := false;
   {*********************************************}
```

```
end;

procedure mpos;
{ returns position of mouse, coordinates mx, my.
  if mbt=1, left button was pressed
  if mbt=2, right button was pressed
  if mbt=3, both buttons were pressed  }
begin
   regs.ax := 3;
   intr($33, regs);
   with regs do
   begin
      mbt := bx;
      mx := cx;
      my := dx
   end
end;

procedure mput;
{ put the mouse cursor at coordinates mx,my.   legal values must be suppled }
begin
   regs.ax := 4;
   regs.cx := mx;
   regs.dx := my;
   intr($33, regs)
end;

procedure mvlimit;
{ set min and max vertical limits for cursor positions }
begin
   regs.ax := 8;
   regs.cx := minpos;
   regs.dx := maxpos;
   intr($33, regs);

{*********************************************}
   {New global variables                         }
   {*********************************************}

MinVLim := minpos;
   MaxVLim := maxpos;
   {*********************************************} end;

procedure mhlimit;
{ set min and max vertical limits for cursor positions }
begin
   regs.ax := 7;
   regs.cx := minpos;
   regs.dx := maxpos;
   intr($33, regs);

{*********************************************}
   {New global variables                         }
   {*********************************************}
```

```
   MinHLim := minpos;
   MaxHLim := maxpos;
   {*******************************************}
end;

(*-procedure mtext;
{ select the text cursor.  select=0 gives software cursor, select=1 gives
  hardware cursor.  For select=0 specify screen mask and cursor mask in mask1,
  mask2.  For select=1, specify mask1=0 and mas2=no. scan lines in cursor}
begin
   regs.ax := 10;
   regs.cx := mask1;
   regs.dx := mask2;
   intr($33, regs)
end;-*)

end.
unit prtscr;
{
 interface that allows for the printing of graphics screens during
 fish monitoring.  It does this by transferring a line at a time
 in between calls to data processing.
}
interface
uses disptool,bmiconst,dos,graph,u_header,bmidisp,oldview,crt;
type
    screen_line_buffer_type=record
                            width,height:word;
                            data:array[0..Ymax,0..3] of byte;
                            end;
    screen_buffer_type=array[0..Xmax div 8,0..Ymax] of byte;
    state_type =(dumped,grabbed,pressed);
    print_screenobj = object
                    procedure vector_restore;
                    procedure vector_save(device:pointer);
                    procedure process;
                  private
                    msg:string;
                    old_handler:pointer;
                    screen_buffer:^screen_buffer_type;
                    screen_line_buffer:^screen_line_buffer_type;
                    strip :word;
                    status:state_type;
                    out_device:^text;
                    procedure grab;
                    procedure dump;
                    end;
var print_screen        :print_screenobj;
implementation
    {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
procedure Print_screen_handler;
{$F-}
interrupt;
begin
print_screen.status:=pressed;
```

```
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure print_screenobj.vector_restore;
begin
SetIntVec($5,old_handler);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure print_screenobj.vector_save(device:pointer);
begin
status:=dumped;
out_device:=device;
GetIntVec($5,old_handler);
SetIntVec($5,@print_screen_handler);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure print_screenobj.grab;
var  mem_ptr:pointer;
     i,j,k:word;
     x,y:integer;
     scr8:byte;
     LocalView:ViewObj;
begin
if not printer_status(0,msg) then
   begin
   display_message(msg,'');
   Sound(200);
   Delay(250);
   NoSound;
   status:=dumped;
   exit;
   end;
Mark(mem_ptr);
if sizeof(screen_line_buffer^)>maxavail then
   begin
   status:=dumped;
   display_message('Not enough memory for print screen operation.','');
   exit;
   end
   else New(Screen_line_buffer);
if sizeof(screen_buffer^)>maxavail then
   begin
   Release(mem_ptr);
   status:=dumped;
   display_message('Not enough memory for print screen operation.','');
   exit;
   end
   else New(Screen_buffer);
LocalView.save;
SetViewPort(0,0,Xmax,Ymax,ClipOn);
for i:=0 to 79 do
    begin
    GetImage(i*8,0,i*8+7,Ymax,Screen_line_buffer^);
    for j:=0 to Ymax do
        begin
        scr8:=0;
        for k:=0 to 2 do scr8 := scr8 or Screen_Line_buffer^.data[j][k];
        screen_buffer^[i][j] := scr8;
        end;
    end;
display_message('Screen is saved to memory.','');
```

```
LocalView.restore;
strip:=0;
status:=grabbed;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure print_screenobj.dump;
var j:word;

begin
if printer_status(0,msg) then
    if strip<80 then
       begin
       write(out_device^,''#224#1); {480 bytes}
       for j:=Ymax downto 0 do write(out_device^,Chr(screen_buffer^[strip][j]));
       write(out_device^,''#24#13);
       Inc(strip);
       end
    else
       begin
       status:=dumped;
       Dispose(Screen_buffer);
       Dispose(Screen_line_buffer);
       end;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure print_screenobj.process;
begin
case status of
     grabbed :dump;
     pressed :grab;
     end;
end;
end.unit timedate;
   {*********************************************************************}
   {                                                                     }
   { Copyright (c) Biological Monitoring, Inc. 1987, 1990                }
   {                                                                     }
   { This unit contains time and date display procedures                 }
   {                                                                     }
   {*********************************************************************}
interface uses
  graph,
  bmiconst;

function TimerSecsElapsed(TimerStart:LongInt):LongInt;
function Seconds_update:Word;
procedure Time_update(current_menu_ptr:Pointer;location:Word);
procedure Date_update(current_menu_ptr:Pointer;location:Word);
function timegr      :String;

implementation uses
   dos,
```

```
    bmimenux,
    oldview,
    menulogo;
var year,month,day,dayofweek,rtm,rth,rts,rtu:Word;
    ygr                     :String[4];
    mgr,dgr,mingr,hgr       :String[2];
    parent_menu             : ^menu;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}

{The number of ticks is multiplied by 5 and divided by 91 to return  }
{18.2 ticks per second               2/11/91 - MK                    } function TimerSecsElapsed(TimerStart:LongInt):LongInt;
var
   Now                  :LongInt;
begin
   Now:=TimerNow;
   if Now>TimerStart then
     TimerSecsElapsed:=(Now-TimerStart)*5 div 91
   else
     TimerSecsElapsed:=((Now+1572480)-TimerStart)*5 div 91;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
function Seconds_update;         { real-time second display }
type
   Time_rec            =record
                          rth,rtm,rts,rtu    :Word;
                        end;

var secgr               :String[2];
    time                :Time_rec;
begin
   View.save;
   with time do
     begin
       Gettime(rth,rtm,rts,rtu);  { read the clock }
       Str(rts,secgr);
       SetTextStyle(DefaultFont,HorizDir,1);
       if rts<10 then secgr:='0'+secgr;
     end;

SetViewPort(565,10,580,26,Clipon);
   SetTextJustify(LeftText,CenterText);
   SetColor(LightGreen);
   ClearViewPort;
   OutTextXY(0,8,secgr);          { display seconds  and restore previous viewpo
   View.restore;
   Seconds_update:=time.rts;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Time_update(current_menu_ptr:Pointer;location:Word);
var
   Timestr              :String[6];

begin
   parent_menu:=current_menu_ptr;
   View.save;
```

```
    Gettime(rth,rtm,rts,rtu);
    if parent_menu^.oldrtm=rtm then Exit;
    parent_menu^.oldrtm:=rtm;
    Str(rtm,mingr);
    Str(rth,hgr);
    if rtm<10 then mingr:='0'+mingr;
    if rth<10 then hgr:='0'+hgr;
    Timestr:=hgr+':'+mingr;
    if location=0 then
      begin
        SetTextStyle(DefaultFont,HorizDir,1);
        SetViewPort(500,10,564,26,Clipon);
        SetColor(LightGreen);
        SetTextJustify(RightText,CenterText);
        Timestr:=Timestr+':';
      end;
    ClearViewPort;
    with parent_menu^ do
        if location=0 then
          begin
             {MoveTo(64,8);}
             OutTextXY(64,8,Timestr);
          end
        else
             display(parent_menu,2); { redisplay the time } if GoToMonitoring then check_for_old_file:=False;
    if rth+rtm=0 then
      begin
          Date_update(parent_menu,location);
          check_for_old_file := true;
      end;
    if setup_data.misc.Automatic_name then
      if location=0 then {added IsMidnight boolean to Auto_name proc 4/10/91 - MK} if rth+rtm=0 then Auto_Name(parent_menu^,True,True) {Fish Monitoring}
        else
          begin
             { nothing }
          end
      else
        if check_for_old_file then {Update main menu}
          begin
            Auto_name(parent_menu^,false,false);
            Monitor_Period_Name(parent_menu,3);
            check_for_old_file:=False;
          end;
    View.restore;
end;

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Date_update(current_menu_ptr:Pointer;location:Word);
begin
  parent_menu:=current_menu_ptr;
  GetDate(year,month,day,dayofweek);
  Str(year,ygr);
  {ygr:=Copy(ygr,3,2);}              {remarked out to force 4 char year string - 1/
```

```
      Str(month,mgr);
      if month<10 then mgr:='0'+mgr;
      Str(day,dgr);
      if day<10 then dgr:='0'+dgr;
      parent_menu^.Datestr:=mgr+'/'+dgr+'/'+ygr;
      View.save;
      if location=0 then           { Fish Monitoring }
        begin
          SetTextStyle(DefaultFont,HorizDir,1);
          SetViewPort(500,27,583,43,Clipon);
          SetColor(LightGreen);
          SetTextJustify(RightText,CenterText);
          ClearViewPort;
          with parent_menu^ do if location=0 then OutTextXY(81,8,Datestr);
        end
      else
        begin
          display(parent_menu,1); { show the date }
        end;
      View.restore;

end;
   {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
   function timegr      :String;
   var
      sngr : string;
   begin
      GetDate(year,month,day,dayofweek);
      Str(year,ygr);
      ygr:=Copy(ygr,3,2);
      Str(month:2,mgr);
      Str(day,dgr);
      if day<10 then dgr:='0'+dgr;
      Gettime(rth,rtm,rts,rtu);
      Str(rtm,mingr);
      if rtm<10 then mingr:='0'+mingr;
      Str(rth,hgr);
      if rth<10 then hgr:='0'+hgr;
      str(rts,sngr);
      if rts<10 then sngr := '0'+sngr;
      timegr:=mgr+'/'+dgr+'/'+ygr+' '+hgr+':'+mingr;
   end;
end.
unit alarmhan;
{

This module is the interface to the DAS-16 didgit outputs for digital
alarms.

The interface is an object that insulates the caller from the details
about the DAS-16.  To activate an input, simply call the activate
method and tell it how long you like the alarm to be on in seconds.

Then all you have to do is repeatedly call the monitor method over and
over in the main loop of the bio-sensor.  When the time has expired the
monitor will automatically turn off the alarm outputs at the appropriate
time.

}
```

```
interface uses bmiconst,crt,das16;

const
   number_of_alarms = 4;
   sampler      = 1;
   biological   = 0;
   physchemical = 2;
   bio_phys     = 3;

type
   alarm_handler = object
                     procedure init;
                     procedure activate(chan,duration : integer);
                     procedure deactivate(chan : integer);
                     procedure monitor;
                     function alarms_active : boolean;
                     function active(chan : integer) : boolean;
                     private channel_expires: array[0..number_of_alarms-1] of longint;
                     channel_active : array[0..number_of_alarms-1] of boolean;
                     procedure write_to_d16;
                   end;
var
   alarm_out : alarm_handler;

implementation function alarm_handler.active(chan : integer) : boolean;
{
 determines if a given output channel is active.
}
begin
 active := channel_active[chan];
end;

procedure alarm_handler.init;
var
 channel : integer;
begin
   for channel := 0 to number_of_alarms -1 do
      begin
         channel_expires[channel] := 0;
         channel_active[channel] := false;
      end;
   write_to_d16; { set the proper outputs }
end;

procedure alarm_handler.write_to_d16;
{
 This function handles calculating what port value to write to the
 DAS-16 in order to get the proper outputs activated.
}
var
   bin_count,
```

```
        channel,out_val : integer;
begin
   out_val := 0; { start by outputting the absence of a signal }
   bin_count := 1; { counter to keep track of what value to output}
   for channel:=0 to number_of_alarms-1 do
      begin
         if channel_active[channel] then
            out_val := out_val + bin_count;
         bin_count := bin_count * 2;
      end;
   d16.bous(out_val);
end;

function alarm_handler.alarms_active: boolean;
{

Determines if there are any alarms currently active.  This function
 only determines the logical state of the alarm outputs, it does not
 query the hardware to insure that the alarms are indeed on.

}
var
   active_alarms : boolean;
   channel : integer;
begin active_alarms := false;

for channel := 0 to number_of_alarms-1 do
      if channel_active[channel] then
         active_alarms := true;

alarms_active := active_alarms;

end;

procedure alarm_handler.activate(chan,duration : integer);
{

This function will activate a given channel for a duration of
 seconds.  If the monitor method is called often enough the alarm
 will expire in "duration" seconds.

}
begin
   { only operate on valid channels }
   if not (chan in [0..number_of_alarms-1]) then exit;
   channel_active[chan] := true;
   channel_expires[chan] := timernow + 18 * longint(duration);
   write_to_d16; { make sure the proper outputs are on }
end;

procedure alarm_handler.deactivate(chan : integer);
{
 This function will deactivate a given channel.  If the channel
 is already inactive, the system will not be adversely effected.
}
```

```
begin
  { deativate the channel }
  channel_active[chan] := false;
  write_to_d16; { make sure the proper outputs are on }
end;

procedure alarm_handler.monitor;
{
 This channel monitors the expiration times of the channels and deactivates
 the channels as needed.  This function makes use of the constant
 variable TIMERNOW (defined in BMICONST) that gives the current clock tick
 of the CPU.  The expiration times are recorded in terms of timer ticks
 (18.2 a second) since this give a flat time system that requires no
 conversion to compare times.
}
var
  channel_num : integer;
begin
    for channel_num := 0 to number_of_alarms -1 do
        { see if the channel is active }
        if channel_active[channel_num] then
            { yes, now see if the time duration on the given
              channel has expired }
            if timernow >= channel_expires[channel_num] then
                deactivate(channel_num); { turn the alarm output off }
end;

end.
program bio;
{**********************************************************************
{
{ Copyright (c) Biological Monitoring, Inc. 1987, 1991
{
{ Waterloo project to be delivered March 1991
{ Use Compile/Build after change in Options/Compile/Conditional defines
{ Compiler directives list:
{          SCOUT         - adds Hydrolab SCOUT interface for physiochemical data
{                          uses serial port COM2
{          SCOUTDAC      - outputs SCOUT data to an additional D/A output
{                          use only with SCOUT directive enabled
{          ANALOGPH      - analog physiochemical interface
{                          uses DASH-16 board
{          NOLOGO        - suppresses initial logo screen for faster execution
{                          Never use in final version!
{          SPECTRUM      - spectral analysis of fish ventilatory waveform enabled
{          RINGBACK      - use password to call back the station which initialize
{          EXP           - experimental version with 12 fish tanks enabled
{                          cannot be enabled together with ANALOGPH.
{                          If disabled 8 fish tanks are used.
{          PROTECT       - If defined, enables parallel key copy protection.
{                          See BMISECUR.PAS.
{          FAHRENHEIT    - Sets Scout(R) automatic configuration to ½F.
{                          If disabled configuration set to ½C.
{          JTU           - Sets maximum turbidity to 200 Jackson Turbidity Units
{                          Otherwise sets max to 300 Formazine Turbidity Units
{          RAWDATA       - Allows dumping raw data to disk when Alt F1 is pressed
{          MICROCHANNEL
```

```
{                    - use for uCDAS16 A/D board
{         WATERLOO   - Determines if there should be an external signal
{                      present to trigger the water sampler in case of a
{                      Biological Alarm
{*****************************************************************************

{
*****************************************************************************
Waterloo Compiler directives needed:
analogph - scout - scoutdac - protect - ringback - waterloo Sydney Compiler directives needed:
scout - protect - ringback - microchannel NOTE: Sydney.tp in the D:\50 directory does not have the microchannel
directive because BMI does not have a microchannel board or machine
on which to test.

*****************************************************************************
}

{$N-}                              { No math coprocessor}
{$E-}                              { No emulation }

{$IFDEF EXP}
  {$IFDEF ANALOGPH}
    writeln('You can''t define analogph and have the EXP version too');
  {$ENDIF}
{$ENDIF}

{$IFDEF SPECTRUM}
{$N+}                              { Use math coprocessor for spectral analysis }
{$ENDIF} uses
{.U-}
  Graph,                           { graphics library }
  dos,                             { operating system library }
  crt,                             { display library }
{.U+}
  disptool,
  das16,
  mouse,                           { mouse library }
  bmiconst,                        { constant definitions and data types }
  bmikey,                          { keyboard handler }
  (*-bmident,-*)                   { data entry library }
  filecopy,                        { file copying library}
  bmisecur,                        { hardware key/security unit }
  bmiinit,                         { initialization routines }
  timedate,                        { time and date functions }
  menulogo,                        { menu system }
  bmimenux,                        { menu manipulations }
  bmidisp,                         { data display }
  files,                           { disk maintenance }
  alarmhan,                        { handler to trigger alarm outputs }
{.U-}
  printer,                         { printer communication }
{.U+}
  U_header,                        { printing the header with setup data }
```

```
        prtscr,                         { print screen }
        bmimodem,                       { communication with remote computer or termin
        dgt_rtne                        { digital I/O routines}

{$IFDEF SPECTRUM}
        ,tp4fft                         { Discrete Fourier transformation }
        ,xmm_unit
{$ENDIF}
{$IFDEF SCOUT}
        ,U_Scout                        { Scout interface library }
{$ENDIF}
        ;
const {$IFDEF SPECTRUM}
    no_of_decades       =8;             {For spectrum display}
{$ENDIF}
    Xtal                =10;            {timer clock rate jumper setting} var
{$IFDEF SPECTRUM}
    FFT_Data            :complex_array_type;
    FFT_Window          :real_vector_ptr;
    sincos,FFT2         :complex_vector_ptr;
    XMM                 :XMMObj;
{$ENDIF}
    decay               :Real;          { variables for data acqusition } minimum_threshold, skip,skip_index,
    elapsed_minutes     :Integer;

processing_count    : Word;
    absolute_count      :longint;
    extra_parameters,
    refresh,
    waveform_analysis   :Boolean;

nul                 :Text;          { dummmy printer output }

{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Shift_sample_history(chx:Integer);
  { Shifts the samples collected from channel chx by 1 }
  { Used in moving average algorithm                   }
  { Called by Alarm_Sensor procedure                   }
  var i                 :Integer;
begin
  with PL do
    begin
      for i:=1 to setup_data.bio.sample_size.actual-1 do
        begin
          period_freqs[i][chx]:=period_freqs[i+1][chx];
          period_amplitudes[i][chx]:=period_amplitudes[i+1][chx];
          direction_changes[i][chx]:=direction_changes[i+1][chx];
        end;
      period_freqs[setup_data.bio.sample_size.actual][chx]:=period_sum_freq[ch
      period_amplitudes[setup_data.bio.sample_size.actual][chx]:=period_sum_am
      direction_changes[setup_data.bio.sample_size.actual][chx]:=direction_cha
```

```
      end;
  end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
  function ParseBioStr(BStr:String;Num:Integer):String;

{*****************************************************************}
    {This function parses the data string for output to the printer or file.}
    {It is called only from procedure Alarm_Sensor. BStr is an element of  }
    {array Biostr[x], defined in procedure Alarm_Sensor.  Returned string  }
    {contains data selected for output during printer/file option setup    }
    {in Log Info/Setup/Misc/Printer or /File options.                      }
    {******************* 10/27/90 - MK ****************************} var
      S                       :String;
      count,
      i                       :Integer;
    begin
      count:=0;
      S:=Copy(BStr,1,2);              {copy ' *', ' W', or ' ' from left of BioStr}
      for i:=0 to 4 do
        begin
          if Num=1 then               { 1 = disk }
            begin
              if setup_data.misc.PrinterFileOpt.fileopt[i+1]then
                begin
                  S:=S+Copy(BStr,3+(i*5),5);
                  Inc(count);
                end;
            end
          else if Num=2 then          { 2 = printer }
            begin
              if setup_data.misc.PrinterFileOpt.printopt[i+1]then
                begin
                  S:=S+Copy(BStr,3+(i*5),5);
                  Inc(count);
                end;
            end
          else
            S:=S+' #.##';
        end;
      if((Num=1) and setup_data.misc.PrinterFileOpt.fileopt[6]) or
        ((Num=2) and setup_data.misc.PrinterFileOpt.printopt[6])then
        S:=S+Copy(BStr,28,7);
      ParseBioStr:=S;
    end;

{$IFDEF ANALOGPH}
  function CheckAnalogPhysChemAlarm:Boolean;
    {*****************************************************************}
    { This function is called by End_processing to determine the alarm status}
    { of the analog physiochemical sensors.  It is FALSE if no alarm exists, }
    { TRUE and  if any of the sensors are outside their respective limits.   }
    {                        12/1/90 - Mark Kaynor                           }
    {*****************************************************************}
    var
      B                       :Boolean;
      Index                   :Integer;
```

```
    begin
      Index:=number_of_fish;
      B:=False;
      with setup_data.Analog_Phys do
        begin
          if setup_data.assignment[Index]=0 then
            with Ammonia do
              if(actual<min) or(actual>max)then B:=True;
          Inc(Index);
          if setup_data.assignment[Index]=0 then
            with Temperature do
              if(actual<min) or(actual>max)then B:=True;
          Inc(Index);
          if setup_data.assignment[Index]=0 then
            with pH do
              if(actual<min) or(actual>max)then B:=True;
          Inc(Index);
          if setup_data.assignment[Index]=0 then
            with Conductivity do
              if(actual<min) or(actual>max)then B:=True;
          Inc(Index);
          if setup_data.assignment[Index]=0 then
            with O2 do
              if(actual<min) or(actual>max)then B:=True;
          Inc(Index);
          if setup_data.assignment[Index]=0 then
            with Turbidity do
              if(actual<min) or(actual>max)then B:=True;
          Inc(Index);
          if setup_data.assignment[Index]=0 then
            with extra1 do
              if(actual<min) or(actual>max)then B:=True;
          Inc(Index);
          if setup_data.assignment[Index]=0 then
            with extra2 do
              if(actual<min) or(actual>max)then B:=True;
        end;
      CheckAnalogPhysChemAlarm:=B;
    end;
{$ENDIF}

{$IFDEF SCOUT}
  function CheckScoutPhysChemAlarm:Boolean;
    {****************************************************************}
    { This function is called by End_processing to determine the alarm status}
    { of the Scout physiochemical sensors.  It is FALSE if no alarm exists,  }
    { and TRUE if any of the sensors are outside their respective limits,    }
    { assuming the parameter is in ACTIVE state.                             }
    {                          12/1/90 - Mark Kaynor                         }
    {****************************************************************}
  var
    B                  :Boolean;
    Index              :Integer;
  begin
    B:=False;
{$IFDEF ANALOGPH}
    Index:=number_of_fish+number_of_analog_parameters;
{$ELSE}
    Index := number_of_fish;
{$ENDIF}
```

```
         with setup_data.Scout_Phys do
           begin
             if setup_data.assignment[Index]=0 then
               with Temperature do
                 if(actual<min) or(actual>max)then B:=True;
             Inc(Index);
             if setup_data.assignment[Index]=0 then
               with O2 do
                 if(actual<min) or(actual>max)then B:=True;
{$IFNDEF SCOUTDAC}
             Inc(Index);
             if setup_data.assignment[Index]=0 then
               with Conductivity do
                 if(actual<min) or(actual>max)then B:=True;
             Inc(Index);
             if setup_data.assignment[Index]=0 then
               with pH do
                 if(actual<min) or(actual>max)then B:=True;

{ next two for later if needed - 12/1/90 - Mark Kaynor}
           { with O2p do
               if (actual < min) or (actual > max) then B := TRUE;}
           { with battery do
               if (actual < min) or (actual > max) then B := TRUE;}
{$ENDIF}
           end;
       CheckScoutPhysChemAlarm:=B;
     end;
{$ENDIF} function Is_Parameter_in_Alarm(Channel_active:Integer;Prec:RealDatatype):Strin
{
This function determins if the record passed to it exceeds either it's
minimum or maximum value.  If if the actual value is outside the range,
the function returns a 'P ' to be printed by the caller to denote an
physiochemical alarm on the printout and diskfile.

modified to check for channeal activity..if a given channel is not active
it does not check for an alarm like it should.
called from:
Alarm_sensor Written by : MAJ - 1/14/91

}
   var
     tstring              :String;
   begin
     if Channel_active=0 then
       begin
         with Prec do
           if(actual<min) or(actual>max)then
             tstring:='P '
           else
             tstring:='  ';
       end
     else
       tstring:='  ';
     Is_Parameter_in_Alarm:=tstring;
```

```
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure Alarm_Sensor(var current_menu:menu;var Remote:RemoteObj;ScoutDataLoc
                AnalogAlarm,ScoutAlarm:Boolean);
{ Performs statistical analysis of fish data and checks physiochemical data
{ Called by End_Processing procedure
{

This is a key procedure to the Bio-Sensor System.  It calculates the
  mean frequency and amplitude of each fish in the bio-sensor.

The bio-sensor keeps track of the mean frequencies and amplitudes over
  a period minutes and calculates the standard deviation.  When the mean
  frequency gets out of range of the other samples collected by a certain
  amount (usually 4 standard deviations) an alarm is triggered.

This procedure also monitors a variety of physiochemical parameters from
  such input sources as the SCOUT or analog PH equipment such as that
  supplied to CANADA.  If a given reading is out of range an alarm is
  triggered.

When an alarm is triggered a number of digital IO channels are activated
  to control extraneous events.
  digital output 0 - triggers the water sampler
  digital output 1 - triggers the biological alarm
  digital output 2 - triggers the physiochemical alarm
  digital output 3 - triggers an alarm when both a biological and
                     physiochemical alarms occur.
} var k,i,
Index,
reference_warning,
active_warning        :Integer;
mfreq,
meanfreq              :array[0..number_of_fish-1]of Real;
msg                   :String;
hstring               :String[10];
Biostr                :array[0..number_of_fish-1]of String[36];

BioAlarm              :String[5];

StdStr,                        {StdStr and MavStr allow '----' }
{in BioStr during calibration  }

MavStr                :String[6];

TempStr,
Timestr               :String[30]; { extended the length of these to
                                     allow complete alarm messages
                                     MAJ-MK 10/15/91 } analog_phystr         :String[60];

scout_phystr          :String[40];
greenalarm,
yellowalarm,
```

```
        (*- dummy, -*)
        redalarm              :Boolean;
        DigitalIn,
        DigitalOut            :BooleanArray4;

begin
    active_warning:=0;reference_warning:=0;
    Timestr:=Timegr;
    { change made to prevent a crash MAJ 1/29/91 }
    if DiskFree(0)<50000 then
      with current_menu do
        begin
          Period_name:='NUL';
          Assign(Biofile,Period_name);
          Rewrite(Biofile);
          Close(Biofile);
          SetBkColor(RED);
          Alarm_flag:=True;
          display_message('Disk is full. Data are not written to disk.',
                          'Move files to the floppy disk,')
        end;

analog_phystr:=' ';
    scout_phystr:=' ';
    Index:=number_of_fish;
{$IFDEF ANALOGPH}
    {
    check to see if any of the analog physiochemical parameters are
    out of range.  IE. dissolved oxygen too high or too low.
    }
    with setup_data do
      begin
        if assignment[Index]=0 then
          Str(Analog_Phys.Ammonia.actual:5:1,hstring)
        else hstring:='I....';
        analog_phystr:=analog_phystr+hstring+Is_Parameter_in_Alarm(assignment[In
        Inc(Index);
        if assignment[Index]=0 then Str(Analog_Phys.Temperature.actual:5:1,hstri
        else hstring:='I....';
        analog_phystr:=analog_phystr+hstring+Is_Parameter_in_Alarm(assignment[In
        Inc(Index);
        if assignment[Index]=0 then Str(Analog_Phys.O2.actual:4:1,hstring)
        else hstring:='I...';
        analog_phystr:=analog_phystr+hstring+Is_Parameter_in_Alarm(assignment[In
        Inc(Index);
        if assignment[Index]=0 then Str(Analog_Phys.pH.actual:4:1,hstring)
        else hstring:='I...';
        analog_phystr:=analog_phystr+hstring+Is_Parameter_in_Alarm(assignment[In
        Inc(Index);
        if assignment[Index]=0 then Str(Analog_Phys.Conductivity.actual:5:0,hstr
        else hstring:='I....';
        analog_phystr:=analog_phystr+hstring+Is_Parameter_in_Alarm(assignment[In
        Inc(Index);
        if assignment[Index]=0 then Str(Analog_Phys.Turbidity.actual:5:1,hstring
        else hstring:='I...';
        analog_phystr:=analog_phystr+hstring+Is_Parameter_in_Alarm(assignment[In
        Inc(Index);
        if extra_parameters then
          begin
            if assignment[Index]=0 then Str(Analog_Phys.extra1.actual:5:0,hstrin
```

```
                else hstring:= I....';
                analog_phystr:=analog_phystr+hstring+Is_Parameter_in_Alarm(assignmen
                Inc(Index);
                if assignment[Index]=0 then Str(Analog_Phys.extra2.actual:5:0,hstrin
                else hstring:='I....';
                analog_phystr:=analog_phystr+hstring+Is_Parameter_in_Alarm(assignmen
                Inc(Index);
              end
            else
              Inc(Index,2);
        end;
     Index:=number_of_fish+number_of_analog_parameters; { Fix PG 1/15/91}
{$ELSE}
   Index := number_of_fish;
{$ENDIF}
{$IFDEF SCOUT}
      if (setup_data.Scout_Phys.Data_Valid) or (scout.scout_state = valid_data) th
        begin
          hstring := '';
          with setup_data do
            begin
              if assignment[Index]=0 then
                begin
                  Str(Scout_Phys.Temperature.actual:5:1,hstring);
                  scout_phystr:=scout_phystr+hstring+Is_Parameter_in_Alarm(assignm
                  hstring:='';
                end
              else
                Scout_Phystr:=Scout_phystr+'I....   ';
              Inc(Index);
              if assignment[Index]=0 then
                begin
                  Str(Scout_Phys.O2.actual:4:1,hstring);
                  scout_phystr:=scout_phystr+hstring+Is_Parameter_in_Alarm(assignm
                  hstring:='';
                end
              else
                Scout_phystr:=Scout_Phystr+'I...   ';
              Inc(Index);
              if number_of_scout_parameters >= 3 then
                begin
                  if assignment[Index]=0 then
                    begin
                      Str(Scout_Phys.pH.actual:4:1,hstring);
                      scout_phystr:=scout_phystr+hstring+Is_Parameter_in_Alarm(ass
                      hstring:='';
                    end
                  else
                    Scout_phystr:=Scout_phystr+'I...   ';
                  Inc(Index);
                end;
              if number_of_scout_parameters >= 4 then
                begin
                  if assignment[Index]=0 then
                    begin
                      Str(Scout_Phys.Conductivity.actual:5:0,hstring);
                      scout_phystr:=scout_phystr+hstring+Is_Parameter_in_Alarm(ass
                      hstring:='';
                    end
                  else
```

```
                        scout_phystr:=Scout_phystr+'I....  ';
                    Inc(Index);
                end;
            end;
        end
    else
        if (not setup_Data.scout_phys.data_valid) or (scout.scout_state <> valid_d
            case scout.scout_state of
                valid_data,
                reconnected:
                                        scout_phystr:='  Configured';
                disconnected:
                                        scout_phystr:='  Disconnected';
                else
                    scout_phystr:=                  '  ERROR';
            end;

{$ENDIF}

{ This part of the code was nearly impossible to read so I rearranged it }
    { and indented it, etc.   MK - 2/6/91                                    } if elapsed_minutes=setup_data.bio.assessment_interval.actual then {end of as
        begin
            redalarm:=False;
            yellowalarm:=False;
            greenalarm:=False;

{
              this loop calculates the mean frequency, standard deviation and
              other parameters such as mean amplitude etc.
            }
            for k:=0 to number_of_fish-1 do
                begin                       {channel loop}
                    if setup_data.assignment[k]=2 then {skip calculations if inactive}
                        begin
                            Biostr[k]:=' I';
                            MavStr:='....';
                            StdStr:='......';
                        end
                    else begin                   {if active}
                            with setup_data.bio do
                                mfreq[k]:=PL.period_sum_freq[k]/
                                        (2.0*acquisition_period*assessment_interval.actual);
                            { this has to be calculated independent of calibration - PG}
                            with PL do
                                if calibration[k]then
                                    begin               {calibration}
                                        Biostr[k]:=' *';
                                        StdStr:='-----';
                                        MavStr:='----';
                                        sample_num[k]:=sample_num[k]+1;
                                        if setup_data.bio.moving_average then period_freqs[sample_
                                        AlarmSensorS1[k]:=Sqr(mfreq[k])+AlarmSensorS1[k];
                                        AlarmSensorS2[k]:=mfreq[k]+AlarmSensorS2[k];
                                        warning_count[k]:=0;
                                        if(mfreq[k]<setup_data.bio.minimum_frequency.actual)then
                                            begin
```

```
            warning[k]:=True;
            Biostr[k]:='W*';
            if setup_data.assignment[k]=0 then Inc(active_warning)
            if setup_data.assignment[k]=1 then Inc(reference_warni
          end;
          with setup_data.bio do
            if sample_num[k]=sample_size.actual then
              begin       {end calibration}
                meanfreq[k]:=AlarmSensorS2[k]/sample_size.actual;
                sdev[k]:=Sqrt(Abs((AlarmSensorS1[k]-
                              Sqr(AlarmSensorS2[k])/sample_size
                              (sample_size.actual-1)));
                AlarmSensorS1[k]:=0;AlarmSensorS2[k]:=0;
                sample_num[k]:=0;
                calibration[k]:=False;
              end;
      end             {calibration}
    else with setup_data.bio do
      begin           {if not calibration}
        if moving_average then
          begin
            AlarmSensorS1[k]:=0;
            AlarmSensorS2[k]:=0;
            for i:=1 to sample_size.actual do
              begin
                AlarmSensorS1[k]:=Sqr(period_freqs[i][k]/
                              (2.0*acquisition_period*asse
                AlarmSensorS2[k]:=period_freqs[i][k]/
                              (2.0*acquisition_period*assessme
              end;
          end;
        meanfreq[k]:=AlarmSensorS2[k]/sample_size.actual;
        if setup_data.assignment[k]<2 then
          Str(meanfreq[k]:4:2,MavStr)
        else MavStr:='....';

sdev[k]:=Sqrt(Abs((AlarmSensorS1[k]-
                      Sqr(AlarmSensorS2[k])/sample_size.actua
                      (sample_size.actual-1)));
        if setup_data.assignment[k]<2 then
          Str(sdev[k]:5:3,StdStr)
        else StdStr:='.....';
        if(Abs(mfreq[k]-meanfreq[k])>Acceptable_std_dev.actual*sde
        or(mfreq[k]<minimum_frequency.actual)then
          begin    {warning}
            warning[k]:=True;
            Biostr[k]:=' W';
            if setup_data.assignment[k]=0 then Inc(active_warning)
            if setup_data.assignment[k]=1 then Inc(reference_warni
            warning_count[k]:=warning_count[k]+1;
            if((warning_count[k]>=Recalc_after_warnings.actual) an
              then calibration[k]:=True;
          end       {warning}
        else
          begin    {no warning}
            Biostr[k]:='  ';
            warning[k]:=False;
            warning_count[k]:=0;
            if moving_average then Shift_sample_history(k);
          end;     {no warning}
```

```
                end;            {if not calibration}
            end;                {if active} if setup_data.assignment[k]>1 then
            hstring:='....'
        else Str(mfreq[k]:4:2,hstring);

Biostr[k]:=Biostr[k]+hstring+' ';  {average frequency} if setup_data.assignment[k]>1 then
            hstring:='....'
        else
            with PL do
                if period_sum_freq[k]>0 then
                    Str(max_input/4096*period_sum_amplitude[k]/period_sum_freq[k]:
                else
                    hstring:='0.00';

Biostr[k]:=Biostr[k]+hstring+' ';  {average amplitude} if setup_data.assignment[k]>1 then
            hstring:='....'
        else
            Str(PL.last_freq[k]/(2*60.0):4:2,hstring);

Biostr[k]:=Biostr[k]+hstring+' ';  {last minute frequency} if setup_data.assignment[k]>1 then
            hstring:='....'
        else
            Str(PL.last_amplitude[k]:4:2,hstring);

Biostr[k]:=Biostr[k]+hstring+' ';  {last minute amplitude}

Biostr[k]:=Biostr[k]+MavStr+' ';   {moving average}

Biostr[k]:=Biostr[k]+StdStr+' ';   {std. deviation} end;                        {channel loop}

{
 the following check to see what kind of alarm occurred if any
 See Dave to understand the logic and rationale behind the
 A,B and C alarms.
}
    if active_warning>=setup_data.bio.warnings_for_alarm.actual then
        begin
            if reference_warning=0 then
                begin
                    redalarm:=True;
                    BioAlarm:='A ';
                end
            else
                begin
                    yellowalarm:=True;
                    {$IFDEF EXP}
                    BioAlarm:='B ';
```

```
                {$ELSE}
                BioAlarm:='A ';
                {$ENDIF}
              end;
          end
        else if active_warning+reference_warning>=setup_data.bio.warnings_for_al
          begin
            greenalarm:=True;
            {$IFDEF EXP }
            BioAlarm:='C ';
            {$ELSE}
            BioAlarm:='A ';
            {$ENDIF}
          end
        else BioAlarm:=' ';
      with current_menu do
        begin
          Append(Biofile);
          Write(Biofile,Timestr);
          for k:=0 to number_of_fish-1 do
            Write(Biofile,ParseBioStr(Biostr[k],1)); {file=1,printer=2}
          Write(Biofile,BioAlarm);
          WriteLn(Biofile,' '+analog_phystr+scout_phystr);
          Close(Biofile);
        end;

(*    {call function DGT_IO.InDta - set array DigitalIn = digital inputs} if DGT_IO.InDta then display_message('','Error reading digital inputs');
      DigitalIn:=DGT_IO.digit;

{reset the DGT_IO.digit array elements to FALSE and init array DigitalOu
      DGT_IO.Init(board_num);
      DigitalOut:=DGT_IO.digit; *)

{check for physiochemical alarms}
      if ScoutAlarm then TempStr:='Scout (R) physiochemical';
      if AnalogAlarm then TempStr:='Physiochemical';

{if physiochemical alarm then display status and set array element TRUE}
      if (AnalogAlarm or ScoutAlarm)
          and not (redalarm or yellowalarm or greenalarm) then
        begin
          Remote.Alarm_Start(TempStr);
          Alarm_Display(TempStr);
          with alarm_out do
            begin
              { turn on the sampler and the physiochemical outputs }
              activate(sampler,setup_data.misc.alarm_duration.actual);
              activate(physchemical,setup_data.misc.alarm_duration.actual);
            end;
{         DigitalOut[PhysChemAlarmOutput]:=True;
          DGT_IO.AlarmSet:=True;}
        end;

{check for biological alarms}

{
      The following code sees what alarms ocurred and then triggers
      the appropriate alarm
```

```
      }
      if redalarm then TempStr:='Biological';
      if yellowalarm then TempStr:='Biological B';
      if greenalarm then TempStr:='Biological C';

if AnalogAlarm or ScoutAlarm then
          TempStr := TempStr + ' & Physiochemical';

{if biological alarm then display message and set array element TRUE}
      if redalarm or greenalarm or yellowalarm then
         begin (*

{$IFDEF WATERLOO }
             { make sure that the RTU isn't inhibiting the sampler }
             if DigitalIn[IntSamplerOverrideInput] then {$ELSE}
              if DigitalOut[IntSamplerOutput] then
             {$ENDIF}
                DigitalOut[IntSamplerOutput]:=False
             else
                DigitalOut[IntSamplerOutput]:=True;
             DigitalOut[BioAlarmOutput]:=True;
             DGT_IO.AlarmSet:=True;

*)

if ScoutAlarm or AnalogAlarm then
                   begin
                       { have both physiochemical and bio alarm so trigger
                         the phys/biological alarm output and the sampler }
                       with alarm_out do
                           begin
                               activate(sampler,setup_data.misc.alarm_duration.actual);
                               activate(bio_phys,setup_data.misc.alarm_duration.actual)
                           end;
                   end
               else
                   { trigger just a biological alarm and the sampler }
                   begin
                       with alarm_out do
                           begin
                               activate(sampler,setup_data.misc.alarm_duration.actual);
                               activate(biological,setup_data.misc.alarm_duration.actua
                           end;
                   end;
            Remote.Alarm_Start(TempStr);
            Alarm_Display(TempStr);
         end;

(*   {set alarm time for elapsed timer - New functions above - 2/8/91 - MK}
     DGT_IO.TimerStart:=TimerNow;

{set digital outputs via call to DGT_IO.OutDta function}
     DGT_IO.digit:=DigitalOut;
     if DGT_IO.OutDta then display_message('','Digital output error'); *)

current_menu.Alarm_flag:=redalarm or yellowalarm or greenalarm
```

```
                                        or ScoutAlarm or AnalogAlarm;
         if Printer_status(0,msg)then with current_menu do
           begin
             Write(printer_output^,#15+Timestr);
             for k:=0 to number_of_fish-1 do
               Write(printer_output^,ParseBioStr(Biostr[k],2));
             Write(printer_output^,BioAlarm);
{$IFDEF ANALOGPH}
             WriteLn(printer_output^,analog_phystr);
{$ENDIF}
{$IFDEF SCOUT}
             calc_ScoutDataLoc(ScoutDataLoc);
{$IFDEF ANALOGPH}
             for i:=1 to ScoutDataLoc do
               Write(printer_output^,' ');
             Write(printer_output^,'        Scout :');
{$ENDIF}
             WriteLn(printer_output^,scout_phystr);
{$ENDIF}
           end;

if(redalarm or yellowalarm or greenalarm)then {calibration after alarm}
           for k:=0 to number_of_fish-1 do with PL do
             begin
               {warning[k]:=False;}
               warning_count[k]:=0;
(***************************************************************************
   Remarked out to disable mandatory recalibration after alarm
   as requested by Dave - 2/6/91 - MK, corrected - 2/8/91 - PG
         calibration[k]:=TRUE;
****************************************************************************)
             end;

end;                        {end of assessment period}
   end;
   {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$IFDEF SPECTRUM}
  procedure Spectrum_display(ch:integer;var msg:string;FirstCycle:boolean);
  {
   Spectrum display plots the waveform spectrum generated by the DFFT in
   the experimental 6012X unit.  It uses extensive use of Extended memory
   so be careful when modifying.
  }
  var i,j:word;
  begin
  with setup_data.wave do
  if FFT then with XMM do
             begin
               with MoveX do
                   begin
                   length:=sizeof(complex)*vector_size;
                   sourcehandle:=handle[ch];
                   sourceoffset:=0;
                   desthandle:=0;
                   destoffset:=longint(FFT2);
                   end;
               if not MoveExtended then
                 begin
                 Str(Error,msg);
```

```
                    display_message('Extended memory move error:'+msg,'');
                    end;
                for i:=0 to Vector_size div 2-1 do
                    Amplitude_and_phase(FFT2^[i]);
            ClearViewPort;
            if skip<0 then skip:=0;
            Plot_dB_grid(refresh,firstcycle,skip,Vector_size,no_of_decades);
            if waveform_analysis then with PL do
                FS_display(last_freq[ch]/(2.0*acquisition_period),
                            last_amplitude[ch],sdev[ch],ch);
            if not FirstCycle then
                begin
                if FFT2^[0].x>0 then
                    MoveTo(0,Round(-0.4343*2*ln(FFT2^[0].x/max_input)*Ysize/no_o
                for j:=1 to Vector_size div(2*(skip+1))-1 do
                    if FFT2^[j].x>0 then
                        LineTo((j*LongInt(2*Xsize))*(skip+1) div Vector_size,
                        Round(-0.4343*2*ln(FFT2^[j].x/max_input)*Ysize/no_of_dec
                end;
            end;
    end;
{$ENDIF}
    {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
    procedure End_processing(var first_cycle:Boolean;channum:Integer;PlotWidth:Wor
                            var xpt,ypt        :Integer;var current_menu:menu;va
                            var msg:String;ScoutDataLoc:Integer);
    {
    This procedure acts as an interface between the alarm sensor system that
    evaluates if an alarm has ocurred. It also handles resetting the
    frequency and amplitude arrays.

}
    var
        tsec100,tdayofweek  :Word;    { used to calculate start of interval for hist
                                        files - MAJ 1/19/91 }
        i,q,q1              :Integer;
{$IFDEF SCOUT}
        Scout_Error         :Word;
{$ENDIF}
        AnalogAlarm,
        ScoutAlarm          :Boolean;

begin
    AnalogAlarm:=False;
    ScoutAlarm:=False;
    first_cycle:=False;            { used for first minute of monitoring only }
    for q:=0 to number_of_fish-1 do
        begin                       {fish process}
        with PL do
            if last_freq[q]>0 then
                last_amplitude[q]:=max_input/4096*old_sum_amplitude[q]/last_freq[q]
            else
                last_amplitude[q]:=0;
        end;

{$IFDEF SPECTRUM}
    if setup_data.wave.FFT then
        begin
        for q:=0 to number_of_fish div 2 -1 do with setup_data.wave do with XMM do
            begin
```

```
                Four(FFT_Data[q]^,sincos,Vector_size,1);
                Split_spectrum(FFT_Data[q]^,FFT2^,Vector_size);
                with MoveX do
                    begin
                    length:=sizeof(complex)*vector_size;
                    sourcehandle:=0;
                    sourceoffset:=longint(FFT_Data[q]);
                    desthandle:=handle[2*q];
                    destoffset:=0;
                    end;
                if not MoveExtended then
                    begin
                    Str(Error,msg);
                    display_message('Extended memory move error:'+msg,'');
                    end;
                with MoveX do
                    begin
                    length:=sizeof(complex)*vector_size;
                    sourcehandle:=0;
                    sourceoffset:=longint(FFT2);
                    desthandle:=handle[2*q+1];
                    destoffset:=0;
                    end;
                if not MoveExtended then
                    begin
                    Str(Error,msg);
                    display_message('Extended memory move error:'+msg,'');
                    end;
                end;

if status=spectrum_amplitude then spectrum_display(channum,msg,first_cycle);
    end; {FFT}
{$ENDIF}

{$IFDEF SCOUT}
    Scout.scan(setup_data.Scout_Phys,msg,TRUE);

if (scout.scout_state = valid_data) then
        ScoutAlarm:=CheckScoutPhysChemAlarm
    else
        ScoutAlarm:= false;

with setup_data.Scout_Phys do
      begin
        if not Data_Valid then
          begin
            Temperature.actual:=0;
            O2.actual:=0;
          end;
  {$IFDEF SCOUTDAC}
        DAC_O2.Write(Temperature.actual,O2.actual);
  {$ENDIF}
      end;

{$ENDIF}

{$IFDEF ANALOGPH}
    Phys_scan;
    AnalogAlarm:=CheckAnalogPhysChemAlarm;
```

```
{$ENDIF}

Inc(elapsed_minutes);
    Alarm_Sensor(current_menu,Remote,ScoutDataLoc,AnalogAlarm,ScoutAlarm);
    with PL do
        case status of
            general : begin
                            General_Display(last_freq,last_amplitude,warning,
                                        setup_data,True);
                            Remote.General_Display(last_freq,last_amplitude,
                                        warning,setup_data,first_cycle,True);
                      end;
            waveform_plot: begin
                            FS_display(last_freq[channum]/(2.0*acquisition_period),
                                    last_amplitude[channum],sdev[channum],channum);
                            Remote.FS_display(last_freq[channum]/(2.0*acquisition_pe
                                    last_amplitude[channum],sdev[channum],channum);
                           end;
        end; {case} if elapsed_minutes=setup_data.bio.assessment_interval.actual then {end of as
       with PL do with startofinterval do
          begin
            getdate(year,month,day,tdayofweek);
            gettime(hour,min,sec,tsec100);
            FillChar(period_sum_freq,SizeOf(period_sum_freq),0);
            FillChar(period_sum_amplitude,SizeOf(period_sum_amplitude),0);
            elapsed_minutes:=0;
          end;
    UpdatePowerLossFiles;          { save history after data update - 2/4/1991 -
    if status=waveform_plot then MoveTo(xpt,ypt);
    Remote.Data.BarUpdate:=True;   {need to update bars on general status screen
    Remote.Data.Initialize.Date_erase := false; { set here so that the date gets
    Remote.TimeDateUpdate(xpt+Xo,ypt+Yo-Ysize);
    if not KeyInstalled(*-(0)-*)then SecurityExit;
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$IFDEF RAWDATA}
    procedure EndRawDataCollection;
    {
    This procedure handles the ending of collections of RAW data from
    the A/D board.
    }
    var S1,S2 :string[12];
    begin
    with RawDataRecGlb do
            begin
            DoCollect := FALSE;
            CollectOK := FALSE;
            str (TimerSecsElapsed (Timer),S1);
            sound (500);
            delay (50);
            nosound;
            Display_message ('Raw data collection complete.',S1+' seconds elapsed dur
            str (RawDataRecGlb.NumSamples,S2);
            writeln (DataFile);
            writeln (DataFile,'    Total elapsed time = '+S1+' seconds,   Total samples
            Close (DataFile);
            end;
    end;
```

```
{$ENDIF}
  {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
  procedure Data_processing(new_count:word;channum:Integer;PlotWidth:Word;
                            var xpt,ypt:Integer;var msg:string;var Remote:Remote
                            var current_menu:menu);
  { Reads collected data from DMA buffer, determines frequency and amplitude }
  { and plots waveform.                                                       }
  { Processes DMA locations starting from processing_count until new_count    }
  { Called by End_Processing and Fish_Monitoring procedure task list          }

{
   This function is probably the most crucial piece of code in the
   bio-sensor. It gets data from the A/D DMA buffer and determines when
   a peak in a fish's waveform takes place. This is important because
   counting the peaks is how the bio-sensor determines the frequency of
   ventilatory action.  This frequency is then in turn used to assess if
   the Bio-Sensor is working properly.
  }
  var xpt_erase,
    ch,chx,pt          : Integer;
    vector_position    : Word;
    or_direction,and_direction:boolean;
    s1,s2,s3 : string;
  begin {
   while there is data in the DMA buffer from the Bio-Sensor,
   process it.  The DMA buffer is a circular buffer meaning that
   if you let processing go to long, you will eventually "wrap around"
   the end of the buffer and start overwriting data collected.
  } repeat
      ch:=absolute_count mod number_of_channels;
      vector_position:=absolute_count div number_of_channels;

if ch<number_of_fish then
        begin
          if processing_count<DMA_buf_count
            then pt:=AcquisitionData[0]^[processing_count]shr 4-2048
            else pt:=AcquisitionData[1]^[processing_count-DMA_buf_count]shr 4-2
{$IFDEF RAWDATA}
          {
           THIS CODE IS CRITICAL TO PHASE II.
           TO SAVE SPACE YOU SHOULD WRITE JUST THE VALUE OF
           PT WHICH IS A TWO BYTE INTEGER.  THIS FILE MUST ALSO
           BE OF TYPE INTEGER.  THIS WILL ALLOW FOR LONGER PERIODS
           OF LOGGING RAW DATA TO DISK FOR LATER ANALYSIS.
          }
          with RawDataRecGlb do
            begin
              if CollectOK and not DoCollect then
                if ch = 0 then
                  DoCollect := TRUE;
              if DoCollect then
                write (DataFile,pt*max_input/2048:7:3);
            end;   {with}
{$ENDIF}
```

```
{$IFDEF SPECTRUM}
{
this code collects data for doing the FFT when the spectal analysis
option is used
}
        if setup_data.wave.FFT then {pack data for FFT}
            if ch mod 2 = 0 then
                FFT_Data[ch div 2]^[vector_position].x:= {convert to IEEE 32-bit
                FFT_Window^[vector_position]* {includes FFT and windowing correc
                pt*0.5*max_input/(2048.0*(setup_data.wave.Vector_size div 2)*Bla
            else
                FFT_Data[ch div 2]^[vector_position].y:= {convert to IEEE 32-bit
                FFT_Window^[vector_position]* {includes FFT and windowing correc
                pt*0.5*max_input/(2048.0*(setup_data.wave.Vector_size div 2)*Bla
{$ENDIF} if waveform_analysis then
              begin
                if setup_data.wave.automatic_threshold then
                  begin dynamic_threshold[ch]:=dynamic_threshold[ch]*decay;

if dynamic_threshold[ch]<minimum_threshold then
                      threshold[ch]:=minimum_threshold
                    else
                      threshold[ch]:=Round(dynamic_threshold[ch]);
                  end;

{
           the next bit of code is the critical part.
           it detects if the waveform is rising or falling and where
           the peaks are ocurring within the waveform.  With each peak
           the sum_amplitude array is incremented to count a peak.

The amplitude is calculated as a peak to peak amplitude.
           That is to say the amplitude is difference between the height
           of the positive peak and the height of the negative peak.

Because of the nature of the bio-electric field and the nature
           of the fish exposure chambers, the fish acts as a natural
           dipole.  This effect in turn polarizes the signal depending on
           which way the fish is facing in the tank.  The polarity can be
           calculated as to whether or not amplitude is more positive or
           negative.  When the signal changes polarity you can be assured
           that the fish has changed direction.  As per the previous phase
           I research it has been noted that when a toxicant is present
           the fish tends to not change direction as often.
        }
                if rise[ch]then
                  begin              {+slope}
                    Inc(poscount[ch]);
                    if pt>pospeak[ch]then pospeak[ch]:=pt;
                    if pospeak[ch]-pt>threshold[ch]then
                       begin           {detect -slope}
                          Amplitude[ch]:=pospeak[ch]-negpeak[ch];
```

```
                    Sum_amplitude[ch]:=Sum_amplitude[ch]+Amplitude[ch];
                    dynamic_threshold[ch]:=0.01*setup_data.wave.dynamic_thresh
                    current_freq[ch]:=current_freq[ch]+1;
                    negpeak[ch]:=pt;
                    rise[ch]:=False;
                    { following code detects and counts changes }
                    { in the fish direction                     }
(*                     direction[ch]:=poscount[ch]>=negcount[ch];
                    for chx:=1 to setup_data.wave.maxdirection.actual do
                        old_direction[ch][chx]:=old_direction[ch][chx-1];
                    old_direction[ch][0]:=direction[ch];
                    or_direction:=FALSE;
                    and_direction:=TRUE;
                    for chx:=0 to setup_data.wave.maxdirection.actual do
                        begin
                        or_direction:=or_direction or old_direction[ch][chx];
                        and_direction:=and_direction and old_direction[ch][chx
                        end;
                    if not or_direction and new_direction[ch] then
                        begin
                        new_direction[ch]:=FALSE;
                        Inc(Direction_change[ch]);
                        end;
                    if and_direction and not new_direction[ch] then
                        begin
                        new_direction[ch]:=TRUE;
                        Inc(Direction_change[ch]);
                        end; *)
                    negcount[ch]:=0;
                end;               {detect -slope}
            end                    {+slope}
        else
            begin                  {-slope}
                inc(negcount[ch]);
                if pt<negpeak[ch]then negpeak[ch]:=pt;
                if pt-negpeak[ch]>threshold[ch]then
                    begin          {detect +slope}
                    Amplitude[ch]:=pospeak[ch]-negpeak[ch];
                    Sum_amplitude[ch]:=Sum_amplitude[ch]+Amplitude[ch];
                    dynamic_threshold[ch]:=0.01*setup_data.wave.dynamic_thresh
                    current_freq[ch]:=current_freq[ch]+1;
                    pospeak[ch]:=pt;
                    rise[ch]:=True;
                    poscount[ch]:=0;
                end;               {detect +slope}
            end;                   {-slope}
    end;

{
this code plots the waveform when the user is on the
individual waveform status screen.

It also sends textronix 4200+ code to the modem for
remote viewing when a remote communications session is
active.
}
if (ch=channum) and(status=waveform_plot)then
    begin                  {for real-time plot}
        Dec(skip_index);
        if skip_index<=0 then
```

```
                    begin
                      SetColor(Blue);
                      Inc(xpt,1-skip_index); {fix}
                      if refresh then xpt:=0;
                      refresh:=FALSE;
                      xpt:=xpt mod Xsize; {fix}
                      if xpt<= -skip_index then xpt:=0;
                      xpt_erase:=xpt+PlotWidth div 2; {fix}
                      if skip_index<0 then
                        Bar(xpt,0,xpt_erase-skip_index,Ysize)
                      else
                        Line(xpt_erase,0,xpt_erase,Ysize); {fix}
                      ypt:=Ysize div 2-pt div 16;
                      with Remote do
                        with Data do with PL do
                          if(xpt=0) and(terminal_type=Tek4010) or Terminal_refresh t
                            Plot_modem_setup(current_menu,xpt+Xo,ypt+Yo-Ysize,ch,
                                             last_freq[ch],last_amplitude[ch],sdev[c
                      if waveform_analysis then
                        if rise[ch]then
                          begin
                            if rise[ch]<>oldrise then Remote.Color(2);
                            SetColor(LightRed);
                          end
                        else
                          begin
                            if rise[ch]<>oldrise then Remote.Color(3);
                            SetColor(LightGreen);
                          end
                      else
                        begin
                          SetColor(Yellow);
                          Remote.Color(7);
                        end;

if xpt>0 then
                        begin
                          LineTo(xpt,ypt);
                          Remote.Plot_Modem(xpt+Xo,Yo-Ysize+ypt);
                        end
                      else
                        begin
                          MoveTo(xpt,ypt);
                          Remote.Erase_trace(Yo-Ysize+ypt);
                        end;

oldrise:=rise[ch];
                      skip_index:=skip;
                    end;
              end;
          end;

{$IFDEF RAWDATA}

{I changed the following line to number_of_fish-1 from number_of _fish because
 the writeln wasn't being called with the 12 channel version. 4/29/91 - MK} if (ch = number_of_fish-1) and RawDataRecGlb.DoCollect then
            begin
              writeln (RawDataRecGlb.DataFile);
```

```
                inc (RawDataRecGlb.NumSamples);
            end;

with RawDataRecGlb do
            if DoCollect then
                if (NumSamples >= MaxSamples) then EndRawDataCollection;

{$ENDIF}

Inc(processing_count);
        Inc(absolute_count);

if processing_count=DMA_buf_count*2 then
            processing_count:=0;

{
         this code determines if a minutes worth of samples have been
         collected since the last time the biological parameters were
         assessed.
        }
        if absolute_count=setup_data.wave.vector_size*number_of_channels then
            begin absolute_count:=0;
            if waveform_analysis then with PL do
                begin
                last_freq:=current_freq;
                old_sum_amplitude:=Sum_amplitude;
                for chx:=0 to number_of_fish-1 do
                    begin
                        period_sum_freq[chx]:=period_sum_freq[chx]+current_freq[chx];
                        period_sum_amplitude[chx]:=period_sum_amplitude[chx]+
                                                  Sum_amplitude[chx];
                    end;
                FillChar(current_freq,SizeOf(current_freq),0);
                FillChar(Sum_amplitude,SizeOf(Sum_amplitude),0);
                FillChar(direction_changes,sizeof(direction_changes),0);
                End_processing(PL.FirstCycle,channum,PlotWidth,xpt,ypt,current_menu,
                        Remote,msg,current_menu.ScoutDataLoc);
                end;
            end;

until processing_count=new_count;
    { keep processing data until the data in the DMA buffer until the
      buffer has been cleared } end;

procedure FrequencyAndAmplitudeInit(var GotMonitoring : boolean);
{
 FrequencyAndAmplitudeInit performs the initializations of the
 array data used during EndProcessing to determine if there is an
 alarm - MAJ 5/14/91
}
var i,j : integer;
begin
    for i:=0 to number_of_fish-1 do
        begin
            if (not GoToMonitoring) or (InitializePLRecGlB) then
            with PL do
```

```
                    begin
                      FirstCycle:=True;
                      period_sum_amplitude[i]:=0;
                      period_sum_freq[i]:=0;
                      last_amplitude[i]:=0;
                      last_freq[i]:=0;
                      calibration[i]:=True;
                      sdev[i]:=0;
                      sample_num[i]:=0;
                      warning_count[i]:=0;
                      warning[i]:=False;

if setup_data.bio.moving_average then
                        for j:=1 to max_samples do
                          begin
                            period_freqs[j][i]:=0;
                            period_amplitudes[j][i]:=0;
                            direction_changes[j][i]:=0;
                          end;

end;

for j:=1 to maxdirlimit do old_direction[i][j]:=FALSE;
               threshold[i]:=minimum_threshold;
               rise[i]:=False;
               direction[i]:=FALSE;
               new_direction[i]:=FALSE;
               AlarmSensorS1[i]:=0;
               AlarmSensorS2[i]:=0;
               pospeak[i]:=0;
               negpeak[i]:=0;
               poscount[i]:=0;
               negcount[i]:=0;
               Sum_amplitude[i]:=0;
               direction_change[i]:=0;
               current_freq[i]:=0;
               Amplitude[i]:=0;
               dynamic_threshold[i]:=threshold[i];
           end;

GoToMonitoring:=False;
end;

{$IFDEF RAWDATA}
procedure InitRawDataRec(var RawDataRecGlb : RawDataRecord);
{
 Initializes the raw data record - moved here from
 Fish_monitoring 5/14/91 - MAJ
}
begin
     with RawDataRecGlb do
        begin
           CollectOK := FALSE;
           DoCollect := FALSE;
           NumSamples := 0;
           Timer := 0;
        end;
end;
```

```
{$ENDIF}
   {ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
{$F+}
   procedure Fish_Monitoring(current_menu_ptr:Pointer;item:Word);
{$F-}
   { Performs biological and physiochemical monitoring and handles remote commu
   { Called by main }
const    dayticksmod18    =24*60*60*91 div 5 div 18;
  var
     tdayofweek,tsec100,          { temp variables created to be able to
                                    mark time and date for the history
                                    files - 1/18/90 MAJ }
     PlotWidth,Result,
     new_count,buffer_time,
     number_of_datafiles :Word;
     channum,oldchannum,
     i,j                 :Integer;
     filecopy            :File_Obj;
     AltWasPressed, dummy,ctrl          :boolean;
     LocalKey            :Char;
     msg,msg2            :String;
     mem_required,
     time,oldtime        :longint;
     seconds,oldseconds,
     xpt,ypt    :Integer;
     PlotView            :ViewPortType;
     current_menu        : ^menu;
     Remote              :RemoteObj;
     Mempointer,
     ExitSave,
     DMA_pointer         :Pointer; { memory location of DMA buffer }
     RVar                :file;
     rate                :real;
     timer               :longint;
     sparekey            :char;
     corner_voltage      :Integer;
     difference          :Word;

{$IFDEF RAWDATA}
    RawDataFileName,
    S1,S2               : string[12];
    L1,L2               : longint;
    Hr,Mn,Sc,Hn,
    Yr,Mo,Dy,Dw         : word;
    ii                  : integer;
{$ENDIF}

{$IFDEF SPECTRUM}
    procedure CleanupExtendedMemory(j:integer);
    {
     this procedure releases any extended memory allocated by the
     system when doing spectal analysis.
    }
    var i:integer;
    begin
    if j>=0 then for i:=j downto 0 do
        if XMM.FreeExtended(XMM.handle[i]) then;
    with XMM do if ReleaseHMA and QueryA20 then if DisableA20 then;
```

```
        end;
{$ENDIF} procedure Stop_DMA; far;        { Error handler which stops DMA   }
    begin
      ExitProc:=ExitSave;
      d16.dma_int_disable;
      print_screen.vector_restore;
{$IFDEF SPECTRUM}
      if setup_data.wave.FFT then CleanupExtendedMemory(number_of_fish-1);
{$ENDIF}
      Remote.Modem_Cleanup(current_menu^);
{$IFDEF SCOUT}
      Scout.Close;
{$ENDIF}
      Release(Mempointer);        {deallocate buffers}
      if Exitcode<>0 then
        begin
        CloseGraph;
        Writeln('Exit code=',ExitCode,' Error address=',
             Seg(ErrorAddr),':',Ofs(ErrorAddr));
        Writeln('Please contact Biologocal Monitoring Inc.');
        Writeln('Press Enter to quit.');
        sparekey:=Readkey;
        end;
    end;

procedure out_of_memory(msg:string);
    begin
        check_for_old_file:=False;
        with current_menu^ do
            begin
            oldrtm:=100;                  { greater than 59 to ensure time refreshi
            redraw:=True;
            end;
        write(#7);
        display_message(msg,'Press Space Bar.');
        sparekey:=Readkey;
    end;

function DMA_Init(var d16 : D16obj;var rate : real;mempointer : pointer):boolean
{
 handles the initialization of the D16 data acquisition board
 moved here from Fish_monitoring 5/14/91 - MAJ
}
begin
    display_message('Allocating Data Acquisition Buffer.','Please Wait...');
    d16.malloc(AcquisitionData,SizeOf(Integer)*DMA_buf_count*2);
    rate:=setup_data.wave.vector_size/acquisition_period;
    buffer_time:= DMA_buf_count*2*longint(acquisition_time) div
              (longint(number_of_channels)*setup_data.wave.vector_size);
    display_message('Please Wait...','DMA initialization in progress.');
    d16.aindma(AcquisitionData,chanlo,chanhi,Xtal,DMA_buf_count*2,rate);
                                               { start data acquisition } if d16.err_code <> 0 then
```

```
        begin
        Stop_DMA;
        out_of_memory(d16.err_msg);
        DMA_Init:=FALSE;
        end
        else
        DMA_init:=TRUE;
     display_message('DMA initialization successful.','Thanks you for waiting.');
end;

{$IFDEF RAWDATA}
procedure StartRawDataCollection;
{
 This procedure sets toggles on the collection of Raw Data collection
 and sets up the raw data collection file moved here out of the actual code in Fish Monitoring
 MAJ  5/14/91
}
var
   ii : integer;
begin
     if not RawDataRecGlb.DoCollect then
                     begin
                        L1 := DiskFree (0);
                        with setup_data do
                          RawDataRecGlb.MaxSamples := wave.vector_size*bio.assessmen
                        L2 := RawDataRecGlb.MaxSamples*7+350;
                        if L1 > L2 then
                           begin
                              GetTime (Hr,Mn,Sc,Hn);
                              GetDate (Yr,Mo,Dy,Dw);
                              str (Mo,S1);
                              if Mo < 10 then S1 := '0'+S1;
                              str (Dy,S2);
                              if Dy < 10 then S1 := '0'+S2;
                              RawDataFileName := S1 + S2;
                              str (Hr,S1);
                              if Hr < 10 then S1 := '0'+S1;
                              str (Mn,S2);
                              if Mn < 10 then S2 := '0'+S2;
                              RawDataFileName := RawDataFileName+S1+S2+'.RAW';
                              str (setup_data.bio.assessment_interval.actual:1,S1);
                              str (setup_data.wave.sampling_frequency.actual:1:2,S2);
                              with RawDataRecGlb do
                                 begin
                                    Assign (DataFile,RawDataFileName);
                                    SetTextBuf (DataFile,Buffer);
                                    ReWrite (DataFile);
                                    CollectOK := TRUE;
                                    NumSamples := 0;

{For now, we'll set the following variable MaxSamples here -
 later it will be a menu selection. - 4/26/91 - MK}

{ How about one assesment interval? - 4/28/91 - PG }

{ Looks fine to me - MK 4/29/91 - but what if we want it to be < assessment
   interval?  I think an eventual menu option is best - L8R, tho...}
```

```
                        writeln (DataFile,'                      File name =
                        writeln (DataFile,'              Assessment interval =
                        writeln (DataFile,'                Sampling frequency =
                        str (Round (setup_data.wave.sampling_frequency.actua
                                    setup_data.bio.assessment_interval.actua
                                    60),S1);
                        writeln (DataFile,'Samples per assessment interval =
                        str (MaxSamples,S1);
                        writeln (DataFile,'Samples/channel to be collected =
                        writeln (DataFile);
                        for ii := 0 to number_of_fish-1 do
                        begin
                           str (ii:7,S1);
                           write (DataFile,S1);
                        end;
                        writeln (DataFile);
                        Timer := TimerNow;

end; {with}

Display_message ('Raw data logging enabled.','');
                  end
               else
                  begin
                  str (L1 div 1024,S1);
                  str (L2 div 1024,S2);
                  Display_Message ('Only '+S1+' KB of space left on fixed di
                                   'Minimum of '+S2+' KB required to save ra
                  end;
               end
                  else msg:='Raw data log in progress. Can not start new log f
end;
{$ENDIF} begin

{$IFDEF RAWDATA}
   InitRawDataRec(RawDataRecGlb);
{$ENDIF}

Mark(Mempointer);              {record buffers starting memory}
      if not KeyInstalled then SecurityExit;
      current_menu:=current_menu_ptr;
      current_menu^.Alarm_flag:=False;
      skip:=0;
      skip_index:=0;
      current_menu^.printer_on:=True;
      current_menu^.printer_output:= @lst;
      DGT_IO.AlarmSet:=False;
      DGT_IO.TimerStart:=TimerNow;
      oldtime:=TimerNow div 18;

with current_menu^ do { Prevent overwriting old file PG 3/3/1991 }
           if Period_name=Old_Period_Name then
              begin
              Sound(200);delay(200);NoSound;
              refresh:=False;
```

```
                    Monitor_Period_Name(current_menu,3);
                    if mshown then
                        mhide;
                    end;
{$IFDEF SCOUT}
    scout.Setup;
    scout.invoke;
{    Scout_timing:=Round(setup_data.wave.Vector_size*50.0/60);} {Ten seconds bef
{$ENDIF}

SetViewPort(0,0,GetMaxX,GetMaxY,ClipOn);
    ClearViewPort;
    Frame;
    Remote.Open_port;

number_of_datafiles:=0;
    processing_count:=0;
    absolute_count:=0;
    PlotWidth:=3;
    Filecopy.in_progress:=False;
    refresh:=True;
    AltWasPressed:=TRUE;

{$IFDEF SPECTRUM}
    if setup_data.wave.FFT then with setup_data.wave do
        begin
        XMM.initialized:=FALSE;
        if XMM.Installed then begin
                            Result:=XMM.version;
                            Str(Hi(Result),msg);
                            Str(Lo(Result),msg2);
                            if Lo(result)<10 then msg2:='0'+msg2;
                            msg:=msg+'.'+msg2;
                            end
                      else begin
                            out_of_memory('XMM driver not installed');
                            exit;
                            end;
        Result:=XMM.QueryTotalFree;
        Str(Result,msg2);
        new_count:=(sizeof(complex)*number_of_fish * vector_size) div 1024;
        if Result<new_count
            then begin
                Str(new_count,msg);
                out_of_memory(msg+' kB extended memory required. '+msg2+' kB foun
                exit;
                end;

if not XMM.QueryA20 then if XMM.EnableA20 then;  { get ready for HMA acces
        if XMM.RequestHMA($FFFF) then   { grab HMA }
            begin
            FFT_window:=ptr($FFFF,$10);  { Allocate to High Memory Area }
            FFT2:=ptr($FFFF,$8000);
            mem_required:=vector_size*sizeof(complex)*(number_of_fish div 2+1);
            if maxavail<mem_required then
                begin
                if XMM.ReleaseHMA then;   { set HMA free }
                out_of_memory('Not enough memory to start monitoring. Free some mem
                exit;
```

```
                end;
            end
        else    { when HMA is not available }
            begin
            mem_required:=vector_size*(sizeof(single)+sizeof(complex)*(number_of_f
            if maxavail<mem_required then
                begin
                out_of_memory('Not enough memory to start monitoring. Free some mem
                exit;
                end
            else    { get DOS memory }
                begin
                GetMem(FFT_window,vector_size*sizeof(single));
                GetMem(FFT2,Vector_size*sizeof(complex));
                end;
            end;

for i:=0 to number_of_fish div 2 -1 do
            GetMem(FFT_Data[i],vector_size*SizeOf(complex));
{        Result:=$FFFF;
        if XMM.RequestUMB(Result,new_count) then
            if XMM.ReleaseUMB(new_count) then;
}
{ XMS v 2.04   driver does not support UMB }

GetMem(sincos,vector_size div 2 *SizeOf(complex));
        Create_tables(sincos,FFT2,FFT_window,Vector_size);

for i:=0 to number_of_fish-1 do
            if not XMM.AllocateExtended(sizeof(complex)*vector_size div 1024,XMM.
                begin
                Str(XMM.Error,msg);
                CleanupExtendedMemory(i-1);
                out_of_memory('Failed to allocate extended memory. Error:'+msg);
                exit;
                end;
        display_message('XMS driver version '+msg,'Extended memory available:  '+m Delay(1000);
        end;
{$ENDIF}

{$IFDEF ANALOGPH}
    with setup_data.Analog_Phys do
        begin
        Ammonia.actual:=0;
        Turbidity.actual:=0;
        Temperature.actual:=0;
        pH.actual:=0;
        Conductivity.actual:=0;
        O2.actual:=0;
        extra1.actual:=0;
        extra2.actual:=0;
        end;
{$ENDIF} with setup_data.wave do
        begin
```

```
{          automatic_threshold:=True; }
           decay:=Exp(-1.0/(sampling_frequency.actual*Time_constant.actual));
           minimum_threshold:=Round(409.5*Min_threshold.actual);
         end;

{ 5/14/91 - moved this code out of FishMonitoring to make the code
        easier to read MAJ }
      FrequencyAndAmplitudeInit(GotoMonitoring);

{$IFDEF SCOUT}
      setup_data.Scout_Phys.Data_Valid:=False;
{$ENDIF}

{$IFDEF SPECTRUM}
      waveform_analysis:=True;
{$ELSE}
    waveform_analysis:=TRUE;
{$ENDIF} status:=general;
      channum:=0;oldchannum:=0;
      elapsed_minutes:=0;
      oldseconds:=100;

{ mark the start of the montoring interval for the history files } with PL.startofinterval do
        begin
          getdate(year,month,day,tdayofweek);
          gettime(hour,min,sec,tsec100);
        end;

ctrl:=False;
      dummy:=Printer_status(0,msg);
      msg2:='';
{
   Installed this assign because otherwise setup file was being overwritten
   with the current settings regardless of the users wishes to make the
   setup data permenant.  so this temp file name is created to be used by
   powerloss recovery as well - MAJ 2/5/91
}
      Auto_Name(current_menu^,True,False);

Assign(Setup_file,PowerLossSetupFileName); {Create temporary setup file}
      Rewrite(Setup_file,1);
      BlockWrite(Setup_file,setup_data,SizeOf(setup_data),Result);
      Close(Setup_file);

UpdatePowerLossFiles;
      timer:=TimerNow;
      print_screen.vector_save(current_menu^.printer_output);
      ExitSave:=ExitProc;      { save old exit procedure pointer }
      ExitProc:=@Stop_DMA;
      if not DMA_Init(d16,rate,mempointer) then exit;
      with setup_data.wave do
          corner_voltage:= Round((5.2970452 -0.20408314*corner_frequency.actual
```

```
                                    -0.00148581*sqr(corner_frequency.actual))/5.0*40
    d16.aous(0,corner_voltage);
    delay(500);
{$IFDEF SCOUT}
    Scout.scan(setup_data.Scout_Phys,msg,TRUE);
    with setup_data.Scout_Phys do
      begin
         trigger:=True;
         if not Data_Valid then
           begin
              Temperature.actual:=0;
              O2.actual:=0;
           end;
      {$IFDEF SCOUTDAC}
         DAC_O2.Write(Temperature.actual,O2.actual);
      {$ENDIF}
      end;
{$ENDIF}
{$IFDEF ANALOGPH}
  Phys_scan;
{$ENDIF} alarm_out.init;

repeat   {big loop which controls everything during monitoring }
      with Remote do with Data do if (Command_state=Tek_mode)
                              and Terminal_refresh then with PL do
        case status of
          waveform_plot:Remote.Plot_modem_setup(current_menu^,
                                         Xo+1,Yo-Ysize div 2,channum,last
                                         last_amplitude[channum],sdev[cha
          general:Remote.General_Status(current_menu^.Logo_polygon,FirstCycle,Tr
        end;
      if refresh then with PL do
        begin
          case status of
             waveform_plot:Plot_setup(channum,'Time','Amplitude',status,last_freq
                                last_amplitude[channum],sdev[channum],ref
{$IFDEF SPECTRUM}
             spectrum_amplitude:begin
                                Plot_setup(channum,'Frequency','Amplitude',stat
                                   last_amplitude[channum],sdev[channum
                                spectrum_display(channum,msg,FirstCycle);
                                end;
{$ENDIF}
             else General_Setup(refresh,FirstCycle,msg,warning,setup_data,True,la
                             last_amplitude,current_menu^);
          end;                    {case}
          refresh:=FALSE;
          xpt:=-1;
          if not (Remote.Command_state in [Password_Query,Modem_off]) then msg2:
          if Remote.Command_state=Modem_off then msg2:='Modem is off.';
          dummy:=Printer_status(0,msg);
          if current_menu^.printer_on then
            display_message('Data echoed to printer. '+msg,msg2)
          else
            display_message('Data not echoed to printer. '+msg,msg2);
          msg:='';  msg2:='';
          AltWasPressed:=TRUE;
```

```
         end;

if(oldchannum<>channum) and (status<>general)then with PL do
         begin
            oldchannum:=channum;
            Plot_refresh(channum,last_freq[channum]/(2.0*acquisition_period),
                         last_amplitude[channum],sdev[channum]);

{$IFDEF SPECTRUM }
            if status=spectrum_amplitude then
               spectrum_display(channum,msg,FirstCycle);
            {$ENDIF}

Remote.Plot_refresh(xpt,ypt,channum,last_freq[channum],
                         last_amplitude[channum],sdev[channum]);
            MoveTo(xpt,ypt);
         end;

if TimerNow<>timer then
         begin
            new_count:=d16.count;        { index of last A/D acquisition }
            if new_count < processing_count then
               begin
                  difference := 2*dma_buf_count - processing_count + new_count;
               end
            else
               begin
                  difference := new_count-processing_count;
               end;

timer:=TimerNow;
         end;

if new_count<>processing_count then
         Data_processing(new_count,channum,PlotWidth,xpt,ypt,msg,Remote,current_m time := TimerNow div 18;

if time<>oldtime then
         begin
                              {new second}
{$IFDEF SCOUT}
            Scout.scan(setup_data.Scout_Phys,msg,FALSE);
{$ENDIF}
            (* if DGT_IO.AlarmSet then
               if TimerSecsElapsed(DGT_IO.TimerStart)>setup_data.misc.alarm_duratio
                  DGT_IO.Init(board_num); *)

alarm_out.monitor;

(*
   This code was removed because the buffer time is way to short to be
   accurate and even when it does determine a supposed loss of data
   it doesn't take any action on processing to either remove the data that
   might be bogus or note that this occurred in any of the log files or
   printout
   MAJ 8/21/91
```

```
              if (time-oldtime+dayticksmod18) mod dayticksmod18 >buffer_time then
                  begin
                      msg:='Data processing interrupted by data transfer...';
                      if Remote.Data.DCDHigh then Send_to_Modem(msg+Remote_prompt);
                  end;
*)
                  if AltPressed then if not AltWasPressed then
                      begin
{$IFDEF RAWDATA}
                          Fkey_display('Raw data collection: F1-Start   '#13'F2-Estimate    '#13
                                        'F4-Move to floppy'#13#10,Yellow,White,Cyan);
{$ENDIF}
                          AltWasPressed:=TRUE;
                      end
                  else
                  else
                  if AltWasPressed then
                      begin
                          Fkey_display('F2-Estimate    '#13'F4-Move data    '#13+
{$IFDEF SPECTRUM}
                                        'F9-FFT    '#13+
{$ENDIF}
                                        'F10-Toggle printer    '#13+
                                        #17#196#217'-Change   '#13'Esc-Quit'#13#10,Yellow,White,Cyan);
                          AltWasPressed:=FALSE;
                      end;

Seconds:=Seconds_update;
              with Remote do
                  if DCD_Changed then Modem_Carrier_Control; {change in modem status}
              if seconds<oldseconds then Time_update(current_menu,0);
              oldseconds:=seconds;
              oldtime:=time;
              print_screen.process;
              {str(difference:6,msg);}
          end;

(*     if TimerNow<>timer then
                              { see if any new data has built up that needs
                                to be processed so that remote.handler,
                                when active can halt remote processing and
                                catch up on data processing.  This is so
                                that the remote user does not get the
                                impression that the Bio-Sensor(r) has
                                locked up MAJ 6/12/91}
          begin
          new_count:=d16.count;          { index of last A/D acquisition }
          timer:=TimerNow;
*)

Remote.Handler(current_menu^,difference,setup_data.wave.sampling_freque
(* end; *)

LocalKey:=Getkey;
      with Remote.Data do
```

```
        if(LocalKey=#0) and DCDHigh then { read remote only if local keybord is
          begin
            LocalKey:=key;
            key:=#0;
          end;

if LocalKey<>#0 then
      begin                           {keybord scan}
        if status=waveform_plot then GetViewSettings(PlotView);

case LocalKey of
          UArr,
          RArr:channum:=(channum+1) mod number_of_fish;
          LArr,
          DArr:channum:=(channum+number_of_fish-1) mod number_of_fish;

F2:with Filecopy do if not in_progress then
                Estimate('BM?',current_menu^.Period_name,msg2,msg);

F4:with Filecopy do if not in_progress then
                begin
                  Estimate('BM?',current_menu^.Period_name,msg2,msg);
                  msg:='                                              ';
                  display_message(msg,msg2);
                  Initialize('BM?',msg);
                end;
          AF2:with Filecopy do if not in_progress then
                Estimate('RAW',current_menu^.Period_name,msg2,msg);

AF4:with Filecopy do if not in_progress then
                begin
                  Estimate('RAW',current_menu^.Period_name,msg2,msg);
                  msg:='                                              ';
                  display_message(msg,msg2);
                  Initialize('RAW',msg);
                end;
          F8:begin
              if status=waveform_plot then
                begin
                  {fix linethickness toggle}
                  PlotWidth:=(PlotWidth+2) mod 4;
                  SetLineStyle(SolidLn,0,PlotWidth); {fix}
                end;
            end;

{$IFDEF SPECTRUM}
          F9:begin
              status:=spectrum_amplitude;
              refresh:=True;
            end;
{$ENDIF}
          F10:with current_menu^ do
                begin
                  dummy:=Printer_status(0,msg);
                  printer_on:=not printer_on;
                  if printer_on then
                    begin
                      display_message('Data echoed to printer. '+msg,'');
                      printer_output:= @lst;
                    end
```

```
                    else
                      begin
                        printer_output:= @nul;
                        display_message('Data not echoed to printer. '+msg,'');
                      end;
                    msg:='';
                  end;

{$IFDEF RAWDATA}
                  { try to turn on Raw Data colleciton }
            AF1: StartRawDataCollection;

AF2:with Filecopy do if not in_progress then
                  Estimate('RAW',current_menu^.Period_name,msg2,msg);

AF3:with RawDataRecGlb do
                  if DoCollect then { if collecting raw data, turn off
                                      raw data collection }
                    EndRawDataCollection;

{ moves raw data to floppies }
            AF4:with Filecopy do if not in_progress then
                  begin
                    Estimate('RAW',current_menu^.Period_name,msg2,msg);
                    msg:='                                               ';
                    display_message(msg,msg2);
                    Initialize('RAW',msg2);
                  end;
{$ENDIF}

',',
            '<':if skip<=10 then
                  begin
                    Inc(skip);
                    if status=spectrum_amplitude then refresh:=True;
                  end;

'.',
            '>':if skip>= -10 then
                  begin
                    Dec(skip);
                    refresh:=status=spectrum_amplitude;
                  end;
            'R',
            'r':begin
                  skip:=0;           {reset waveform speed}
                  refresh:=status=spectrum_amplitude;
                end;
            'C',
            'c':begin                 {clear alarm red screen}
                  SetBkColor(Blue);
                  Remote.Alarm_Stop;
                  current_menu^.Alarm_flag:=False;
                end;
            Esc,
            MEsc:if Filecopy.in_progress then
```

```
            begin
              msg:='Please wait until file copying is complete';
              display_message(msg,msg2);
              Write(#7);
            end
          else ctrl:=True;

Enter:begin
              status:=(status+1) mod max_status;
              refresh:=True;
              Remote.Data.Terminal_refresh:=True;
            end;

AltS:begin
            (* DGT_IO.digit[IntSamplerOutput]:=not(DGT_IO.digit[IntSample
              if DGT_IO.digit[IntSamplerOutput]then
                display_message('','Internal sampler override is ON ********
              else
                display_message('','Internal sampler override is OFF');
              dummy:=DGT_IO.OutDta; *);
              if alarm_out.active(sampler) then
                begin
                    alarm_out.deactivate(sampler);
                    display_message('','Internal sampler override is OFF');
                end
              else
                begin
                    display_message('','Internal sampler override is ON ***
                    alarm_out.activate(sampler,maxint);
                end;
          end;

end;                     {case}
     if status=waveform_plot then MoveTo(xpt,ypt);
     LocalKey:=#0;
   end;                       {scan}

{
 this code handles the end of a transfer of a set of
 .BMI files to floppy disk.
}
with Filecopy do if in_progress then
  begin
    msg:=Transfer;
    if msg='' then
      msg:=Next_File_Message
    else
      begin
        in_progress:=False;
        Sound(400);
        if Total_Filecount=filecount then
            begin
              delay(200);
              Sound(440);
              delay(200);
              Sound(600);
              delay(400);
              msg2:='                                       ';
            end;
```

```pascal
            delay(200);
            NoSound;
          end;
      end;

if(msg<>'') or (msg2<>'')then
       begin
         display_message(msg,msg2);
         msg:='';msg2:='';
       end;

with Remote do
        if not(Data.CommErrCode in[0,10])then ModemErrMsg;
{$IFDEF SCOUT}
       if Scout.Error<>0 then display_message('',Scout.Msg);
{$ENDIF} until ctrl;  { Here is the end of the big loop !!!!!}

{$IFDEF RAWDATA}
     with RawDataRecGlb do
         if DoCollect then EndRawDataCollection;
{$ENDIF}

{$IFDEF SCOUTDAC}
     DAC_02.Write(0,0);
{$ENDIF}
     SetBkColor(Blue);
     TextBox(40,150,600,210,white,RED,4,'Resetting modem - please wait..');
     Remote.Modem_Cleanup(current_menu^);

{$IFDEF SCOUT}
     Scout.Close; { clear the scout }
{$ENDIF}

{DGT_IO.Init(board_num);}
     alarm_out.init; { make sure all the alarm outs are off }

NoSound;
     Stop_DMA;

Assign(RVar,RecoveryFileNameOne);  { Erase history files}
     Erase(RVar);

Assign(RVar,RecoveryFileNameTwo);
     Erase(RVar);

Erase(Setup_file);  { Erase temporary setup file }

SetColor(white);

check_for_old_file:=False;

with current_menu^ do
       begin
         EraseEmptyFiles;
         oldrtm:=100;                  { greater than 59 to ensure time refreshing }
```

```
      redraw:=True;
      Old_Period_Name:=Period_Name;
    end;
  PL.PeriodName:='';
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
procedure GraphAbort(msg:String);
{
 trap function called when the BGI graphics system fails
}
begin
  WriteLn(msg,': ',GraphErrorMsg(GraphResult));
  Halt(1);
end;
{ÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜÜ}
  {main}
var z,zz                :Integer;
    i                   :Word;
    Pstr                :String[30];

Metapointer         :Pointer;
    main_menu           :menu;
    dummy               :Char;

procedure EgaVgaDriverproc; External;
{$L EGAVGA.OBJ }
procedure SansSerifFontproc; External;
{$L SANS.OBJ }
procedure TriplexFontproc; External;
{$L TRIP.OBJ } begin powerlossrecoveryglb := false;
  Fetch_setup_data(SetupFileName);

checkbreak:=False;              {disable ctrl break except for testing - MK 1/
                   set checkbreak to FALSE if you do not want
                   control -C to abort your program -- MJ 1/15/91}
  extra_parameters:=False;
  if ParamCount>0 then
    for z:=1 to ParamCount do
      begin
        Pstr:=ParamStr(z);
        for zz:=1 to Length(Pstr)do
          Pstr[zz]:=Upcase(Pstr[zz]);
        if Pos('/XD',Pstr)>0 then extra_parameters:=True;
      end;

{ load and link in the VGA graphics driver and the fonts that
    are needed by the program
  }
  if RegisterBGIdriver(@EgaVgaDriverproc)<0 then GraphAbort('EGA/VGA');
  if RegisterBGIfont(@SansSerifFontproc)<0 then GraphAbort('SansSerif');
  if RegisterBGIfont(@TriplexFontproc)<0 then GraphAbort('Triplex');
  Assign(nul,'NUL');
  Rewrite(nul);
```

```
    InitializePLRecGlb := False;
    GoToMonitoring:=False;
    PL.PeriodName:='';
    { necessary to avoid rewriting of data file in procedure Header in U_HEADER}

{
      check to see if the bio-sensor is starting up from a power loss system
      or if it starting up normally
    }
    RestoreDataFromPowerLoss(GoToMonitoring);
    i:=IoResult;
    if i<>0 then TextExit('History Files '+IOcheck(i));
{$IFDEF SCOUT}
    scout.setup;
    Scout.configuration(TRUE);  { TRUE tells the user that scout is being
                                  configured.  It is also used as a debugging
                                  mode that will display any invalid data
                                  received during the configuration of the
                                  scout PG-MAJ 06/28/91 }
    scout.close; { close the scout down until needed, this way useless data
                   will not build up in the data buffer }

{ alert the user to the fact that it could not detect the
      hydrolab scout }
    if (scout.scout_state=disconnected) and not GoToMonitoring then
       begin
          if keypressed then dummy:=Readkey;
          TextBackground(RED);
          WriteLn('Scout(R) disconnected or communication error. Do you want to cont
          if Readkey in['n','N']then
             begin
                WriteLn('Program aborted');
                Halt;
             end;
       end;
{$ENDIF}

(********************************************************************)

Initialize(Metapointer,main_menu);

(********************************************************************)
   {     Moved above statement to BEFORE call to                              }
   {         "if not Scout_Configuration and not GoToMonitoring then"         }
   {         so the Scout warning and (Y/N) prompt below are skipped if       }
   {         GoToMonitoring is TRUE  - 1/18/91 - MK                           }
   {                                                                          }
   {     Moved above call after the call to "if not Scout..." because         }
   {         GoToMonitoring is checked in the same statement. 1/24/1991 PG    }
   {                                                                          }
   { Yeah, but GoToMonitoring is set in INITIALIZE, so you get random results}
   { if INITIALIZE is not called first.  1/25/91 - MK                         }
   {                                                                          }
   { Yeah, but then it's in graphics mode and the message is not displayed.   }
   { How about we move the check for GoToMonitoring out here above the        }
   { "if not Scout ....." call.  1/25/91 - MK                                 }
   {                                                                          }
```

```
{ I think it is a splenaid idea - 1/27/91 - PG                                  }
(********************************************************************)
i:=0;
if not main_menu.Read_metafile('logo2.cgm',i)then
  begin
    CloseGraph;
    TextExit('LOGO2.CGM File '+IOcheck(i));
  end;
if setup_data.bio.assessment_interval.actual=0 then
  begin
    CloseGraph;
    Sound(400);delay(500);NoSound;
    TextExit('Default settings file (BMI.PRF) is corrupted. Program aborted');
  end;
SetColor(white);
check_for_old_file:=True;
with main_menu do
  begin
    Old_Period_Name:='';
    Period_name:='';
    { installed this fix to allow for power recovery with manual
      file names 6/6/91 MAJ }
    if (GotoMonitoring) and not (setup_data.Misc.AutoMatic_Name)
        and not (InitializePlRecGLB) then
            Period_Name := Pl.PeriodName { restore only if the PL record
                                          was good }
    else
      if (GotoMonitoring) and not (setup_data.Misc.AutoMatic_Name) then
        Auto_Name(Main_Menu,False,False);

oldrtm:=100;             { greater than 59 to ensure time refreshing }

{ following code sets up the menu system defined in
      BMImenuX
    }
    Data[0].description:='LOG INFORMATION';
    Data[0].task:=Time_update;
    Data[1].description:='Today''s date:';
    Data[1].data_type:=dat;
    Data[1].task:=Change_date;
    Data[2].description:='Time of day:';
    Data[2].data_type:=tim;
    Data[2].task:=Change_time_of_day;
    Data[3].description:='Monitor Period Name:';

Data[3].data_ptr:= @Period_name;
    Data[3].data_type:=story;
    Data[3].task:=Monitor_Period_Name;
    Data[4].description:='Bio-Sensor Setup';
    Data[4].data_type:=NoDataType;
    Data[4].task:=Setup;
    Data[5].description:='Start Fish Monitoring';
    Data[5].data_type:=NoDataType;
    Data[5].task:=Fish_Monitoring;
    Data[6].description:='End Program';
    Data[6].data_type:=NoDataType;
    Data[6].task:=nothing;
    Data[7].task:=diskinfo;
    draw((Xmax+1) div 20,(Ymax+1) div 5,Blue,Magenta,ThickWidth,
```

```
            SolidFill,Soli( _n,SansSerifFont,HorizDir,., 1.6,6, @main_menu);
      EraseEmptyFiles;
    end;
  Release(Metapointer);            { kill small fish logo }
  CloseGraph;                      { fixed memory release - PG 3/7/91 }
  Initialize(Metapointer,main_menu);
  CloseGraph;
  Flush_Keyboard_Buffer;
  Close(nul);
  TextMode(LastMode);
end.
```

What is claimed is:

1. A method for processing and assessing a bio-electric waveform as generated by neuromuscular activity of aquatic organisms, comprising the steps of:
   a) non-contact monitoring of ventilatory and locomotor behavior variables of aquatic organisms;
   b) converting the ventilatory and locomotor behavior variables into frequency components;
   c) selecting one of two waveform processing techniques for quantifying the monitored ventilatory and locomotor behavior frequencies;
   d) comparing the monitored quantified ventilatory and locomotor behavior frequencies with a mean frequency changing with time and one of plus and minus a predetermined number of standard deviations;
   e) generating, based on the comparison in said step d), a warning when the ventilatory and locomotor behavior frequencies of the aquatic organisms are one of statistically greater than and less than a predetermined value; and
   f) outputting an alarm when an alarm state occurs when a predetermined number of warnings are simultaneously generated for a predetermined number of aquatic organisms.

2. A method according to claim 1, wherein said one of two waveform processing techniques for quantifying the ventilatory and locomotor behavior frequencies selected in said step c) includes:
   aa) a dynamic threshold level waveform processing technique; and
   bb) a static threshold level waveform processing technique.

3. A method according to claim 2, wherein said dynamic threshold level waveform processing technique comprises:
   i) determining a peak amplitude voltage of a first waveform;
   ii) determining whether a second waveform is forming another peak;
   iii) counting two consecutive threshold crossings of said first and second waveforms as one ventilatory cycle;
   iv) determining a dynamic threshold value based on a peak-to-peak voltage of said first and second waveforms and a time elapsed from a previously established peak;
   v) comparing the dynamic threshold value with the difference between the previously established peak and a present data point; and
   vi) adjusting a threshold level based on the dynamic threshold value.

4. A method according to claim 2, wherein the static threshold level waveform processing technique comprises the steps of:
   i) determining a threshold crossing of the ventilatory behavior frequency of aquatic organisms; and
   ii) counting two consecutive threshold crossings as one ventilatory cycle for determining the alarm state.

5. A method according to claim 1, wherein said step b) further comprises calculating an assessment interval equal to an amount of time in which one of the aquatic organisms ventilates a predetermined number of times.

6. A method according to claim 5, wherein said step (d) comprises the substep of comparing a present ventilatory and locomotor behavioral frequency of one of the aquatic organisms to past ventilatory and locomotor behavioral frequencies averaged over a predetermined number of assessment intervals and one of plus and minus a predetermined number of standard deviations.

7. A method according to claim 5, further comprising the substep of re-calculating an assessment interval when one of the aquatic organisms consecutively generates the predetermined number of warnings without the alarm occurring.

8. An apparatus for processing and assessing a bio-electric waveform as generated by neuromuscular activity of aquatic organisms, comprising:
   means for sensing and quantifying ventilatory behavior and locomotor behavior of aquatic organisms into data and the apparatus outputting the data as behavioral frequencies; and
   means for selecting a waveform processing technique, including a dynamic threshold level processing technique and a static threshold level processing technique, and for comparing the behavioral frequency with a predetermined behavioral frequency changing with time in accordance with the selected processing technique, generating a warning when the behavioral frequency of one of the aquatic organisms is one of statistically greater than and less than the predetermined behavior frequency and outputting an alarm when the behavioral frequency of more than a predetermined number of the aquatic organisms is one of statistically greater than and less than the predetermined behavioral frequency.

9. An apparatus for processing and assessing a bio-electric waveform as generated by neuromuscular activities of aquatic organisms, comprising:
   a sensor for sensing and quantifying ventilatory behavior and locomotor behavior of aquatic organisms into data and outputting the data as a behavioral frequency;
   a processor for selecting a waveform processing technique, including a dynamic threshold level processing technique and a static threshold level processing technique, and comparing the behavioral frequency with a predetermined frequency changing with time in accordance with the selected processing technique and outputting a warning signal when the behavioral frequency of one of the aquatic organisms is one of statistically greater than and less than a predetermined behavioral frequency; and
   an alarm circuit for receiving the warning alarm signal and generating an alarm when the behavioral frequency of a predetermined number of the aquatic organisms is one of statistically greater than and less than the predetermined behavioral frequency during a predetermined interval.

10. A method for processing and assessing a bio-electric waveform as generated by the neuromuscular activity of aquatic organisms and converting the bio-electric waveform into behavioral frequencies, each of said aquatic organisms is in a tank and considered as a separate channel, said method comprising the steps of:
   a) monitoring behavioral frequencies generated by neuromuscular activity of the aquatic organisms;
   b) processing a predetermined number of assessment intervals, an assessment interval equal to an amount of time in which one of the aquatic organisms performs neuromuscular activity a predetermined number of times;
   c) selecting one of two waveform processing techniques for processing the behavioral frequencies including:

(i) a dynamic threshold level waveform processing technique, comprising:
- a1) determining a peak amplitude voltage of a first waveform;
- b1) determining whether a second waveform is producing another peak;
- c1) counting two consecutive threshold crossings of said first and second waveforms as one ventilatory cycle;
- d1) determining a dynamic threshold value based on a peak-to-peak voltage of said first and second waveforms and a time elapsed from a previously established peak;
- e1) comparing the dynamic threshold value with the difference between the previously established peak and a pre-set data point; and
- f1) adjusting the threshold level based on the dynamic threshold value; and ii) a static threshold level waveform processing technique, comprising:
- a2) determining a threshold crossing of the behavioral frequencies of one of the aquatic organisms; and
- b2) counting two consecutive threshold crossings as one behavioral cycle for determining a warning state; and d) calibrating each separate channel, including the substeps of:
- i) determining the mean behavioral frequency and standard deviation for each channel, a calibration period being equal to the predetermined number of assessment intervals multiplied by a number of samples required for a statistical event; and
- ii) continuously adjusting an acceptable range of behavioral frequencies;

e) comparing a current processed one of the behavioral frequencies of one of the aquatic organisms to past processed behavioral frequencies of the aquatic organisms averaged over the predetermined number of assessment intervals and one of plus and minus a predetermined number of standard deviations;

f) generating a warning when the comparison is one of statistically greater than and less than the acceptable range of behavioral frequencies; and g) generating an alarm when a predetermined number of the aquatic organisms are in simultaneous warning states.

11. A method according to claim 10, wherein said continuously adjusting substep ii) in said step d) comprises the step of continuously adjusting an acceptable range of behavioral frequencies by choosing a different standard deviation taken around a behavioral mean.

12. A method according to claim 11, further comprising the step of recalibrating the respective channel when a single one of the aquatic organisms consecutively generates a predetermined number of the warnings.

13. A method for processing and assessing a bio-electric waveform as generated by neuromuscular activity of aquatic organisms and converting the bio-electric waveform into behavioral frequency comprising the steps of:

a) monitoring behavioral frequency generated by neuromuscular activity of the aquatic organisms;

b) selecting one of two waveform processing techniques for quantifying the monitored behavioral frequency, said one of two waveform processing techniques including:

i) a dynamic threshold level waveform processing technique, including the steps of:
- a1) determining a peak amplitude voltage of a first waveform;
- b1) determining whether a second waveform is producing another peak;
- c1) counting two consecutive threshold crossings of said first and second waveforms as one behavioral cycle;
- d1) determining a dynamic threshold value based on a peak-to-peak voltage of said first and second waveforms and a time elapsed from a previously established peak;
- e1) comparing the dynamic threshold value with the difference between the previously established peak and a present data point; and
- f1) adjusting a threshold level based on the dynamic threshold value; and ii) a static threshold level waveform processing technique including:
- a2) determining a threshold crossing of the behavioral frequency of one of the aquatic organisms; and
- b2) counting two consecutive threshold crossings as one behavioral cycle for determining a warning state;

c) comparing the monitored quantified behavioral frequency with a mean frequency plus or minus a predetermined number of standard deviations; and d) determining, based on the comparison in said step c), to send an alarm.

14. A method according to claim 13, wherein said behavioral frequency includes data based on one of ventilatory rate, turns and episodes, and quivers.

* * * * *